US009925241B2

(12) United States Patent
Suh et al.

(10) Patent No.: US 9,925,241 B2
(45) Date of Patent: Mar. 27, 2018

(54) MUTATED FIBROBLAST GROWTH FACTOR (FGF) 1 AND METHODS OF USE

(71) Applicant: Salk Institute for Biological Studies, La Jolla, CA (US)

(72) Inventors: Jae Myoung Suh, San Diego, CA (US); Michael Downes, San Diego, CA (US); Ronald M. Evans, La Jolla, CA (US); Annette Atkins, San Diego, CA (US); Ruth T. Yu, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 14/520,178

(22) Filed: Oct. 21, 2014

(65) Prior Publication Data
US 2015/0111821 A1    Apr. 23, 2015

Related U.S. Application Data

(60) Provisional application No. 61/893,766, filed on Oct. 21, 2013, provisional application No. 61/949,945, filed on Mar. 7, 2014, provisional application No. 61/975,530, filed on Apr. 4, 2014, provisional application No. 62/019,185, filed on Jun. 30, 2014, provisional application No. 62/046,038, filed on Sep. 4, 2014.

(51) Int. Cl.
*A61K 38/00* (2006.01)
*A61K 38/18* (2006.01)
*A61K 31/7088* (2006.01)
*A61K 45/06* (2006.01)
*C07K 14/50* (2006.01)
*A61K 31/421* (2006.01)
*A61K 31/422* (2006.01)
*A61K 31/4439* (2006.01)

(52) U.S. Cl.
CPC ........ *A61K 38/1825* (2013.01); *A61K 31/421* (2013.01); *A61K 31/422* (2013.01); *A61K 31/4439* (2013.01); *A61K 31/7088* (2013.01); *A61K 45/06* (2013.01); *C07K 14/501* (2013.01)

(58) Field of Classification Search
None
See application file for complete search history.

(56) References Cited

U.S. PATENT DOCUMENTS

| 5,132,408 | A | 7/1992 | Baird et al. |
| 5,478,804 | A | 12/1995 | Calabresi et al. |
| 5,885,960 | A | 3/1999 | Nies |
| 6,326,484 | B1 | 12/2001 | Gage et al. |
| 6,982,170 | B1 | 1/2006 | Maciag et al. |
| 7,491,697 | B2 | 2/2009 | Beals et al. |
| 7,582,607 | B2 | 9/2009 | Frye et al. |
| 7,595,296 | B1 * | 9/2009 | Blaber et al. ........... 514/1.1 |
| 7,622,445 | B2 | 11/2009 | Frye et al. |
| 7,655,627 | B2 | 2/2010 | Frye et al. |
| 7,700,558 | B2 | 4/2010 | Thomason et al. |
| 7,723,050 | B2 | 5/2010 | Urdea et al. |
| 7,776,825 | B1 | 8/2010 | Blaber et al. |
| 7,790,682 | B1 | 9/2010 | Blaber et al. |
| 7,956,033 | B2 | 6/2011 | Cheng et al. |
| 8,053,408 | B2 | 11/2011 | Thomason et al. |
| 8,168,591 | B2 | 5/2012 | Takada et al. |
| 8,372,952 | B2 | 2/2013 | Smith et al. |
| 8,535,912 | B2 | 9/2013 | Sonoda |
| 8,642,546 | B2 | 2/2014 | Belouski et al. |
| 8,889,426 | B2 | 11/2014 | Mohammadi et al. |
| 8,889,621 | B2 | 11/2014 | Mohammadi et al. |
| 8,906,854 | B2 | 12/2014 | Jonker et al. |
| 8,951,966 | B2 | 2/2015 | Ling et al. |
| 8,999,929 | B2 | 4/2015 | Mohammadi et al. |
| 9,072,708 | B2 | 7/2015 | Jonker et al. |
| 9,272,017 | B2 | 3/2016 | Mohammadi et al. |
| 9,446,097 | B2 | 9/2016 | Jonker et al. |
| 9,464,126 | B2 | 10/2016 | Mohammadi et al. |
| 9,474,785 | B2 | 10/2016 | Mohammadi et al. |
| 2003/0008820 | A1 * | 1/2003 | Kwan ............... C07K 14/50 514/9.1 |

(Continued)

FOREIGN PATENT DOCUMENTS

CN    1890371 A    1/2007
EP    0 420 222 A1    4/1991

(Continued)

OTHER PUBLICATIONS

Sequence Identity BLAST, Feb. 23, 2015.*
Brych et al, Structure and stability effects of mutations designed to increase the primary sequence symmetry within the core region of a beta-trefoil, Protein Science (2001), 10:2587-2599.*
Storz et al. (Intellectual Property Issues: Therapeutics, Vaccines and Molecular Diagnostics, Springer Science & Business Media, May 11, 2012).*
Beenken and Mohammadi, "The FGF Family: Biology, Pathophysiology and Therapy," *Nat Rev Drug Discov.* 8:235-253, 2009.
Bossard et al., "Translokin is an Intracellular Mediator of FGF-2 Trafficking," *Nat Cell Biol.* 5:433-439, 2003.
Czajkowsky et al., "Fc-Fusion Proteins: New Developments and Future Perspectives," *EMBO Mol Med.* 4:1015-1028, 2012.
Dubey et al., "Spackling the Crack: Stabilizing Human Fibroblast Growth Factor-1 by Targeting the N and C Terminus β-Strand Interactions," *J Mol Biol.* 371:256-268, 2007.
Dutchak et al., "Fibroblast Growth Factor-21 Regulates PPARγ Activity and the Antidiabetic Actions of Thiazolidinediones," *Cell* 148:556-567, 2012.

(Continued)

*Primary Examiner* — Jennifer Pitrak McDonald
*Assistant Examiner* — Sergio Coffa
(74) *Attorney, Agent, or Firm* — Klarquist Sparkman, LLP

(57) ABSTRACT

The present disclosure provides FGF1 mutant proteins, such as those having an N-terminal deletion, point mutation(s), or combinations thereof, which can reduce blood glucose in a mammal. Such mutant FGF1 proteins can be part of a chimeric protein that includes a β-Klotho-binding protein, an FGFR1c-binding protein, a β-Klotho-binding protein and a FGFR1c-binding protein, a C-terminal region from FGF19 or FGF21. In some examples, mutant FGF1 proteins have reduced mitogenic activity. Also provided are nucleic acid molecules that encode such proteins, and vectors and cells that include such nucleic acids. Methods of using the disclosed molecules to reduce blood glucose levels are also provided.

15 Claims, 46 Drawing Sheets

(56) References Cited

U.S. PATENT DOCUMENTS

| | | | |
|---|---|---|---|
| 2004/0082564 A1* | 4/2004 | Arrhenius et al. | 514/210.21 |
| 2004/0259780 A1 | 12/2004 | Glasebrook et al. | |
| 2006/0217310 A1 | 9/2006 | Chiu et al. | |
| 2007/0099834 A1 | 5/2007 | Takada et al. | |
| 2007/0142278 A1 | 6/2007 | Beals et al. | |
| 2007/0237768 A1 | 10/2007 | Glaesner et al. | |
| 2007/0265200 A1 | 11/2007 | Glaesner et al. | |
| 2007/0293430 A1 | 12/2007 | Frye et al. | |
| 2007/0299007 A1 | 12/2007 | Frye et al. | |
| 2008/0103096 A1 | 5/2008 | Frye et al. | |
| 2008/0176790 A1 | 7/2008 | DeFrees | |
| 2008/0255045 A1 | 10/2008 | Cujec et al. | |
| 2008/0260703 A1 | 10/2008 | Riordan et al. | |
| 2008/0261875 A1 | 10/2008 | Etgen et al. | |
| 2009/0111742 A1 | 4/2009 | Kharitonenkov et al. | |
| 2009/0118190 A1 | 5/2009 | Beals et al. | |
| 2009/0305986 A1 | 12/2009 | Belouski et al. | |
| 2010/0062984 A1 | 3/2010 | Kumar et al. | |
| 2010/0158914 A1 | 6/2010 | Desnoyers | |
| 2010/0184665 A1 | 7/2010 | Suzuki et al. | |
| 2010/0216715 A1 | 8/2010 | Tagmose et al. | |
| 2010/0285131 A1 | 11/2010 | Belouski et al. | |
| 2010/0286042 A1 | 11/2010 | Imamura et al. | |
| 2010/0323954 A1 | 12/2010 | Li et al. | |
| 2011/0053841 A1 | 3/2011 | Yayon et al. | |
| 2011/0104152 A1 | 5/2011 | Sonoda | |
| 2011/0150901 A1 | 6/2011 | Smith et al. | |
| 2011/0172401 A1 | 7/2011 | Cujec et al. | |
| 2011/0190207 A1 | 8/2011 | Mohammadi et al. | |
| 2011/0195077 A1 | 8/2011 | Glass et al. | |
| 2012/0052069 A1 | 3/2012 | Belouski et al. | |
| 2012/0288886 A1 | 11/2012 | Mohammadi et al. | |
| 2013/0023474 A1 | 1/2013 | Ling et al. | |
| 2013/0058896 A1 | 3/2013 | Takada et al. | |
| 2013/0116171 A1 | 5/2013 | Jonker et al. | |
| 2013/0130983 A1 | 5/2013 | Blaber et al. | |
| 2013/0184211 A1 | 7/2013 | Mohammadi et al. | |
| 2013/0197191 A1 | 8/2013 | Smith et al. | |
| 2013/0231277 A1 | 9/2013 | Mohammadi et al. | |
| 2013/0331316 A1 | 12/2013 | Mohammadi et al. | |
| 2013/0331317 A1 | 12/2013 | Mohammadi et al. | |
| 2013/0331325 A1 | 12/2013 | Mohammadi et al. | |
| 2014/0094406 A1 | 4/2014 | Mohammadi et al. | |
| 2014/0107022 A1 | 4/2014 | Mohammadi et al. | |
| 2014/0155316 A1 | 6/2014 | Mohammadi et al. | |
| 2014/0171361 A1 | 6/2014 | Jonker et al. | |
| 2014/0243260 A1 | 8/2014 | Mohammadi et al. | |
| 2015/0065419 A1 | 3/2015 | Jonker et al. | |
| 2015/0111821 A1 | 4/2015 | Suh et al. | |
| 2015/0343022 A1 | 12/2015 | Jonker et al. | |
| 2016/0206695 A1 | 7/2016 | Suh et al. | |
| 2016/0237133 A1 | 8/2016 | Suh et al. | |
| 2016/0354440 A1 | 12/2016 | Jonker et al. | |
| 2017/0056475 A1 | 3/2017 | Jonker et al. | |

FOREIGN PATENT DOCUMENTS

| | | |
|---|---|---|
| EP | 0 645 451 B1 | 8/2001 |
| WO | WO 2002/036732 A2 | 5/2002 |
| WO | WO 03/052378 A2 | 6/2003 |
| WO | WO 2004/003179 A1 | 1/2004 |
| WO | WO 2004/108167 A1 | 12/2004 |
| WO | WO 2005/063807 A2 | 7/2005 |
| WO | WO 2006/028714 A1 | 3/2006 |
| WO | WO 2008/038287 A2 | 4/2008 |
| WO | WO 2008/047235 A2 | 4/2008 |
| WO | WO 2010/075037 A1 | 7/2010 |
| WO | WO 2010/129600 A2 | 11/2010 |
| WO | WO 2010/135491 A2 | 11/2010 |
| WO | WO 2011/047267 A1 | 4/2011 |
| WO | WO 2011/068893 A1 | 6/2011 |
| WO | WO 2011/130729 A2 | 10/2011 |
| WO | WO 2012/010553 A1 | 1/2012 |
| WO | WO 2012/062078 A1 | 5/2012 |
| WO | WO 2012/066075 A1 | 5/2012 |
| WO | WO 2012/140650 A2 | 10/2012 |
| WO | WO 2013/006486 A2 | 1/2013 |
| WO | WO 2013/033452 A2 | 3/2013 |
| WO | WO 2013/090919 A1 | 6/2013 |
| WO | WO 2013/131091 A1 | 9/2013 |
| WO | WO 2013/184958 A1 | 12/2013 |
| WO | WO 2013/184960 A2 | 12/2013 |
| WO | WO 2013/184962 A1 | 12/2013 |
| WO | WO 2014/085365 A2 | 6/2014 |
| WO | WO 2015/061331 A1 | 4/2015 |
| WO | WO 2015/061351 A1 | 4/2015 |
| WO | WO 2015/061361 A1 | 4/2015 |
| WO | WO 2015/065897 A1 | 5/2015 |
| WO | WO 2015/149069 A1 | 10/2015 |
| WO | WO 2015/183890 A2 | 12/2015 |
| WO | WO 2016/089945 A1 | 6/2016 |
| WO | WO 2016/172153 A2 | 10/2016 |
| WO | WO 2016/172156 A2 | 10/2016 |
| WO | WO 2016/172290 A1 | 10/2016 |

OTHER PUBLICATIONS

Fowler, "Diabetes Treatment, Part 2: Oral Agents for Glycemic Management," *Clin. Diabetes* 25:131-134, 2007.

Goetz et al., "Conversion of a Paracrine Fibroblast Growth Factor into an Endocrine Fibroblast Growth Factor," *J Biol Chem.* 287:29134-29146, 2012.

Hevener et al., "Muscle-Specific *Pparg* Deletion Causes Insulin Resistance," *Nat Med.* 9:1491-1497 (2003).

Imamura et al., "Recovery of Mitogenic Activity of a Growth Factor Mutant with a Nuclear Translocation Sequence," *Science* 249:1567-1570, 1990.

Imamura et al., "Identification of the Domain Within Fibroblast Growth Factor-1 Responsible for Heparin-Dependence," *Biochim Biophys Acta.* 1266:124-130, 1995.

Itoh and Ornitz, "Fibroblast Growth Factors: From Molecular Evolution to Roles in Development, Metabolism and Disease," *J Biochem.* 149:121-130,2011.

Jonker et al., "A PPARγ-FGF1 Axis is Required for Adaptive Adipose Remodelling and Metabolic Homeostasis," *Nature* 485:391-394, 2012.

Kharitonenkov et al., "FGF-21 as a Novel Metabolic Regulator," *J Clin Invest.* 115:1627-1635, 2005.

Kobielak et al., "Protease Resistant Variants of FGF1 with Prolonged Biological Activity," *Protein Pept Lett.* 21:434-443, 2014.

Lee and Blaber, "The Interaction Between Thermodynamic Stability and Buried Free Cysteines in Regulating the Functional Half-Life of Fibroblast Growth Factor-1," *J Mol Biol.* 393:113-127, 2009.

Lehrke and Lazar, "The Many Faces of PPARγ," *Cell* 123:993-999, 2005.

Li et al., "Strong Suppression of Feeding by a Peptide Containing Both the Nuclear Localization Sequence of Fibroblast Growth Factor-1 and a Cell Membrane-Permeable Sequence," *Neuroscience Lett.* 255:41-44, 1998.

Lin et al., "Role of the Nuclear Localization Sequence in Fibroblast Growth Factor1-Stimulated Mitogenic Pathways," *J Biol Chem.* 271:5305-5308, 1996.

Mori et al., "Direct Binding of Integrin αvβ3 to FGF1 Plays a Role in FGF1 Signaling," *J Biol Chem* 283:18066-18075, 2008.

Motomura et al., "An FGF1:FGF2 Chimeric Growth Factor Exhibits Universal FGF Receptor Specificity, Enhanced Stability and Augmented Activity Useful for Epithelial Proliferation and Radioprotection," *Biochim Biophys Acta.* 1780:1432-1440, 2008.

Nakayama et al., "Post Treatment With an FGF Chimeric Growth Factor Enhances Epithelial Cell Proliferation to Improve Recovery From Radiation-Induced Intestinal Damage," *Int J Radiat Oncol Biol Phys.* 78:860-867, 2010.

Niu et al., "Solid-Phase Polyethylene Glycol Conjugation Using Hydrophobicinteraction Chromatography," *J Chromatogr. A* 1327:66-72, 2014.

Reid, "Choosing GLP-1 Receptor Agonists or DPP-4 Inhibitors: Weighing the Clinical Trial Evidence," *Clin. Diabetes* 30:3-12, 2012.

(56) References Cited

OTHER PUBLICATIONS

Ripsin et al., "Management of Blood Glucose in Type 2 Diabetes Mellitus," *Am. Fam. Physician* 79:29-36, 2009.
Sasaki et al., "Effects of Fibroblast Growth Factors and Related Peptides on Food Intake by Rats," *Physiol Behav.* 56:211-218, 1994.
Smith et al., "FGF21 Can Be Mimicked In Vitro and In Vivo by a Novel Anti-FGFR1c/b-Klotho Bispecific Protein," *PLoS ONE* 8:e61432, 2013.
Suh et al., "Endocrinization of FGF1 Produces a Neomorphic and Potent Insulin Sensitizer," *Nature* 513:436-439, 2014.
Sun and Scherer, "The PPARγ-FGF1 Axis: An Unexpected Mediator of Adipose Tissue Homeostasis," *Cell Res.* 22:1416-1418, 2012.
Suzuki et al., "Feeding Suppression by Fibroblast Growth Factor-1 is Accompanied by Selective Induction of Heat Shock Protein 27 in Hypothalamic Astrocytes," *Eur J Neurosci.* 13:2299-2308, 2001.
Van Dijk et al., "Quantification of Hepatic Carbohydrate Metabolism in Conscious Mice Using Serial Blood and Urine Spots," *Anal Biochem.* 322:1-13, 2003.
Wang et al., "A Novel Monoclonal Antibody to Fibroblast Growth Factor 2 Effectively Inhibits Growth of Hepatocellular Carcinoma Xenografts," *Mol Cancer Ther.* 11:864-872, 2012.
Wei et al., "Fibroblast Growth Factor 21 Promotes Bone Loss by Potentiating the Effects of Peroxisome Proliferator-Activated Receptor γ," *Proc Natl Acad Sci. USA* 109:3143-3148, 2012.
Wu et al., "Amelioration of Type 2 Diabetes by Antibody-Mediated Activation of Fibroblast Growth Factor Receptor 1," *Sci Transl Med.* 3:113ra126, 2011.
Wu and Li, "Chapter 13—Understanding the Structure-Function Relationship Between Fgf19 and Its Mitogenic and Metabolic Activities," in *Endocrine FGFs and Klothos*, Makoto Kuro-o (ed.), pp. 195-213, Landes Bioscience and Springer Science+Business Media, 2012.
Xia et al., "Pharmacokinetic Properties of $2^{nd}$-Generation Fibroblast Growth F°actor-1 Mutants for Therapeutic Application," *PLoS ONE* 7:e48210, 2012.
Zakrzewska et al., "Design of Fully Acctive FGF-1 Variants with Increased Stability," *Protein Eng Des Sel.* 17:603-611, 2004.
Zakrzewska et al., "Increased Protein Stability of FGF1 Can Compensate for Its Reduced Affinity for Heparin," *J Biol Chem.* 284:25388-25403, 2009.
Zhu et al., "Three-Dimensional Structures of Acidic and Basic Fibroblast Growth Factors," *Science* 251:90-93, 1991.
Zinn et al., "Imaging Tc-99m-Labeled FGF-1 Targeting in Rats," *Nucl Med Biol.* 27:407-414, 2000.
International Search Report and Written Opinion mailed on Feb. 20, 2015 for PCT/US2014/061638 (21 pages).
Xia et al., "Pharmacokinetic Properties of $2^{nd}$-Generation Fibroblast Growth Factor-1 Mutants for Therapeutic Application," *PLoS ONE* 7:e48210, 2012.
Wu et al., "Separating Mitogenic and Metabolic Activities of Fibroblast Growth Factor 19 (FGF19)," *Proc Natl Acad Sci U.S.A.* 107:14158-14163, 2010.
European Patent Office, European Search Report from EP 11769740.9, dated Dec. 5, 2013 (10 pages).
Hutley et al., "Fibroblast Growth Factor 1," *Diabetes* 53:3097-3106, 2004.
Ikezono and Hanai, "The Effect of Satiation of the Acidic Fibroblast Growth Factor-Like Activity on Ingestion of Soyamalt and Soybean Milk"; *Int J Obesity* 25(S2):S142, 2001. Abstract P403.
Inchovska et al., "Fibroblast Growth Factors Promote Pancreatic Cell Proliferation in Normal and STZ-Treated Hamsters," *Arch Med Sci.* 2:90-93, 2006.
Inchovska et al., "Role of FGF1, FGF2 and FGF7 in the Development of the Pancreas of Diabetic Hamsters," *Acta morphologica et anthropologica* 12:79-85, 2007.
Inchovska et al., "Role of FGF1, FGF2, FGF7 in the Development of Pancreas from Control and Streptozotocin-Treated Hamsters," *Cell Proliferation* 39:537-550, 2006.
International Search Report from PCT/US2011/032541, dated Jan. 19, 2012 (4 pages).
Kilkenny et al.; "Fibroblast Growth Factor Receptor-1 Signaling in Pancreatic Islet Beta-Cells is Modulated by the Extracellular Matrix," *Mol EndocrinoL.* 22:196-205, 2008.
Lee and Blaber, "Structural Basis of Conserved Cysteine in the Fibroblast Growth Factor Family: Evidence for a Vestigial Half-Cystine," *J Mol Biol.* 393:128-139, 2009.
Ogneva et al., "The Effect of In Vitro Fibroblast Growth Factors on Cell Proliferation in Pancreas from Normal and Streptozoticin-Treated Rats," *Diabetes Res Clin Practice* 57:11-16, 2002.
Widberg et al., "Fibroblast Growth Factor Receptor 1 is a Key Regulator of Early Adipogenic Events in Human Preadipocytes"; *Am J Physiol Endocrinol Metab.* 296:E121-E131, 2009.
Youseff et al., "Diabetes Mellitus, Obesity, and Hepatic Steatosis," *Semin Gastrointest Dis.* 13:17-30, 2002.
Abraham et al., "Human Basic Fibroblast Growth Factor: Nucleotide Sequence and Genomic Organization," *EMBO J.* 5(10): 2523-2528, 1986.
Andrukhova et al., "FGF23 Acts Directly on Renal Proximal Tubules to Induce Phosphaturia Through Activation of the ERK1/2-SKG1 Signaling Pathway," *Bone*51:621-628, 2012.
Beenken & Mohammadi, "The Structural Biology of the FGF19 Subfamily," *Adv Exp Med Biol.* 728:1-24, 2012.
Beenken et al., "Plasticity in Interactions of Fibroblast Growth Factor 1 (FGF1) N Terminus With FGF Receptors Underlies Promiscuity of FGF1," *J Biol Chem.* 287:3067-3078, 2012.
Beenken, "Structural and biochemical Studies of FGF-FGFR Complexes," Thesis, Sep. 2011.
Cassidy et al., "Elevated Frequency of Diabetes Mellitus in Hospitalized Manic-Depressive Patients," *Am J Psychiatry* 156:1417-1420, 1999.
Esch et al., "Primary Structure of Bovine Pituitary Basic Fibroblast Growth Factor (FGF) and Comparison with the Amino-Terminal Sequence of Bovine Brain Acidic FGF," *PNAS* 82:6507-6511, 1985.
Finan et al., "A Rationally Designed Monomeric Peptide Triagonist Corrects Obesity and Diabetes in Rodents," *Nat Med.* 21:27-36, 2015.
Ge et al., "Characterization of a FGF19 Variant with Altered Receptor Specificity Revealed a Central Role for FGFR1c in the Regulation of Glucose Metabolism," *PloS ONE* 7:e33603, 2012.
Goetz et al., "Isolated C-Terminal Tail of FGF23 Alleviates Hypophosphatemia by Inhibiting FGF23-FGFR-Klotho Complex Formation," *Proc Natl Acad Sci USA* 107:407-412, 2010.
Goetz et al., "Klotho Coreceptors Inhibit Signaling by Paracrine Fibroblast Growth Factor 8 Subfamily Ligands," *Mol Cell Biol.* 32:1944-1954, 2012.
Goetz et al., "Molecular Insights Into the Klotho-Dependent, Endocrine Mode of Action of Fibroblast Growth Factor 19 Subfamily Members," *Mol Cell Biol.* 27:3417-3428, 2007.
Hwang and Weis, "Steroid-Induced Diabetes: A Clinical and Molecular Approach to Understanding and Treatment," *Diabetes Metab Res Rev.* 30:96-102, 2014.
Igarashi et al., "Characterization of Recombinant Human Fibroblast Growth Factor (FGF)-10 Reveals Functional Similarities with Keratinocyte Growth Factor (FGF-7)," *J Biol Chem.* 273:13230-13235, 1998.
Irwin et al., "A Novel CCK-8/GLP-1 Hybrid Peptide Exhibiting Prominent Insulinotropic, Glucose-Lowering, and Satiety Actions With Significant Therapeutic Potential in High-Fat-Fed Mice," *Diabetes* 64:2996-3009, 2015.
Kharitonenkov et al., "FGF-21/FGF-21 Receptor Interaction and Activation is Determined by βKlotho," *J Cell Physiol.* 215:1-7, 2008.
Kharitonenkov et al., "The Metabolic State of Diabetic Monkeys is Regulated by Fibroblast Growth Factor-21," *Endocrinology* 148:774-781, 2007.
Kurosu et al., "The Klotho Gene Family as a Regulator of Endocrine Fibroblast Growth Factors," *Mol Cell Endocrin.* 299:72-78,2009.
Kurosu et al., "Tissue-Specific Expression of βKlotho and Fibroblast Growth Factor (FGF) Receptor Isoforms Determines Metabolic Activity of FGF19 and FGF21," *J Biol Chem.* 282:26687-26695, 2007.
Micanovic et al., "Different Roles of N- and C-Termini in the Functional Activity of FGF21," *J Cell Physiol.* 219:227-234, 2009.

(56) References Cited

OTHER PUBLICATIONS

Mohammadi et al., "Structural Basis for Fibroblast Growth Factor Receptor Activation," *Cytokine Growth Factor Rev.* 16:107-137, 2005.

O'Harte et al., "Novel Dual Agonist Peptide Analogues Derived From Dogfish Glucagon Show Promising in vitro Insulin Releasing Actions and Antihyperglycaemic Activity in Mice," *Mol Cell Endocrinol.* 431:133-144, 2016.

Olsen et al., "Insights Into the Molecular Basis for Fibroblast Growth Factor Receptor Autoinhibition and Ligand-Binding Promiscuity," *Proc Natl Acad Sci. USA* 101:935-940, 2004.

Ono et al., "Novel Regulation of Fibroblast Growth Factor 2 (FGF20-Mediated Cell Growth by Polysialic Acid," *J Biol Chem.* 287:3710-3722, 2012.

Poa and Edgar, "Insulin Resistance Is Associated With Hypercortisolemia in Polynesian Patients Treated With Antipsychotic Medication," *Diabetes Care* 30:1425-1429, 2007.

Presta et al., "Structure-Function Relationship of Basic Fibroblast Growth Factor: Site-Directed Mutagenesis of a Putative Heparin-Binding and Receptor-Binding Region," *Biochem Biophys Res Commun.* 185:1098-1107, 1992.

Rafacho et al., "Glucocorticoid Treatment and Endocrine Pancreas Function: Implications for Glucose Homeostasis, Insulin Resistance and Diabetes," *J Endocrinol.* 223:R49-R62, 2014.

Razzaque, "The FGF23-Klotho Axis: Endocrine Regulation of Phosphate Homeostasis," *Nat Rev Endocrinol.* 5:611-619, 2009.

Schlessinger et al., "Crystal Structure of a Ternary FGF-FGFR-Heparin Complex Reveals a Dual Role for Heparin in FGFR Binding and Dimerization," *Mol. Cell* 6:743-750, 2000.

Thompson et al., "Energetic Characterization of the Basic Fibroblast Growth Factor-Heparin Interaction: Identification of the Heparin Binding Domains," *Biochem.* 33:3831-3840, 1994.

Wu et al., "C-Terminal Tail of FGF19 Determines Its Specificity Toward Klotho Co-Receptors," *J Biol Chem.* 283:33304-33309, 2008.

Wu et al., "Selective Activation of FGFR4 by an FGF19 Variant Does Not Improve Glucose Metabolism in ob/ob Mice," *Proc Natl Acad Sci. USA* 106:14379-14384, 2009.

Wu et al., "FGF19-Induced Hepatocyte Proliferation is Mediated Through FGFR4 Activation," *J Biol Chem.* 285:5165-5170, 2010.

Wu et al., "FGF19 Regulates Cell Proliferation, Glucose and Bile Acid Metabolism via FGFR4-Dependent and Independent Pathways," *PLoS One* 6:e17868, 2011.

Wu et al., "A Unique FGF23 With the Ability to Activate FGFR Signaling Through Both αKlotho and βKlotho," *J Mol Biol.* 418:82-89, 2012.

Yao et al., "Expression and Pharmacological Evaluation of Fusion Protein FGF21-L-Fc," *Acta Pharmaceutica Sinica* 46:787-792, 2011 (with English abstract).

Yie et al., "FGF21 N- and C-Termini Play Different Roles in Receptor Interaction and Activation," *FEBS Lett.* 583:19-24, 2009.

Zhang et al., "Receptor Specificity of the Fibroblast Growth Factor Family: The Complete Mammalian FGF Family," *J Biol Chem.* 281:15694-15700, 2006.

CN 201380039848.9 Office Action dated Oct. 8, 2016 (with English Translation) (23 pages).

EP 13799858.9 Extended Search Report dated May 3, 2016 (13 pages).

PCT/US2013/028888 International Search Report and Written Opinion dated Jul. 23, 2013 (15 pages).

PCT/US2013/044589 International Search Report and Written Opinion dated Nov. 13, 2013 (9 pages).

PCT/US2013/044592 International Search Report and Written Opinion dated Jan. 17, 2014 (13 pages).

PCT/US2013/044594 International Search Report and Written Opinion dated Nov. 13, 2013 (9 pages).

PCT/US2014/017367 International Search Report and Written Opinion dated Jun. 18, 2014 (9 pages).

EP 11769740-9 Office Action dated Jul. 29, 2016 (5 pages).

Liu et al., "Effective Treatment of Steatosis and Steatohepatitis by Fibroblast Growth Factor 1 in Mouse Models of Nonalcoholic Fatty Liver Disease," *Proc Natl Acad Sci USA* 113:2288-2293, 2016.

Luo et al., "A Nontumorigenic Variant of FGF19 Treats Cholestatic Liver Diseases," *Sci Transl Med.* 6:247ra 100, 2014.

Ohta and Itoh, "Roles of FGFs as Adipokines in Adipose Tissue Development, Remodeling and Metabolism," *Frontiers in Endocrinology*, vol. 5, No. FEB, Article 18, pp. 1-4, 2014.

Zhou et al., "Separating Tumorigenicity from Bile Acid Regulatory Activity for Endocrine Hormone FGF19," *Cancer Res.* 74:3306-3316, 2014.

PCT/US2016/028368 Invitation to Pay Additional Fees dated Jul. 28, 2016 (2 pages).

PCT/US2016/028562 International Search Report dated Jul. 29, 2016 (4 pages).

PCT/US2016/028562 Written Opinion dated Jul. 29, 2016 (5 pages).

PCT/US2011/032848 International Search Report dated Jan. 19, 2012 (4 pages).

PCT/US2011/032848 Written Opinion dated Jan. 19, 2012 (5 pages).

PCT/US2014/061624 International Search Report dated Dec. 23, 2014 (6 pages).

PCT/US2014/061624 Written Opinion dated Dec. 23, 2014 (5 pages).

PCT/US2014/061593 International Search Report dated Dec. 23, 2014 (6 pages).

PCT/US2014/061593 Written Opinion dated Dec. 23, 2014 (5 pages).

Brewster et al., "Heparin-independent mitogenicity in an endothelial and smooth muscle cell chimeric growth factor (S130K-HBGAM)," *Am J Surg* 188:575-579, 2004.

Brewster et al., "Improving endothelial healing with novel chimeric mitogens," *Am J Surg.* 192:589-593, 2006.

Klingenberg et al., "Effects of Mutations of a Phosphorylation Site in an Exposed Loop in Acidic Fibroblast growth Factor," *J Biol Chem.* 274:18081-18086, 1999.

Shireman et al., "The S130K fibroblast growth factor-1 mutant induces heparin-independent proliferation and is resistant to thrombin degradation in fibrin glue," *J Vasc Surg.* 31:382-390, 2000.

PCT/US2016/028365 International Search Report and Written Opinion dated Dec. 8, 2016 (15 pages).

Adams et al., "LY2405319, an Engineered FGF21 Variant, Improves the Metabolic Status of Diabetic Monkeys," *PLoS One* 8:e65763, 2013

PCT/US2015/051402 International Search Report dated Oct. 5, 2016 (9 pages).

PCT/US2015/051402 Written Opinion dated Oct. 5, 2016 (8 pages).

PCT/US2015/051406 International Search Report dated Oct. 5, 2016 (12 pages).

PCT/US2015/051406 Written Opinion dated Oct. 5, 2016 (6 pages).

PCT/US2015/066683 International Search Report dated Oct. 5, 2016 (8 pages).

PCT/US2015/066683 Written Opinion dated Oct. 5, 2016 (8 pages).

PCT/US2016/028368 International Search Report dated Oct. 5, 2016 (5 pages).

PCT/US2016/028368 Written Opinion dated Oct. 5, 2016 (6 pages).

Fathallah et al., "Drug-Induced Hyperglycaemia and Diabetes," *Drug Safety* 38:1153-1168, 2015.

Guo et al., "Risk of Diabetes Mellitus Associated With Atypical Antipsychotic Use Among Patients With Bipolar Disorder: A Retrospective, Population-Based, Case-Control Study," *J Clin. Psychiatry* 67:1055-1061, 2006.

Perez et al., "Glucocorticoid-induced hyperglycemia," *J. Diabetes* 6:9-20, 2014.

Tamez-Perez et al., "Steroid hyperglycemia: Prevalence, early detection and therapeutic recommendations: A narrative review," *World J. Diabetes* 6:1073-1081, 2015.

Van Raalte & Diamant, "Steroid diabetes: from mechanism to treatment?," *Neth J Med.* 72:62-72, 2014.

PCT/US2016/059190 International Search Report and Written Opinion dated Jan. 19, 2017 (11 pages).

(56) References Cited

OTHER PUBLICATIONS

EP14856609.4 Extended European Search Report dated May 10, 2017 (9 pages).
Royce et al., "Incorporation of polymer microspheres within fibrin scaffolds for the controlled delivery of FGF-1," *J Biomater Sci Polymer Edn.* 15:1327-1336, 2004.
Xia et al.,"An S116R Phosphorylation Site Mutation in Human Fibroblast Growth Factor-1 Differentially Affects Mitogenic and Glucose-Lowering Activities," *J Pharm Sci.* 105:3507-3519, 2016.
PCTUS2017044678 International Search Report and Written Opinion dated Oct. 24, 2017 (18 pages).
Accession No. 1605206A, Sep. 14, 1996.
CN 201380039848.9 Office Action dated Jun. 8, 2017 (with English translation) (18 pages).

* cited by examiner

FIG. 1

| | | |
|---|---|---|
| | wtFGF1(1-140αα) | FNLPPGNYKK PKLLYCSNGG HFLRILPDGT VDGTRDRSDQ HIQLQLSAES VGEVYIKSTE TGQYLAMDTD<br>GLLYGSQTPN EECLFLERLE ENHYNTYISK KHAEKNWFVG LKKNGSCKRG PRTHYGQKAI LFLPLPVSSD |

N-terminal deletions:

| | | |
|---|---|---|
| 1. | $FGF1^{\Delta NT}$(10-140αα) | ---------K PKLLYCSNGG HFLRILPDGT VDGTRDRSDQ HIQLQLSAES VGEVYIKSTE TGQYLAMDTD<br>GLLYGSQTPN EECLFLERLE ENHYNTYISK KHAEKNWFVG LKKNGSCKRG PRTHYGQKAI LFLPLPVSSD |
| 2. | $FGF1^{\Delta NT2}$(14-140αα) | ---------- ---LYCSNGG HFLRILPDGT VDGTRDRSDQ HIQLQLSAES VGEVYIKSTE TGQYLAMDTD<br>GLLYGSQTPN EECLFLERLE ENHYNTYISK KHAEKNWFVG LKKNGSCKRG PRTHYGQKAI LFLPLPVSSD |
| 3. | $FGF1^{\Delta NT3}$(12-140αα) | ---------- -KLLYCSNGG HFLRILPDGT VDGTRDRSDQ HIQLQLSAES VGEVYIKSTE TGQYLAMDTD<br>GLLYGSQTPN EECLFLERLE ENHYNTYISK KHAEKNWFVG LKKNGSCKRG PRTHYGQKAI LFLPLPVSSD |

Point mutations:

| | | |
|---|---|---|
| 4. | FGF1(1-140αα)<br>K12V,N95V | FNLPPGNYKK PVLLYCSNGG HFLRILPDGT VDGTRDRSDQ HIQLQLSAES VGEVYIKSTE TGQYLAMDTD<br>GLLYGSQTPN EECLFLERLE ENHYVTYISK KHAEKNWFVG LKKNGSCKRG PRTHYGQKAI LFLPLPVSSD |
| 5. | FGF1(1-140αα)<br>K12V,L46V,E87V,<br>LFLVLPVSSD<br>N95V,P134V | FNLPPGNYKK PVLLYCSNGG HFLRILPDGT VDGTRDRSDQ HIQLQVSAES VGEVYIKSTE TGQYLAMDTD<br>GLLYGSQTPN EECLFLVRLE ENHYVTYISK KHAEKNWFVG LKKNGSCKRG PRTHYGQKAI |

Mutations to heparan binding domain:

| | | |
|---|---|---|
| 6. | FGF1(7-140αα)<br>K118N | ------NYKK PKLLYCSNGG HFLRILPDGT VDGTRDRSDQ HIQLQLSAES VGEVYIKSTE TGQYLAMDTD<br>GLLYGSQTPN EECLFLERLE ENHYNTYISK KHAEKNWFVG LKKNGSCNRG PRTHYGQKAI LFLPLPVSSD |
| 7. | FGF1(7-140αα)<br>K118E | ------NYKK PKLLYCSNGG HFLRILPDGT VDGTRDRSDQ HIQLQLSAES VGEVYIKSTE TGQYLAMDTD<br>GLLYGSQTPN EECLFLERLE ENHYNTYISK KHAEKNWFVG LKKNGSCERG PRTHYGQKAI LFLPLPVSSD |

FIG. 3A

M1 Deletions

| | | | | | | | |
|---|---|---|---|---|---|---|---|
| FGF1(1-140aa)M1 K12V,C117V,P134V | FNLPPGNYKK GLLYGSQTPN | PVLLYCSNGG EECLFLERLE | HFLRILPDGT ENHYNTYISK | VDGTRDRSDQ KHAEKNWFVG | HIQLQLSAES LKKNGSVKRG | VGEVYIKSTE PRTHYGQKAI | TGQYLAMDTD LFLVLPVSSD |
| FGF1(1-140aa)M1a K12V,M95V,C117V,P134V | FNLPPGNYKK GLLYGSQTPN | PVLLYCSNGG EECLFLERLE | HFLRILPDGT ENHYVTYISK | VDGTRDRSDQ KHAEKNWFVG | HIQLQLSAES LKKNGSVKRG | VGEVYIKSTE PRTHYGQKAI | TGQYLAMDTD LFLVLPVSSD |
| FGF1ΔNT1(1-140aa)M1 K12V,C117V,P134V | ----------K GLLYGSQTPN | PVLLYCSNGG EECLFLERLE | HFLRILPDGT ENHYNTYISK | VDGTRDRSDQ KHAEKNWFVG | HIQLQLSAES LKKNGSVKRG | VGEVYIKSTE PRTHYGQKAI | TGQYLAMDTD LFLVLPVSSD |
| FGF1ΔNT3(1-140aa)M1 K12V,C117V,P134V | ----------- GLLYGSQTPN | -VLLYCSNGG EECLFLERLE | HFLRILPDGT ENHYNTYISK | VDGTRDRSDQ KHAEKNWFVG | HIQLQLSAES LKKNGSVKRG | VGEVYIKSTE PRTHYGQKAI | TGQ

FIG. 3B
M2 Deletions

```
FGF1(1-140aa)M2                    FNLPPGNYKK  PKLLYCSNGG  HFLRILPDGT  VDGTRDRSDQ  HIQFQLSAES  VGEVYIKSTE  TGQYLAMDTD
L44F,C83T,C117V,F132N              GLLYGSQTPN  EEVLFLERLE  ENHYNTYISK  KHAEKNWFVG  LKKNGSYKRG  PRTHYGQKAI  LWLPLPVSSD

FGF1(1-140aa)M2a                   FNLPPGNYKK  PKLLYCSNGG  HFLRILPDGT  VDGTRDRSDQ  HIQFQLSAES  VGEVYIKSTE  TGQYLAMDTD
L44F,C83T,C117V,F132N              GLLYGSQTPN  EEVLFLERLE  ENHYNTYISK  KHAEKNWFVG  LKKNGSYKRG  PRTHYGQKAI  LWLPLPVSSD

FGF1(1-140aa)M2b                   FNLPPGNYKK  PVLLYCSNGG  HFLRILPDGT  VDGTRDRSDQ  HIQFQLSAES  VGEVYIKSTE  TGQYLAMDTD
N7V,L44F,C83T,C

FIG. 3C
M3 Deletions

| Construct | Sequence |
|---|---|
| FGF1(1-140αα)M3 L44F,M67I,L73V,V109L L111I,C117V,A103G,R119G Δ104-106 Δ120-122 | FNLPPGNYKK PKLLYCSNGG HFLRILPDGT VDGTRDRSDQ HIQFQLSAES VGEVYIKSTE TGQYLAIDTD GLVYGSQTPN EECLFLERLE ENHYNTYISK KHG----WFLG IKKNGSVKG- --THYGQKAI LFLPLPVSSD |
| FGF1(1-140αα)M3a K12V,L44F,M67I,L73V,V109L L111I,C117V,A103G,R119G Δ104-106 Δ120-122 | FNLPPGNYKK PVLLYCSNGG HFLRILPDGT VDGTRDRSDQ HIQFQLSAES VGEVYIKSTE TGQYLAIDTD GLVYGSQTPN EECLFLERLE ENHYNTYISK KHG----WFLG IKKNGSVKG- --THYGQKAI LFLPLPVSSD |
| FGF1(1-140αα)M3b N17,L44F,M67I,N95K,V109L L111I,C117V,A103G,R119G Δ104-106 Δ120-122 | FNLPPGNYKK PVLLYCSNGG HFLRILPDGT VDGTRDRSDQ HIQFQLSAES VGEVYIKSTE TGQYLAIDTD GLVYGSQTPN EECLFLERLE ENHVVTYISK KHG----WFLG IKKNGSVKG- --THYGQKAI LFLPLPVSSD |
| FGF1(1-140αα)M3c N17,L44F,M67I,N95K,V109L L111I,C117V,A103G,R119G Δ104-106 Δ120-122 | FNLPPGNYKK PVLLYCSNGG HFLRILPDGT VDGTRDRSDQ HIQFQLSAES VGEVYIKSTE TGQYLAIDTD GLVYGSQTPN EECLFLERLE ENHVVTYISK KHG----WFLG IKKNGSVKG- --THYGQKAI LFLPLPVSSD |
| FGF1 ΔNT1(1-140αα)M3 L44F,M67I,L73V,V109L L111I,C117V,A103G,R119G Δ104-106 Δ120-122 | -------K PKLLYCSNGG HFLRILPDGT VDGTRDRSDQ HIQFQLSAES VGEVYIKSTE TGQYLAIDTD GLVYGSQTPN EECLFLERLE ENHYNTYISK KHG----WFLG IKKNGSVKG- --THYGQKAI LFLPLPVSSD |
| FGF1 ΔNT2(1-140αα)M3 L44F,M67I,L73V,V109L L111I,C117V,A103G,R119G Δ104-106 Δ120-122 | -------- -KLLYCSNGG HFLRILPDGT VDGTRDRSDQ HIQFQLSAES VGEVYIKSTE TGQYLAIDTD GLVYGSQTPN EECLFLERLE ENHYNTYISK KHG----WFLG IKKNGSVKG- --THYGQKAI LFLPLPVSSD |
| FGF1 ΔNT2(1-140αα)M3a K12V,L44F,M67I,L73V,V109L L111I,C117V,A103G,R119G Δ104-106 Δ120-122 | -------K PVLLYCSNGG HFLRILPDGT VDGTRDRSDQ HIQFQLSAES VGEVYIKSTE TGQYLAIDTD GLVYGSQTPN EECLFLERLE ENHYNTYISK KHG----WFLG IKKNGSVKG- --THYGQKAI LFLPLPVSSD |
| FGF1 ΔNT3(1-140αα)M3a N17,L44F,M67I,L73V,V109L L111I,C117V,A103G,R119G Δ104-106 Δ120-122 | -------- -VLLYCSNGG HFLRILPDGT VDGTRDRSDQ HIQFQLSAES VGEVYIKSTE TGQYLAIDTD GLVYGSQTPN EECLFLERLE ENHYNTYISK KHG----WFLG IKKNGSVKG- --THYGQKAI LFLPLPVSSD |

FIG. 3D

```
FGF1 ΔNT1 (1-140αα) M3b          ---------M PKLLYCSNGG HFLRILPDGT VDGTRDRSDQ HIQFQLSAES VGEVYIKSTE TGQYLAMDTD
L44F,M67I,I73V,N95V,V109L        GLVYGSQTPN EECLFLERLE ENHYVTYISK KHG----WFLG IKKN

FIG. 4A

| | | | | | | | |
|---|---|---|---|---|---|---|---|
| 1. | FGF1(1-140aa) K12V,N95V,K118N | FNLPPGNYKK GLLYGSQTPN | PVLLYCSNGG EECLFLERLE | HFLRILPDGT

FIG. 4B

13. FGF14ΔNT2 (12-140αα)  ---------- -VLLYCSNGG HFLRILPDGT VDGTRDRSDQ HIQLQLSAES VGEVYIKSTE TGQYLAMDTD
    K12V,N95V,K118E         GILYGSQTPN EECLFLERLE ENHYVTYISK KHAERNWFVG LKKNGSCKRG PRTHYGQKAI LFLPLFVSSD

14. FGF14ΔNT (10-140αα)     --------K PKLLYCSNGG HFLRILPDGT VDGTRDRSDQ HIQLQLSAES VGEVYIKSTE TGQYLAMDTD
    K118N                   GILYGSQTPN EECLFLERL

| | |
|---|---|
| FGF$^{\Delta NT3}$(1-140αα) | ---------- -VLLYCSNGG HFLRILPDGT VDGTRDRSDP HIQLQLIAES VGEVYIKSTE TGQYLAMDTD |
| K12V Q40P, S47I, H93G, N95V | GLLYGSQTPN EECLFLERLE ENGYVTYISK KHAEKNWFVG LKKNGSCKRG PRTHYGQKAI LFLPLPVSSD |
| FGF1$^{\Delta NT}$(1-140αα) | ---------K PKLLYCSNGG HFLRILPDGT VDGTRDRSDQ HIQLQLSAES VGEVYIKSTE TGQYLAMDTD |
| C117P, K118V | GLLYGSQTPN EECLFLERLE ENHYNTYISK KHAEKNWFVG LKKNGSPVRG PRTHYGQKAI LFLPLPVSSD |
| FGF1$^{\Delta NT3}$(1-140αα) | ---------- -KLLYCSNGG HFLRILPDGT VDGTRDRSDQ HIQLQLSAES VGEVYIKSTE TGQYLAMDTD |
| C117P, K118V | GLLYGSQTPN EECLFLERLE ENHYNTYISK KHAEKNWFVG LKKNGSPVRG PRTHYGQKAI LFLPLPVSSD |
| FGF1(1-140αα) | FNLPPGNYKK PVLLYCSNGG HFLRILPDGT VDGTRDRSDQ HIQLQLSAES VGEVYIKSTE TGQYLAMDTD |
| K12V, N95V, C117P, K118V | GLLYGSQTPN EECLFLERLE ENHYVTYISK KHAEKNWFVG LKKNGSPVRG PRTHYGQKAI LFLPLPVSSD |
| FGF1(1-140αα) | FNLPPGNYKK PKLLYCSNGG HFLRILPDGT VDGTEDRSDQ HIQLQLSAES VGEVYIKSTE TGQYLAMDTD |
| R35E FGF1 Antagonist | GLLYGSQTPN EECLFLERLE ENHYNTYISK KHAEKNWFVG LKKNGSCKRG PRTHYGQKAI LFLPLPVSSD |

FIG. 6A

FGF21 chimeras

```
human FGF21          MDSDETGFEH SGLWVSVLAG LLLGACQAHP IPDSSPLLQF GGQVRQRYLY TDDAQQTEAH LEIREDGTVG
mature sequence      GAADQSPESL LQLKALKPGV IQILGVKTSR FLCQRPDGAL YGSLHFDPEA CSFRELLLED GYNVYQSEAH
                     GLPLHLPGNK SPHRDPAPRG PARFLPLPGL PPALPEPPGI LAPQPPDVGS SDPLSMVGPS QGRSPSYAS p168-S203 hFGF21C-tail    PGL PPALPEPPGI LAPQPPDVGS SDPLSMVGPS QGRSPSYAS
&klotho binding K12V,N98V FGF1-      FNLPPGNYKK PVLLYCSNGG HFLRILPDGT VDGTRDRSDQ HIQLQLSAES VGEVYIKSTE TGQYLAMDTD
FGF21C-tail          GLLYGSQTPN EECLFLERLE EMHYNTYISK KHAEKNWFVG LKKNGSCKRG PRTHYGQKAI LFLPLPGL
                     PPALPEPPGI LAPQPPDVGS SDPLSMVGPS QGRSPSYAS FGF1ΔNT-FGF21C-tail        -------K PKLLYCSNGG HFLRILPDGT VDGTRDRSDQ HIQLQLSAES VGEVYIKSTE TGQYLAMDTD
K12-L135FGF1         GLLYGSQTPN EECLFLERLE EMHYNTYISK KHAEKNWFVG LKKNGSCKRG PRTHYGQKAI LFLPLPGL
                     PPALPEPPGI LAPQPPDVGS SDPLSMVGPS QGRSPSYAS FGF1ΔNT-FGF21C-tail        -------- -KLLYCSNGG HFLRILPDGT VDGTRDRSDQ HIQLQLSAES VGEVYIKSTE TGQYLAMDTD
K22-L135FGF1         GLLYGSQTPN EECLFLERLE EMHYNTYISK KHAEKNWFVG LKKNGSCKRG PRTHYGQKAI LFLPLPGL
                     PPALPEPPGI LAPQPPDVGS SDPLSMVGPS QGRSPSYAS M1-FGF21C-tail             --------K PVLLYCSNGG HFLRILPDGT VDGTRDRSDQ HIQLQLSAES VGEVYIKSTE TGQYLAMDTD
K12V,C117V,P134V FGF1 GLLYGSQTPN EECLFLERLE EMHYNTYISK KHAEKNWFVG LKKNGSVKRG PRTHYGQKAI LFLVLPGL
                     PPALPEPPGI LAPQPPDVGS SDPLSMVGPS QGRSPSYAS M1-FGF21C-tail             -------- -KLLYCSNGG HFLRILPDGT VDGTRDRSDQ HIQLQLSAES VGEVYIKSTE TGQYLAMDTD
K12V,C117V,P134V FGF1 GLLYGSQTPN EECLFLERLE EMHYNTYISK KHAEKNWFVG LKKNGSVKRG PRTHYGQKAI LFLVLPGL
                     PPALPEPPGI LAPQPPDVGS SDPLSMVGPS QGRSPSYAS M1-FGF21C-tail       FNLPPGNYKK PVLLYCSNGG HFLRILPDGT VDGTRDRSDQ HIQLQLSAES VGEVYIKSTE TGQYLAMDTD
K12V,C117V,P134V FGF1 GLLYGSQTPN EECLFLERLE EMHYNTYISK KHAEKNWFVG LKKNGSVKRG PRTHYGQKAI LFLVLPGL
                     PPALPEPPGI LAPQPPDVGS SDPLSMVGPS QGRSPSYAS M2-FGF21C-tail             --------K PKLLYCSNGG HFLRILPDGT VDGTRDRSDQ HIQWQLSAES VGEVYIKSTE TGQYLAMDTD
L14R,C87T,C117V,P122W FGF1 GLLYGSQTPN EETLFLERLE EMHYNTYISK KHAEKNWFVG LKKNGSVKRG PRTHYGQKAI LWLPLPGL
                     PPALPEPPGI LAPQPPDVGS SDPLSMVGPS QGRSPSYAS
```

FIG. 6B

```
M2-FGF21C-tail      ---------- -KLLYCSNGG HFLRILPDGT VDGTRDRSDQ HIQFQLSAES VGEVYIKSTE TGQYLAMDTD
L44E,C83T,C117V,F132W FGF1  GLIYGSQTPN EETLFLERLE ENHYNTYISK KHAEKNWFVG LKKNGSVKRG PRTHYGQKAI LWLPLPGL
                    PPALPEPPGI LAPQPPDVGS SDPLSMVGPS QGRSPSYAS M2-FGF21C-tail      FNLPPGNYKK PKLLYCSNGG HFLRILPDGT VDGTRDRSDQ HIQFQLSAES VGEVYIKSTE TGQYLAMDTD
L44E,C83T,C117V,F132W FGF1  GLIYGSQTPN EETLFLERLE ENHYNTYISK KHAEKNWFVG LKKNGSVKRG PRTHYGQKAI LWLPLPGL
                    PPALPEPPGI LAPQPPDVGS SDPLSMVGPS QGRSPSYAS M3-FGF21C-tail      ---------K PKLLYCSNGG HFLRILPDGT VDGTRDRSDQ HIQFQLSAES VGEVYIKSTE TGQYLAIDTD
L44E,M67I,L72Y,V105L  EECLFLERLE ENHYNTYISK KHG----WFLG IKKNGSVKG- ---THYGQKAI LFLPLPGL
L111I,C117V,A103G,R119G GLIVYGSQTPN
Δ104-106,Δ120-122   PPALPEPPG

FIG. 7A

FGF19 chimeras

FIG. 7B

```
M2-FGF19C-tail            ---------- -KLLYCSNGG HFLRILPDGT VDGTRDRSDQ HIQFQLSAES VGEVVIKSTE TGQYLAMDTD
L44F,C83T,C117V,P122W FGF1  GLLYGSQTPN EETLFLERLE ENHYNTYISK KHAEKNWFVG LKKNGSVKRG PRTHYGQKAI LWLPLLP
                          MVTEPEDLR GHLESDMFSS PLETDSMDPF GLVTGLEAVR SPSFEK M3-FGF19C-tail            ENLPPGNYKK PKLLYCSNGG HFLRILPDGT VDGTRDRSDQ HIQFQLSAES VGEVVIKSTE TGQYLAIDTD
L44F,M61I,L73V,V105L       GLVYGSQTPN EECLFLERLE ENHYNTYISK KHG---WELG IKKNGSVKG- ---THYGQKAI LFLPLLP
L121I,C117V,A103G,R119G    MVTEPEDLR GHLESDMFSS PLETDSMDPF GLVTGLEAVR SPSFEK
Δ104-106 Δ120-122

M3-FGF19C-tail            ---------- K PKLLYCSNGG HFLRILPDGT VDGTRDRSDQ HIQFQLSAES VGEVVIKSTE TGQYLAIDTD
L44F,M61I,L73V,V105L       GLVYGSQTPN EECLFLERLE ENHYNTYISK KHG---WELG IKKNGSVKG- ---THYGQKAI LFLPLLP
L121I,C117V,A103G,R119G    MVTEPEDLR GHLESDMFSS PLETDSMDPF GLVTGLEAVR SPSFEK
Δ104-106 Δ120-122

M3-FGF19C-tail            ---------- -KLLYCSNGG HFLRILPDGT VDGTRDRSDQ HIQFQLSAES VGEVVIKSTE TGQYLAIDTD
L44F,M61I,L73V,V105L       GLVYGSQTPN EECLFLERLE ENHYNTYISK KHG---WELG IKKNGSVKG- ---THYGQKAI LFLPLLP
L121I,C117V,A103G,R119G    MVTEPEDLR GHLESDMFSS PLETDSMDPF GLVTGLEAVR SPSFEK
Δ104-106 Δ120-122
```

*Mutant peptide descriptions*
M1: K12V/C117V/P134V
M2: L44F/C83T/C117V/F132W
M3: L44F/M67I/L73V/V109L/L111I/C117V/A103G/R119G/Δ104-106/Δ120-122
M4: N95V/K12V/C117V
M5: K12V/L46V/E87V/N95V/C117V/P134V

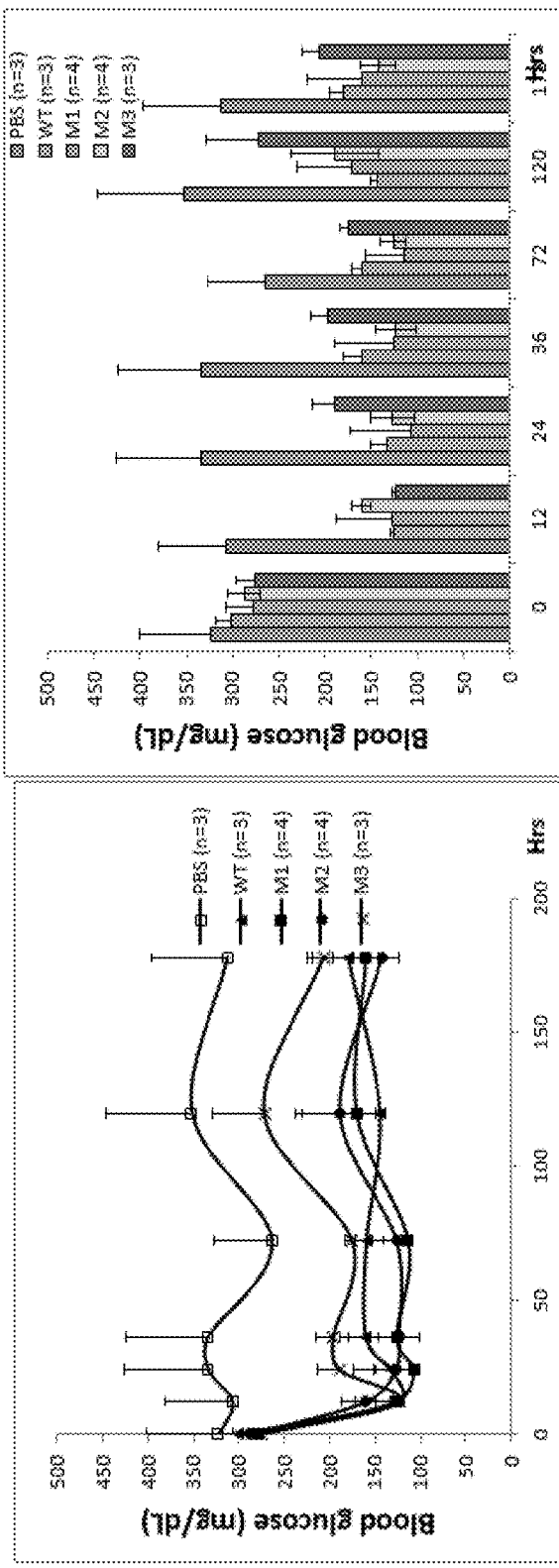
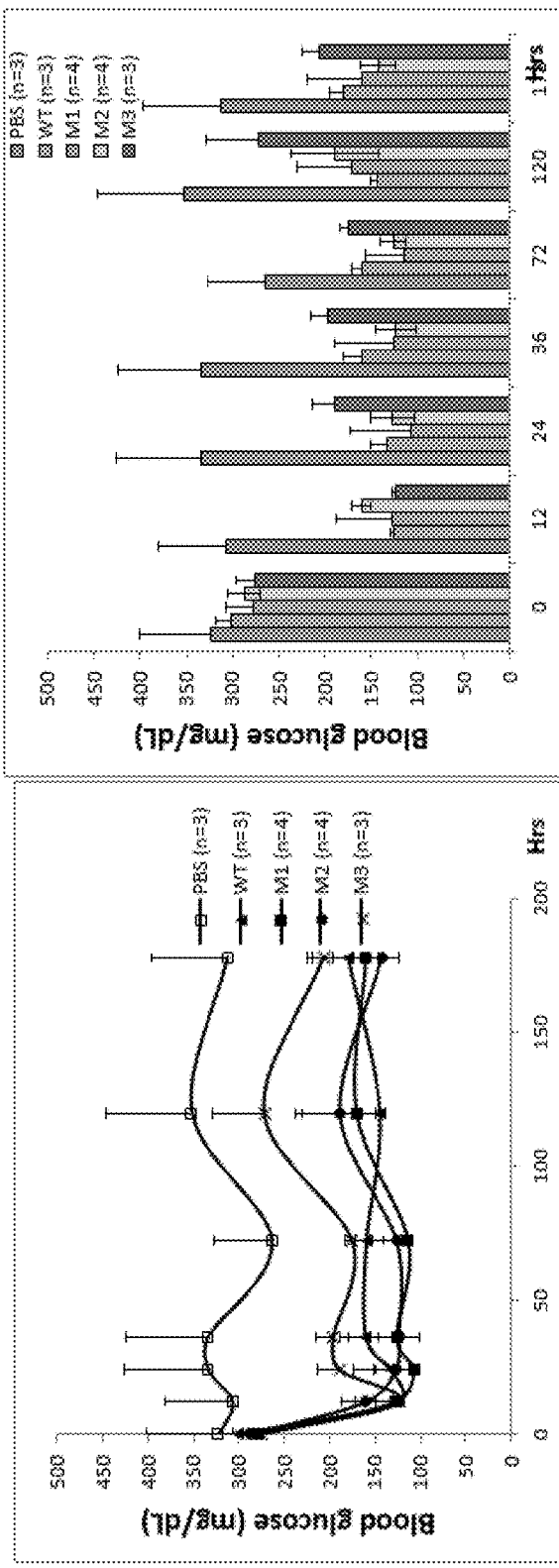
FIG. 11B
FIG. 11A

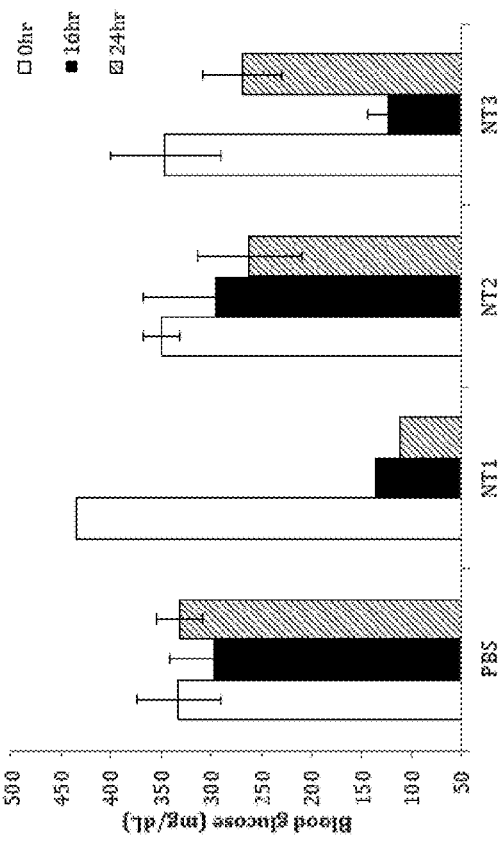
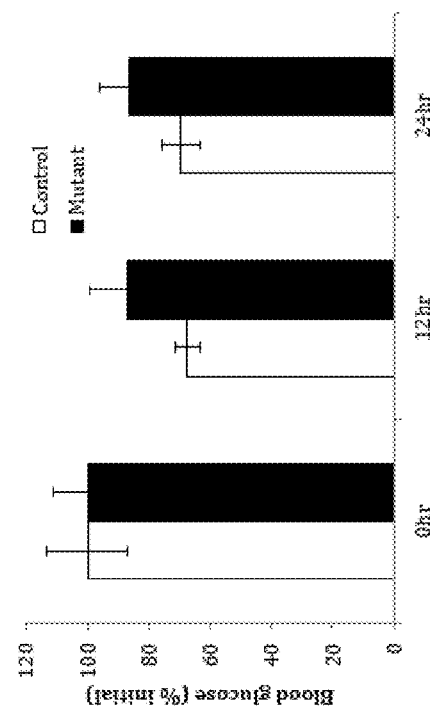
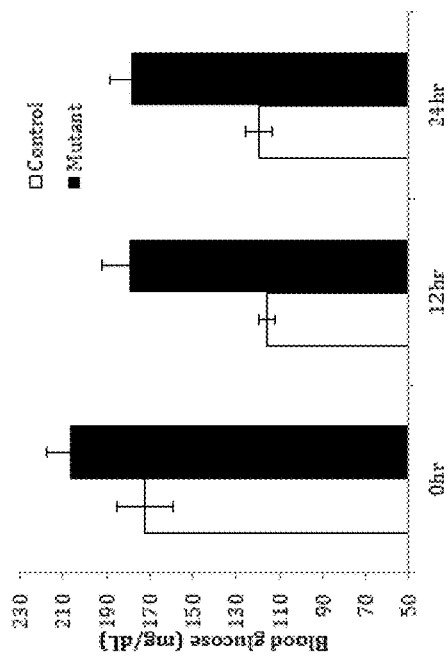
FIG. 16
FIG. 17A
FIG. 17B

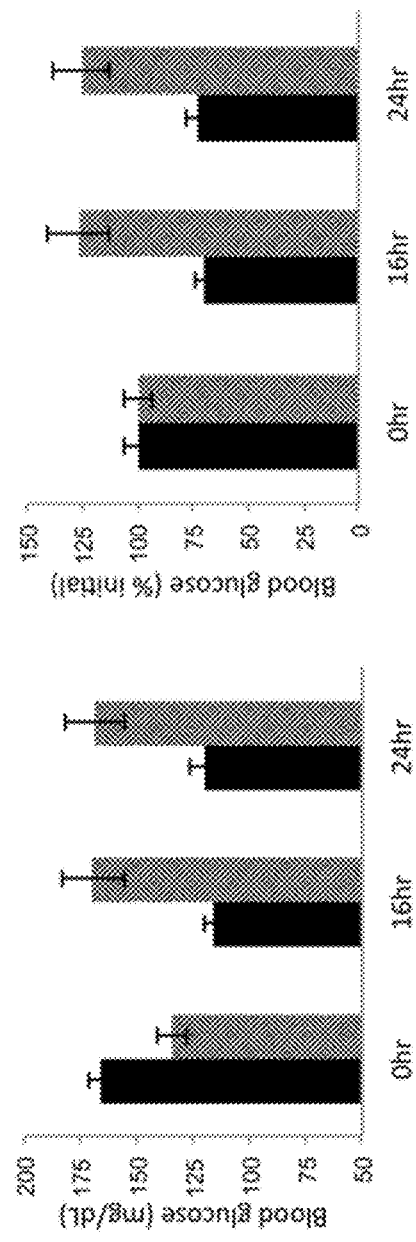
FIG. 18A
FIG. 18B
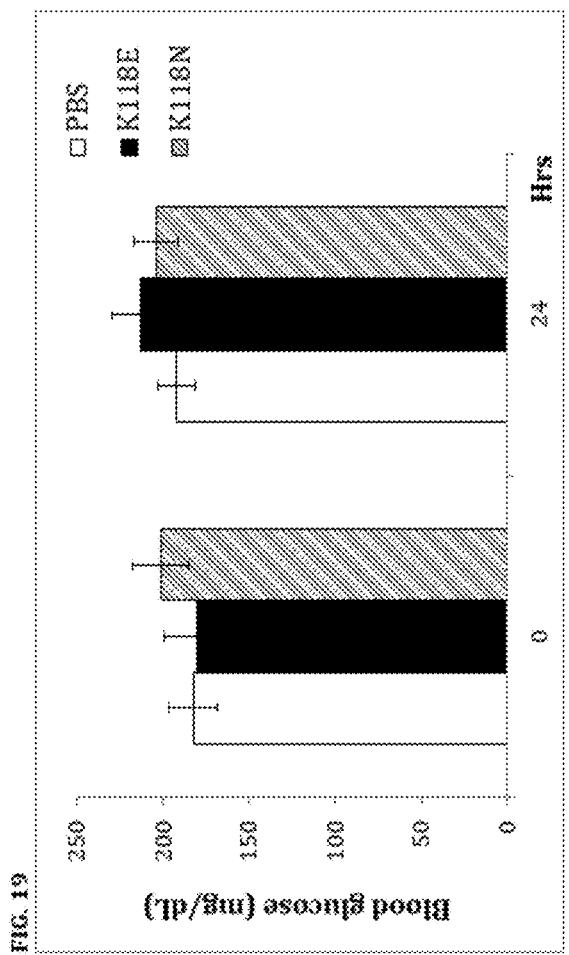
FIG. 19

FIG. 20

```
wtFGF1(1-140aa)              FNLPPGNYKK PKLLYCSNGG HFLRILPDGT VDGTRDRSDQ HIQLQLSAES VGEVYIKSTE TGQYLAMDTD
                             GLLYGSQTPN EECLFLERLE ENHYNTYISK KHAEKNWFVG LKKNGSCKRG PRTHYGQKAI LFLPLPVSSD

FGF1(1-140aa) KKK            FNLPPGNYKK PKLLYCSNGG HFLRILPDGT VDGTRDRSDQ HIQLQLSAES VGEVYIKSTE TGQYLAMDTD
K112D,K113Q,K118V            GLLYGSQTPN EECLFLERLE ENHYNTYISK KHAEKNWFVG LKKNGSCVRG PRTHYGQKAI LFLPLPVSSD

FGF1(1-140aa) KKK            FNLPPGNYKK PKLLYCSNGG HFLRILPDGT VDGTRDRSDQ HIQLQLSAES VGEVYIKSTE TGQYLAMDTD
K112D,K113Q,C117V,K118V      GLLYGSQTPN EECLFLERLE ENHYNTYISK KHAEKNWFVG LKKNGSVVRG PRTHYGQKAI LFLPLPVSSD

FGF1 ΔNT(1-140aa) KKK        ---------K PKLLYCSNGG HFLRILPDGT VDGTRDRSDQ HIQLQLSAES VGEVYIKSTE TGQYLAMDTD
K112D,K113Q,K118V            GLLYGSQTPN EECLFLERLE ENHYNT

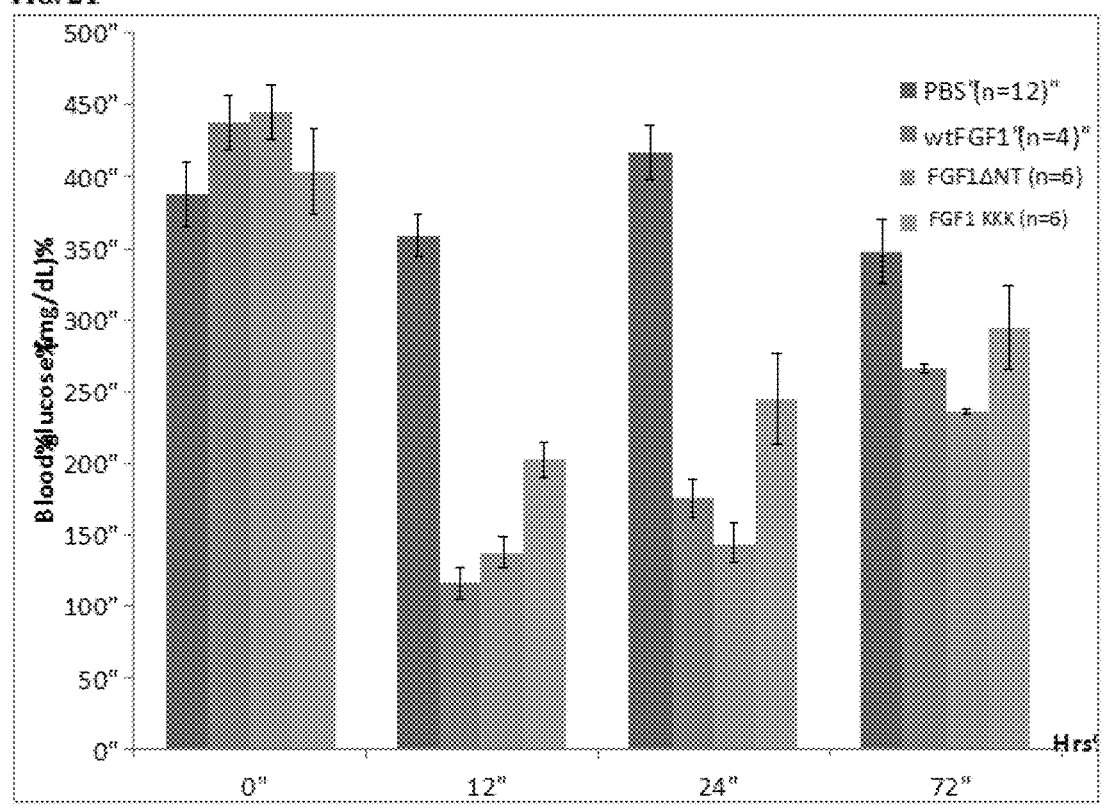

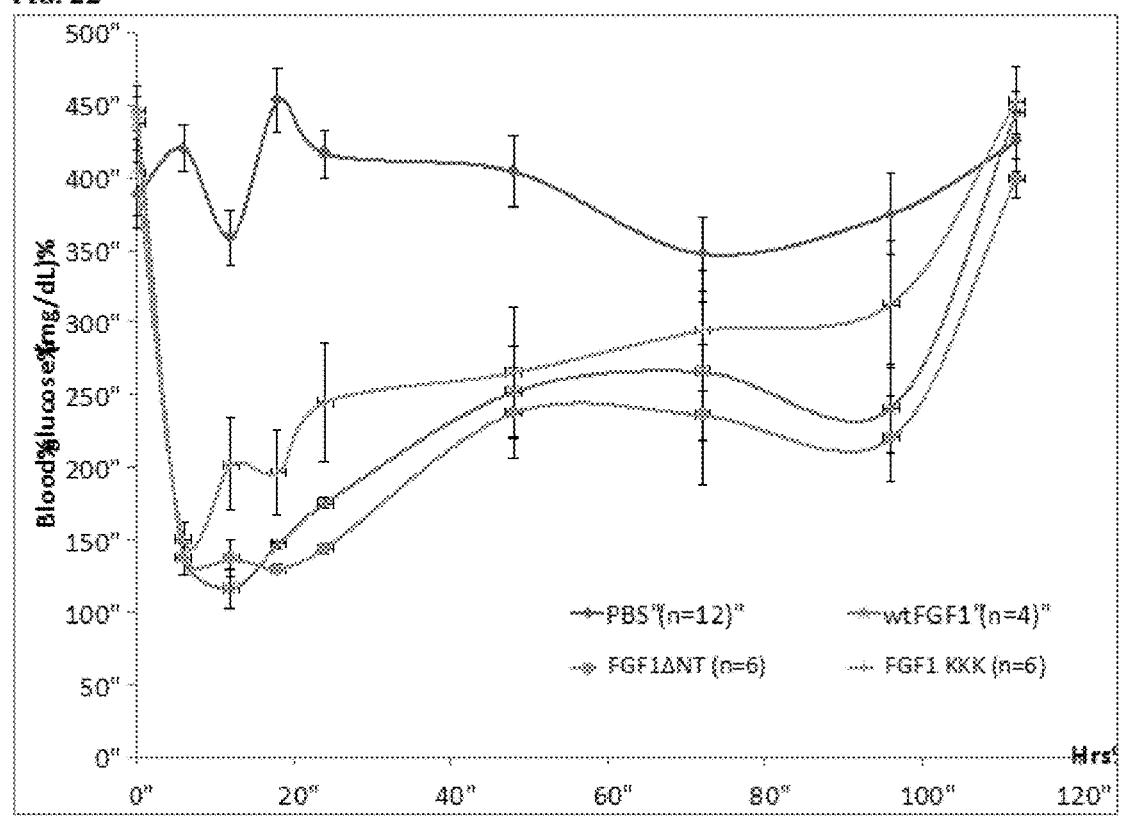

FIG. 26
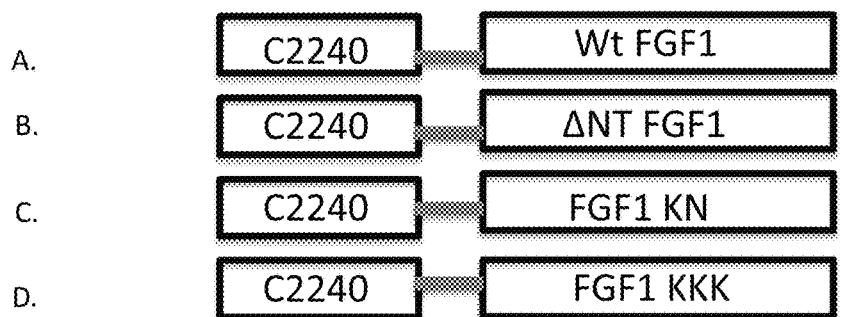
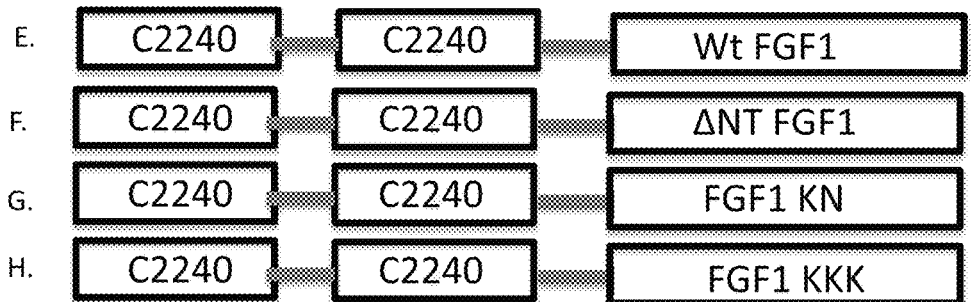

FIG. 27

| | | | | | | |
|---|---|---|---|---|---|---|
| FGF1(1-140αα) R35E C117V | FMLPPGNYKK PKLLYCSNGG HPLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSVVRG PRTHYGQKAI LFLPLPVSSD |
| FGF1(1-140αα) R35E C117V KKK | FMLPPGNYKK PKLLYCSNGG HPLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSVVRG PRTHYGQKAI LFLPLPVSSD |
| FGF1(1-140αα) R35E C117V K12V,N95V | FMLPPGNVKK PVLLYCSNGG HPLRILPDGT VDGTRDRSDQ HIQLQLSAES VGEVYIKSTE T

FIG. 28

```
FGF1(1-140αα)                FNLPPGNYKK PKLLYCSNGG HFLRILPDGT VDGTVDRSDQ HIQLQLSAES VGEVYIKSTE TGQYLAMDTD
R35V C117V                   GLLYGSQTPN EECLFLERLE ENHYNTYISK KHAEKNWFVG LKKNGSVKRG PRTHYGQKAI LFLPLPVSSD

FGF1(1-140αα)                FNLPPGNYKK PKLLYCSNGG HFLRILPDGT VDGTVDRSDQ HIQLQLSAES VGEVYIKSTE TGQYLAMDTD
R35V C117V, KKK              GLLYGSQTPN EECLFLERLE ENHYNTYISK KHAEKNWFVG LDQNGSVVRG PRTHYGQKAI LFLPLPVSSD

FGF1(1-140αα)                FNLPPGNYKK PVLLYCSNGG HFLRILPDGT VDGTVDRSDQ HIQLQLSAES VGEVYIKSTE TGQYLAMDTD
K12V,R35V,N95V,C117V         GLLYGSQTPN EECLFLERLE ENHYVTYISK KHAEKNWFVG LKKNGSVKRG PRTHYGQKAI LFLPLPVSSD

FGF1ΔNT(10-140αα)            ---------K PKLLYCSNGG HFLRILPDGT VDGTVDRSDQ HIQLQLSAES VGEVYIKSTE TGQYLAMDTD
R35V,C117V                   GLLYGSQTPN EECLFLERLE ENHYNTYISK KHAEKNWFVG LKKNGSVKRG PRTHYGQKAI LFLPLPVSSD

FGF1ΔNTKNKKK(10-140αα)       ---------K PVLLYCSNGG HFLRILPDGT VDGTVDRSDQ HIQLQLSAES VGEVYIKSTE TGQYLAMDTD
K112D,K113Q,K118V K12V,      GLLYGSQTPN EECLFLERLE ENHYVTYISK KHAEKNWFVG LDQNGSVVRG PRTHYGQKAI LFLPLPVSSD
N95V C117V R35V

FGF1 KKK(KN)(1-140αα)        FNLPPGNYKK PVLLYCSNGG HFLRILPDGT VDGTVDRSDQ HIQLQLSAES VGEVYIKSTE TGQYLAMDTD
K112D,K113Q,K118V            GLLYGSQTPN EECLFLERLE ENHYVTYISK KHAEKNWFVG LDQNGSVVRG PRTHYGQKAI LFLPLPVSSD
K12V,N95V C117V R35V

FGF1ΔNT1(10-140αα)M2KN       ---------K PVLLYCSNGG HFLRILPDGT VDGTVDRSDQ HIQFQLSAES VGEVYIKSTE TGQYLAMDTD
K12V,L44F,C83T, N95V         GLLYGSQTPN EETLFLERLE ENHYVTYISK KHAEKNWFVG LKKNGSVKRG PRTHYGQKAI LWLPLPVSSD
C117V,F132W R35v

FGF1ΔNT1(10-140αα)M2KNKKK    ---------K PVLLYCSNGG HFLRILPDGT VDGTVDRSDQ HIQFQLSAES VGEVYIKSTE TGQYLAMDTD
K12V,L44F,C83T, N95V         GLLYGSQTPN EETLFLERLE ENHYVTYISK KHAEKNWFVG LDQNGSVVRG PRTHYGQKAI LWLPLPVSSD
C117V,F132W, R35V
```

FIG. 29

```
FGF1(1-140αα)   FNLPPGNYKK PKLLYCSNGG HFLRILPDGT VDGTRDRSDQ HIQLQLSAES VGEVYIKSTE TGQYLAMDTD
C117V, KKKR     GLLYGSQTPN EECLFLERLE ENHYNTYISK KHAEKNWFVG LKQNGSVVVG PRTHYGQKAI LFLPLPVSSD

FGF1(1-140αα)   FNLPPGNYKK PVLLYCSNGG HFLRILPDGT VDGTRDRSDQ HIQLQLSAES VGEVYIKSTE TGQYLAMDTD
C117V KY        GLLYGSQTPN EECLFLERLE ENHVNTYISK KHAEKNWFVG LKKNGSVKRG PRTHYGQKAI LFLPLPVSSD

FGF1(1-140αα)   FNLPPGNYKK PVLLYCSNGG HFLRILPDGT VDGTRDRSDQ HIQLQLSAES VGEVYIKSTE TGQYLAMDTD
C117V KK        GLLYGSQTPN EECLFLVRLE ENHYNTYISK KHAEKNWFVG LKKNGSVKRG PRTHYGQKAI LFLPLPVSSD

FGF1(1-140αα)   FNLPPGNYKK PVLLYCSNGG HFLRILPDGT VDGTRDRSDQ HIQLQLSAES VGEVYIKSTE TGQYLAMDTD
C117V KKY       GLLYGSQTPN EECLFLVRLE ENHVNTYISK KHAEKNWFVG LKKNGSVKRG PRTHYGQKAI LFLPLPVSSD

FGF1(1-140αα)   FNLPPGNYKK PVLLYCSNGG HFLRILPDGT VDGTRDRSDQ HIQLQLSAES VGEVYIKSTE TGQYLAMDTD
C117V KNY       GLLYGSQTPN EECLFLERLE ENHVVTYISK KHAEKNWFVG LKKNGSVKRG PRTHYGQKAI LFLPLPVSSD
```

FIG. 30A

```
FGF1(1-140αα)               FNLPPGNYKK PVLLYCSNGG HFLRILPDGT VDGTRDRSDQ HIQLQLSAES VGEVYIKSTE TGQYLAMDTD
K12V,N95V,C117V             GLLYGSQTPN EECLFLERLE ENHYVTYISK KHAEKNWFVG LKKNGSVKRG PRTHYGQKAI LFLPLPVSSD

FGF1(1-140αα)               FNLPPGNYKK PVLLYCSNGG HFLRILPDGT VDGTRDRSDQ HIQLQVSAES VGEVYIKSTE TGQYLAMDTD
K12V,L46V,E87V,N95V,        GLLYGSQTPN EECLFLVRLE ENHYVTYISK KHAEKNWFVG LKKNGSVKRG PRTHYGQKAI LFLVLPVSSD
P134V,C117V

Salk_030 FGF1  (1-140αα)    FNLPPGNYKK PKLLYCSNGG HFLRILPDGT VDGTRDRSDQ HIQLQLSAES VGEVYIKSTE TGQYLAMDTD
C117V,K118V                 GLLYGSQTPN EECLFLERLE ENHYNTYISK KHAEKNWFVG LKKNGSVVRG PRTHYGQKAI LFLPLPVSSD Salk_031 FGF1ΔNT1C(10-140αα) ---------K PVLLYCSNGG HFLRILPDGT VDGTRDRSDQ HIQLQLSAES VGEVYIKSTE TGQYLAMDTD
K12V,N95V,C83T,C117V        GLLYGSQTPN EETLFLERLE ENHYVTYISK KHAEKNWFVG LKKNGSVKRG PRTHYGQKAI LFLPLPVSSD Salk_032 FGF1ΔNT1C(10-140αα) ---------K PVLLYTSNGG HFLRILPDGT VDGTRDRSDQ HIQLQLSAES VGEVYIKSTE TGQYLAMDTD
K12V,N95V,C16T,C83S,C117A   GLLYGSQTPN EESLFLERLE ENHYVTYISK KHAEKNWFVG LKKNGSAKRG PRTHYGQKAI LFLPLPVSSD Salk_035 FGF1ΔNT1(10-140αα)      ---------K PKLLYCSNGG YFLRILPDGT VDGTRDRSDQ HIQFQLSAES VGEVYIKSTE TGQYLAMDTD
H21Y,L44F,H102Y,F108Y,C117V     GLLYGSQTPN EECLFLERLE ENHYNTYISK KYAEKNWYVG LKKNGSVKRG PRTHYGQKAI LFLPLPVSSD Salk_036 FGF1ΔNT1(10-140αα)      ---------K PVLLYCSNGG YFLRILPDGT VDGTRDRSDQ HIQFQLSAES VGEVYIKSTE TGQYLAMDTD
K12V,H21Y,L44F,N95V,            GLLYGSQTPN EECLFLERLE ENHYVTYISK KYAEKNWYVG LKKNGSVKRG PRTHYGQKAI LFLPLPVSSD
H102Y,F108Y,C117V Salk_037 FGF1(1-140αα)          FNLPPGNYKK PVLLYCSNGG YFLRILPDGT VDGTRDRSDQ HIQFQLSAES VGEVYIKSTE TGQYLAMDTD
K12V,H21Y,L44F,N95V,            GLLYGSQTPN EECLFLERLE ENHYVTYISK KYAEKNWYVG LKKNGSVKRG PRTHYGQKAI LFLPLPVSSD
H102Y,F108Y,C117V (ΔHBS)                      FNLPPGNYKK PVLLYCSNGG HFLRILPDGT VDGTRDRSDQ HIQLQLSAES VGEVYIKSTE TGQYLAMDTD
K112D,K113Q,K118V           GLLYGSQTPN EECLFLERLE ENHYVTYISK KHAEKNWFVG LDQNGSCVRG PRTHYGQKAI LFLPLPVSSD
```

FIG. 30B

```
wtFGF1DHBS-FGF21C-tail    FNLPPGNYKK PKLLYCSNGG HFLRILPDGT VDGTRDRSDQ HIQLQLSAES VGEVYIKSTE TGQYLAMDTD
                          GLIYGSQTPN EECLFLERLE ENHYNTYISK KHAEKNWFVG LDQNGSCVRG PRTHYGQKAI LFLPLPgl
                          ppalpeppgi lapqppdvgs sdpismvgps qgrspsyas wtFGF1DHBS-FGF19C-tail    FNLPPGNYKK PKLLYCSNGG HFLRILPDGT VDGTRDRSDQ HIQLQLSAES VGEVYIKSTE TGQYLAMDTD
                          GLIYGSQTPN EECLFLERLE ENHYNTYISK KHAEKNWFVG LDQNGSCVRG PRTHYGQKAI LFLPLLP
                          mvpeepedir ghlesdmfss pietdsmdpf glvtgleavr spsfek Salk_033 ntFGF21/1        HPIPDSS PLLQFGGGVK PKLLYCSNGG HFLRILPDGT VDGTRDRSDQ HIQLQLSAES VGEVYIKSTE TGQYLAMDTD
C117V                     GLIYGSQTPN EECLFLERLE ENHYNTYISK KHAEKNWFVG LKKNGSVKRG PRTHYGQKAI LFLPLPVSSD Salk_034 ntFGF21/1a       -----GSQVK PKLLYCSNGG HFLRILPDGT VDGTRDRSDQ HIQLQLSAES VGEVYIKSTE TGQYLAMDTD
C117V                     GLIYGSQTPN EECLFLERLE ENHYNTYISK KHAEKNWFVG LKKNGSVKRG PRTHYGQKAI LFLPLPVSSD Salk_015                  FNLPPGNYKK PKLLYCSNGG HFLRILPDGT VDGTRDRSDQ HIQLQLSAES VGEVYIKSTE TGQYLAMDTD
wtFGF1-FGF21C-tail        GLIYGSQTPN EECLFLERLE ENHYNTYISK KHAEKNWFVG LKKNGSCKRG PRTHYGQKAI LFLPLPgl
                          ppalpeppgi lapqppdvgs sdpismvgps qgrspsyas Salk_019                  FNLPPGNYKK PKLLYCSNGG HFLRILPDGT VDGTRDRSDQ HIQLQLSAES VGEVYIKSTE TGQYLAMDTD
wtFGF1-FGF19C-tail        GLIYGSQTPN EECLFLERLE ENHYNTYISK KHAEKNWFVG LKKNGSCKRG PRTHYGQKAI LFLPLLP
                          mvpeepedir ghlesdmfss pietdsmdpf glvtgleavr spsfek
```

FIG. 30C

```
Salk_009
FGF1 ΔNTΔC(10-140αα)                    K PVLLYCSNGG HFLRILPDGT VDGTRDRSDQ HIQLQLSAES VGEVYIKSTE TGQYLAMDTD
K12V,N95V,C117V          GLLYGSQTPN EECLFLERLE ENHYVTYISK KHAEKNWFVG LKKNGSVKRG PRTHYGQKAI LFLPLPVS

FIG. 30D

```
Salk_014
FGF1(1-140αα)C117V  FNLPPGNYKK PKLLYCSNGG HFLRILPDGT VDGTRDRSDQ HIQLQLSAES VGEVYIKSTE TGQYLAMDTD
                    GLLYGSQTPN EECLFLERLE ENHYNTYISK KHAEKNWFVG LKKNGSVKRG PRTHYGQKAI LFLPLPVSSD Salk_022
FGF1(1-140αα)KKK(KN)     FNLPPGNYKK PVLLYCSNGG HFLRILPDGT VDGTRDRSDQ HIQLQLSAES VGEVYIKSTE TGQYLAMDTD
K112D,K113Q,K118V        GLLYGSQTPN EECLFLERLE ENHYVTYISK KHAEKNWFVG LDQNGSVVRG PRTHYGQKAI LFLPLPVSSD
K12V,N95V,C117V Salk_023
FGF1(10-140αα)M2KN  ---------K PVLLYCSNGG HFLRILPDGT VDGTRDRSDQ HIQFQLSAES VGEVYIKSTE TGQYLAMDTD
K12V,L44F,C83T,     GLLYGSQTPN EETLFLERLE ENHYVTYISK KHAEKNWFVG LKKNGSVKRG PRTHYGQKAI LWLPLPVSSD
N95V C117V,F132W Salk_024
FGF1(1-140αα)       FNLPPGNYKK PKLLYCSNGG HFLRILPDGT VDGTEDRSDQ HIQLQLSAES VGEVYIKSTE TGQYLAMDTD
R35E, C117V         GLLYGSQTPN EECLFLERLE ENHYNTYISK KHAEKNWFVG LKKNGSVKRG PRTHYGQKAI LFLPLPVSSD
```

FIG. 30E

Salk_025
FGF1(1-140αα)KY FNLPPGNYKK PVLLYCSNGG HFLRILPDGT VDGTRDRSDQ HIQLQLSAES VGEVYIKSTE TGQYLAMDTD
K12V,Y94V, C117V GLLYGSQTPN EECLFLERLE ENHVNTYISK KHAEKNWFVG LKKNGSVKRG PRTHYGQKAI LFLPLPVSSD Salk_026
FGF1(1-140αα) KE FNLPPGNYKK PVLLYCSNGG HFLRILPDGT VDGTRDRSDQ HIQLQLSAES VGEVYIKSTE TGQYLAMDTD
K12V,E87V, C117V GLLYGSQTPN EECLFLVRLE ENHYNTYISK KHAEKNWFVG LKKNGSVKRG PRTHYGQKAI LFLPLPVSSD Salk_027
FGF1(1-140αα) KKKR FNLPPGNYKK PKLLYCSNGG HFLRILPDGT VDGTRDRSDQ HIQLQLSAES VGEVYIKSTE TGQYLAMDTD
K112D,K113Q, GLLYGSQTPN EECLFLERLE ENHYNTYISK KHAEKNWFVG LDQNGSVVVG PRTHYGQKAI LFLPLPVSSD
C117V, K118V, R119V Salk_028
FGF1(1-140αα) KN FNLPPGNYKK PVLLYCSNGG HFLRILPDGT VDGTEDRSDQ HIQLQLSAES VGEVYIKSTE TGQYLAMDTD
R35E, K12V, GLLYGSQTPN EECLFLERLE ENHYVTYISK KHAEKNWFVG LKKNGSVKRG PRTHYGQKAI LFLPLPVSSD
N95V, C117V Salk_029
FGF1(10-140αα) KN ---------K PVLLYCSNGG HFLRILPDGT VDGTEDRSDQ HIQLQLSAES VGEVYIKSTE TGQYLAMDTD
R35E, C117V GLLYGSQTPN EECLFLERLE ENHYVTYISK KHAEKNWFVG LKKNGSVKRG PRTHYGQKAI LFLPLPVSSD

FIG. 31

```
                    K12 Y15
    PNLFDGNKRPKLLYCSNG------GHFLRILPDGTVDGTRDRSDQHIQLQLSARSVGEVYIKSTETGQYLAMDTEGLLYGSQHP--EEE
    PALPEDGGAAFPPGHFKDPKRLYCKNG------GFFLRIHPDGRVDGVREKSDPHVKLQLQAEERGVVSIKGVCANRYLAMKEDGRLLASKCV-TEE
                                  N95
        E87 Y24N95             K112K113 K118
    CLFLERLEENHYNTYISKRHAEKNWFVGL------KKNGSCKRGPRTHYGQKAILFLPLPVSSD                        FGF1
    CFFFERLESNNYNTYRSRKYTSS--WYVALKRTGQYKLGSKTGPGQKAILFLPMSAKS                              FGF2
```

| Interaction | Residues | FGF1 | FGF2 |
|---|---|---|---|
| Identified FGF1 receptor interactions | Y15, E87, Y94, N95 | □ | □ |
| Predicted to be at receptor interface | K12 | □ | □ |
| Heparin binding site | K112, K113, K118 | □ | K113R |
| Salt bridge with D2 of receptor | R35 | □ | □ |

US 9,925,241 B2

MUTATED FIBROBLAST GROWTH FACTOR (FGF) 1 AND METHODS OF USE

CROSS-REFERENCE TO RELATED APPLICATIONS

This application claims priority to U.S. Provisional Application No. 61/893,766 filed Oct. 21, 2013, U.S. Provisional Application No. 61/949,945 filed Mar. 7, 2014, U.S. Provisional Application No. 61/975,530 filed Apr. 4, 2014, U.S. Provisional Application No. 62/019,185 filed Jun. 30, 2014, and U.S. Provisional Application No. 62/046,038 filed Sep. 4, 2014, all herein incorporated by reference.

ACKNOWLEDGEMENT OF GOVERNMENT SUPPORT

This invention was made with government support under Grant Nos. DK057978, DK090962, HL088093, HL105278 and ES010337 awarded by The National Institutes of Health, National Human Genome Research Institute. The government has certain rights in the invention.

FIELD

This application provides mutated FGF1 proteins, FGFR1c-binding protein multimers, nucleic acids encoding such proteins, and methods of their use, for example to treat a metabolic disease.

BACKGROUND

Type 2 diabetes and obesity are leading causes of mortality and are associated with the Western lifestyle, which is characterized by excessive nutritional intake and lack of exercise. A central player in the pathophysiology of these diseases is the nuclear hormone receptor (NHR) PPARγ, a lipid sensor and master regulator of adipogenesis. PPARγ is also the molecular target for the thiazolidinedione (TZD)-class of insulin sensitizers, which command a large share of the current oral anti-diabetic drug market. However, there are numerous side effects associated with the use of TZDs such as weight gain, liver toxicity, upper respiratory tract infection, headache, back pain, hyperglycemia, fatigue, sinusitis, diarrhea, hypoglycemia, mild to moderate edema, and anemia. Thus, the identification of new insulin sensitizers is needed.

SUMMARY

It is shown herein that mutants of fibroblast growth factor (FGF) 1 having reduced or eliminated mitogenic activity can be used to reduce blood glucose in a mammal. Based on these observations, methods for reducing blood glucose in a mammal, for example to treat a metabolic disease, are disclosed. Such FGF1 mutants can have an N-terminal truncation, point mutations, or combinations thereof, for example to reduce the mitogenic activity of the native FGF1 protein. Such FGF1 mutants can be used alone or in combination with other agents, such as other glucose reducing agents, such as thiazolidinedione.

In some examples, the FGF1 mutant is part of a chimeric protein, such as one that includes at least 10, at least 20, at least 30, at least 40, at least 42, at least 43, at least 44, at least 45, at least 46, at least 47, at least 48, at least 49, or at least 50 contiguous amino acids from a C-terminal end of FGF19 or FGF21.

In some examples, the FGF1 mutant is part of a chimeric protein, such as one that includes at least 10, at least 20, at least 30, at least 35, at least 40, at least 50, at least 60, at least 70, at least 80, at least 90, at least 100, at least 120, at least 150, at least 180, or at least 200 amino acids (such as 20-500, 20 to 250, 30 to 200, 35 to 180, 37 to 90, or 37 to 180 amino acids) of a protein that selectively binds to beta-Klotho (β-Klotho), such as SEQ ID NO: 121, 122, 123, 124, 125, 126, 127, 128, 129, 130, 131, 132, 133, 134, 135, 136, 137, 138, 139, 140, 141, 142, 143, 144, 145 or 146.

In some examples, the FGF1 mutant is part of a chimeric protein, such as one that includes at least 10, at least 20, at least 30, at least 35, at least 40, at least 50, at least 60, at least 70, at least 80, at least 90, at least 100, at least 120, at least 150, at least 180, or at least 200 amino acids (such as 20-500, 20 to 250, 30 to 200, 35 to 180, 37 to 90, or 37 to 180 amino acids) of a protein that selectively binds to FGFR1c, such as SEQ ID NO: 147, 148, 149, 150, 151, 152, 153, 154, 155, 156, 157, 158, 159, 160, 161, 162, 163, 164, 165, 166, 167, or multimers thereof (e.g., dimers, timers), such as SEQ ID NO: 190.

In some examples, the FGF1 mutant is part of a chimeric protein, such as one that includes at least 10, at least 20, at least 30, at least 35, at least 40, at least 50, at least 60, at least 70, at least 80, at least 90, at least 100, at least 120, at least 150, at least 180, or at least 200 amino acids (such as 20-500, 20 to 250, 30 to 200, 35 to 180, 37 to 90, or 37 to 180 amino acids) of a protein that selectively binds to β-Klotho, and that includes at least 10, at least 20, at least 30, at least 35, at least 40, at least 50, at least 60, at least 70, at least 80, at least 90, at least 100, at least 120, at least 150, at least 180, or at least 200 amino acids (such as 20-500, 20 to 250, 30 to 200, 35 to 180, 37 to 90, or 37 to 180 amino acids) of a protein that selectively binds to FGFR1c, such as SEQ ID NO: 168, 169, 170 or 171.

In some examples, chimeric proteins include a linker between the FGF1 mutant and the FGF19, FGF21, FGFR1c-binding, or β-Klotho-binding sequence. In some examples, use of the disclosed methods result in one or more of: reduction in triglycerides, decrease in insulin resistance, reduction of hyperinsulinemia, increase in glucose tolerance, or reduction of hyperglycemia in a mammal.

Provided herein are mutated FGF1 proteins, which can include deletion of an N-terminal portion of FGF1, point mutations (such as amino acid substitutions, deletions, additions, or combinations thereof), or combinations of N-terminal deletions and point mutations, and methods of their use to lower glucose, for example to treat a metabolic disease. In some examples, such mutations reduce the mitogenicity of mature FGF1 (e.g., SEQ ID NO: 5), such as a reduction of at least 20%, at least 50%, at least 75% or at least 90%. In some examples, the mutant FGF1 protein is a truncated version of the mature protein (e.g., SEQ ID NO: 5), which can include for example deletion of at least 5, at least 6, at least 10, at least 11, at least 12, at least 13, or at least 20 consecutive N-terminal amino acids. In some examples, one or more of the deleted N-terminal amino acids are replaced with corresponding amino acids from FGF21 (or any FGF having low affinity for FGFR4, including FGF3, FGF5, FGF7, FGF9 and FGF10), such as at least 1, at least 2, at least 3, at least 4, at least 5, at least 10, or at least 15, such as 1, 2, 3, 4, 5, 6, 7, 8, 9, 10, 11, 12, 13, 14, 15, 16, 17, 18, 19, or 20 corresponding amino acids from FGF21 (e.g., see SEQ ID NOS: 21, 219, 221, 222 and 223). In some examples, the mutant FGF1 protein is a mutated version of the mature protein (e.g., SEQ ID NO: 5), such as one containing at least 1, at least 2, at least 3, at least 4, at least 5, at least 6, at least 7, at least 8, at least 9 or at least 10 amino acid substitutions (such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41 substitutions), such as one or more of those shown in Table 1. In some examples, the mutant FGF1 protein includes both an N-terminal truncation and point mutations. In some examples, the mutant FGF1 protein includes at least 120 consecutive amino acids from amino acids 5-141 of FGF1 (e.g., of SEQ ID NO: 2 or 4), (which in some examples can include 1-20 point mutations, such as substitutions, deletions, or additions).

In some examples, the FGF1 mutants provided herein are used to generate a chimeric protein, such as an FGF1/FGF21, FGF1/FGF19, FGF1/β-Klotho-binding protein, FGF1/FGFR1c-binding protein or FGF1/β-Klotho-binding protein/FGFR1c-binding protein. For example, the C-terminal end or the N-terminal end of the disclosed FGF1 mutants can be joined directly or indirectly to the N-terminal end of a C-terminal fragment of FGF21 or FGF19, such as SEQ ID NO: 86 or 100, respectively. Similarly, the C-terminal end of the disclosed FGF1 mutants can be joined directly or indirectly to the N-terminal end of a β-Klotho binding domain (such as SEQ ID NO: 121, 122, 123, 124, 125, 126, 127, 128, 129, 130, 131, 132, 133, 134, 135, 136, 137, 138, 139, 140, 141, 142, 143, 144, 145, 146 or β-Klotho binding portion of SEQ ID NO: 168, 169, 170 or 171), or the N-terminal end of the disclosed FGF1 mutants can be joined directly or indirectly to the C-terminal end of a β-Klotho-binding domain. In addition, the C-terminal end of the disclosed FGF1 mutants can be joined directly or indirectly to the N-terminal end of a FGFR1c-binding domain (such as SEQ ID NO: 147, 148, 149, 150, 151, 152, 153, 154, 155, 156, 157, 158, 159, 160, 161, 162, 163, 164, 165, 166, 167 or 190), or the N-terminal end of the disclosed FGF1 mutants can be joined directly or indirectly to the C-terminal end of a FGFR1c-binding domain. In some examples, the C-terminal end of the disclosed FGF1 mutants can be joined directly or indirectly to an FGFR1c-binding domain (such as any of SEQ ID NOS: 147, 148, 149, 150, 151, 152, 153, 154, 155, 156, 157, 158, 159, 160, 161, 162, 163, 164, 165, 166, 167, 190 or FGFR1c-binding portion of 168, 169, 170 or 171) and a β-Klotho-binding domain, the N-terminal end of the disclosed FGF1 mutants can be joined directly or indirectly to the C-terminal end of a FGFR1c-binding domain and a β-Klotho-binding domain, or both (such as SEQ ID NO: 168, 169, 170 or 171). Such chimeric proteins can be used to reduce blood glucose in a mammal, for example to treat a metabolic disease.

Specific exemplary FGF1 mutant proteins are shown in SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 113, 114, 115, 116, 117, 118, 119, 120, 191, 192, 193, 194, 195, 196, 197, 198, 199, 200, 201, 202, 203, 204, 205, 206, 207, 208, 209, 210, 211, 212, 213, 214, 215, 216, 217, 218, 225, 226, 227, 228, 229, 230, 231, 232, 233, 234, 235, 236, 237 and 238, which can be used to generate any of the chimeras provided herein. Specific exemplary FGF1/FGF21 chimeras are shown in SEQ ID NOS: 87, 88, 89, 90, 91, 92, 93, 94, 95, 96, 97, 98, 219, 221, 222, and 223. Specific exemplary FGF1/FGF19 chimeras are shown in SEQ ID NOS: 101, 102, 103, 104, 105, 106, 107, 108, 109, 110, 111, 112, 220, and 224. Specific exemplary FGF1/β-Klotho-binding chimeras are shown in FIGS. 23-25 (and in SEQ ID NOS: 173, 174, 175, 177, 178, 179, 181, 182, 183, 185, 186, and 187). Specific exemplary FGF1/FGFR1c-binding chimeras are shown in FIGS. 23J and 24I (and in SEQ ID NOS: 188 and 189). Specific exemplary β-Klotho-binding/FGFR1c-binding chimeras that can be linked directly or indirectly to an N- or C-terminal end of a FGF1 mutant protein are shown in SEQ ID NOS: 168, 169, 170 and 171.

Also provided are FGFR1c-binding protein dimers and multimers (such as trimers) and their use to treat metabolic disease. An example is shown in FIG. 25E (also see SEQ ID NO: 190).

Also provided are isolated nucleic acid molecules encoding the disclosed mutant FGF1 proteins (which includes chimeras), and the FGFR1c binding proteins. Vectors and cells that include such nucleic acid molecules are also provided.

Methods of using the disclosed mutant FGF1 proteins and FGFR1c binding protein multimers (or nucleic acid molecules encoding such) are provided, such as a mutated mature FGF1 protein having a deletion of at least six contiguous N-terminal amino acids, at least one point mutation, or combinations thereof, for example to reduce or eliminate mitogenic activity. In some examples the methods include administering a therapeutically effective amount of a disclosed mutant FGF1 protein or FGFR1c binding protein (or nucleic acid molecules encoding such) to reduce blood glucose in a mammal, such as a decrease of at least 5%. In some examples the methods include administering a therapeutically effective amount of a disclosed mutant FGF1 protein or FGFR1c binding protein multimer (or nucleic acid molecules encoding such) to treat a metabolic disease in a mammal. Exemplary metabolic diseases that can be treated with the disclosed methods include but are not limited to: diabetes (such as type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), and cardiovascular diseases (e.g., hypertension). In some examples, one or more of these diseases are treated simultaneously with the disclosed FGF21 mutants. Also provided are methods of reducing fed and fasting blood glucose, improving insulin sensitivity and glucose tolerance, reducing systemic chronic inflammation, ameliorating hepatic steatosis in a mammal, reducing food intake, or combinations thereof, by administering a therapeutically effective amount of a disclosed mutant FGF1 protein or FGFR1c binding protein multimer (or nucleic acid molecules encoding such).

The foregoing and other objects and features of the disclosure will become more apparent from the following detailed description, which proceeds with reference to the accompanying figures.

BRIEF DESCRIPTION OF THE DRAWINGS

FIG. 1 shows an exemplary wild-type mature FGF1 sequence (SEQ ID NO: 5), N-terminal deletions that can be made to mature FGF1 (SEQ ID NOS: 7, 8 and 9), point mutations that can be made to mature FGF1 (SEQ ID NOS: 10 and 11), and mutations to the heparan binding domain of FGF1 (SEQ ID NOS: 12 and 13).

12). This shows that the non-mitogenic FGF1 variant rFGF1$^{\Delta NT}$ (SEQ ID NO: 7) has equivalent efficacy as wild-type FGF1 in lowering blood glucose levels in ob/ob diabetic mice. (B) Diet induced obese (DIO) mice treated with control vehicle (PBS, open bars), rFGF1 (0.5 mg/kg subcutaneous, filled bars), or rFGF1$^{\Delta NT}$ (0.5 mg/kg subcutaneous, striped bars) at indicated times (n=10). This shows that the non-mitogenic FGF1 variant rFGF1$^{\Delta NT}$ has equivalent efficacy as wild-type FGF1 in lowering blood glucose levels in high fat diet fed obese mice. Subcutaneous injections of vehicle (PBS) or rFGF1 (0.5 mg/kg) were performed on ad lib fed mice. Values are means±SEM. Statistics by two-tailed t test. *P<0.05, **P<0.01.

Figure 2A:
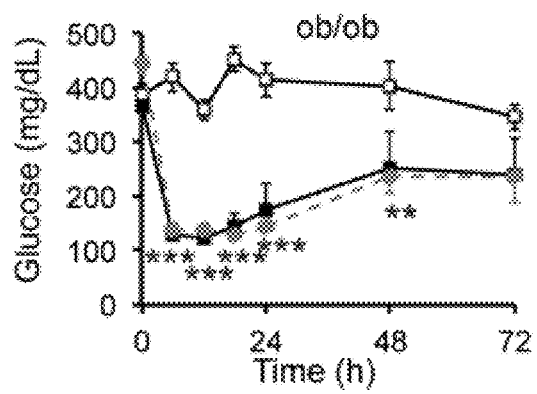
FIGS. 2A and 2B are graphs showing blood glucose levels of (A) ob/ob mice treated with control vehicle (PBS, open symbols), rFGF1 (0.5 mg/kg subcutaneous, filled symbols), or rFGF1$^{\Delta NT}$ (0.5 mg/kg subcutaneous, dashed line, n=8-
Figure 2B:
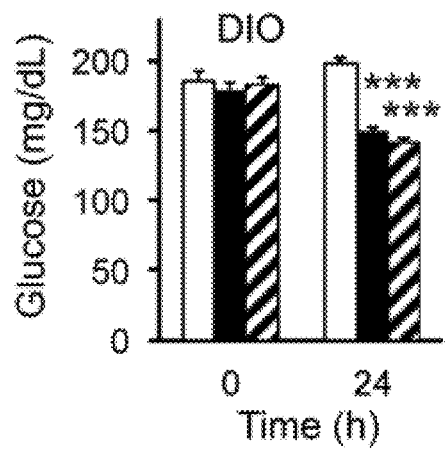
Figure 2C:
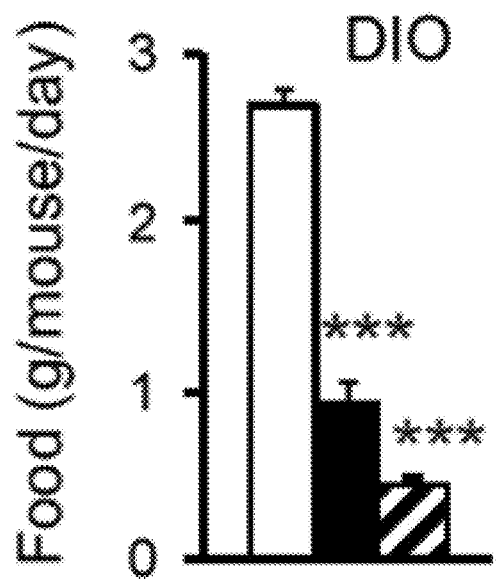

FIG. 2C is a graph showing food intake in DIO mice after control vehicle (PBS, open bar), rFGF1 (0.5 mg/kg subcutaneous, filled bars), or rFGF1$^{\Delta NT}$ (0.5 mg/kg subcutaneous, striped bar) treatment (n=5).

FIGS. 3A-3D show how an exemplary wild-type mature FGF1 sequence (SEQ ID NO: 5) can be mutated to include mutations that increase thermostability of FGF1 (M1, M2 and M3 deletions, SEQ ID NOS: 22, 28, and 40, respectively), which can be combined with FGF1 N-terminal deletions and/or point mutations (SEQ ID NOS: 23, 24, 25, 26, 27, 29, 30, 31, 32, 33, 34, 35, 36, 37, 38, 39, 41, 42, 43, 44, 45, 46, 47, 48, 49, 50 and 51).

FIGS. 4A-4B show additional FGF1 mutant sequences that can be generated from an exemplary wild-type mature FGF1 sequence (SEQ ID NO: 5) to include N-terminal deletions and/or point mutations (SEQ ID NOS: 52, 53, 54, 55, 56, 57, 58, 59, 60, 61, 62, 63, 64, 65, and 66).

FIGS. 5A-5B show additional FGF1 mutant sequences that can be generated from an exemplary wild-type mature FGF1 sequence (SEQ ID NO: 5) to include N-terminal deletions and/or point mutations (SEQ ID NOS: 68, 69, 70, 71, 72, 73, 74, 75, 76, 77, 78, 79, 80, 81, 82, 83, and 84).

FIGS. 6A-6B show FGF21 (SEQ ID NO: 20) and a C-terminal portion of FGF21 (SEQ ID NO: 86) that binds to beta-klotho, and how they can be attached to FGF1 mutants described herein to form FGF1/FGF21 chimeric proteins (SEQ ID NOS: 87, 88, 89, 90, 91, 92, 93, 94, 95, 96, 97, and 98). The FGF1/FGF21 chimeras shown can further include one or more of K12V and N95V FGF1 non mitogenic mutations (or other mutations disclosed herein, such as those listed in Table 1) that have longer glucose lowering duration.

FIGS. 7A-7B show FGF19 (SEQ ID NO: 99) and a C-terminal portion of FGF19 (SEQ ID NO: 100) that binds to beta-klotho, and how they can be attached to FGF1 mutants described herein to form FGF1/FGF19 chimeric proteins (SEQ ID NOS: 101, 102, 103, 104, 105, 106, 107, 108, 109, 110, 111, and 112). The FGF1/FGF19 chimeras shown can further include one or more of K12V and N95V FGF1 non mitogenic mutations that have longer glucose lowering duration.

Figure 8:
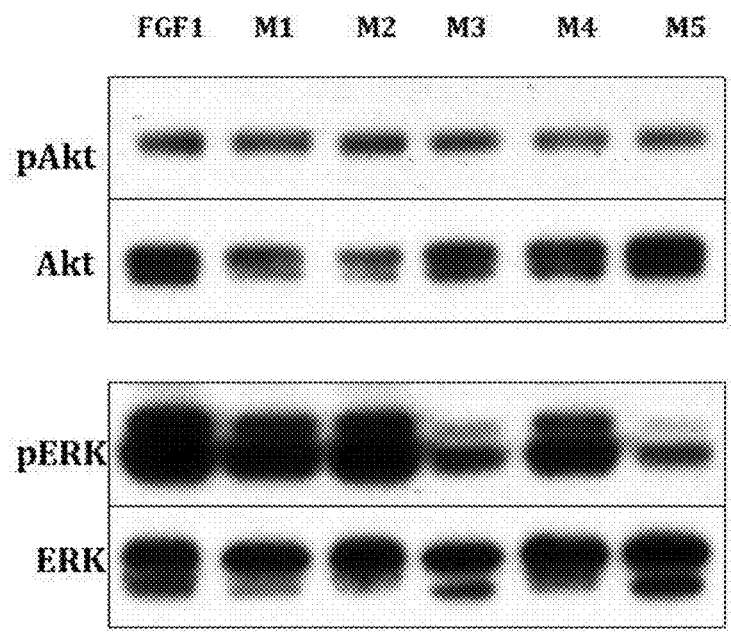

FIG. 8 is a digital image showing the effect of intracellular signaling with M1 thru M5 peptides (SEQ ID NOS: 22, 28, 40, 54 and 212, respectively). HEK293 cells were serum starved and then treated with the indicated peptides at 10 ng/ml concentration for 15 min. Total cell lysates were subject to western blots with indicated antibodies.

Figure 9:
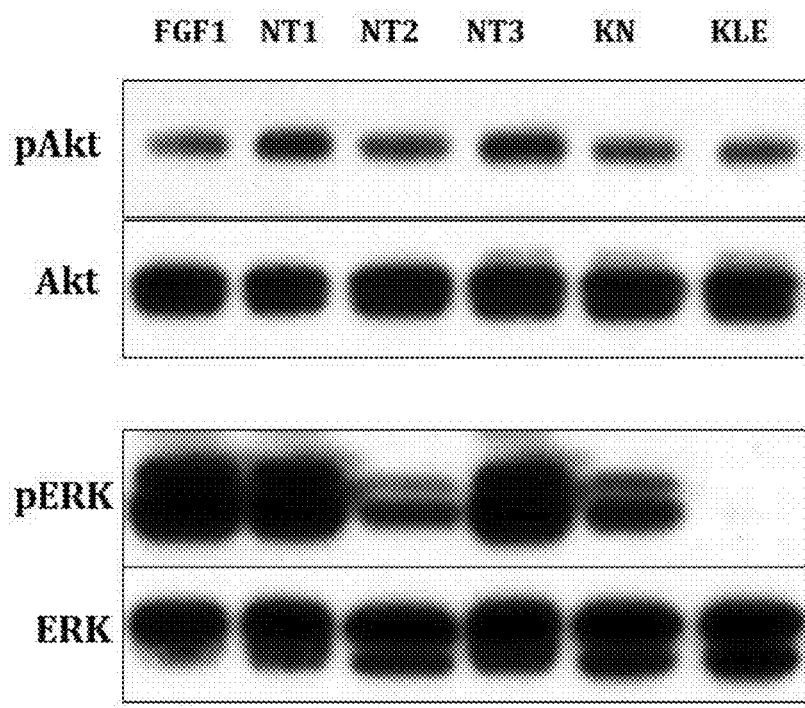

FIG. 9 is a digital image showing peptides NT1 (SEQ ID NO: 7), NT2 (SEQ ID NO: 8), or NT3 (SEQ ID NO: 9) KN (SEQ ID NO: 10), and KLE (SEQ ID NO: 11) and their ability to affect intracellular signaling. HEK293 cells were serum starved and then treated with the indicated peptides at 10 ng/ml concentration for 15 min. Total cell lysates were subject to western blots with indicated antibodies.

Figure 10:
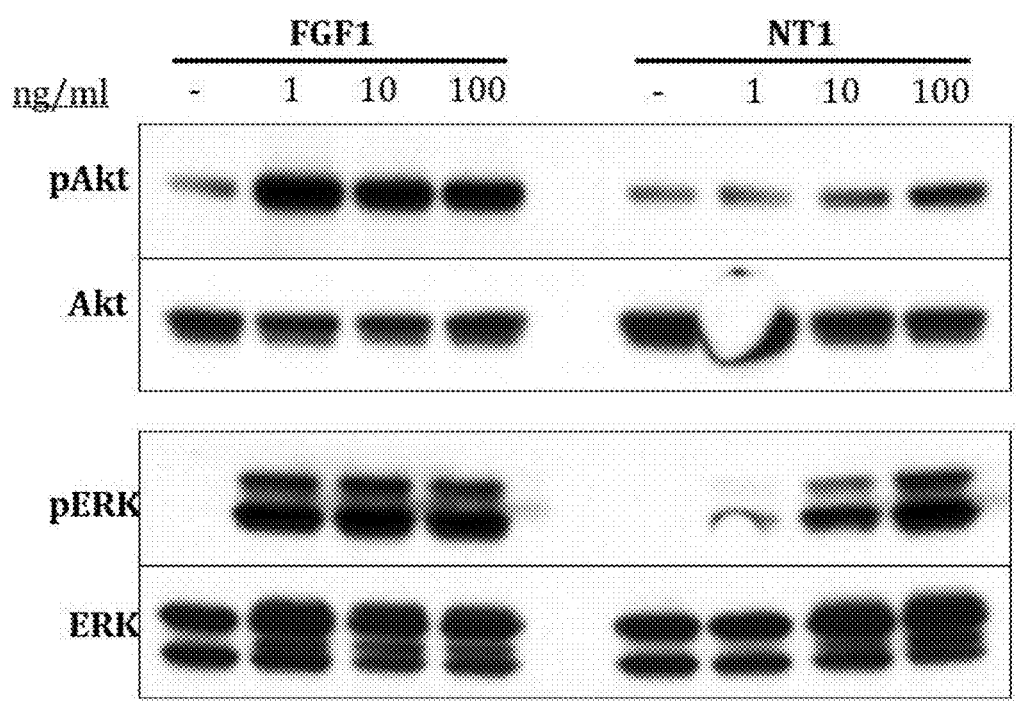

FIG. 10 is a digital image showing peptides FGF1 (SEQ ID NO: 5) and NT1 (SEQ ID NO: 7) and their ability to affect intracellular signaling. HEK293 cells were serum starved and then treated with the indicated peptides at 10 ng/ml concentration for 15 min. Total cell lysates were subject to western blots with indicated antibodies.

FIGS. 11A and 11B are graphs showing the glucose lowering effects for M1, M2, and M3 in ob/ob mice. Mice were 5 mo old C57BL/6J ob/ob on normal chow. The peptides were injected SQ (0.5 mg/kg).

Figure 12:
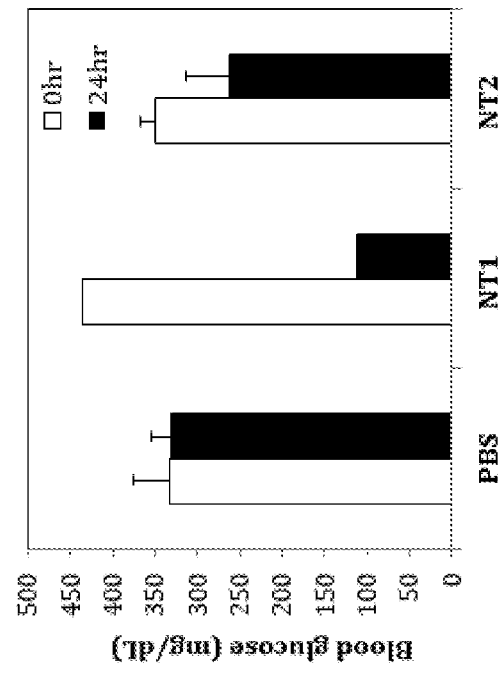

FIG. 12 shows in vivo glucose lowering effects correlate with FGFR mediated signaling. Mice were 5 mo old C57BL/6J ob/ob on normal chow. The peptides NT1 (SEQ ID NO: 7) and NT2 (SEQ ID NO: 8), were injected SQ (0.5 mg/kg).

Figure 13:
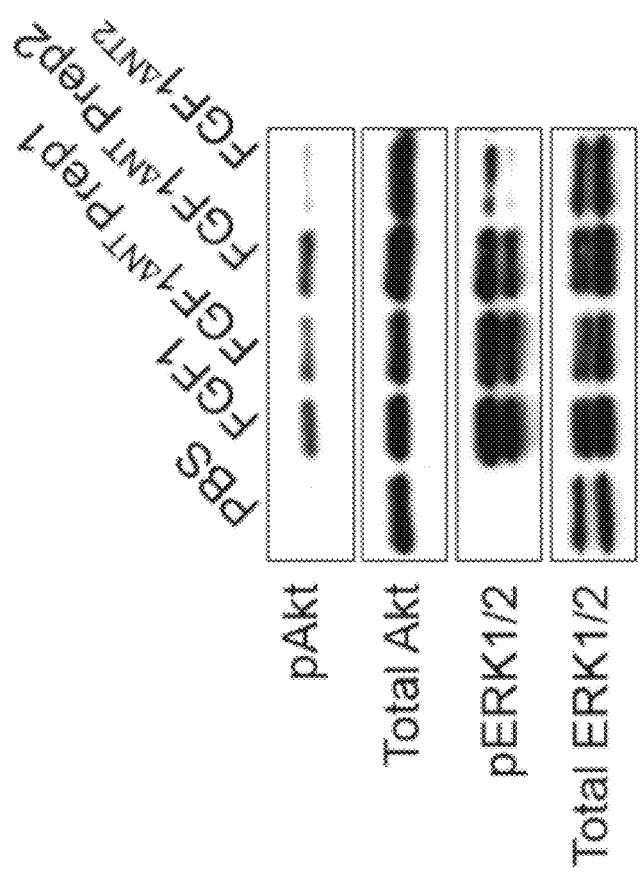

FIG. 13 is a digital image showing that the in vivo glucose lowering effect correlate with FGFR mediated signaling. Serum starved HEK 293 cells were treated with indicated peptides (10 ng/ml) for 15 min and subject to western blot. FGF1$^{\Delta NTPrep1}$ and FGF1$^{\Delta NTPrep2}$ are the same sequence, just independent preparations of the protein.

Figure 14:
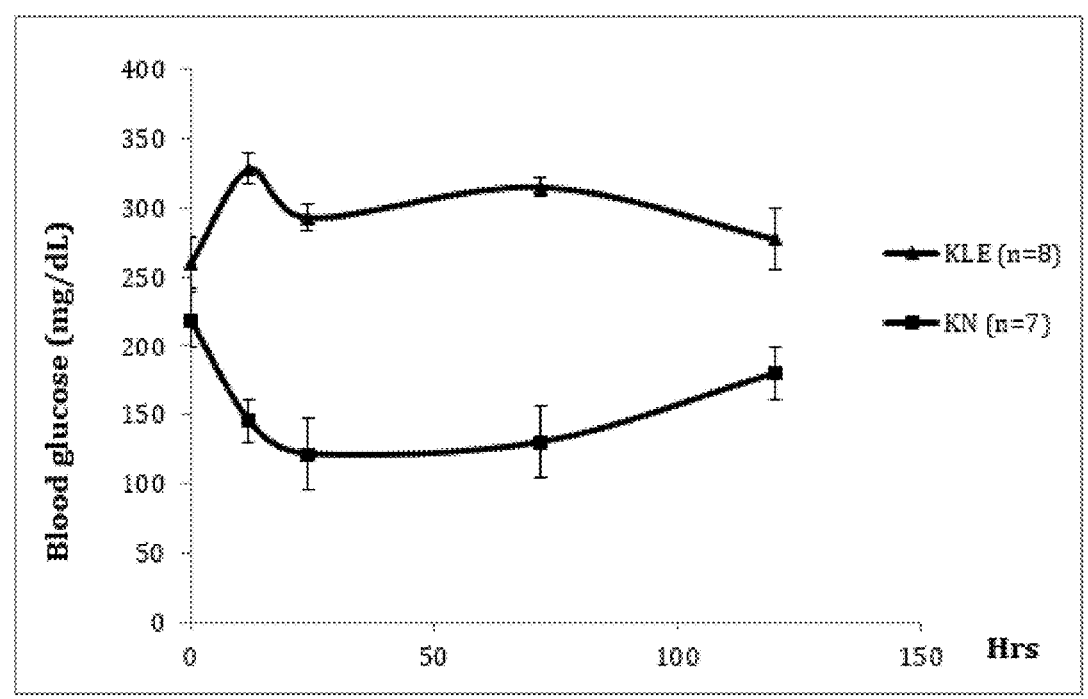

FIG. 14 is a graph showing blood glucose levels 0 to 120 hrs following administration of a single injection of FGF1-KLE (SEQ ID NO: 11) or FGF1-KN (SEQ ID NO: 10). The FGF1-KN mutant retained the ability to lower glucose for 120 hrs while FGF1-KLE fails to lower glucose.

Figures 15A, 15B, 15C:
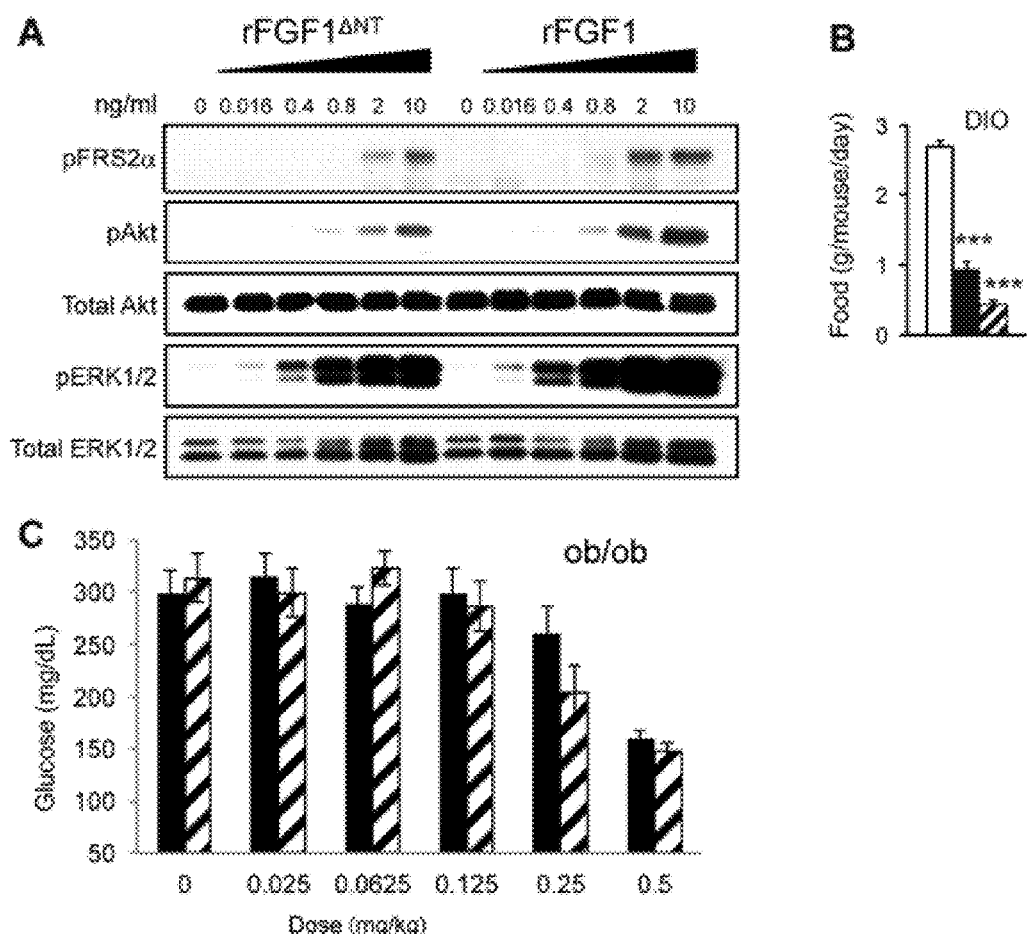
Figure 23:
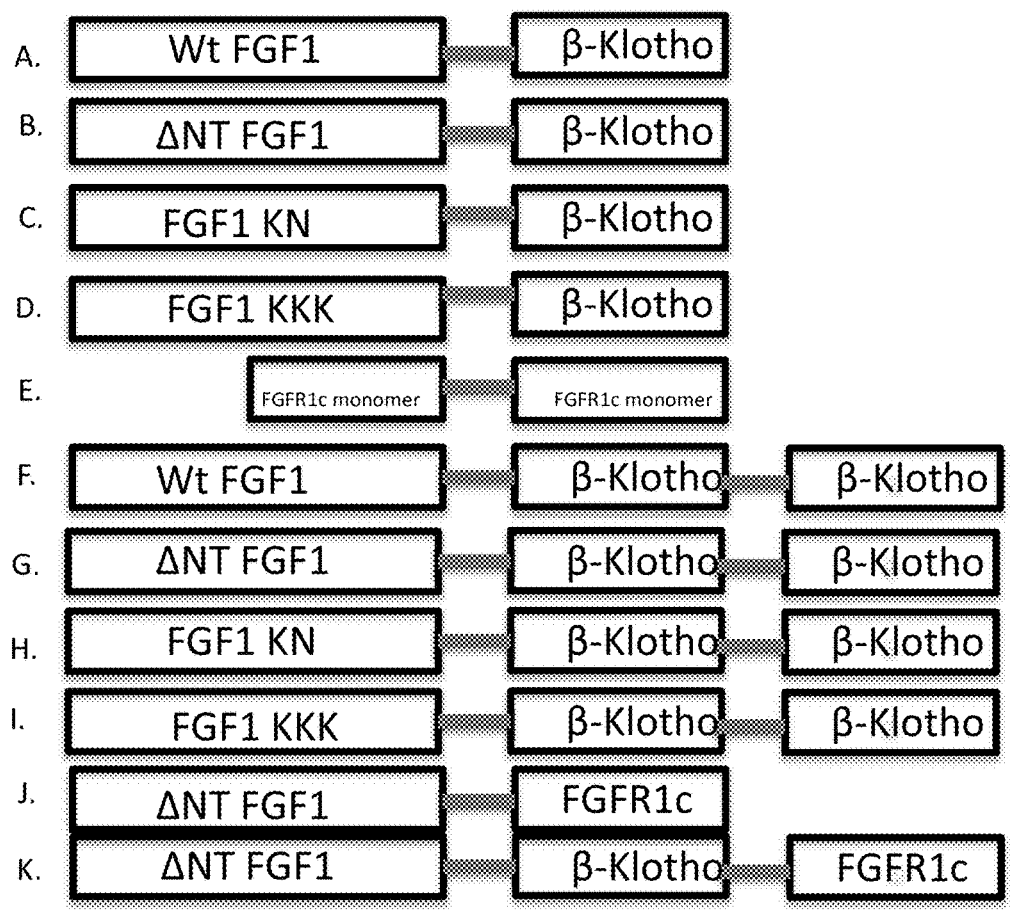
Figure 24:
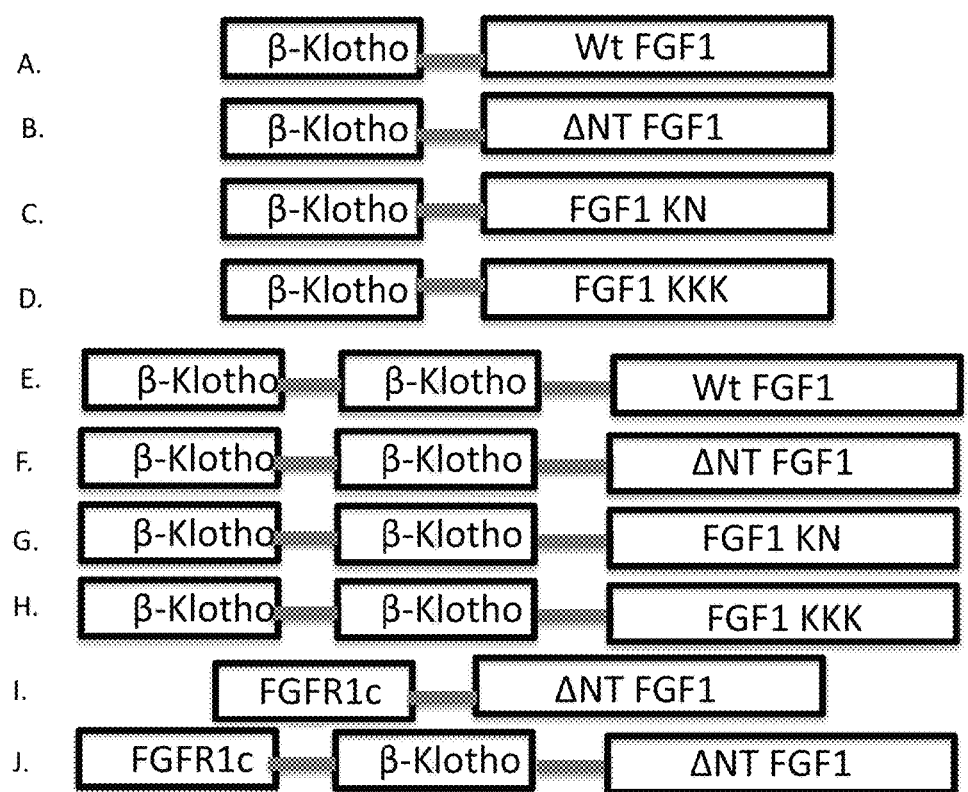
Figure 25:
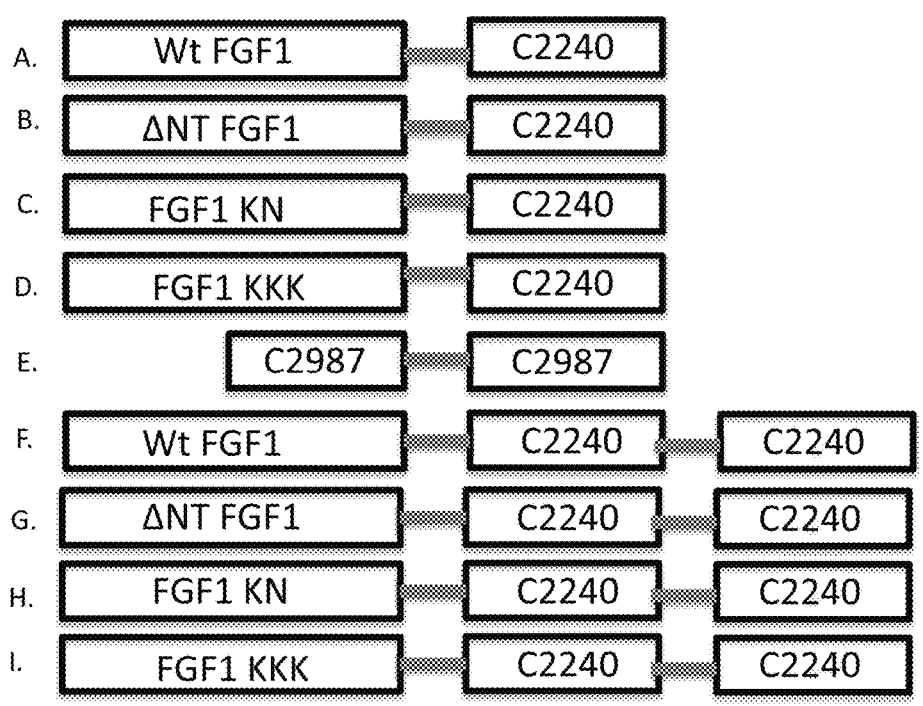

FIG. 15A compares the dose response of downstream FGFR signaling induced by rFGF1 (SEQ ID NO: 5) and NT1 (rFGF1$^{\Delta NT}$, SEQ ID NO: 7). FIG. 15B is the same as FIG. 2C. FIG. 15C compares the dose response of rFGF1 and NT1 in lowering glucose in ob/ob mice. A. Western blot showing intracellular signaling in serum starved HEK293 cells after a 15 min treatment with the indicated concentrations of PBS (vehicle), rFGF1$^{\Delta NT}$, or rFGF1. B. Food intake in DIO mice during 24 hr period after injection of control vehicle (PBS, open bar), rFGF1 (0.5 mg/kg subcutaneous, filled bars), or rFGF$^{\Delta NT}$ (0.5 mg/kg subcutaneous, striped bar, n=5). C. Dose response of glucose lowering effects of subcutaneously delivered rFGF1$^{\Delta NT}$ (striped bars) in comparison to rFGF1 (filled bars) in 12 week old ob/ob mice (n=6-12). ***P<0.005.

FIG. 16 is a bar graph showing blood glucose levels 0 hr, 16 hrs, or 24 hrs following administration of PBS, NT1 (FGF1$^{\Delta NT}$, SEQ ID NO: 7), NT2 (FGF1$^{\Delta NT2}$, SEQ ID NO: 8), or NT3 (FGF1$^{\Delta NT3}$, SEQ ID NO: 9). Note that if the N-terminus is truncated at 14 amino acids, glucose lowering ability is substantially decreased (NT2). Mice were 5 mo old C57BL/6J ob/ob on normal chow. The peptides were injected SQ (0.5 mg/kg).

FIGS. 17A and 17B are bar graphs showing that NT1 (SEQ ID NO: 7) fails to lower blood glucose levels in HFD-fed aP2-Cre; FGFR1 f/f mice (mutant FGFR1KO mice). Blood glucose levels in 8 month old HFD-fed wild-type FGFR1 f/f (control open bars) or adipose-specific FGFR1 knockout (mutant, R1KO, aP2-Cre; FGFR1 f/f, filled bars) mice after NT1 treatment (murine rFGF1$^{\Delta NT}$, 0.5 mg/kg subcutaneous injection, n=5 per group). Values are means±SEM. (A) shows the raw blood glucose levels, (B) shows the data normalized to initial blood glucose as 100%.

FIGS. 18A and 18B are bar graphs showing that mouse rFGF1 (amino acids 1-15 of SEQ ID NO 4) fails to lower blood glucose levels in HFD-fed aP2-Cre; FGFR1 f/f mice (FGFR1 KO, filled bars). Blood glucose levels in 8 month old HFD-fed wild type (FGFR1 f/f, black bars) or adipose-specific FGFR1 knockout (R1 KO, aP2-Cre; FGFR1 f/f, dotted bars) mice after rFGF1 treatment (murine rFGF1, 0.5 mg/kg subcutaneous injection, n–=5 per group). Values are means±SEM. (A) shows the raw blood glucose levels, (B) shows the data normalized to initial blood glucose as 100%.

Murine FGF1 (amino acids 1-15 of SEQ ID NO 4) is ~96% homologous to the human sequence (SEQ ID NO: 5)

FIG. 19 is a bar graph showing that FGF1 mutations K118E (SEQ ID NO: 12) and K118N (SEQ ID NO: 13) fail to lower blood glucose levels in DIO mice. Blood glucose levels in 7 months HFD-fed C57BL/6J mice after PBS (open bar), K118E (filled bar), and K118N (hatched bar) treatment (0.5 mg/kg subcutaneous injection, n=4-8 per group). Values are means±SEM.

FIG. 20 shows a native FGF1 sequence (SEQ ID NO: 5) and eight heparan binding mutant FGF1 KKK analogs (SEQ ID NOS: 113, 114, 115, 116, 117, 118, 119, and 120).

FIGS. 21 and 22 show that FGF1 heparan binding mutant KKK lowers glucose.

FIGS. 23-26 show exemplary arrangements of FGF1 mutant/β-Klotho-binding chimeras and FGFR1c-binding protein dimers. Exemplary sequences are shown in SEQ ID NOS: 172, 173, 174, 175, 176, 177, 178, 179, 180, 181, 182, 183, 184, 185, 186, 187, 188, 189 and 190. Although monomers or dimers of FGFR1c- or β-Klotho-binding proteins are shown, in some examples greater multimers are used, such as trimers, etc. In addition, the FGF1 mutant/β-Klotho-binding chimeras can be made into FGF1 mutant/FGFR1c-binding chimeras by replacing the β-Klotho-binding portion with an FGFR1c-binding portion (e.g., as shown in FIGS. 23J and 24I for ΔNT FGF1). Furthermore, FGFR1c-binding portion(s) can be included in the FGF1 mutant/β-Klotho-binding chimeras (e.g., as shown in FIGS. 23K and 24J for ΔNT FGF1). The sequence of CC2240 is shown in SEQ ID NO: 121 and C2987 in SEQ ID NO: 148.

FIG. 27 shows exemplary FGF1 mutant sequences that include an R35E substitution (SEQ ID NOS: 191-198).

FIG. 28 shows exemplary FGF1 mutant sequences that include an R35V substitution (SEQ ID NOS: 199-206).

FIG. 29 shows exemplary FGF1 mutant sequences (SEQ ID NOS: 207-211). This free cysteine (C117) forms intermolecular disulfide bonds that lead to protein aggregation. The mutation to valine is designed to improve stability, hence it is introduced in combination with other point mutations. KKKR are putative heparin binding residues. KY, KE, KEY, KNY are various combinations of point mutations to residues that interact with the FGF receptors (K=K12, E=E87, Y=Y94, N=N95).

FIGS. 30A-30E show exemplary FGF1 mutant sequences that are mutated to (A) increase stability (SEQ ID NOS: 54, 212-218 and 113), (B) chimeras (SEQ ID NOS: 219-224), (C) increase stability and decrease mitogenicity (SEQ ID NOS: 225-229, (D) increase stability and decrease mitogenicity (SEQ ID NOS: 230-233), and (E) increase stability and decrease mitogenicity (SEQ ID NOS:234-238).

FIG. 31 shows an alignment of FGF1 (SEQ ID NO: 5) and FGF2 (SEQ ID NO: 85), with amino acids that form beta strands in bold, and other relevant residues highlighted and their interaction noted.

FIGS. 32A-32D are graphs showing the affect of FGF1 mutations on blood glucose lowering and feeding effects in vivo. Peptides KN (Salk_004, SEQ ID NO: 10), KKK (Salk_010, SEQ ID NO: 226), FGF1 (SEQ ID NO: 5), KLE (Salk_011, SEQ ID NO: 11), FGF1$^{\Delta NT}$ (NT1) (SEQ ID NO: 7) and FGF1$^{\Delta NTKN}$ (Salk_009, SEQ ID NO: 225) were tested.

Figure 33A:
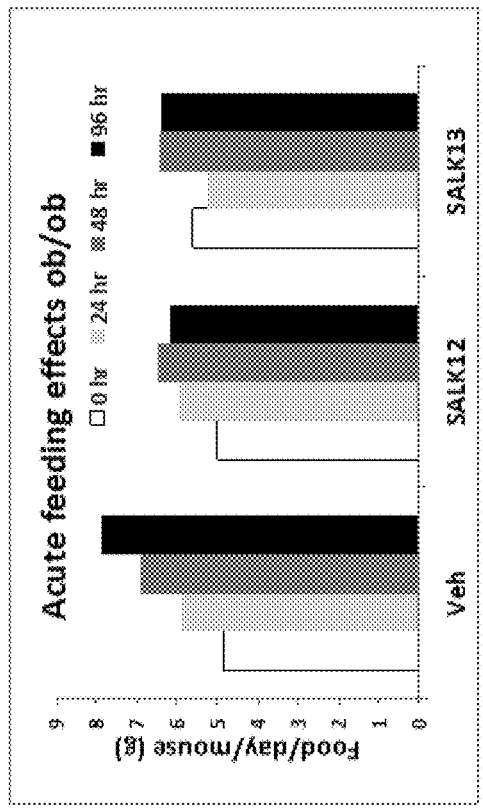
Figure 33B:
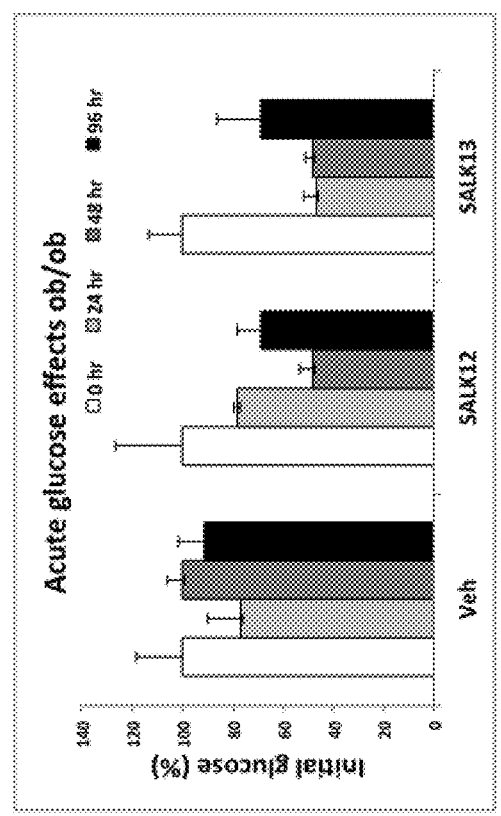

FIGS. 33A-33B are bar graphs showing the affect of FGF1 mutations on (A) blood glucose lowering and (B) feeding effects in vivo. Peptides FGF1 (SEQ ID NO: 5), Salk_013 (SEQ ID NO: 31), and Salk_012 (SEQ ID NO: 79) were tested.

Figure 34B:
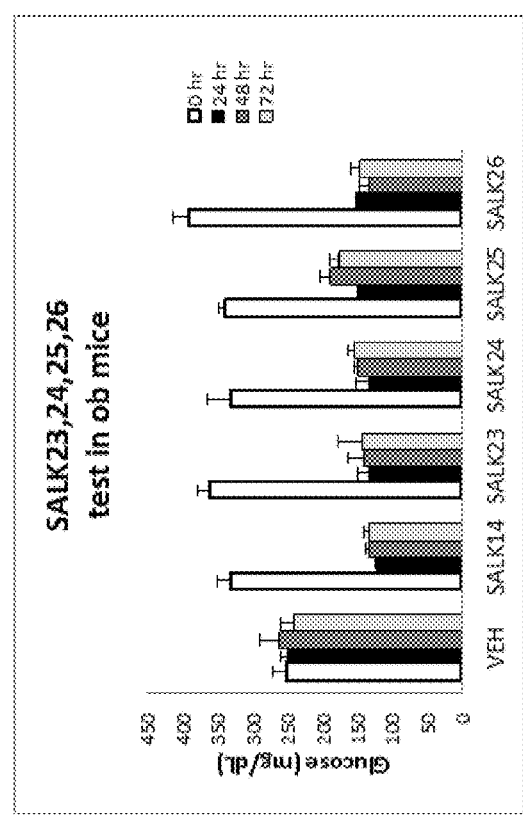
Figure 34A:
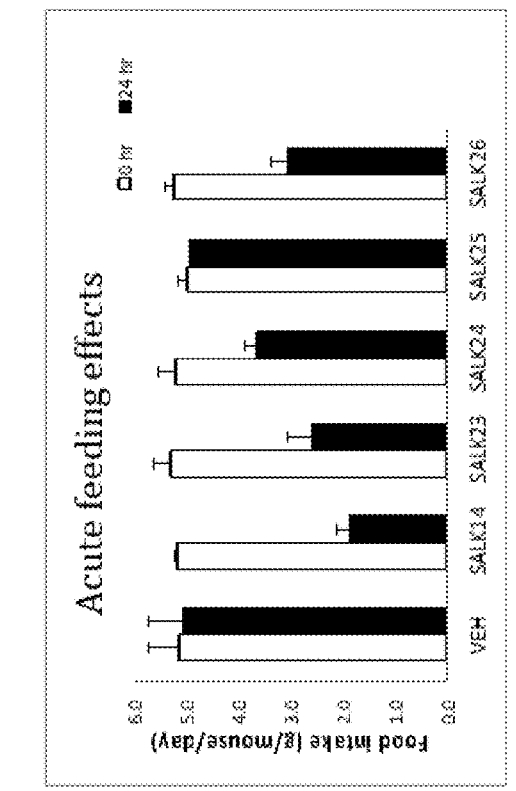

FIGS. 34A-34B are bar graphs showing the affect of FGF1 mutations on (A) blood glucose lowering and (B) feeding effects in vivo. Peptides Salk_014 (SEQ ID NO: 230), Salk_024 (SEQ ID NO: 84), Salk_025 (SEQ ID NO: 208), Salk_026 (SEQ ID NO: 209), and Salk_023 (SEQ ID NO: 38) were tested.

Figures 35A, 35B:
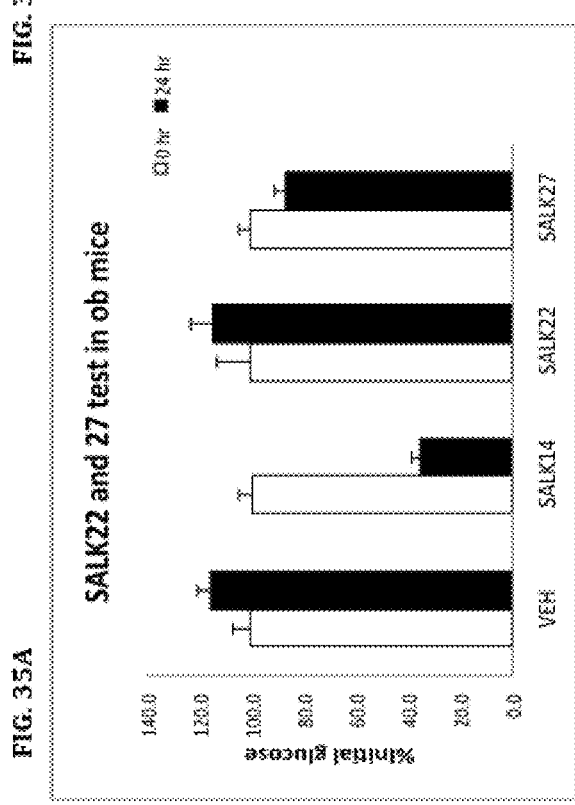

FIGS. 35A-35B are bar graphs showing the affect of FGF1 mutations on (A) blood glucose lowering and (B) feeding effects in vivo. Peptides Salk_014 (SEQ ID NO: 230), Salk_024 (SEQ ID NO: 84), Salk_025 (SEQ ID NO: 208), and Salk_026 (SEQ ID NO: 209), and Salk_023 (SEQ ID NO: 38) were tested.

Figure 36A:
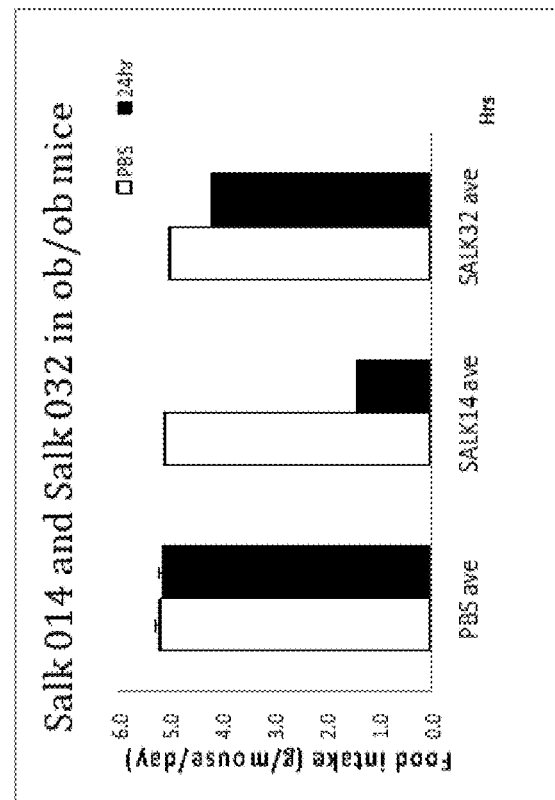
Figure 36B:
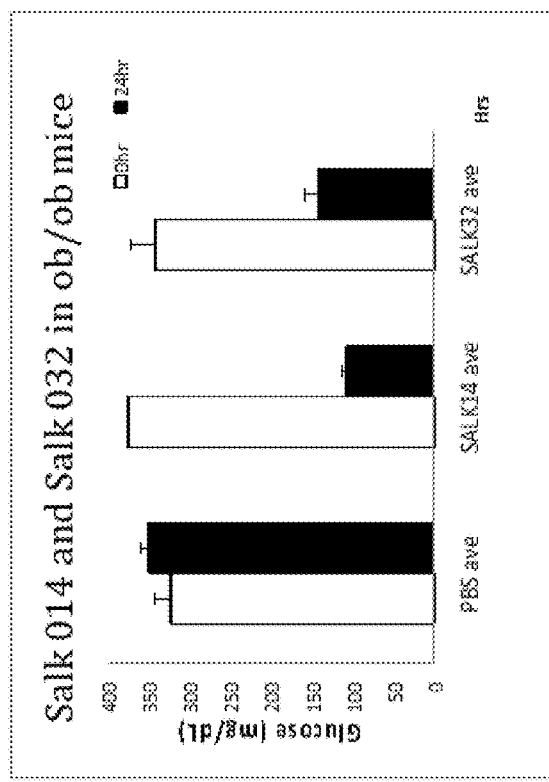

FIGS. 36A-36B are bar graphs showing the affect of FGF1 mutations on (A) blood glucose lowering and (B) feeding effects in vivo. Peptides Salk_014 (SEQ ID NO: 230) and Salk_032 (SEQ ID NO: 215) were tested.

Figure 37A:
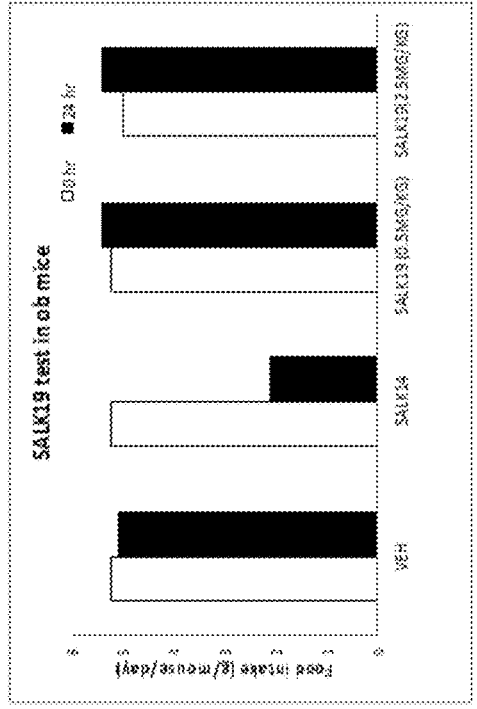
Figure 37B:
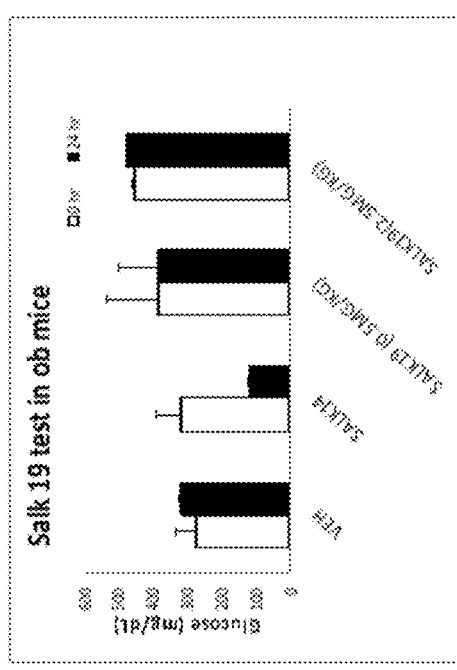

FIGS. 37A-37B are bar graphs showing the affect of a FGF1-FGF19 chimera on (A) blood glucose lowering and (B) feeding effects in vivo. Peptides Salk_014 (SEQ ID NO: 230) and Salk_019 (SEQ ID NO: 224) were tested.

Figure 38:
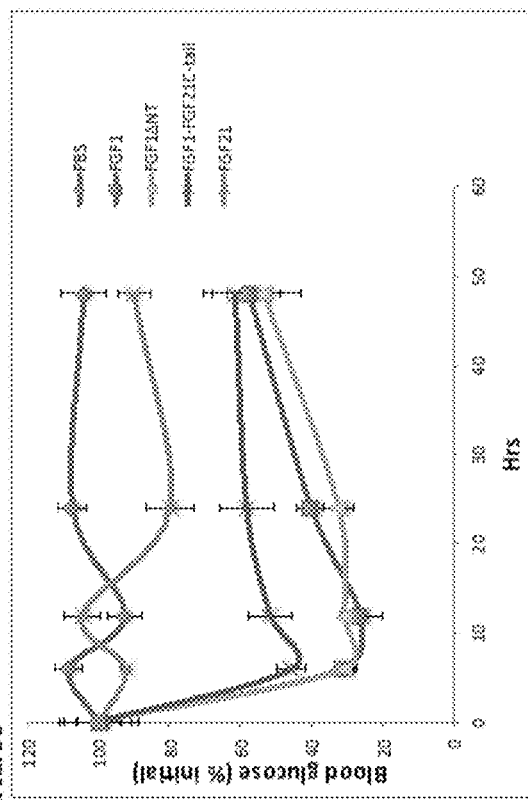

FIG. 38 is a bar graph showing the affect of a FGF1-FGF21 chimera on (A) blood glucose lowering and (B) feeding effects in vivo. Peptides FGF1 (SEQ ID NO: 5), FGF1$^{\Delta NT}$ (SEQ ID NO: 7), FGF21 (SEQ ID 20) and FGF1-FGF21 chimera (SEQ ID NO: 114+SEQ ID NO: 86) were tested.

SEQUENCE LISTING

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NOS: 1 and 2 provide an exemplary human FGF1 nucleic acid and protein sequences, respectively. Source: GenBank Accession Nos: BC032697.1 and AAH32697.1. Heparan binding residues are amino acids 127-129 and 133-134.

SEQ ID NOS: 3 and 4 provide an exemplary mouse FGF1 nucleic acid and protein sequences, respectively. Source: GenBank Accession Nos: BC037601.1 and AAH37601.1.

SEQ ID NO: 5 provides an exemplary mature form of FGF1 (140 aa, sometimes referred to in the art as FGF1 15-154)

SEQ ID NO: 6 provides an exemplary mature form of FGF1 with an N-terminal deletion.

SEQ ID NO: 7 provides an exemplary mature form of FGF1 with an N-terminal deletion (FGF1$^{\Delta NT}$(10-140αα)).

SEQ ID NO: 8 provides an exemplary mature form of FGF1 with an N-terminal deletion (FGF1$^{\Delta NT2}$(14-140αα)).

SEQ ID NO: 9 provides an exemplary mature form of FGF1 with an N-terminal deletion (FGF1$^{\Delta NT3}$(12-140αα)).

SEQ ID NO: 10 provides an exemplary mature form of FGF1 with point mutations (K12V, N95V, wherein numbering refers to SEQ ID NO: 5) to reduce mitogenic activity.

SEQ ID NO: 11 provides an exemplary mature form of FGF1 with point mutations (K12V, L46V, E87V, N95V, P134V, wherein numbering refers to SEQ ID NO: 5) to reduce mitogenic activity.

SEQ ID NOS: 12 and 13 provide exemplary mature forms of FGF1 with mutations in the heparan binding domain (K118N or K118E, respectively, wherein numbering refers to SEQ ID NO: 5). In some examples these sequences further include MFNLPPG at their N-terminus. Such proteins have reduced mitogenicity as compared to wild-type FGF1.

SEQ ID NOS: 14-17 provide exemplary mutated FGF1 nuclear export sequences.

SEQ ID NO: 18 provides a coding sequence for SEQ ID NO: 6.

SEQ ID NOS: 19 and 20 provide an exemplary human FGF21 nucleic acid and protein sequence. Obtained from GenBank Accession Nos. AY359086 and AAQ89444.1. The mature form of FGF21 is about amino acids 21-208.

SEQ ID NO: 21 provides an exemplary N-terminally truncated form of FGF1, wherein the four N-terminal amino acids are from FGF21 (amino acids 40-43 of SEQ ID NO: 20).

SEQ ID NO: 22 provides an exemplary mature form of FGF1 with point mutations (K12V, C117V and P134V wherein numbering refers to SEQ ID NO: 5) to reduce mitogenic activity and increase thermostability. From Xia et al., *PLoS One.* 7(11):e48210, 2012.

SEQ ID NO: 23 (FGF1(1-140αα)M1a) provides an exemplary mature form of FGF1 with point mutations (K12V, N95V, C117V, and P134V wherein numbering refers to SEQ ID NO: 5) to reduce mitogenic activity and increase thermostability.

SEQ ID NO: 24 (FGF1$^{\Delta NT1}$ (1-140αα)M1) provides an exemplary N-terminally truncated form of FGF1 with point mutations (K12V, C117V, and P134V wherein numbering refers to SEQ ID NO: 5) to reduce mitogenic activity and increase thermostability.

SEQ ID NO: 25 (FGF1$^{\Delta NT3}$ (1-140αα)M1a) provides an exemplary N-terminally truncated form of FGF1 with point mutations (K12V, C117V, and P134V wherein numbering refers to SEQ ID NO: 5) to reduce mitogenic activity and increase thermostability.

SEQ ID NO: 26 (FGF1$^{\Delta NT1}$ (1-140αα)M1a) provides an exemplary N-terminally truncated form of FGF1 with point mutations (K12V, N95V, C117V, and P134V wherein numbering refers to SEQ ID NO: 5) to reduce mitogenic activity, and increase thermostability.

SEQ ID NO: 27 (FGF1$^{\Delta NT3}$ (1-140αα)M1a) provides an exemplary N-terminally truncated form of FGF1 with point mutations (K12V, N95V, C117V, and P134V wherein numbering refers to SEQ ID NO: 5) to reduce mitogenic activity, and increase thermostability SEQ ID NO: 28 (FGF1(1-140αα)M2) provides an exemplary mature form of FGF1 with point mutations (L44F, C83T, C117V, and F132W wherein numbering refers to SEQ ID NO: 5) to reduce mitogenic activity and increase thermostability. From Xia et al., *PLoS One.* 7(11):e48210, 2012.

SEQ ID NO: 29 (FGF1(1-140αα)M2a) provides an exemplary mature form of FGF1 with point mutations (L44F, C83T, N95V, C117V, and F132W wherein numbering refers to SEQ ID NO: 5) to reduce mitogenic activity and increase thermostability.

SEQ ID NO: 30 (FGF1(1-140αα)M2b) provides an exemplary mature form of FGF1 with point mutations (K12V, L44F, C83T, C117V, and F132W wherein numbering refers to SEQ ID NO: 5) to reduce mitogenic activity and increase thermostability.

SEQ ID NO: 31 (FGF1(1-140αα)M2c) provides an exemplary mature form of FGF1 with point mutations (K12V, L44F, C83T, N95V, C117V, and F132W wherein numbering refers to SEQ ID NO: 5) to reduce mitogenic activity and increase thermostability.

SEQ ID NO: 32 (FGF1$^{\Delta NT1}$(10-140αα)M2) provides an exemplary N-terminally truncated form of FGF1 with point mutations (L44F, C83T, C117V, and F132W wherein numbering refers to SEQ ID NO: 5) to reduce mitogenic activity and increase thermostability.

SEQ ID NO: 33 (FGF1$^{\Delta NT3}$(12-140αα)M2) provides an exemplary N-terminally truncated form of FGF1 with point mutations (L44F, C83T, C117V, and F132W wherein numbering refers to SEQ ID NO: 5) to reduce mitogenic activity and increase thermostability.

SEQ ID NO: 34 (FGF1$^{\Delta NT1}$(10-140αα)M2a) provides an exemplary N-terminally truncated form of FGF1 with point mutations (L44F, C83T, N95V, C117V, and F132W wherein numbering refers to SEQ ID NO: 5) to reduce mitogenic activity and increase thermostability.

SEQ ID NO: 35 (FGF1$^{\Delta NT3}$(12-140αα)M2a) provides an exemplary N-terminally truncated form of FGF1 with point mutations (L44F, C83T, N95V, C117V, and F132W wherein numbering refers to SEQ ID NO: 5) to reduce mitogenic activity and increase thermostability.

SEQ ID NO: 36 (FGF1$^{\Delta NT1}$(10-140αα)M2b) provides an exemplary N-terminally truncated form of FGF1 with point mutations (K12V, L44F, C83T, C117V, and F132W wherein numbering refers to SEQ ID NO: 5) to reduce mitogenic activity and increase thermostability.

SEQ ID NO: 37 (FGF1$^{\Delta NT3}$(12-140αα)M2b) provides an exemplary N-terminally truncated form of FGF1 with point mutations (K12V, L44F, C83T, C117V, and F132W wherein numbering refers to SEQ ID NO: 5) to reduce mitogenic activity and increase thermostability.

SEQ ID NO: 38 (FGF1$^{\Delta NT1}$(10-140αα)M2c) provides an exemplary N-terminally truncated form of FGF1 with point mutations (K12V, L44F, C83T, N95V, and C117V, F132W wherein numbering refers to SEQ ID NO: 5) to reduce mitogenic activity and increase thermostability.

SEQ ID NO: 39 (FGF1$^{\Delta NT3}$(12-140αα)M2c) provides an exemplary N-terminally truncated form of FGF1 with point mutations (K12V, L44F, C83T, N95V, and C117V, F132W wherein numbering refers to SEQ ID NO: 5) to reduce mitogenic activity and increase thermostability.

SEQ ID NO: 40 (FGF1(1-140αα)M3) provides an exemplary mature form of FGF1 with mutations (L44F, M67I, L73V, V109L, L111I, C117V, A103G, R119G Δ104-106, and Δ120-122, wherein numbering refers to SEQ ID NO: 5) to reduce mitogenic activity and increase thermostability. From Xia et al., *PLoS One.* 7(11):e48210, 2012.

SEQ ID NO: 41 (FGF1(1-140αα)M3a) provides an exemplary mature form of FGF1 with mutations (K12V, L44F, M67I, L73V, V109L, L111I, C117V, A103G, R119G, Δ104-106, and Δ120-122 wherein numbering refers to SEQ ID NO: 5) to reduce mitogenic activity and increase thermostability.

SEQ ID NO: 42 (FGF1(1-140αα)M3b) provides an exemplary mature form of FGF1 with mutations (K12V, L44F, M67I, L73V, N95V, V109L, L111I, C117V, A103G, R119G, Δ104-106, and Δ120-122 wherein numbering refers to SEQ ID NO: 5) to reduce mitogenic activity and increase thermostability.

SEQ ID NO: 43 (FGF1(1-140αα)M3c) provides an exemplary mature form of FGF1 with mutations (K12V, L44F, M67I, L73V, N95V, V109L, L111I, C117V, A103G, R119G, Δ104-106, and Δ120-122 wherein numbering refers to SEQ ID NO: 5) to reduce mitogenic activity and increase thermostability.

SEQ ID NO: 44 (FGF1$^{\Delta NT1}$ (1-140αα)M3) provides an exemplary N-terminally truncated form of FGF1 with mutations (L44F, M67I, L73V, V109L, L111I, C117V, A103G, R119G, Δ104-106, and Δ120-122 wherein numbering refers to SEQ ID NO: 5) to reduce mitogenic activity and increase thermostability.

SEQ ID NO: 45 (FGF1$^{\Delta NT3}$ (1-140αα)M3) provides an exemplary N-terminally truncated form of FGF1 with mutations (L44F, M67I, L73V, V109L, L111I, C117V, A103G, R119G, Δ104-106, and Δ120-122 wherein numbering refers to SEQ ID NO: 5) to reduce mitogenic activity and increase thermostability.

SEQ ID NO: 46 (FGF1$^{\Delta NT1}$ (1-140αα)M3a) provides an exemplary N-terminally truncated form of FGF1 with mutations (K12V, L44F, M67I, L73V, V109L, L111I, C117V, A103G, R119G, Δ104-106, and Δ120-122 wherein numbering refers to SEQ ID NO: 5) to reduce mitogenic activity and increase thermostability.

SEQ ID NO: 47 (FGF1$^{\Delta NT3}$ (1-140αα)M3a) provides an exemplary N-terminally truncated form of FGF1 with mutations (K12V, L44F, M67I, L73V, V109L, L111I, C117V, A103G, R119G, Δ104-106, and Δ120-122 wherein numbering refers to SEQ ID NO: 5) to reduce mitogenic activity and increase thermostability.

SEQ ID NO: 48 (FGF1$^{\Delta NT1}$ (1-140αα)M3b) provides an exemplary N-terminally truncated form of FGF1 with mutations (L44F, M67I, L73V, N95V, V109L, L111I, C117V, A103G, R119G, Δ104-106, and Δ120-122 wherein numbering refers to SEQ ID NO: 5) to reduce mitogenic activity and increase thermostability.

SEQ ID NO: 49 (FGF1$^{\Delta NT3}$ (1-140αα)M3b) provides an exemplary N-terminally truncated form of FGF1 with mutations (L44F, M67I, L73V, N95V, V109L, L111I, C117V, A103G, R119G, Δ104-106, and Δ120-122 wherein numbering refers to SEQ ID NO: 5) to reduce mitogenic activity and increase thermostability.

SEQ ID NO: 50 (FGF1$^{\Delta NT1}$ (1-140αα)M3c) provides an exemplary N-terminally truncated form of FGF1 with mutations (K12V, L44F, M67I, L73V, N95V, V109L, L111I, C117V, A103G, R119G, Δ104-106, and Δ120-122 wherein numbering refers to SEQ ID NO: 5) to reduce mitogenic activity and increase thermostability.

SEQ ID NO: 51 (FGF1$^{\Delta NT3}$ (1-140αα)M3c) provides an exemplary N-terminally truncated form of FGF1 with point mutations (K12V, L44F, M67I, L73V, N95V, V109L, L111I, C117V, A103G, R119G, Δ104-106, and Δ120-122 wherein numbering refers to SEQ ID NO: 5) to reduce mitogenic activity and increase thermostability.

SEQ ID NO: 52 (FGF1 (1-140αα) provides an exemplary mature form of FGF1 with point mutations (K12V, N95V, and K118N wherein numbering refers to SEQ ID NO: 5).

SEQ ID NO: 53 (FGF1 (1-140αα) provides an exemplary mature form of FGF1 with point mutations (K12V, N95, and K118E wherein numbering refers to SEQ ID NO: 5).

SEQ ID NO: 54 FGF1 (1-140αα) K12V, N95V, C117V provides an exemplary mature form of FGF1 with point mutations (K12V, N95V, and C117V wherein numbering refers to SEQ ID NO: 5).

SEQ ID NO: 55 (FGF1 (1-140αα) provides an exemplary mature form of FGF1 with point mutations (K12V, N95V, C117V, and K118N wherein numbering refers to SEQ ID NO: 5).

SEQ ID NO: 56 (FGF1 (1-140αα) provides an exemplary mature form of FGF1 with point mutations (K12V, N95V, C117V, and K118E wherein numbering refers to SEQ ID NO: 5).

SEQ ID NO: 57 (FGF1$^{\Delta NT}$ (10-140αα) provides an exemplary N-terminally truncated FGF1 with point mutations (K12V and N95V, wherein numbering refers to SEQ ID NO: 5).

SEQ ID NO: 58 (FGF1$^{\Delta NT2}$ (12-140αα) provides an exemplary N-terminally truncated FGF1 with point mutations (K12V, and N95V, wherein numbering refers to SEQ ID NO: 5).

SEQ ID NO: 59 (FGF1$^{\Delta NT}$ (10-140αα) provides an exemplary N-terminally truncated FGF1 with a point mutation (K12V, wherein numbering refers to SEQ ID NO: 5).

SEQ ID NO: 60 (FGF1$^{\Delta NT2}$ (12-140αα) provides an exemplary N-terminally truncated FGF1 with a point mutation (K12V, wherein numbering refers to SEQ ID NO: 5).

SEQ ID NO: 61 (FGF1$^{\Delta NT}$ (10-140αα) provides an exemplary N-terminally truncated FGF1 with a point mutation (N95V, wherein numbering refers to SEQ ID NO: 5).

SEQ ID NO: 62 (FGF1$^{\Delta NT2}$ (12-140αα) provides an exemplary N-terminally truncated FGF1 with a point mutation (N95V, wherein numbering refers to SEQ ID NO: 5).

SEQ ID NO: 63 (FGF1$^{\Delta NT}$ (10-140αα) provides an exemplary N-terminally truncated FGF1 with point mutations (K12V, N95V, and K118N, wherein numbering refers to SEQ ID NO: 5).

SEQ ID NO: 64 (FGF1$^{\Delta NT2}$ (12-140αα) provides an exemplary N-terminally truncated FGF1 with point mutations (K12V, N95V, and K118E, wherein numbering refers to SEQ ID NO: 5).

SEQ ID NO: 65 (FGF1$^{\Delta NT}$ (10-140αα) provides an exemplary N-terminally truncated FGF1 with a point mutation (K118N, wherein numbering refers to SEQ ID NO: 5).

SEQ ID NO: 66 (FGF1$^{\Delta NT2}$ (12-140αα) provides an exemplary N-terminally truncated FGF1 with a point mutation (K118E, wherein numbering refers to SEQ ID NO: 5).

SEQ ID NO: 67 (FGF1 (1-140αα) provides an exemplary mature form of FGF1 with point mutations (K9T and N10T wherein numbering refers to SEQ ID NO: 5).

SEQ ID NO: 68 (FGF1 (1-140αα) provides an exemplary mature form of FGF1 with point mutations (K9T, N10T, and N95V, wherein numbering refers to SEQ ID NO: 5).

SEQ ID NO: 69 (FGF1 (1-140αα) provides an exemplary mature form of FGF1 with point mutations (K9T, N10T, and K118N, wherein numbering refers to SEQ ID NO: 5).

SEQ ID NO: 70 (FGF1 (1-140αα) provides an exemplary mature form of FGF1 with a mutant NLS sequence.

SEQ ID NO: 71 (FGF1$^{\Delta NT}$ (1-140αα) provides an exemplary N-terminally truncated form of FGF1 with point mutations (Q40P and S47I, wherein numbering refers to SEQ ID NO: 5).

SEQ ID NO: 72 (FGF1$^{\Delta NT3}$ (1-140αα) provides an exemplary N-terminally truncated form of FGF1 with point mutations (Q40P and S47I, wherein numbering refers to SEQ ID NO: 5).

SEQ ID NO: 73 (FGF1 (1-140αα) provides an exemplary mature form of FGF1 with point mutations (K12V, Q40P, S47I, and N95V wherein numbering refers to SEQ ID NO: 5).

SEQ ID NO: 74 FGF1$^{\Delta NT}$ (1-140αα) provides an exemplary N-terminally truncated form of FGF1 with point mutations (K12V, Q40P, S47I, and N95V, wherein numbering refers to SEQ ID NO: 5).

SEQ ID NO: 75 (FGF1$^{\Delta NT3}$ (1-140αα) provides an exemplary N-terminally truncated form of FGF1 with point mutations (K12V, Q40P, S47I, and N95V, wherein numbering refers to SEQ ID NO: 5).

SEQ ID NO: 76 (FGF1$^{\Delta NT}$ (1-140αα) provides an exemplary N-terminally truncated form of FGF1 with point mutations (Q40P, S47I, and H93G, wherein numbering refers to SEQ ID NO: 5).

SEQ ID NO: 77 (FGF1$^{\Delta NT3}$ (1-140αα) provides an exemplary N-terminally truncated form of FGF1 with point mutations (Q40P, S47I, and H93G, wherein numbering refers to SEQ ID NO: 5).

SEQ ID NO: 78 (FGF1 (1-140αα) provides an exemplary mature form of FGF1 with point mutations (K12V, Q40P, S47I, H93G, and N95V, wherein numbering refers to SEQ ID NO: 5).

SEQ ID NO: 79 (FGF1$^{\Delta NT}$ (1-140αα) provides an exemplary N-terminally truncated form of FGF1 with point mutations (K12V, Q40P, S47I, H93G, and N95V, wherein numbering refers to SEQ ID NO: 5).

SEQ ID NO: 80 (FGF1$^{\Delta NT3}$ (1-140αα) provides an exemplary N-terminally truncated form of FGF1 with point mutations (K12V, Q40P, S47I, H93G, and N95V, wherein numbering refers to SEQ ID NO: 5).

SEQ ID NO: 81 (FGF1$^{\Delta NT}$ (1-140αα) provides an exemplary N-terminally truncated form of FGF1 with point mutations (C117P and K118V, wherein numbering refers to SEQ ID NO: 5).

SEQ ID NO: 82 (FGF1$^{\Delta NT3}$ (1-140αα) provides an exemplary N-terminally truncated form of FGF1 with point mutations (C117P and K118V, wherein numbering refers to SEQ ID NO: 5).

SEQ ID NO: 83 (FGF1 (1-140αα) provides an exemplary mature form of FGF1 with point mutations (K12V, N95V, C117P, and K118V, wherein numbering refers to SEQ ID NO: 5).

SEQ ID NO: 84 (FGF1 (1-140αα) provides an exemplary mature form of FGF1 with a point mutation (R35E, wherein numbering refers to SEQ ID NO: 5). Such an antagonist can be used to treat hypoglycemia or type I diabetes.

SEQ ID NO: 85 provides an exemplary portion of an FGF2 protein sequence.

SEQ ID NO: 86 provides an exemplary C-terminal FGF21 protein sequence (P$^{168}$-S$^{209}$hFGF21$^{C\text{-}tail}$). This fragment can be attached at its N-terminus to the C-terminus of any FGF1 mutant provided herein to generate an FGF1/FGF21 chimera.

SEQ ID NO: 87 provides an exemplary FGF1/FGF21 chimera, which contains the K12V and N95V FGF1 point mutations. The FGF21 portion is amino acids 136 to 177.

SEQ ID NO: 88 provides an exemplary FGF1/FGF21 chimera (FGF1$^{\Delta NT}$-FGF21$^{C\text{-}tail}$). The FGF21 portion is amino acids 127 to 168.

SEQ ID NO: 89 provides an exemplary FGF1/FGF21 chimera (FGF1$^{\Delta NT3}$-FGF21$^{C\text{-}tail}$) The FGF21 portion is amino acids 125 to 166.

SEQ ID NO: 90 provides an exemplary FGF1/FGF21 chimera (M1-FGF21$^{C\text{-}tail}$). The FGF1 portion includes point mutations K$^{12}$V, C$^{117}$V, and P$^{134}$V. The FGF21 portion is amino acids 127 to 168.

SEQ ID NO: 91 provides an exemplary FGF1/FGF21 chimera (M1-FGF21$^{C\text{-}tail}$). The FGF1 portion includes point mutations K$^{12}$V, C$^{117}$V, and P$^{134}$V. The FGF21 portion is amino acids 125 to 166.

SEQ ID NO: 92 provides an exemplary FGF1/FGF21 chimera (M1-FGF21$^{C\text{-}tail}$). The FGF1 portion includes point mutations K$^{12}$V, C$^{117}$V, and P$^{134}$V. The FGF21 portion is amino acids 136 to 177.

SEQ ID NO: 93 provides an exemplary FGF1/FGF21 chimera (M2-FGF21$^{C\text{-}tail}$). The FGF1 portion includes point mutations L$^{44}$F, C$^{83}$T, C$^{117}$V, and F$^{132}$W. The FGF21 portion is amino acids 127 to 168.

SEQ ID NO: 94 provides an exemplary FGF1/FGF21 chimera (M2-FGF21$^{C\text{-}tail}$). The FGF1 portion includes point mutations L$^{44}$F, C$^{83}$T, C$^{117}$V, and F$^{132}$W. The FGF21 portion is amino acids 125 to 166.

SEQ ID NO: 95 provides an exemplary FGF1/FGF21 chimera (M2-FGF21$^{C\text{-}tail}$). The FGF1 portion includes point mutations L$^{44}$F, C$^{83}$T, C$^{117}$V, and F$^{132}$W. The FGF21 portion is amino acids 136 to 177.

SEQ ID NO: 96 provides an exemplary FGF1/FGF21 chimera (M3-FGF21$^{C\text{-}tail}$). The FGF1 portion includes mutations L$^{44}$F, M$^{67}$I, L$^{73}$V, V$^{109}$L, L$^{111}$I, C$^{117}$V, A$^{103}$G, R$^{119}$G, Δ$^{104\text{-}106}$ and Δ$^{120\text{-}122}$. The FGF21 portion is amino acids 121 to 162.

SEQ ID NO: 97 provides an exemplary FGF1/FGF21 chimera (M3-FGF21$^{C\text{-}tail}$). The FGF1 portion includes mutations L$^{44}$F, M$^{67}$I, L$^{73}$V, V$^{109}$L, L$^{111}$I, C$^{117}$V, A$^{103}$G, R$^{119}$G, Δ$^{104\text{-}106}$ and Δ$^{120\text{-}122}$. The FGF21 portion is amino acids 119 to 160.

SEQ ID NO: 98 provides an exemplary FGF1/FGF21 chimera (M3-FGF21$^{C\text{-}tail}$). The FGF1 portion includes mutations L$^{44}$F, M$^{67}$I, L$^{73}$V, V$^{109}$L, L$^{111}$I, C$^{117}$V, A$^{103}$G, R$^{119}$G, Δ$^{104\text{-}106}$ and Δ$^{120\text{-}122}$. The FGF21 portion is amino acids 130 to 171.

SEQ ID NO: 99 provides an exemplary FGF19 protein sequence. The mature form of FGF19 is amino acids 23 to 216.

SEQ ID NO: 100 provides an exemplary C-terminal FGF19 protein sequence (L$^{169}$-K$^{216}$ h FGF19C-tail). This fragment can be attached at its N-terminus to the C-terminus of any FGF1 mutant provided herein to generate an FGF1/FGF19 chimera.

SEQ ID NO: 101 provides an exemplary FGF1/FGF19 chimera. The FGF1 portion includes point mutations K$^{12}$V, and N$^{95}$V. The FGF19 portion is amino acids 136 to 183.

SEQ ID NO: 102 provides an exemplary FGF1/FGF19 chimera (FGF1$^{\Delta NT}$-FGF19$^{C\text{-}tail}$). The FGF19 portion is amino acids 127 to 174.

SEQ ID NO: 103 provides an exemplary FGF1/FGF19 chimera (FGF1$^{\Delta NT3}$-FGF19$^{C\text{-}tail}$). The FGF19 portion is amino acids 125 to 172.

SEQ ID NO: 104 provides an exemplary FGF1/FGF19 chimera (M1-FGF19$^{C\text{-}tail}$). The FGF1 portion includes point mutations K$^{12}$V, C$^{117}$V, and P$^{134}$V. The FGF19 portion is amino acids 136 to 183.

SEQ ID NO: 105 provides an exemplary FGF1/FGF19 chimera (M1-FGF19$^{C\text{-}tail}$). The FGF1 portion includes point mutations K$^{12}$V, C$^{117}$V, and P$^{134}$V. The FGF19 portion is amino acids 127 to 174.

SEQ ID NO: 106 provides an exemplary FGF1/FGF19 chimera (M1-FGF19$^{C\text{-}tail}$). The FGF1 portion includes point mutations K$^{12}$V, C$^{117}$V, and P$^{134}$V. The FGF19 portion is amino acids 125 to 172.

SEQ ID NO: 107 provides an exemplary FGF1/FGF19 chimera (M2-FGF19$^{C\text{-}tail}$). The FGF1 portion includes point mutations L$^{44}$F, C$^{83}$T, C$^{117}$V, and F$^{132}$W. The FGF19 portion is amino acids 136 to 183.

SEQ ID NO: 108 provides an exemplary FGF1/FGF19 chimera (M2-FGF19$^{C\text{-}tail}$). The FGF1 portion includes point mutations L$^{44}$F, C$^{83}$T, C$^{117}$V, and F$^{132}$W. The FGF19 portion is amino acids 127 to 174.

SEQ ID NO: 109 provides an exemplary FGF1/FGF19 chimera (M2-FGF19$^{C\text{-}tail}$). The FGF1 portion includes point mutations L$^{44}$F, C$^{83}$T, C$^{117}$V, and F$^{132}$W. The FGF19 portion is amino acids 125 to 172.

SEQ ID NO: 110 provides an exemplary FGF1/FGF19 chimera (M3-FGF19$^{C\text{-}tail}$). The FGF1 portion includes mutations L$^{44}$F, M$^{67}$I, L$^{73}$V, V$^{109}$L, L$^{111}$I, C$^{117}$V, A$^{103}$G, R$^{119}$G, Δ$^{104\text{-}106}$ and Δ$^{120\text{-}122}$. The FGF19 portion is amino acids 130 to 177.

SEQ ID NO: 111 provides an exemplary FGF1/FGF19 chimera (M3-FGF19$^{C\text{-}tail}$). The FGF1 portion includes mutations L$^{44}$F, M$^{67}$I, L$^{73}$V, V$^{109}$L, L$^{111}$I, C$^{117}$V, A$^{103}$G, R$^{119}$G, Δ$^{104\text{-}106}$ and Δ$^{120\text{-}122}$. The FGF19 portion is amino acids 121 to 168.

SEQ ID NO: 112 provides an exemplary FGF1/FGF19 chimera (M3-FGF19$^{C\text{-}tail}$). The FGF1 portion includes mutations L$^{44}$F, M$^{67}$I, L$^{73}$V, V$^{109}$L, L$^{111}$I, C$^{117}$V, A$^{103}$G, R$^{119}$G, Δ$^{104\text{-}106}$ and Δ$^{120\text{-}122}$. The FGF19 portion is amino acids 119 to 166.

SEQ ID NO: 113 provides an exemplary FGF1 heparan binding KKK mutant analog K112D, K113Q, K118V (wherein numbering refers to SEQ ID NO: 5).

SEQ ID NO: 114 provides an exemplary FGF1 heparan binding KKK mutant analog with mutations K112D, K113Q, C117V, K118V (wherein numbering refers to SEQ ID NO: 5).

SEQ ID NO: 115 provides an exemplary FGF1 heparan binding KKK mutant analog with an N-terminal truncation and mutations K112D, K113Q, K118V (wherein numbering refers to SEQ ID NO: 5).

SEQ ID NO: 116 provides an exemplary FGF1 heparan binding KKK mutant analog with an N-terminal truncation and mutations K112D, K113Q, K118V (wherein numbering refers to SEQ ID NO: 5).

SEQ ID NO: 117 provides an exemplary FGF1 heparan binding KKK mutant analog with an N-terminal truncation and mutations K112D, K113Q, C117V, K118V (wherein numbering refers to SEQ ID NO: 5).

SEQ ID NO: 118 provides an exemplary FGF1 heparan binding KKK mutant analog with an N-terminal truncation and mutations K112D, K113Q, C117V, K118V (wherein numbering refers to SEQ ID NO: 5).

SEQ ID NO: 119 provides an exemplary FGF1 heparan binding KKK mutant analog with mutations K12V, N95V, K112D, K113Q, K118V (wherein numbering refers to SEQ ID NO: 5).

SEQ ID NO: 120 provides an exemplary FGF1 heparan binding KKK mutant analog with mutations K12V, N95V, K112D, K113Q, C117V, K118V (wherein numbering refers to SEQ ID NO: 5).

SEQ ID NO: 121 provides an exemplary β-Klotho binding protein dimer sequence (C2240) that can be attached at its N- or C-terminus directly or indirectly to any of the FGF1 mutants provided herein to generate a chimeric protein.

SEQ ID NO: 122 provides an exemplary β-Klotho binding protein sequence that can be attached at its N- or C-terminus directly or indirectly to any of the FGF1 mutants provided herein to generate a chimeric protein.

SEQ ID NOs: 123-130 provide exemplary β-Klotho binding protein sequences that can be attached at their N- or C-termini directly or indirectly to any of the FGF1 mutants provided herein to generate a chimeric protein. In addition, each can be linked to SEQ ID NO: 122 via a linker and then the resulting chimera attached at its N- or C-terminus directly or indirectly to any of the FGF1 mutants provided herein to generate a chimeric protein.

SEQ ID NOs: 131-140 provide exemplary β-Klotho binding protein sequences that can be attached at their N- or C-termini directly or indirectly to any of the FGF1 mutants provided herein to generate a chimeric protein.

SEQ ID NO: 141 provides an exemplary β-Klotho binding protein sequence that can be attached at its N- or C-terminus directly or indirectly to any of the FGF1 mutants provided herein to generate a chimeric protein. In addition, it can be linked to any of SEQ ID NOS: 142-143 via a linker and then the resulting chimera attached at its N- or C-terminus directly or indirectly to any of the FGF1 mutants provided herein to generate a chimeric protein.

SEQ ID NO: 142 provides an exemplary β-Klotho binding protein sequence that can be attached at its N- or C-terminus directly or indirectly to any of the FGF1 mutants provided herein to generate a chimeric protein. In addition, it can be linked to SEQ ID NO: 141 via a linker and then the resulting chimera attached at its N- or C-terminus directly or indirectly to any of the FGF1 mutants provided herein to generate a chimeric protein.

SEQ ID NO: 143 provides an exemplary β-Klotho binding protein sequence that can be attached at its N- or C-terminus directly or indirectly to any of the FGF1 mutants provided herein to generate a chimeric protein. In addition, it can be linked to SEQ ID NO: 141 via a linker and then the resulting chimera attached at its N- or C-terminus directly or indirectly to any of the FGF1 mutants provided herein to generate a chimeric protein.

SEQ ID NOs: 144-146 provide exemplary β-Klotho binding protein sequences that can be attached at their N- or C-termini directly or indirectly to any of the FGF1 mutants provided herein to generate a chimeric protein.

SEQ ID NO: 147 provides an exemplary FGFR1c binding protein sequence that can be attached at its N- or C-terminus directly or indirectly to any of the FGF1 mutants provided herein to generate a chimeric protein. In addition, it can be linked to itself one or more times to generate an FGFR1c multimer, such as a dimer or a trimer.

SEQ ID NO: 148 (C2987) provides an exemplary FGFR1c binding protein sequence that can be attached at its N- or C-terminus directly or indirectly to any of the FGF1 mutants provided herein to generate a chimeric protein. In addition, it can be linked to itself one or more times to generate an FGFR1c multimer, such as a dimer or a trimer.

SEQ ID NOS: 149-167 provide exemplary FGFR1c binding protein sequences that can be attached at their N- or C-termini directly or indirectly to any of the FGF1 mutants provided herein to generate a chimeric protein. In addition, each can be linked to itself one or more times to generate an FGFR1c multimer, such as a dimer or a trimer, or combinations of these binding proteins can be linked together.

SEQ ID NOs: 168-171 provide exemplary β-Klotho-FGFR1c binding protein sequences that can be attached at their N- or C-termini directly or indirectly to any of the FGF1 mutants provided herein to generate a chimeric protein.

SEQ ID NO: 172 provides an exemplary WT-FGF1/β-Klotho binding protein chimera sequence (C2240). This is represented in FIG. 25A.

SEQ ID NO: 173 provides an exemplary ΔNT FGF1/β-Klotho binding protein chimera sequence (C2240). This is represented in FIG. 25B.

SEQ ID NO: 174 provides an exemplary FGF1 KN/β-Klotho binding protein chimera sequence (C2240). This is represented in FIG. 25C.

SEQ ID NO: 175 provides an exemplary FGF1KKK/β-Klotho binding protein chimera sequence (C2240). This is represented in FIG. 25D.

SEQ ID NO: 176 provides an exemplary WT-FGF1/β-Klotho binding protein chimera sequence (C2240) with two β-Klotho binding protein portions. This is represented in FIG. 25F.

SEQ ID NO: 177 provides an exemplary ΔNT FGF1/β-Klotho binding protein chimera sequence (C2240) with two β-Klotho binding protein portions. This is represented in FIG. 25G.

SEQ ID NO: 178 provides an exemplary FGF1 KN/β-Klotho binding protein chimera sequence (C2240) with two β-Klotho binding protein portions. This is represented in FIG. 25H.

SEQ ID NO: 179 provides an exemplary FGF1 KKK/β-Klotho binding protein chimera sequence (C2240) with two β-Klotho binding protein portions. This is represented in FIG. 25I.

SEQ ID NO: 180 provides an exemplary WT-FGF1/β-Klotho binding protein chimera sequence (C2240). This is represented in FIG. 26A.

SEQ ID NO: 181 provides an exemplary ΔNT FGF1/β-Klotho binding protein chimera sequence (C2240). This is represented in FIG. 26B.

SEQ ID NO: 182 provides an exemplary FGF1 KN/β-Klotho binding protein chimera sequence (C2240). This is represented in FIG. 26C.

SEQ ID NO: 183 provides an exemplary FGF1KKK/β-Klotho binding protein chimera sequence (C2240). This is represented in FIG. 26D.

SEQ ID NO: 184 provides an exemplary WT-FGF1/β-Klotho binding protein chimera sequence (C2240) with two β-Klotho binding protein portions. This is represented in FIG. 26F.

SEQ ID NO: 185 provides an exemplary dNT FGF1/β-Klotho binding protein chimera sequence (C2240) with two β-Klotho binding protein portions. This is represented in FIG. 26F.

SEQ ID NO: 186 provides an exemplary FGF1 KN/β-Klotho binding protein chimera sequence (C2240) with two β-Klotho binding protein portions. This is represented in FIG. 25H.

SEQ ID NO: 187 provides an exemplary FGF1KKK/β-Klotho binding protein chimera sequence (C2240) with two β-Klotho binding protein portions. This is represented in FIG. 25I.

SEQ ID NO: 188 provides an exemplary ΔNT FGF1/FGFR1c-binding protein chimera sequence (C2987). This is represented in FIG. 23J.

SEQ ID NO: 189 provides an exemplary ΔNT FGF1/FGFR1c-binding protein chimera sequence (C2987). This is represented in FIG. 24I.

SEQ ID NO: 190 provides an exemplary FGFR1c dimer chimera sequence (C2987). This is represented in FIG. 25E.

SEQ ID NO: 191 (FGF1(1-140αα) R35E, C117V) provides an exemplary mature form of FGF1 with mutations (R35E and C117V, wherein numbering refers to SEQ ID NO: 5) to reduce mitogenic activity and increase thermostability.

SEQ ID NO: 192 (FGF1(1-140αα) R35E, C117V, KKK) provides an exemplary mature form of FGF1 with mutations (R35E, K112D, K113Q, C117V, and K118V wherein numbering refers to SEQ ID NO: 5) to reduce mitogenic activity and increase thermostability.

SEQ ID NO: 193 (FGF1(1-140αα) R35E, C117V K12V, N95V) provides an exemplary mature form of FGF1 with mutations (K12V, R35E, N95V, and C117V wherein numbering refers to SEQ ID NO: 5) to reduce mitogenic activity and increase thermostability.

SEQ ID NO: 194 ($FGF1^{\Delta NT1}$ (10-140αα) R35E, C117V) provides an exemplary N-terminally truncated form of FGF1 with mutations (R35E and C117V, wherein numbering refers to SEQ ID NO: 5) to reduce mitogenic activity and increase thermostability.

SEQ ID NO: 195 ($FGF1^{\Delta NTKN}$ KKK (10-140αα)) provides an exemplary N-terminally truncated form of FGF1 with mutations (K112D, K113Q, K118V, K12V, N95V, C117V, and R35E, wherein numbering refers to SEQ ID NO: 5) to reduce mitogenic activity and increase thermostability.

SEQ ID NO: 196 (FGF1 KKK (KN) (1-140αα)) provides an exemplary mature form of FGF1 with mutations (K112D, K113Q, K118V, K12V, N95V, C117V, and R35E, wherein numbering refers to SEQ ID NO: 5) to reduce mitogenic activity and increase thermostability.

SEQ ID NO: 197 ($FGF1^{\Delta NT1}$ (10-140αα) M2KN) provides an exemplary N-terminally truncated form of FGF1 with mutations (K12V, L44F, R35E, C83T, N95V, C117V, and F132W, wherein numbering refers to SEQ ID NO: 5) to reduce mitogenic activity and increase thermostability.

SEQ ID NO: 198 ($FGF1^{\Delta NT1}$ (10-140αα) M2KNKKK) provides an exemplary N-terminally truncated form of FGF1 with mutations (K12V, L44F, R35E, C83T, N95V, C117V, K112D, K113Q, K118V, and F132W, wherein numbering refers to SEQ ID NO: 5) to reduce mitogenic activity and increase thermostability.

SEQ ID NO: 199 (FGF1(1-140αα) R35V, C117V) provides an exemplary mature form of FGF1 with mutations (R35V and C117V, wherein numbering refers to SEQ ID NO: 5) to reduce mitogenic activity and increase thermostability.

SEQ ID NO: 200 (FGF1(1-140αα) R35V, C117V, KKK) provides an exemplary mature form of FGF1 with mutations (R35V, K112D, K113Q, C117V, and K118V wherein numbering refers to SEQ ID NO: 5) to reduce mitogenic activity and increase thermostability.

SEQ ID NO: 201 (FGF1(1-140αα) K12V, R35V, N95V, C117V) provides an exemplary mature form of FGF1 with mutations (K12V, R35V, N95V, and C117V wherein numbering refers to SEQ ID NO: 5) to reduce mitogenic activity and increase thermostability.

SEQ ID NO: 202 ($FGF1^{\Delta NT1}$ (10-140αα) R35V, C117V) provides an exemplary N-terminally truncated form of FGF1 with mutations (R35V and C117V, wherein numbering refers to SEQ ID NO: 5) to reduce mitogenic activity and increase thermostability.

SEQ ID NO: 203 ($FGF1^{\Delta NTKN}$ KKK (10-140αα)) provides an exemplary N-terminally truncated form of FGF1 with mutations (K112D, K113Q, K118V K12V, N95V, C117V, and R35V, wherein numbering refers to SEQ ID NO: 5) to reduce mitogenic activity and increase thermostability.

SEQ ID NO: 204 (FGF1 KKK (KN) (1-140αα)) provides an exemplary mature form of FGF1 with mutations (K112D, K113Q, K118V, K12V, N95V, C117V, and R35V, wherein numbering refers to SEQ ID NO: 5) to reduce mitogenic activity and increase thermostability.

SEQ ID NO: 205 ($FGF1^{\Delta NT1}$ (10-140αα)M2KN) provides an exemplary N-terminally truncated form of FGF1 with mutations (K12V, L44F, R35V, C83T, N95V, C117V, and F132W, wherein numbering refers to SEQ ID NO: 5) to reduce mitogenic activity and increase thermostability.

SEQ ID NO: 206 ($FGF1^{\Delta NT1}$ (10-140αα) M2KNKKK) provides an exemplary N-terminally truncated form of FGF1 with mutations (K12V, L44F, R35V, C83T, N95V, C117V, K112D, K113Q, K118V, and F132W, wherein numbering refers to SEQ ID NO: 5) to reduce mitogenic activity and increase thermostability.

SEQ ID NO: 207 (FGF1-140αα) C117V, KKKR provides an exemplary mature form of FGF1 with mutations (K112D, K113Q, C117V, K118V, R119V, wherein numbering refers to SEQ ID NO: 5) to reduce mitogenic activity and increase thermostability.

SEQ ID NO: 208 (FGF1-140αα) C117V, KY provides an exemplary mature form of FGF1 with mutations (K12V, Y94V, C117V, wherein numbering refers to SEQ ID NO: 5) to reduce mitogenic activity and increase thermostability.

SEQ ID NO: 209 (FGF1-140αα) C117V, KE provides an exemplary mature form of FGF1 with mutations (K12V, E87V, C117V, wherein numbering refers to SEQ ID NO: 5) to reduce mitogenic activity and increase thermostability.

SEQ ID NO: 210 (FGF1-140αα) C117V, KEY provides an exemplary mature form of FGF1 with mutations (K12V, E87V, Y94V, C117V, wherein numbering refers to SEQ ID NO: 5) to reduce mitogenic activity and increase thermostability.

SEQ ID NO: 211 (FGF1-140αα) C117V, KNY provides an exemplary mature form of FGF1 with mutations (K12V, Y94V, N95V, C117V, wherein numbering refers to SEQ ID NO: 5) to reduce mitogenic activity and increase thermostability.

SEQ ID NO: 212 (FGF1-140αα) K12V, L46V, E87V, N95V, C117V, P134V provides an exemplary mature form of FGF1 with point mutations (K12V, L46V, E87V, N95V, C117V, P134V, wherein numbering refers to SEQ ID NO: 5) to reduce mitogenic activity and increase thermostability.

SEQ ID NO: 213 (FGF1-140αα) C117V, K118V provides an exemplary mature form of FGF1 with mutations (C117V and K118V, wherein numbering refers to SEQ ID NO: 5) to reduce mitogenic activity and increase thermostability.

SEQ ID NO: 214 (FGF$^{\Delta NT1C}$ 10-140αα) K12V, N95V, C83T, C117V provides an exemplary N-terminally truncated form of FGF1 with mutations (K12V, N95V, C83T, and C117V, wherein numbering refers to SEQ ID NO: 5) to reduce mitogenic activity and increase thermostability.

SEQ ID NO: 215 (FGF$^{\Delta NT1C}$ 10-140αα) K12V, N95V, C16T, C83S, C117A, provides an exemplary N-terminally truncated form of FGF1 with mutations (K12V, N95V, C16T, C83S, and C117A, wherein numbering refers to SEQ ID NO: 5) to reduce mitogenic activity and increase thermostability.

SEQ ID NO: 216 (FGF$^{\Delta NT1}$ 10-140αα) H21Y, L44F, H102Y, F108Y, C117V, provides an exemplary N-terminally truncated form of FGF1 with mutations (H21Y, L44F, H102Y, F108Y, and C117V, wherein numbering refers to SEQ ID NO: 5) to reduce mitogenic activity and increase thermostability.

SEQ ID NO: 217 (FGF$^{\Delta NT1}$ 10-140αα) K12V, H21Y, L44F, N95V, H102Y, F108Y, C117V, provides an exemplary N-terminally truncated form of FGF1 with mutations (K12V, H21Y, L44F, N95V, H102Y, F108Y, and C117V, wherein numbering refers to SEQ ID NO: 5) to reduce mitogenic activity and increase thermostability.

SEQ ID NO: 218 (FGF1 1-140αα) K12V, H21Y, L44F, N95V, H102Y, F108Y, C117V, provides an exemplary mature form of FGF1 with mutations (K12V, H21Y, L44F, N95V, H102Y, F108Y, and C117V, wherein numbering refers to SEQ ID NO: 5) to reduce mitogenic activity and increase thermostability.

SEQ ID NO: 219 (wtFGF1ΔHBS-FGF21C-tail) provides an exemplary mature form of FGF1 with mutations that reduce the functionality of the heparin binding site to affect serum half-life and receptor affinity (K112D, K113Q, K118V, wherein numbering refers to SEQ ID NO: 5) fused to a portion of FGF21 at the C-terminus (amino acids 136 to 177) to generate a reagent that combines the metabolic benefits of a β klotho-dependent agonist (FGF21) and β klotho-independent agonist (FGF1).

SEQ ID NO: 220 (wtFGF1ΔHBS-FGF19C-tail) provides an exemplary mature form of FGF1 with mutations that reduce the functionality of the heparin binding site to affect serum half-life and receptor affinity (K112D, K113Q, K118V, wherein numbering refers to SEQ ID NO: 5) fused to a portion of FGF19 at the C-terminus (amino acids 138 to 183) to generate a reagent that combines the metabolic benefits of a β klotho-dependent agonist (FGF19) and β klotho-independent agonist (FGF1).

SEQ ID NO: 221 provides an exemplary N-terminally truncated form of FGF1, wherein the 16 N-terminal amino acids are from FGF21 (amino acids 28-43 of SEQ ID NO: 20), and the sequence includes a C117V mutation.

SEQ ID NO: 222 provides an exemplary N-terminally truncated form of FGF1, wherein the four N-terminal amino acids are from FGF21 (amino acids 40-43 of SEQ ID NO: 20), and the sequence includes a C117V mutation.

SEQ ID NO: 223 (wtFGF1-FGF21C-tail) provides an exemplary mature form of FGF1 fused to a portion of FGF21 at the C-terminus (amino acids 136 to 177) to generate a reagent that combines the metabolic benefits of a β klotho-dependent agonist (FGF21) and β klotho-independent agonist (FGF1).

SEQ ID NO: 224 (wtFGF1-FGF19C-tail) provides an exemplary mature form of FGF1 fused to a portion of FGF19 at the C-terminus (amino acids 138 to 183) to generate a reagent that combines the metabolic benefits of a β klotho-dependent agonist (FGF19) and β klotho-independent agonist (FGF1).

SEQ ID NO: 225 (FGF$^{\Delta NT1C}$ 10-140αα) K12V, N95V, C117V, provides an exemplary N-terminally truncated form of FGF1 with mutations (K12V, N95V, and C117V, wherein numbering refers to SEQ ID NO: 5) to reduce the mitogenicity and increase the stability of FGF1.

SEQ ID NO: 226 (FGF1 KKK 1-140αα) K112D, K113Q, K118V, provides an exemplary mature form of FGF1 with mutations (K112D, K113Q, and K118V, wherein numbering refers to SEQ ID NO: 5) to reduce the mitogenicity and increase the stability of FGF1.

SEQ ID NO: 227 (FGF1 1-140αα) K12V, Q40P, S47I, H93G, N95V, provides an exemplary mature form of FGF1 with mutations (K12V, Q40P, S47I, H93G, and N95V, wherein numbering refers to SEQ ID NO: 5) to reduce the mitogenicity and increase the thermal stability of FGF1.

SEQ ID NO: 228 (FGF$^{\Delta NT}$ 10-140αα) K12V, Q40P, S47I, H93G, N95V provides an exemplary N-terminally truncated form of FGF1 with mutations (K12V, Q40P, S47I, H93G, and N95V, wherein numbering refers to SEQ ID NO: 5) to reduce the mitogenicity and increase the thermal stability of FGF1.

SEQ ID NO: 229 (FGF1 1-140αα) M2KN K12V, L44F, C83T, N95V, C117V, F132W provides an exemplary mature form of FGF1 with mutations (K12V, L44F, C83T, N95V, C117V, and F132W, wherein numbering refers to SEQ ID NO: 5) to reduce the mitogenicity without increasing the thermal stability of FGF1.

SEQ ID NO: 230 (FGF1 1-140αα) C117V provides an exemplary mature form of FGF1 with mutation (C117V, wherein numbering refers to SEQ ID NO: 5) to improve the stability of FGF1 by eliminating a free cysteine the can form disulfide bridged aggregated protein.

SEQ ID NO: 231 (FGF1 1-140αα))KKK(KN) K112D, K113Q, K118V, K12V, N95V, C117V provides an exemplary mature form of FGF1 with mutations (K112D, K113Q, K118V, K12V, N95V, and C117V, wherein numbering refers to SEQ ID NO: 5) to reduce mitogenicity and heparan binding, and decrease the potential for protein aggregation of FGF1.

SEQ ID NO: 232 (FGF1 10-140αα) M2KN K12V, L44F, C83T, N95V, C117V, F132W, provides an exemplary N-terminally truncated form of FGF1 with mutations (K12V, L44F, C83T, N95V, C117V, and F132W, wherein numbering refers to SEQ ID NO: 5) to reduce mitogenicity and decrease the potential for protein aggregation of FGF1, without affecting the thermal stability.

SEQ ID NO: 233 (FGF1 1-140αα) R35E, C117V, provides an exemplary mature form of FGF1 with mutations (R35E and C117V, wherein numbering refers to SEQ ID NO: 5) to manipulate the receptor binding affinity/specificity and decrease the potential for protein aggregation of FGF1.

SEQ ID NO: 234 (FGF1 1-140αα) KY K12V, Y94V, C117V, provides an exemplary mature form of FGF1 with mutations (K12V, Y94V, and C117V, wherein numbering refers to SEQ ID NO: 5) to manipulate the receptor binding affinity/specificity and decrease the potential for protein aggregation of FGF1.

SEQ ID NO: 235 (FGF1 1-140αα) KE K12V, E87V, C117V, provides an exemplary mature form of FGF1 with mutations (K12V, E87V, and C117V, wherein numbering refers to SEQ ID NO: 5) to manipulate the receptor binding affinity/specificity and decrease the potential for protein aggregation of FGF1

SEQ ID NO: 236 (FGF1 1-140αα) KKKR K112D, K113Q, C117V, K118V, R119V provides an exemplary mature form of FGF1 with mutations (K112D, K113Q, C117V, K118V, and R119V, wherein numbering refers to SEQ ID NO: 5) to reduce the heparan binding affinity/specificity and decrease the potential for protein aggregation of FGF1.

SEQ ID NO: 237 (FGF1 1-140αα) KN R35E, K12V, N95V, C117V provides an exemplary mature form of FGF1 with mutations (R35E, K12V, N95V, and C117V, wherein numbering refers to SEQ ID NO: 5) to manipulate the receptor binding affinity/specificity and decrease the potential for protein aggregation of FGF1.

SEQ ID NO: 238 (FGF1 10-140αα) KN R35E, C117V provides an exemplary N-terminally truncated form of FGF1 with mutations (R35E and C117V wherein numbering refers to SEQ ID NO: 5) to manipulate the receptor binding affinity/specificity and decrease the potential for protein aggregation of FGF1.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Oct. 21, 2013. All references and GenBank® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Administration: To provide or give a subject an agent, such as a mutated FGF1 protein disclosed herein, by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Beta-Klotho binding domain or protein: A peptide sequence that binds selectively to β-Klotho (such as human β-Klotho, OMIM 61135, GenBank® Accession No. NP_783864.1), but not to other proteins. β-Klotho is a cofactor for FGF21 activity. Such a binding domain can include one or more monomers (wherein the monomers can be the same or different β-Klotho binding proteins), thereby generating a multimer (such as a dimer). In specific examples, such a domain/protein is not an antibody. Exemplary β-Klotho binding proteins can be found in SEQ ID NOS: 121, 122, 123, 124, 125, 126, 127, 128, 129, 130, 131, 132, 133, 134, 135, 136, 137, 138, 139, 140, 141, 142, 143, 144, 145 146, and 168-171 as well as U.S. Pat. No. 8,372,952, U.S. Publication No. 2013/0197191, and Smith et al., PLoS One 8:e61432, 2013, all herein incorporated by reference.

A β-Klotho binding protein "specifically binds" to β-Klotho when the dissociation constant ($K_D$) is at least about $1\times10^{-7}$ M, at least about $1.5\times10^{-7}$, at least about $2\times10^{-7}$, at least about $2.5\times10^{-7}$, at least about $3\times10^{-7}$, at least about at least about $5\times10^{-7}$ M, at least about $1\times10^{-8}$ M, at least about $5\times10^{-8}$, at least about $1\times10^{-9}$, at least about $5\times10^{-9}$, at least about $1\times10^{-10}$, or at least about $5\times10^{-10}$ M. In one embodiment, $K_D$ is measured by a radiolabeled antigen binding assay (RIA) performed with the β-Klotho binding protein and β-Klotho. In another example, $K_D$ is measured using an ELISA assay.

C-terminal portion: A region of a protein sequence that includes a contiguous stretch of amino acids that begins at or near the C-terminal residue of the protein. A C-terminal portion of the protein can be defined by a contiguous stretch of amino acids (e.g., a number of amino acid residues).

Chimeric protein: A protein that includes at least a portion of the sequence of a full-length first protein (e.g., FGF1) and at least a portion of the sequence of a full-length second protein (e.g., FGF19, FGF21, β-Klotho-binding protein, or FGF1Rc-binding protein), where the first and second proteins are different. A chimeric polypeptide also encompasses polypeptides that include two or more non-contiguous portions derived from the same polypeptide. The two different peptides can be joined directly or indirectly, for example using a linker.

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and in some examples diagnosed by demonstrating any one of:

a. Fasting plasma glucose level≥7.0 mmol/l (126 mg/dl);
b. Plasma glucose≥11.1 mmol/l (200 mg/dL) two hours after a 75 g oral glucose load as in a glucose tolerance test;
c. Symptoms of hyperglycemia and casual plasma glucose≥11.1 mmol/l (200 mg/dl);
d. Glycated hemoglobin (Hb A1C)≥6.5%

Effective amount or Therapeutically effective amount: The amount of agent, such as a mutated FGF1 protein (or nucleic acid encoding such) disclosed herein, that is an amount sufficient to prevent, treat (including prophylaxis), reduce and/or ameliorate the symptoms and/or underlying causes of any of a disorder or disease. In one embodiment, an "effective amount" is sufficient to reduce or eliminate a symptom of a disease, such as a diabetes (such as type II diabetes), for example by lowering blood glucose.

Fibroblast Growth Factor 1 (FGF1): OMIM 13220. Includes FGF1 nucleic acid molecules and proteins. A protein that binds to the FGF receptor, and is also known as the acidic FGF. FGF1 sequences are publically available, for example from GenBank® sequence database (e.g., Accession Nos. NP_00791 and NP_034327 provide exemplary FGF1 protein sequences, while Accession Nos. NM_000800 and NM_010197 provide exemplary FGF1 nucleic acid sequences). One of ordinary skill in the art can identify additional FGF1 nucleic acid and protein sequences, including FGF1 variants.

Specific examples of native FGF1 sequences are provided in SEQ ID NOS: 1-5. A native FGF1 sequence is one that does not include a mutation that alters the normal activity of the protein (e.g., activity of SEQ ID NO: 2, 4 or SEQ ID NO: 5). A mutated FGF1 is a variant of FGF1 with different or altered biological activity, such as reduced mitogenicity (e.g., a variant of any of SEQ ID NOS: 1-5, such as one having at least 90%, at least 95%, at least 96%, at least 97%, at least 98% or at least 99% sequence identity to any of SEQ ID NOS: 1-5, but is not a native/wild-type sequence). In one example, such a variant includes an N-terminal truncation, at least one point mutation (such as one or more of those shown in Table 1), or combinations thereof, such as changes that decrease mitogenicity of FGF1. Mutated FGF1 proteins include FGF1 chimeras (e.g., FGF1/FGF19 chimeras). Specific exemplary FGF1 mutant proteins are shown in SEQ ID NOS: 6-13, 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 113, 114, 115, 116, 117, 118, 119, 120, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 and 238.

Fibroblast Growth Factor 19 (FGF19): OMIM 603891. Includes FGF19 nucleic acid molecules and proteins. FGF19 regulates bile acid synthesis and has effects on glucose and lipid metabolism. FGF19 sequences are publically available, for example from the GenBank® sequence database (e.g., Accession Nos. NP_005108.1 and AAQ88669.1 provide exemplary FGF19 protein sequences, while Accession Nos. AY358302.1 and NM_005117.2 provide exemplary FGF19 nucleic acid sequences). One of ordinary skill in the art can identify additional FGF19 nucleic acid and protein sequences, including FGF19 variants.

Fibroblast Growth Factor 21 (FGF21): OMIM 609436. Includes FGF21 nucleic acid molecules and proteins. FGF21 stimulates glucose updated in adipocytes. FGF21 sequences are publically available, for example from the GenBank® sequence database (e.g., Accession Nos. AAQ89444.1, NP_061986, and AAH49592.1 provide exemplary FGF21 protein sequences, while Accession Nos. AY359086.1 and BC049592 provide exemplary FGF21 nucleic acid sequences). One of ordinary skill in the art can identify additional FGF21 nucleic acid and protein sequences, including FGF21 variants.

Fibroblast Growth Factor Receptor 1c (FGFR1c) binding domain or protein: A peptide sequence that binds selectively to FGFR1c (such as human FGFR1c, e.g., GeneBank Accession No. NP_001167536.1 or NP_056934.2), but not to other proteins. FGFR1c is a cofactor for FGF21 activity. Such a binding domain can include one or more monomers (wherein the monomers can be the same or different sequences), thereby generating a multimer (such as a dimer). In specific examples, such a domain/protein is not an antibody. Exemplary FGFR1c-binding proteins can be found in SEQ ID NOS: 147, 148, 149, 150, 151, 152, 153, 154, 155, 156, 157, 158, 159, 160, 161, 162, 163, 164, 165, 166, 167 and portions of 168, 169, 170 and 171, or a multimer thereof such as SEQ ID NO: 190, as well as U.S. Pat. No. 8,372,952, U.S. Publication No. 2013/0197191, and Smith et al., PLoS One 8:e61432, 2013, all herein incorporated by reference. Thus, reference to a FGFR1c-binding protein multimer, includes proteins made using two or more peptides having at least 90%, at least 95%, at least 95%, at least 96%, at least 97%, at least 98%, at least 99% or 100% sequence identity to one or more of SEQ ID NO: 147, 148, 149, 150, 151, 152, 153, 154, 155, 156, 157, 158, 159, 160, 161, 162, 163, 164, 165, 166, 167, and 190.

A FGFR1c binding protein "specifically binds" to FGFR1c when the dissociation constant ($K_D$) is at least about $1\times10^{-7}$ M, at least about $1.5\times10^{-7}$, at least about $2\times10^{-7}$, at least about $2.5\times10^{-7}$, at least about $3\times10^{-7}$, at least about at least about $5\times10^{-7}$ M, at least about $1\times10^{-8}$ M, at least about $5\times10^{-8}$, at least about $1\times10^{-9}$, at least about $5\times10^{-9}$, at least about $1\times10^{-10}$, or at least about $5\times10^{-10}$ M. In one embodiment, $K_D$ is measured by a radiolabeled antigen binding assay (RIA) performed with the FGFR1c-binding protein and FGFR1c. In another example, $K_D$ is measured using an ELISA assay.

Fibroblast Growth Factor Receptor 1c (FGFR1c): Also known as FGFR1 isoform 2. Includes FGFR1c nucleic acid molecules and proteins. FGFR1c and β-Klotho can associate with FGF21 to form a signaling complex. FGFR1c sequences are publically available, for example from the GenBank® sequence database (e.g., Accession Nos. NP_001167536.1 and NP_056934.2 provide exemplary FGFR1c protein sequences). One of ordinary skill in the art can identify additional FGFR1c nucleic acid and protein sequences, including FGFR1c variants.

Fibroblast Growth Factor Receptor 4 (FGFR4): OMIM 134935. Includes FGFR4 nucleic acid molecules and proteins. FGFR4 can bind to some FGF proteins, including FGF1. FGFR4 sequences are publically available, for example from the GenBank® sequence database (e.g., Accession Nos. NM_002011 and AAB25788.1 provide exemplary FGFR4 protein sequences, while Accession Nos. NM_002002 and L03840.1 provide exemplary FGFR4 nucleic acid sequences). One of ordinary skill in the art can identify additional FGFR4 nucleic acid and protein sequences, including FGFR4 variants.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Thus, host cells can be transgenic, in that they include nucleic acid molecules that have been introduced into the cell, such as a nucleic acid molecule encoding a mutant FGF1 protein disclosed herein.

Isolated: An "isolated" biological component (such as a mutated FGF1 protein or nucleic acid molecule) has been substantially separated, produced apart from, or purified away from other biological components in the cell of the organism in which the component naturally occurs, such as other chromosomal and extrachromosomal DNA and RNA, and proteins. Nucleic acids molecules and proteins which have been "isolated" thus include nucleic acids and proteins purified by standard purification methods. The term also embraces nucleic acid molecules and proteins prepared by recombinant expression in a host cell as well as chemically synthesized nucleic acids. A purified or isolated cell, protein, or nucleic acid molecule can be at least 70%, at least 80%, at least 90%, at least 95%, at least 96%, at least 97%, at least 98%, or at least 99% pure.

Linker. A moiety or group of moieties that joins or connects two or more discrete separate peptide or proteins, such as monomer domains, for example to generate a chimeric protein. In one example a linker is a substantially linear moiety. Exemplary linkers that can be used to generate the chimeric proteins provided herein include but are not limited to: peptides, nucleic acid molecules, peptide nucleic acids, and optionally substituted alkylene moieties that have one or more oxygen atoms incorporated in the carbon backbone. A linker can be a portion of a native sequence, a variant thereof, or a synthetic sequence. Linkers can include naturally occurring amino acids, non-naturally occurring amino acids, or a combination of both. In one example a linker is composed of at least 5, at least 10, at least 15 or at least 20 amino acids, such as 5 to 10, 5 to 20, or 5 to 50 amino acids. In one example the linker is a poly alanine.

Mammal: This term includes both human and non-human mammals. Similarly, the term "subject" includes both human and veterinary subjects (such as cats, dogs, cows, and pigs) and rodents (such as mice and rats).

Metabolic disorder/disease: A disease or disorder that results from the disruption of the normal mammalian process of metabolism. Includes metabolic syndrome.

Examples include but are not limited to: (1) glucose utilization disorders and the sequelae associated therewith, including diabetes mellitus (Type I and Type-2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic β-cell destruction; (2) dyslipidemias and their sequelae such as, for example, atherosclerosis, coronary artery disease, cerebrovascular disorders and the like; (3) other conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thromboses, hypercoagulable and prothrombotic states (arterial and venous), hypertension, cardiovascular disease, stroke and heart failure; (4) disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; (5) disorders of cell cycle or cell differentiation processes such as adipose cell tumors, lipomatous carcinomas including, for example, liposarcomas, solid tumors, and neoplasms; (6) neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy and Guillian-Barre syndrome; (7) skin and dermatological disorders and/or disorders of wound healing processes, including erythematosquamous dermatoses; and (8) other disorders such as syndrome X, osteoarthritis, and acute respiratory distress syndrome. Other examples are provided in WO 2014/085365 (herein incorporated by reference).

In specific examples, the metabolic disease includes one or more of (such as at least 2 or at least 3 of): diabetes (such as type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), and cardiovascular diseases (e.g., hypertension).

N-terminal portion: A region of a protein sequence that includes a contiguous stretch of amino acids that begins at or near the N-terminal residue of the protein. An N-terminal portion of the protein can be defined by a contiguous stretch of amino acids (e.g., a number of amino acid residues).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a mutated FGF1 coding sequence). Generally, operably linked DNA sequences are contiguous and, where necessary to join two protein coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the disclosed mutated FGF1 proteins and FGFR1c-binding protein multimers (or nucleic acid molecules encoding such) herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant: A recombinant nucleic acid molecule is one that has a sequence that is not naturally occurring (e.g., a mutated FGF1 or chimeric protein) or has a sequence that is made by an artificial combination of two otherwise separated segments of sequence. This artificial combination can be accomplished by routine methods, such as chemical synthesis or by the artificial manipulation of isolated segments of nucleic acids, such as by genetic engineering techniques. Similarly, a recombinant protein is one encoded for by a recombinant nucleic acid molecule. Similarly, a recombinant or transgenic cell is one that contains a recombinant nucleic acid molecule and expresses a recombinant protein.

Sequence identity of amino acid sequences: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of the mutated FGF1 proteins and coding sequences disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, a mutant FGF1 protein disclosed herein can have at least 80%, at least 85%, at least 90%, at least 91%, at least 92%, at least 95%, at least 96%, at least 97%, at least 98% or at least 99% sequence identity to SEQ ID NO: 5, but is not SEQ ID NO: 5 (which in some examples has one or more, such as 1, 2, 3, 4, 5, 6, 7, 8, 9, or 10 of the mutations or truncations shown in Tables 1 and 2). In addition, exemplary mutated FGF1 proteins have at least 80%, at least 85%, at least 90%, at least 92%, at least 95%, at least 96%, at least 97%, at least 98% or at least 99% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, as well as such sequences schematically shown in FIGS. 23-26 (e.g., at least 80%, at least 85%, at least 90%, at least 92%, at least 95%, at least 96%, at least 97%, at least 98% or at least 99% sequence identity to SEQ ID NO: 173, 174, 175, 177, 178, 179, 181, 182, 183, 185, 186, 187, or 188), and retain the ability to reduce blood glucose levels in vivo.

Similarly, exemplary mutated FGF1 coding sequences in some examples have at least 70%, at least 80%, at least 85%, at least 90%, at least 92%, at least 95%, at least 98%, or at least 99% sequence identity to SEQ ID NO: 18.

Similarly, exemplary β-Klotho-binding domain sequences that can be used in the mutant FGF1 chimeras disclosed herein in some examples have at least 70%, at least 80%, at least 85%, at least 90%, at least 92%, at least 95%, at least 97%, at least 98%, or at least 99% sequence identity to SEQ ID NO: 121, 122, 123, 124, 125, 126, 127, 128, 129, 130, 131, 132, 133, 134, 135, 136, 137, 138, 139, 140, 141, 142, 143, 144, 145, 146 or β-Klotho-binding portions of SEQ ID NO: 168, 169, 170 or 171.

Similarly, exemplary FGFR1c binding sequences that can be used in the mutant FGF1 chimeras disclosed herein in some examples have at least 70%, at least 80%, at least 85%, at least 90%, at least 92%, at least 95%, at least 97%, at least 98%, or at least 99% sequence identity to SEQ ID NO: 147, 148, 149, 150, 151, 152, 153, 154, 155, 156, 157, 158, 159, 160, 161, 162, 163, 164, 165, 166, 167, or FGFR1c-binding portions of SEQ ID NO: 168, 169, 170, 171, or multimers such as SEQ ID NO: 190.

Subject: Any mammal, such as humans, non-human primates, pigs, sheep, cows, dogs, cats, rodents and the like which is to be the recipient of the particular treatment, such as treatment with a mutated FGF1 protein or chimera (or corresponding nucleic acid molecule) provided herein. In two non-limiting examples, a subject is a human subject or a murine subject. In some examples, the subject has one or more metabolic diseases, such as diabetes (e.g., type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), cardiovascular disease (e.g., hypertension), or combinations thereof. In some examples, the subject has elevated blood glucose.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA.

Transgene: An exogenous gene supplied by a vector. In one example, a transgene includes a mutated FGF1 coding sequence (which may be part of a chimera).

Vector: A nucleic acid molecule as introduced into a host cell, thereby producing a transformed host cell. A vector may include nucleic acid sequences that permit it to replicate in the host cell, such as an origin of replication. A vector may also include one or more mutated FGF1 coding sequences (which may be part of a chimera) and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Overview

Provided herein are mutated FGF1 proteins that can include an N-terminal deletion, one or more point mutations (such as amino acid substitutions, deletions, additions, or combinations thereof), or combinations of N-terminal deletions and point mutations. Such mutated FGF1 proteins can be part of a chimeric protein, such as a C-terminal portion of FGF21 or 19 (e.g., SEQ ID NO: 86 or 100, respectively), a β-Klotho binding protein (e.g., SEQ ID NOS: 173, 174, 175, 177, 178, 179, 181, 182, 183, 185, 186, and 187), or an FGFR1c binding protein (e.g., see SEQ ID NOS: 188 and 189), or both a β-Klotho binding protein and an FGFR1c binding protein (e.g., linked directly or indirectly to any of SEQ ID NOS: 168, 169, 170 or 171). Thus, when referring to a mutated FGF1 protein(s) herein, such reference also includes reference to mutated FGF1/FGF21, mutated FGF1/FGF19 chimeras, mutated FGF1/β-Klotho-binding chimeras, mutated FGF1/FGF1Rc-binding chimeras, or mutated FGF1/β-Klotho-binding/FGF1Rc-binding chimeras.

Also provided are methods of using FGF1 mutant proteins or FGF1Rc-binding protein multimers (or their nucleic acid coding sequences) to lower glucose, for example to treat a metabolic disease. In some examples such methods include administering a therapeutically effective amount of a mutated mature FGF21 protein or FGF1Rc-binding protein multimer to the mammal, or a nucleic acid molecule encoding the mutated mature FGF21 protein or FGF1Rc-binding protein multimer or a vector comprising the nucleic acid molecule, thereby reducing the blood glucose, treating the one or more metabolic diseases, or combinations thereof. Exemplary metabolic diseases that can be treated with the disclosed methods include but are not limited to: type 2 diabetes, non-type 2 diabetes, type 1 diabetes, polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), cardiovascular diseases (e.g., hypertension), latent autoimmune diabetes (LAD), or maturity onset diabetes of the young (MODY).

In some examples, mutations in FGF1 reduce the mitogenicity of mature wild-type FGF1 (e.g., SEQ ID NO: 5), such as a reduction of at least 20%, at least 50%, at least 75% or at least 90%. For example, mutated FGF1 can be mutated to decrease binding affinity for heparin and/or heparan sulfate compared to an FGF1 protein without the modification (e.g., a native or wild-type FGF1 protein). Methods of measuring mitogenicity are known in the art. In one example, the method provided in Example 2 is used.

In some examples, the mutant FGF1 protein is a truncated version of the mature protein (e.g., SEQ ID NO: 5), which can include for example deletion of at least 5, at least 6, at least 9, at least 10, at least 11, at least 12, at least 13, at least 14, at least 15, or at least 20 consecutive N-terminal amino acids, such as the N-terminal 5 to 10, 5 to 13, 5, 6, 7, 8, 9, 10, 11, 12, or 13 amino acids of mature FGF1. In some examples, such an N-terminally deleted FGF1 protein has reduced mitogenic activity as compared to wild-type mature FGF1 protein.

In some examples, one or more of the deleted N-terminal amino acids are replaced with corresponding amino acids from FGF21 (e.g., see SEQ ID NO: 20), such as at least 1, at least 2, at least 3, at least 4, at least 5, at least 10, at least 15, or at least 20 amino acids from FGF21, such as 1-5, 1-4, 2-4, 4-6, 4-9, 3-10, 1, 2, 3, 4, 5, 6, 7, 8, 9, or 10 corresponding amino acids from FGF21. An example of an FGF1 mutated protein with an N-terminal deletion having four corresponding N-terminal amino acids from FGF21 is shown in SEQ ID NO: 21 and 222. An example of an FGF1 mutated protein with an N-terminal deletion having 16 N-terminal amino acids from FGF21 is shown in SEQ ID NO: 221. One skilled in the art will appreciate that amino acids from other FGFs besides FGF21 can be used, including those having low affinity for FGFR4, including FGF3, FGF5, FGF7, FGF9 and FGF10. The N-terminal residues of FGF1 include an FGFR4 binding site, and FGFR4 signaling is associated with mitogenic activity. In contrast, FGF21 has low affinity for FGFR4. Thus, replacing the FGFR4 binding residues of FGF1 with those from FGF21 can be used to reduce mitogenicity of the resulting FGF1 mutant protein.

In some examples, mutations in FGF1 increase the thermostability of mature or truncated FGF1 (e.g., SEQ ID NO: 5), such as an increase of at least 20%, at least 50%, at least 75% or at least 90% compared to native FGF1. Exemplary mutations that can be used to increase the thermostability of mutated FGF1 include but are not limited to one or more of: K12V, C117V, C117P, C117T, C117S, C117A and P134V (referred to as M1 mutations), L44F, C83T, C83S, C83A C83V, C117V, C117P, C117T, C117S, C117A and F132W (referred to as M2 mutations), and L44F, M67I, L73V, V109L, L111I, C117V, C117P, C117T, C117S, C117A A103G, R119G, R119V, Δ104-106, and Δ120-122 (referred to as M3 deletions), wherein the numbering refers to SEQ ID NO: 5 (e.g., see Xia et al., PLoS One. 7:e48210, 2012). For example, mutated FGF1 can be mutated to increase the thermostability of the protein compared to an FGF1 protein without the modification (e.g., SEQ ID NO: 5). Methods of measuring thermostability are known in the art. In one example, the method provided in Xia et al., PLoS One. 7:e48210, 2012 is used.

In some examples, the mutant FGF1 protein is a mutated version of the mature protein (e.g., SEQ ID NO: 5), such as one containing at least 1, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or at least 25 amino acid substitutions, such as 1-20, 1-10, 4-8, 5-25, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 amino acid substitutions (such as those shown in Table 1). In some examples, the mutant FGF1 protein includes deletion of one or more amino acids, such as deletion of 1-10, 4-8, 5-10, 1, 2, 3, 4, 5, 6, 7, 8, 9, 10, 11, 12, 13, 14, 15, 16, 17, 18, 19, or 20 amino acid deletions. In some examples, the mutant FGF1 protein includes a combination of amino acid substitutions and deletions, such as at least 1 substitution and at least 1 deletion, such as 1 to 10 substitutions with 1 to 10 deletions.

Exemplary mutations are shown in Table 1 below, with amino acids referenced to either SEQ ID NO: 2 or 5. One skilled in the art will recognize that these mutations can be used singly, or in combination (such as 1-20, 1-10, 4-8, 5-25, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 of these amino acid substitutions and/or deletions). In addition, such mutant FGF1 proteins are part of a chimeric protein, such as with FGF19, FGF21, a protein that selectively binds to β-Klotho, or a protein that selectively binds to FGFR1c.

TABLE 1

Exemplary FGF1 mutations

| Location of Point Mutation Position in SEQ ID NO: 2 | Mutation Citation | Location of Point Mutation Position in SEQ ID NO: 5 |
|---|---|---|
| K24 | K9T | K9 |
| K25 | K10T | K10 |
| K27 | K12V | K12 |
| L29 | L14A | L14 |
| Y30 | Y15F, Y15A, Y15V | Y15 |
| C31 | C16V, C16A, C16T, C16S | C16 |
| H36 | H21Y | H21 |
| R50 | R35E, R35V | R35 |
| Q55 | Q40P | Q40 |
| L59 | L44F | L44 |
| L61 | L46V | L46 |
| S62 | S47I | S47 |
| E64 | E49Q, E49A | E49 |
| Y70 | Y55F, Y55S, Y55A | Y55 |
| M82 | M67I | M67 |
| L88 | L73V | L73 |
| C98 | C83T, C83S, C83A C83V | C83 |
| E102 | E87V, E87A, E87S, E87T | E87 |
| H108 | H93G, H93A | H93 |
| Y109 | Y94V, Y94F, Y94A | Y94 |
| N110 | N95V, N95A, N95S, N95T | N95 |
| H117 | H102Y | H102 |
| A118 | A103G | A103 |
| EKN 119-121 | Δ104-106 | EKN (104-106) |
| F123 | F108Y | F108 |
| V124 | V109L | V109 |
| L126 | L111I | L111 |
| K127 | K112D, K112E, K112Q | K112 |
| K128 | K113Q, K113E, K113D | K113 |
| C132 | C117V, C117P, C117T, C117S, C117A | C117 |
| K133 | K118N, K118E, K118V | K118 |
| R134 | R119G, R119V, R119E | R119 |
| GPR 135-137 | Δ120-122 | GPR (120-122) |
| F147 | F132W | F132 |
| L148 | L133A, L133S | L133 |
| P149 | P134V | P134 |
| L150 | L135A, L135S | L135 |

In some examples, the mutant FGF1 protein includes mutations at one or more of the following positions: K9, K10, K12, L14, Y15, C16, H21, R35, Q40, L44, L46, S47, E49, Y55, M67, L73, C83, L86, E87, H93, Y94, N95, H102, A103, E104, K105, N106, F108, V109, L111, K112, K113, C117, K118, R119, G120, P121, R122, F132, L133, P134, L135, such as one or more of K9, K10, K12, K112, K113, such as 1 to 5, 2 to 5, 3 to 6, 3 to 8, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or all 42 of these positions. In one example, K9 and K10 are replaced with DQ (as in the mutated nuclear localization sequence) or with equivalent residues from FGF21 (or another FGF that does not bind to FGFR4) (wherein the numbering refers to SEQ ID NO: 5).

In some examples, the mutant FGF1 protein includes mutations at 1, 2, 3 or 4 of the following positions: Y15, E87, Y94, and N95 (wherein the numbering refers to SEQ ID NO: 5), such as one or more of Y15F, Y15A, Y15V, E87V, E87A, E87S, E87T, N95V, N95A, N95S, N95T, Y94V, Y94F, and Y94A (such as 1, 2, 3 or 4 of these mutations). For example, E87 or N95 can be replaced with a non-charged amino acid. In addition, Y15 and Y94 can be replaced with an amino acid that destabilizes the hydrophobic interactions. In some examples, the mutant FGF1 protein includes mutations on either side of Y15, E87, Y94, and N95, such as one or more of L14, C16, H93, and T96, such as mutations at 1, 2, 3, or 4 of these positions.

In some examples, the mutant FGF1 protein includes mutations at 1, 2, 3, 4, 5, 6, 7, 8, 9 or 10 of the following positions: Y15, C16, E87, H93, Y94, and N95 (wherein the numbering refers to SEQ ID NO: 5), such as one or more of Y15F, Y15A, Y15V, E87V, E87A, E87S, E87T, H93A, N95V, N95A, N95S, N95T, Y94V, Y94F, and Y94A (such as 1, 2, 3, 4, 5, 6, 7, 8, 9 or 10 of these mutations).

In some examples, the mutant FGF1 protein includes mutations at one or more of the following positions: C16, C83, and C117 (wherein the numbering refers to SEQ ID NO: 5), such as one or more of C16V, C16A, C16T, C16S, C83T, C83S, C83A C83V, C117V, C117P, C117T, C117S, and C117A (such as 1, 2, or 3 of these mutations).

In some examples, the mutant FGF1 protein includes mutations at only one or two of the following positions: E87, Y94, and N95 (wherein the numbering refers to SEQ ID NO: 5), such as one or two of E87V, E87A, E87S, E87T, Y94V, Y94F, Y94A, N95V, N95A, N95S, and N95T.

In some examples, the mutant FGF1 protein includes mutations at 1, 2, or 3 of the following positions: K12, C83, and C117 (wherein the numbering refers to SEQ ID NO: 5), such as one or more of K12V, K12C, C83T, C83S, C83A, C83V, C117V, C117P, C117T, C117S, and C117A (such as 1, 2, or 3 of these mutations, such as K12V, C83T, and C117V).

FIG. 31 shows specific examples of positions that can be mutated in FGF1 to alter its activity. For example, residues that interact with the FGF1 receptor include Y15, E87, Y94 and N95. Thus, in some examples, 1, 2, 3, or 4 of these positions are mutated, for example the amino acid at position 87 and/or 95 of SEQ ID NO: 5 can be changed to a V, A, S or T. In some examples, the amino acid at position 15 and/or 95 of SEQ ID NO: 5 can be changed to a V, A, or F. In some examples, combinations of these changes are made.

FIG. 31 also shows that K12 of FGF1 is predicted to be at the receptor interface. Thus, K12 of SEQ ID NO: 5 can be mutated, for example to a V or C. FIG. 31 also shows that amino acids K112, K113, and K118 are part of the heparin binding site, and thus can be mutated, for example to a E, Q, N, V or D, such as a N, E or V at position K118, and a D, E or Q at positions K112 and K113. FIG. 31 also shows that amino acid R35 of SEQ ID NO: 5 that forms a salt bridge with the D2 domain of the FGF receptor, and thus can be mutated, for example to an E or V.

In some examples, the mutant FGF1 protein includes one or more of K12V, L46V, R35E, R35V, E87V, N95V, K118N, K118E, C117V, and P134V (wherein the numbering refers to SEQ ID NO: 5). In some examples, the point mutation includes replacing amino acid sequence ILFLPLPV (amino acids 145-152 of SEQ ID NO: 2 and 4) to AAALPLPV (SEQ ID NO: 14), ILALPLPV (SEQ ID NO: 15), ILFA-PLPV (SEQ ID NO: 16), or ILFLPAPA (SEQ ID NO: 17). In some examples, such an FGF1 protein with one or more point mutations has reduced mitogenic activity as compared to wild-type mature FGF1 protein. In some examples, the mutant FGF1 protein includes R35E (wherein the numbering refers to SEQ ID NO: 5).

In some examples, the mutant FGF1 protein includes at least 120 consecutive amino acids from amino acids 5-141 of FGF1 (e.g., of SEQ ID NO: 2 or 4), (which in some examples can include further deletion of N-terminal amino acids 1-20 and/or point mutations, such as substitutions, deletions, or additions). In some examples, the mutant FGF1 protein includes at least 120 or at least 130 consecutive amino acids from amino acids 5-141 of FGF1, such as at least 120 consecutive amino acids from amino acids 5-141 of SEQ ID NO: 2 or 4 or at least 120 consecutive amino acids from SEQ ID NO: 5.

In some examples, the mutant FGF1 protein includes both an N-terminal truncation and point mutations. Specific exemplary FGF1 mutant proteins are shown in SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 113, 114, 115, 116, 117, 118, 119, 120, 191, 192, 193, 194, 195, 196, 197, 198, 199, 200, 201, 202, 203, 204, 205, 206, 207, 208, 209, 210, 211, 212, 213, 214, 215, 216, 217, 218, 225, 226, 227, 228, 229, 230, 231, 232, 233, 234, 235, 236, 237 and 238. In some examples, the FGF1 mutant includes an N-terminal deletion, but retains a methionine at the N-terminal position. In some examples, the FGF1 mutant is 120-140 or 125-140 amino acids in length.

In some examples, the FGF1 mutant protein is part of a chimeric protein. For example, one end of the mutant FGF1 mutant protein can be joined directly or indirectly to the end of FGF19 or FGF21, such as a C-terminal region of FGF 19 or FGF21. In some examples, the mutated FGF1 portion of the chimera is at the N-terminus of the chimera, and the FGF19 or FGF21 portion is the C-terminus of the chimera. However, this can be reversed, such that the mutated FGF1 portion of the chimera is the C-terminus of the chimera, and the FGF19 or FGF21 portion is the N-terminus of the chimera. For example, at least 10, at least 20, at least 30, at least 40, at least 41, at least 42, at least 43, at least 44, at least 45, at least 46, at least 47, at least 48, at least 49, at least 50 or at least 60 C-terminal amino acids of FGF19 or FGF21 (such as the C-terminal 60, 55, 50, 49, 48, 47, 46, 45, 44, 43, 42, 41, 40, 35, 30, 25, 20, 15 or 10 amino acids) can be part of the chimera. Examples of C-terminal fragments of FGF21 and FGF19 that can be used are shown in SEQ ID NOS: 86 and 100, respectively. In some examples, the mutant FGF1 and FGF21 or FGF19 portion are linked indirectly through the use of a linker, such as one composed of at least 5, at least 10, at least 15 or at least 20 amino acids. In one example the linker is a poly alanine.

In some examples, the FGF1 mutant protein is part of a chimeric protein with a β-Klotho-binding protein. For example, one end of the mutant FGF1 mutant protein can be joined directly or indirectly to the end of a β-Klotho-binding protein (see for example FIGS. 23-26). In some examples, the mutated FGF1 portion of the chimera is at the N-terminus of the chimera, and the β-Klotho-binding protein portion is the C-terminus of the chimera (e.g., see FIGS. 23B-23D, 23G-23I and 25B-25D, 25G-25I, respectively). However, this can be reversed, such that the mutated FGF1 portion of the chimera is the C-terminus of the chimera, and the β-Klotho binding protein portion is the N-terminus of the chimera (e.g., see FIGS. 24B-24D, 24F-24H and 26B-26D, 26F-26H). Examples of β-Klotho-binding proteins that can be used are shown in SEQ ID NOS: 121, 122, 123, 124, 125, 126, 127, 128, 129, 130, 131, 132, 133, 134, 135, 136, 137, 138, 139, 140, 141, 142, 143, 144, 145 and 146 and β-Klotho-binding portions of SEQ ID NOS: 168, 169, 170, and 171. In some examples, the mutant FGF1 and β-Klotho-binding protein portion are linked indirectly through the use of a linker, such as one composed of at least 5, at least 10, at least 15 or at least 20 amino acids. In one example the linker is a poly alanine.

In some examples, the FGF1 mutant protein is part of a chimeric protein with an FGFR1c-binding protein. For example, one end of the mutant FGF1 mutant protein can be joined directly or indirectly to the end of an FGFR1c-binding protein. In some examples, the mutated FGF1 portion of the chimera is at the N-terminus of the chimera, and the FGFR1c-binding protein portion is the C-terminus of the chimera (e.g., see FIG. 23J). However, this can be reversed, such that the mutated FGF1 portion of the chimera is the C-terminus of the chimera, and the FGFR1c-binding protein portion is the N-terminus of the chimera (e.g., see FIG. 24I). Examples of FGFR1c-binding proteins that can be used are shown in SEQ ID NOS: 147, 148, 149, 150, 151, 152, 153, 154, 155, 156, 157, 158, 159, 160, 161, 162, 163, 164, 165, 166, and 167 and FGFR1c-binding portions of 168, 169, 170 and 171. In some examples, the mutant FGF1 and FGFR1c-binding protein portion are linked indirectly through the use of a linker, such as one composed of at least 5, at least 10, at least 15 or at least 20 amino acids. In one example the linker is a poly alanine.

In some examples, the FGF1 mutant protein is part of a chimeric protein with both an FGFR1c-binding protein and a β-Klotho-binding protein, in any order. For example, one end of the mutant FGF1 mutant protein can be joined directly or indirectly to the end of an FGFR1c-binding/β-Klotho-binding or β-Klotho-binding/FGFR1c-binding chimeric protein. In some examples, the mutated FGF1 portion of the chimera is at the N-terminus of the chimera, and the FGFR1c-binding/β-Klotho-binding or 13-Klotho-binding/FGFR1c-binding chimeric protein portion is the C-terminus of the chimera (e.g., see FIG. 23K). However, this can be reversed, such that the mutated FGF1 portion of the chimera is the C-terminus of the chimera, and the FGFR1c-binding/β-Klotho-binding or β-Klotho-binding/FGFR1c-binding chimeric protein portion is the N-terminus of the chimera (e.g., see FIG. 24J). In one example the FGFR1c-binding/β-Klotho-binding or β-Klotho-binding/FGFR1c-binding chimeric protein is any one of those shown in SEQ ID NOS: 168, 169, 170, and 171. In some examples, the mutant FGF1 and FGFR1c-binding/β-Klotho-binding or β-Klotho-binding/FGFR1c-binding chimeric protein portion are linked indirectly through the use of a linker, such as one composed of at least 5, at least 10, at least 15 or at least 20 amino acids. In one example the linker is a poly alanine. In some examples, the FGF1 mutant protein or chimera including such includes at least 80% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238. Thus, the FGF1 mutant protein can have at least 90%, at least 95%, at least 96%, at least 97%, at least 98% or at least 99% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238 (but is not a native FGF1 sequence, such as SEQ ID NO: 5). In some examples, the FGF1 mutant protein includes or consists of SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 and 238. The disclosure encompasses variants of the disclosed FGF1 mutant proteins, such as SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238 having 1 to 8, 2 to 10, 1 to 5, 1 to 6, or 5 to 10 mutations, such as conservative amino acid substitutions.

In some examples, a mutant FGF1/FGF21 chimera protein includes at least 80% sequence identity to SEQ ID NO: 87, 88, 89, 90, 91, 92, 93, 94, 95, 96, 97, 98, 219, 221, 222, or 223. Thus, the mutant FGF1/FGF21 chimeric protein can have at least 90%, at least 95%, at least 96%, at least 97%, at least 98% or at least 99% sequence identity to SEQ ID NO: 87, 88, 89, 90, 91, 92, 93, 94, 95, 96, 97, 98, 219, 221, 222, or 223. In some examples, the mutant FGF1/FGF21 chimera protein includes or consists of SEQ ID NO: 87, 88, 89, 90, 91, 92, 93, 94, 95, 96, 97, 98, 219, 221, 222, or 223. The disclosure encompasses variants of the disclosed mutant FGF1/FGF21 chimera proteins, such as SEQ ID NO: 87, 88, 89, 90, 91, 92, 93, 94, 95, 96, 97, 98, 219, 221, 222, or 223 having 1-8 mutations, such as conservative amino acid substitutions.

In some examples, a mutant FGF1/FGF19 chimera protein includes at least 80% sequence identity to SEQ ID NO: 101, 102, 103, 104, 105, 106, 107, 108, 109, 110, 111, 112, 220, or 224. Thus, the mutant FGF1/FGF19 chimeric protein can have at least 90%, at least 95%, at least 96%, at least 97%, at least 98% or at least 99% sequence identity to SEQ ID NO: 101, 102, 103, 104, 105, 106, 107, 108, 109, 110, 111, 112, 220, or 224. In some examples, the mutant FGF1/FGF19 chimera protein includes or consists of any of SEQ ID NOS: 101, 102, 103, 104, 105, 106, 107, 108, 109, 110, 111, 112, 220, or 224. The disclosure encompasses variants of the disclosed mutant FGF1/FGF19 chimera proteins, such as SEQ ID NO: 101, 102, 103, 104, 105, 106, 107, 108, 109, 110, 111, 112, 220, or 224 having 1, 2, 3, 4, 5, 6, 7, 8, 9, or 10 mutations, such as conservative amino acid substitutions.

In some examples, a mutant FGF1/β-Klotho-binding protein chimera includes at least 80% sequence identity to SEQ ID NO: 173, 174, 175, 177, 178, 179, 181, 182, 183, 185, 186, or 187. Thus, the mutant FGF1/β-Klotho chimeric protein can have at least 90%, at least 95%, at least 96%, at least 97%, at least 98% or at least 99% sequence identity to SEQ ID NO: 1173, 174, 175, 177, 178, 179, 181, 182, 183, 185, 186, or 187. In some examples, the mutant FGF1/β-Klotho chimera protein includes or consists of SEQ ID NO: 173, 174, 175, 177, 178, 179, 181, 182, 183, 185, 186, or 187. The disclosure encompasses variants of the disclosed mutant FGF1/β-Klotho chimera proteins, such as SEQ ID NO: 173, 174, 175, 177, 178, 179, 181, 182, 183, 185, 186, or 187 having 1, 2, 3, 4, 5, 6, 7, 8, 9, or 10 mutations, such as conservative amino acid substitutions.

In some examples, a mutant FGF1/FGF1Rc-binding protein chimera includes at least 80% sequence identity to any of SEQ ID NOS: 188-189. Thus, the mutant FGF1/FGF1Rc chimeric protein can have at least 90%, at least 95%, at least 96%, at least 97%, at least 98% or at least 99% sequence identity to SEQ ID NO: 188 or 189. In some examples, the mutant FGF1/FGF1Rc chimera protein includes or consists of any of SEQ ID NOS: 188-189. The disclosure encompasses variants of the disclosed mutant FGF1/FGF1Rc chimera proteins, such as SEQ ID NO: 188 or 189 having 1, 2, 3, 4, 5, 6, 7, 8, 9, or 10 mutations, such as conservative amino acid substitutions.

In one example the FGFR1c-binding/β-Klotho-binding or β-Klotho-binding/FGFR1c-binding protein portion of a chimera includes at least 80% sequence identity to SEQ ID NO: 168, 169, 170 or 171, such as at least 90%, at least 95%, at least 96%, at least 97%, at least 98% or at least 99% sequence identity to SEQ ID NO: 168, 169, 170 or 171.

In one example an FGFR1c-binding protein multimer includes at least one monomer having 80% sequence identity to the FGFR1c-binding portion of SEQ ID NO: 147, 148, 149, 150, 151, 152, 153, 154, 155, 156, 157, 158, 159, 160, 161, 162, 163, 164, 165, 166, 167, 168, 169, or 170, such as at least 90%, at least 95%, at least 96%, at least 97%, at least 98% or at least 99% sequence identity to the FGFR1c portion of SEQ ID NO: 147, 148, 149, 150, 151, 152, 153, 154, 155, 156, 157, 158, 159, 160, 161, 162, 163, 164, 165, 166, 167, 168, 169, or 170. In one example an FGFR1c-binding protein dimer includes at least 80% sequence identity SEQ ID NO: 190, such as at least 90%, at least 95%, at least 96%, at least 97%, at least 98% or at least 99% sequence identity to SEQ ID NO: 190.

Also provided are isolated nucleic acid molecules encoding the disclosed mutated FGF1 proteins and chimeras, such as a nucleic acid molecule encoding a protein having at least 80%, at least 85%, at least 90%, at least 95%, at least 98%, or at least 99% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, or 238 (but is not a native FGF1 sequence). One exemplary coding sequence is shown in SEQ ID NO: 18; thus, the disclosure provides sequences having at least 80%, at least 85%, at least 90%, at least 95%, at least 98%, or at least 99% sequence identity to any of SEQ ID NO: 18. Vectors and cells that include such nucleic acid molecules are also provided. For example, such nucleic acid molecules can be expressed in a host cell, such as a bacterium or yeast cell (e.g., E. coli), thereby permitting expression of the mutated FGF1 protein. The resulting mutated FGF1 protein can be purified from the cell.

Methods of using the disclosed mutated FGF1 proteins and chimeras (or nucleic acid molecules encoding such), as well as the FGFR1c-binding protein multimers, are provided. As discussed herein, the mutated mature FGF1 protein can include a deletion of at least six contiguous N-terminal amino acids, at least one point mutation, or combinations thereof. For example, such methods include administering a therapeutically effective amount of a disclosed mutated FGF1 protein or chimeric protein including the mutant FGF1 mutant protein, or FGFR1c-binding protein multimer, (such as at least 0.01, at least 0.1 mg/kg, or at least 0.5 mg/kg) (or nucleic acid molecules encoding such) to reduce blood glucose in a mammal, such as a decrease of at least 5%, at least 10%, at least 25% or at least 50%, for example as compared to administration of no mutant FGF1 mutant protein or FGFR1c-binding protein multimer (e.g., administration of PBS).

In one example, the method is a method of reducing fed and fasting blood glucose, improving insulin sensitivity and glucose tolerance, reducing systemic chronic inflammation, ameliorating hepatic steatosis in a mammal, reducing triglycerides, decreasing insulin resistance, reducing hyperinsulinemia, increasing glucose tolerance, reducing hyperglycemia, reducing food intake, or combinations thereof. Such a method can include administering a therapeutically effective amount of a disclosed mutated FGF1 protein or chimeric protein including the mutant FGF1 mutant protein, or FGFR1c-binding protein multimer, (such as at least 0.5 mg/kg) (or nucleic acid molecules encoding such) to reduce fed and fasting blood glucose, improve insulin sensitivity and glucose tolerance, reduce systemic chronic inflammation, ameliorate hepatic steatosis in a mammal, reduce food intake, or combinations thereof.

In one example, the method is a method of treating a metabolic disease (such as metabolic syndrome, diabetes, or obesity) in a mammal. Such a method can include administering a therapeutically effective amount of a disclosed mutated FGF1 protein or chimeric protein including the mutant FGF1 mutant protein, or FGFR1c-binding protein multimer, (such as at least 0.5 mg/kg) (or nucleic acid molecules encoding such) to treat the metabolic disease.

In some examples, the mammal, such as a human, cat or dog, has diabetes. Methods of administration are routine, and can include subcutaneous, intraperitoneal, intramuscular, or intravenous injection.

In some examples, use of the FGF1 mutants or chimeric proteins including a mutant FGF1 mutant protein, or FGFR1c-binding protein multimer, disclosed herein does not lead to (or significantly reduces, such as a reduction of at least 20%, at least 50%, at least 75%, or at least 90%) the adverse side effects observed with thiazolidinediones (TZDs) therapeutic insulin sensitizers, including weight gain, increased liver steatosis and bone fractures (e.g., reduced affects on bone mineral density, trabecular bone architecture and cortical bone thickness).

Provided are methods of reducing fed and fasting blood glucose, improving insulin sensitivity and glucose tolerance, reducing systemic chronic inflammation, ameliorating hepatic steatosis, reducing food intake, or combinations thereof, in a mammal. Such methods can include administering a therapeutically effective amount of a FGF1 mutant and/or FGFR1c-binding protein multimer disclosed herein, including those that further include a β-Klotho-binding peptide and/or FGFR1c-binding peptide, to the mammal, or a nucleic acid molecule encoding the FGF1 mutant or multimer or a vector comprising the nucleic acid molecule, thereby reducing fed and fasting blood glucose, improving insulin sensitivity and glucose tolerance, reducing systemic chronic inflammation, ameliorating hepatic steatosis, reduce one or more non-HDL lipid levels, reduce food intake, or combinations thereof, in a mammal. In some examples, the fed and fasting blood glucose is reduced in the treated subject by at least 10%, at least 20%, at least 30%, at least 50%, at least 75%, or at least 90% as compared to an absence of administration of the FGF1 mutant and/or FGFR1c-binding protein multimer. In some examples, insulin sensitivity and glucose tolerance is increased in the treated subject by at least 10%, at least 20%, at least 30%, at least 50%, at least 75%, or at least 90% as compared to an absence of administration of the FGF1 mutant and/or FGFR1c-binding protein multimer. In some examples, systemic chronic inflammation is reduced in the treated subject by at least 10%, at least 20%, at least 30%, at least 50%, at least 75%, or at least 90% as compared to an absence of administration of the FGF1 mutant and/or FGFR1c-binding protein multimer. In some examples, hepatic steatosis is reduced in the treated subject by at least 10%, at least 20%, at least 30%, at least 50%, at least 75%, or at least 90% as compared to an absence of administration of the FGF1 mutant and/or FGFR1c-binding protein multimer. In some examples, one or more lipids (such as a non-HDL, for example IDL, LDL and/or VLDL) are reduced in the treated subject by at least 10%, at least 20%, at least 30%, at least 50%, at least 75%, or at least 90% as compared to an absence of administration of the FGF1 mutant and/or FGFR1c-binding multimer In some examples, triglyceride and or cholesterol levels are reduced with the FGF1 mutant and/or FGFR1c-binding protein multimer by at least 10%, at least 20%, at least 30%, at least 50%, at least 75%, or at least 90% as compared to an absence of administration of the FGF1 mutant and/or FGFR1c-binding protein multimer. In some examples, the amount of food intake is reduced in the treated subject by at least 10%, at least 20%, at least 30%, at least 50%, at least 75%, or at least 90% as compared to an absence of administration of the FGF1 mutant and/or FGFR1c-binding protein multimer (such as within 12 hours, within 24 hours, or within 48 hours of the treatment, such as within 12 to 24 hours, within 12 to 36 hours, or within 24 to 48 hours). In some examples, combinations of these reductions are achieved.

Mutated FGF1 Proteins

The present disclosure provides mutated FGF1 proteins that can include an N-terminal deletion, one or more point mutations (such as amino acid substitutions, deletions, additions, or combinations thereof), or combinations of N-terminal deletions and point mutations. Such proteins and corresponding coding sequences can be used in the methods provided herein. In some examples, the disclosed FGF1 mutant proteins have reduced mitogenicity compared to mature native FGF1 (e.g., SEQ ID NO: 5), such as a reduction of at least 20%, at least 50%, at least 75% or at least 90%. For example, mutated FGF1 can be mutated to decrease binding affinity for heparin and/or heparan sulfate compared to a native FGF1 protein without the modification. Methods of measuring mitogenicity are known in the art.

In some examples, the mutant FGF1 protein is a truncated version of the mature protein (e.g., SEQ ID NO: 5), which can include for example deletion of at least 5, at least 6, at least 9, at least 10, at least 11, at least 12, at least 13, at least 14, at least 15, or at least 20 consecutive N-terminal amino acids. Thus, in some examples, the mutant FGF1 protein is a truncated version of the mature protein (e.g., SEQ ID NO: 5), such a deletion of the N-terminal 5, 6, 7, 8, 9, 10, 11, 12, 13, 14, 15, 16, 17, 18, 19 or 20 amino acids shown in SEQ ID NO: 5. Examples of N-terminally truncated FGF1 proteins are shown in SEQ ID NOS: 6, 7, 8, 9, 21, 24, 25, 26, 27, 32, 33, 34, 35, 36, 37, 38, 39, 44, 45, 46, 47, 48, 49, 50, 51, 57, 58, 59, 60, 61, 62, 63, 64, 65, 66, 71, 72, 74, 75, 76, 77, 79, 80, 81, 82, 194, 195, 197, 198, 202, 203, 205, 206, 214, 215, 216, 217, 221, 222, 225, 228, 232, and 238. In some examples, the FGF1 mutant includes an N-terminal deletion, but retains a methionine at the N-terminal position. In some examples, such an N-terminally deleted FGF1 protein has reduced mitogenic activity as compared to wild-type mature FGF1 protein.

In some examples, one or more of the deleted N-terminal amino acids are replaced with corresponding amino acids from FGF21 (e.g., see SEQ ID NO: 20), such as at least 1, at least 2, at least 3, at least 4, at least 5, at least 10, at least 15, or at least 20 amino acids from FGF21, such as 1-5, 1-4, 2-4, 4-6, 4-9, 3-10, 1, 2, 3, 4, 5, 6, 7, 8, 9, or 10 corresponding amino acids from FGF21. An example of an FGF1 mutated protein with an N-terminal deletion having four corresponding N-terminal amino acids from FGF21 is shown in SEQ ID NO: 21. The N-terminal residues of FGF1 include an FGFR4 binding site, and FGFR4 signaling is associated with mitogenic activity. In contrast, FGF21 has low affinity for FGFR4. Thus, replacing the FGFR4 binding residues of FGF1 with those from FGF21 (or from another FGF having low affinity for FGFR4, including FGF3, FGF5, FGF7, FGF9 and FGF10) can be used to reduce mitogenicity of the resulting FGF1 mutant protein.

Thus, in some examples, the mutant FGF1 protein includes at least 120 consecutive amino acids from amino acids 5-141 or 5-155 of FGF1 (e.g., of SEQ ID NO: 2 or 4), (which in some examples can include further deletion of N-terminal amino acids 1-20 and/or point mutations, such as substitutions, deletions, or additions). In some examples, the mutant FGF1 protein includes at least 120 consecutive amino acids from amino acids 1-140 of FGF1 (e.g., of SEQ ID NO: 5), (which in some examples can include further deletion of N-terminal amino acids 1-20 and/or point mutations, such as substitutions, deletions, or additions). Thus, in some examples, the mutant FGF1 protein includes at least 120 consecutive amino acids from amino acids 5-141 of FGF1, such as at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, or at least 140 consecutive amino acids from amino acids 5-141 of SEQ ID NO: 2 or 4 (such as 120-130, 120-135, 130-135, 130-140, or 120-140 consecutive amino acids from amino acids 5-141 of SEQ ID NO: 2 or 4). In some examples, the mutant FGF1 protein includes at least 120 or at least 130 consecutive amino acids from amino acids 5-141 of FGF1, such as at least 120 consecutive amino acids from amino acids 5-141 of SEQ ID NO: 2 or 4 or at least 120 consecutive amino acids from SEQ ID NO: 5. Thus, in some examples, the mutant FGF1 protein includes at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, or at least 140 consecutive amino acids from SEQ ID NO: 5 (such as 120-130, 120-135, or 120-140 consecutive amino acids from SEQ ID NO: 5). Examples of least 120 consecutive amino acids from amino acids 5 to 141 of FGF1 that can be used to generate a mutant FGF1 protein includes but are not limited to amino acids 4 to 140 of SEQ ID NO: 5 and the protein sequence shown in any of SEQ ID NOs: 6, 7, 8, and 9.

In some examples, the mutant FGF1 protein is a mutated version of the mature protein (e.g., SEQ ID NO: 5), or a N-terminal truncation of the mature protein (e.g., SEQ ID NOS: 7, 8, 9), such as one containing at least 1, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acid substitutions, such as 1-20, 1-10, 4-8, 5-12, 5-10, 5-25, 1, 2, 3, 4, 5, 6, 7, 8, 9, 10, 11, 12, 13, 14, or 15 amino acid substitutions. For example, point mutations can be introduced into an FGF1 sequence to decrease mitogenicity, increase stability, decrease binding affinity for heparin and/or heparan sulfate (compared to the portion of a native FGF1 protein without the modification), or combinations thereof. Specific exemplary point mutations that can be used are shown above in Table 1, and exemplary combinations are provided in FIGS. 1, 3A-3D, 4A-4B, 5A-5B, 6A-6B, 20, and 27-30.

In some examples, the mutant FGF1 protein includes mutations (such as a substitution or deletion) at one or more of the following positions K9, K10, K12, L14, Y15, C16, H21, R35, Q40, L44, L46, S47, E49, Y55, M67, L73, C83, L86, E87, H93, Y94, N95, H102, A103, E104, K105, N106, F108, V109, L111, K112, K113, C117, K118, R119, G120, P121, R122, F132, L133, P134, L135, such as one or more of K9, K10, K12, K112, K113, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or all 42 of these positions. In some examples the mutant FGF1 protein has as one or more of K9T, K10T, K12V, L14A, Y15F, Y15A, Y15V, C16V, C16A, C16T, C16S, H21Y, R35E, R35V, Q40P, L44F, L46V, S47I, E49Q, E49A, Y55F, Y55S, Y55A, M67I, L73V, C83T, C83S, C83A C83V, E87V, E87A, E87S, E87T, H93G, H93A, Y94V, Y94F, Y94A, N95V, N95A, N95S, N95T, H102Y, A103G, Δ104-106, F108Y, V109L, L111I, K112D, K112E, K112Q, K113Q, K113E, K113D, C117V, C117P, C117T, C117S, C117A, K118N, K118E, K118V, R119G, R119V, R119E, Δ120-122, F132W, L133A, L133S, P134V, L135A, L135S, (wherein the numbering refers to SEQ ID NO: 5), such as 1 to 5, 1 to 10, 2 to 5, 2 to 10, 2 to 20, 5 to 10, 5 to 40, or 5 to 20 of these mutations, such as 1, 2, 3, 4, 5, 6, 7, 8, 9, 10, 11, 12, 13, 14, 15, 16, 17, 18, 19 or 20 of these mutations.

In some examples, the mutant FGF1 protein includes one or more (such as 2, 3, 4, 5 or 6) of K12V, R35E, R35V, L46V, E87V, N95V, C117V/A, K118N, K118E/V, and P134V (wherein the numbering refers to SEQ ID NO: 5). In some examples, the point mutation includes replacing amino acid sequence ILFLPLPV (amino acids 145-152 of SEQ ID NO: 2 and 4) to AAALPLPV (SEQ ID NO: 14), ILALPLPV (SEQ ID NO: 15), ILFAPLPV (SEQ ID NO: 16), or ILFLPAPA (SEQ ID NO: 17). In some examples, such an FGF1 protein with one or more point mutations has reduced mitogenic activity as compared to wild-type mature FGF1 protein. In some examples, the mutant FGF1 protein includes R35E, (wherein the numbering refers to SEQ ID NO: 5). Examples of FGF1 mutant proteins containing point mutations include but are not limited to the protein sequence shown in SEQ ID NOS: 10, 11, 12, 13, 22, 23, 28, 29, 30, 31, 40, 41, 42, 43, 42, 53, 54, 55, 56, 67, 68, 69, 70, 73, 78, 83, 84, 113, 114, 115, 116, 117, 118, 119, 120, 191, 192, 193, 196, 199, 200, 201, 204, 207, 208, 209, 210, 211, 212, 213, 218, 226, 227, 229, 230, 231, 232, 233, 234, 235, 236, and 237.

In some examples, mutations in FGF1 increase the thermostability of mature or truncated native FGF1. For example, mutations can be made at one or more of the following positions. Exemplary mutations that can be used to increase the thermostability of mutated FGF1 include but are not limited to one or more of: K12, C117, P134, L44, C83, F132, M67, L73, V109, L111, A103, R119, Δ104-106, and Δ120-122, Q40, H93, S47, wherein the numbering refers to SEQ ID NO: 5 (e.g., see Xia et al., PLoS One. 7:e48210, 2012). In some examples, thermostability of FGF1 is increased by using one or more of the following mutations: Q40P and S47I or Q40P, S47I, and H93G (or any other combination of these mutations).

In some examples, the FGF1 mutant protein is part of a chimeric protein. For example, any mutant FGF1 protein provided herein can be joined directly or indirectly to the end of a β-Klotho-binding protein, an FGFR1c binding protein, both a β-Klotho-binding protein and an FGFR1c binding protein, FGF19, or FGF21, such as a C-terminal region of FGF 19 or FGF21. For example, at least 10, at least 20, at least 30, at least 40, at least 41, at least 42, at least 43, at least 44, at least 45, at least 46, at least 47, at least 48, at least 49, at least 50 or at least 60 C-terminal amino acids of FGF19 or FGF21 (such as the C-terminal 60, 55, 50, 49, 48, 47, 46, 45, 44, 43, 42, 41, 40, 35, 30, 25, 20, 15 or 10 amino acids) can be part of the chimera. Examples of C-terminal fragments of FGF21 and FGF19 that can be used are shown in SEQ ID NOS: 86 and 100, respectively. Examples of β-Klotho-binding proteins that can be used are shown in SEQ ID NOS: 121, 122, 123, 124, 125, 126, 127, 128, 129, 130, 131, 132, 133, 134, 135, 136, 137, 138, 139, 140, 141, 142, 143, 144, 145 and 146. Examples of FGFR1c-binding proteins that can be used are shown in SEQ ID NOS: 147, 148, 149, 150, 151, 152, 153, 154, 155, 156, 157, 158, 159, 160, 161, 162, 163, 164, 165, 166, and 167. Examples of β-Klotho-binding/FGFR1c-binding protein chimeras that can be directly or indirectly attached to a mutant FGF1 protein are shown in SEQ ID NOS: 168, 169, 170, and 171.

In some examples, the mutant FGF1 protein includes both an N-terminal truncation and point mutations. Specific exemplary FGF1 mutant proteins are shown in SEQ ID NOS: 6-13, 21-84, 113-120, 191-218 and 225-238. In some examples, the FGF1 mutant protein includes at least 80% sequence identity to any of SEQ ID NOS: 6-13, 21-84, 113-120, 191-218 and 225-238. Thus, the FGF1 mutant protein can have at least 90%, at least 95%, at least 96%, at least 97%, at least 98% or at least 99% sequence identity to any of SEQ ID NOS: 6-13, 21-84, 113-120, 191-218 and 225-238. In some examples, the FGF1 mutant protein includes or consists of any of SEQ ID NOS: 6-13, 21-84, 113-120, 191-218 and 225-238. The disclosure encompasses variants of the disclosed FGF1 mutant proteins, such as any of SEQ ID NOS: 6-13, 21-84, and 113-120, 191-218 and 225-238 having 1 to 20, 1 to 15, 1 to 10, 1 to 8, 2 to 10, 1 to 5, 1 to 6, 2 to 12, 3 to 12, 5 to 12, or 5 to 10 mutations, such as conservative amino acid substitutions. Such mutant FGF1 proteins can be used to generate an FGF1 mutant chimera.

In some examples, the mutant FGF1 protein has at its N-terminus a methionine. In some examples, the mutant FGF1 protein is at least 120 amino acids in length, such as at least 125, at least 130, at least 135, at least 140, at least 145, at least 150, at least 155, at least 160, or at least 175 amino acids in length, such as 120-160, 125-160, 130-160, 150-160, 130-200, 130-180, 130-170, or 120-160 amino acids in length.

Exemplary N-terminally truncated FGF1 sequences and FGF1 point mutations that can be used to generate an FGF1 mutant protein are shown in Tables 1 and 2 (as well as those provided in any of SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 and 238). One skilled in the art will appreciate that any N-terminal truncation in Table 2 (as well as those provided in any of SEQ ID NOS: 6, 7, 8, 9, 21, 24, 25, 26, 27, 32, 33, 34, 35, 36, 37, 38, 39, 44, 45, 46, 47, 48, 49, 50, 51, 57, 58, 59, 60, 61, 62, 63, 64, 65, 66, 71, 72, 74, 75, 76, 77, 79, 80, 81, 82, 194, 195, 197, 198, 202, 203, 205, 206, 214, 215, 216, 217, 221, 222, 225, 228, 232, and 238) can be combined with any FGF1 point mutation in Table 1 or Table 2, to generate an FGF1 mutant protein, and that such an FGF1 mutant protein can be used directly or be used as part of a mutant FGF1/β-Klotho-binding protein chimera, mutant FGF1/FGFR1c-binding protein chimera, mutant FGF1/β-Klotho-binding protein/FGFR1c-binding protein chimera, mutant FGF1/FGF21 or mutant FGF1/FGF19 chimera. In addition, mutations can be made to the sequences shown in the Table, such as one or more of the mutations discussed herein (such as 1, 2, 3, 4, 5, 6, 7, 8, 9, 10, 11, 12, 13, 14, 15, 16, 17, 18, 19, or 20 amino acid substitutions, such as conservative amino acid substitutions, deletions, or additions).

TABLE 2

Exemplary mutations that can be used to generate an FGF1 mutant protein

| FGF1 Point Mutations | FGF1 Fragments |
|---|---|
| FNLPPGNYKK PVLLYCSNGG HFLRILPDGT VDGTRDRSDQ HIQLQLSAES VGEVYIKSTE TGQYLAMDTD GLLYGSQTPN EECLFLERLE ENHYVTYISK KHAEKNWFVG LKKNGSCKRG PRTHYGQKAI LFLPLPVSSD (SEQ ID NO: 10) | PPGNYK KPKLLYCSNG GHFLRILPDG TVDGTRDRSD QHIQLQLSAE SVGEVYIKST ETGQYLAMDT DGLLYGSQTP NEECLFLERL EENHYNTYIS KKHAEKNWFV GLKKNGSCKR GPRTHYGQKA ILFLPLPVSSD (SEQ ID NO: 6) |
| FNLPPGNYKK PVLLYCSNGG HFLRILPDGT VDGTRDRSDQ HIQLQVSAES VGEVYIKSTE TGQYLAMDTD GLLYGSQTPN EECLFLVRLE ENHYVTYISK KHAEKNWFVG LKKNGSCKRG PRTHYGQKAI LFLVLPVSSD (SEQ ID NO: 11) | KPKLLYCSNGG HFLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSCKRG PRTHYGQKAI LFLPLPVSSD (SEQ ID NO: 7) |
| NYKK PKLLYCSNGG HFLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSCNRG PRTHYGQKAI LFLPLPVSSD (SEQ ID NO: 12) | LYCSNGG HFLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSCKRG PRTHYGQKAI LFLPLPVSSD (SEQ ID NO: 8) |
| NYKK PKLLYCSNGG HFLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSCERG PRTHYGQKAI LFLPLPVSSD (SEQ ID NO: 13) | KLLYCSNGG HFLRILPDGT VDGTRDRSDQ HIQLQLSAES VGEVYIKSTE TGQYLAMDTD GLLYGSQTPN EECLFLERLE ENHYNTYISK KHAEKNWFVG LKKNGSCKRG PRTHYGQKAI LFLPLPVSSD (SEQ ID NO: 9) |
| | GGQVKPKLLYCSNG GHFLRILPDG TVDGTRDRSD QHIQLQLSAE SVGEVYIKST ETGQYLAMDT DGLLYGSQTP NEECLFLERL |

TABLE 2-continued

Exemplary mutations that can be used to generate an FGF1 mutant protein

| FGF1 Point Mutations | FGF1 Fragments |
|---|---|
| | EENHYNTYIS KKHAEKNWFV GLKKNGSCKR GPRTHYGQKA ILFLPLPVSSD (SEQ ID NO: 21) |

Exemplary mutant FGF1 proteins are provided in SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 113, 114, 115, 116, 117, 118, 119, 120, 191, 192, 193, 194, 195, 196, 197, 198, 199, 200, 201, 202, 203, 204, 205, 206, 207, 208, 209, 210, 211, 212, 213, 214, 215, 216, 217, 218, 225, 226, 227, 228, 229, 230, 231, 232, 233, 234, 235, 236, 237 and 238, mutant FGF1/FGF21 chimeras in SEQ ID NOS: 87, 88, 89, 90, 91, 92, 93, 94, 95, 96, 97, 98, 219, 221, 222 and 223, mutant FGF1/FGF19 chimeras in SEQ ID NOS: 101, 102, 103, 104, 105, 106, 107, 108, 109, 110, 111, 112, 220 and 224, mutant FGF1/β-Klotho-binding protein chimeras in SEQ ID NOS: 173, 174, 175, 177, 178, 179, 181, 182, 183, 185, 186, and 187, and mutant FGF1/FGFR1c-binding protein chimeras in SEQ ID NOS: 188 and 189. One skilled in the art will recognize that minor variations can be made to these sequences, without adversely affecting the function of the protein (such as its ability to reduce blood glucose). For example, variants of the mutant FGF1 proteins include those having at least 90%, at least 95%, at least 96%, at least 97%, at least 98%, or at least 99% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238 (but are not a native FGF1 sequence, e.g., SEQ ID NO: 5), but retain the ability to treat a metabolic disease, or decrease blood glucose in a mammal (such as a mammal with type II diabetes). Thus, variants of SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238 retaining at least 90%, at least 95%, at least 96%, at least 97%, at least 98%, or at least 99% sequence identity are of use in the disclosed methods.

FGF1

Mature forms of FGF1 (such as SEQ ID NO: 2 or 4) can be mutated to control (e.g., reduce) the mitogenicity of the protein (for example by mutating the nuclear localization sequence (NLS) or the heparan sulfate binding region or both) and to provide glucose-lowering ability to the protein. Mutations can also be introduced into a wild-type mature FGF1 sequence that affects the stability and receptor binding selectivity of the protein.

Exemplary full-length FGF1 proteins are shown in SEQ ID NOS: 2 (human) and 4 (mouse). In some examples, FGF1 includes SEQ ID NO: 2 or 4, but without the N-terminal methionine (thus resulting in a 154 aa FGF1 protein). In addition, the mature/active form of FGF1 is one where a portion of the N-terminus is removed, such as the N-terminal 15, 16, 20, or 21 amino acids from SEQ ID NO: 2 or 4. Thus, in some examples the active form of FGF1 comprises or consists of amino acids 16-155 or 22-155 of SEQ ID NO: 2 or 4 (e.g., see SEQ ID NO: 5). In some examples, the mature form of FGF1 that can be mutated includes SEQ ID NO: 5 with a methionine added to the N-terminus (wherein such a sequence can be mutated as discussed herein). Thus, the mutated mature FGF1 protein can include an N-terminal truncation.

Mutations can be introduced into a wild-type FGF1 (such as SEQ ID NO: 2, 4, or 5). In some examples, multiple types of mutations disclosed herein are made to the FGF1 protein. Although mutations below are noted by a particular amino acid for example in SEQ ID NO: 2, 4 or 5, one skilled in the art will appreciate that the corresponding amino acid can be mutated in any FGF1 sequence. For example, Q40 of SEQ ID NO: 5 corresponds to Q55 of SEQ ID NO: 2 and 4.

In one example, mutations are made to the N-terminal region of FGF1 (such as SEQ ID NO: 2, 4 or 5), such as deletion of the first 14, 15, 16, 17, 18, 19, 20, 21, 22, 23, 24, 25, 26, 27, 28, 29, or 30 amino acids of SEQ ID NO: 2 or 4 (such as deletion of at least the first 14 amino acids of SEQ ID NO: 2 or 4, such as deletion of at least the first 15, at least 16, at least 20, at least 25, or at least 29 amino acids of SEQ ID NO: 2 or 4), deletion of the first 8, 9, 10, 11, 12, 13, 14, 15, 16, 17, 18, 19, or 20 amino acids of SEQ ID NO: 5 (e.g., see SEQ ID NOS: 7, 8 and 9 and FIG. 1).

Mutations can be made to FGF1 (such as SEQ ID NO: 2, 4 or 5) to reduce its mitogenic activity. In some examples, such mutations reduce mitogenic activity by at least 50%, at least 60%, at least 70%, at least 75%, at least 80%, at least 90%, at least 92%, at least 95%, at least 98%, at least 99%, or even complete elimination of detectable mitogenic activity, as compared to a native FGF1 protein without the mutation. Methods of measuring mitogenic activity are known in the art, such as thymidine incorporation into DNA in serum-starved cells (e.g., NIH 3T3 cells) stimulated with the mutated FGF1, methylthiazoletetrazolium (MTT) assay (for example by stimulating serum-starved cells with mutated FGF1 for 24 hr then measuring viable cells), cell number quantification or BrdU incorporation. In some examples, the assay provided by Fu et al., *World J. Gastroenterol.* 10:3590-6, 2004; Klingenberg et al., *J. Biol. Chem.* 274:18081-6, 1999; Shen et al., *Protein Expr Purif.* 81:119-25, 2011, or Zou et al., *Chin. Med. J.* 121:424-429, 2008 is used to measure mitogenic activity. Examples of such mutations include, but are not limited to K12V, R35E, L46V, E87V, N95V, K12V/N95V (e.g., see SEQ ID NO: 10, which can also include a methionine on its N-terminus), and Lys12Val/Pro134Val, Lys12Val/Leu46Val/Glu87Val/Asn95Val/Pro134Val (e.g., see SEQ ID NO: 11, which can also include a methionine on its N-terminus) (wherein the numbering refers to the sequence shown SEQ ID NO: 5). In some examples, a portion of contiguous N-terminal residues are removed, such as amino acids 1-9 of SEQ ID NO: 5, to produce a non-mitogenic form of FGF1. An example is shown in SEQ ID NO: 9.

Mutations that reduce the heparan binding affinity (such as a reduction of at least 10%, at least 20%, at least 50%, or at least 75%, e.g., as compared to a native FGF1 protein without the mutation), can also be used to reduce mitogenic activity, for example by substituting heparan binding residues from a paracrine FGFs into FGF1. In some examples, mitogenicity is reduced or eliminated by deleting the N-terminal region of FGF1 (such as the region that binds FGF4) and replacing some or all of the amino acids deleted with corresponding residues from FGF21.

Mutations can also be introduced into one or both nuclear localization sites (NLS1, amino acids 24-27 of SEQ ID NO: 2 and NLS2, amino acids 115-128 of SEQ ID NO: 4) of FGF1, for example to reduce mitogenicity, as compared to a native FGF1 protein without the mutation. Examples of NLS mutations that can be made to FGF1 include but are not limited to: deleting or mutating all or a part of NLS1 (such as deleting or mutating the lysines), deleting or mutating the lysines in NLS2 such as $^{115}$KK . . . $^{127}$KK . . . , or combinations thereof (wherein the numbering refers to the sequence shown SEQ ID NO: 2). For example, one or more of 24K, 25K, 27K, 115K, 127K or 128K (wherein the numbering refers to the sequence shown SEQ ID NO: 2) or can be mutated (for example changed to an alanine or deleted). Particular examples of such mutations that can be made to the heparan binding site in the NLS2 (KKN . . . KR) domain are shown in SEQ ID NOS: 12 and 13 (K118N or K118E, respectively, wherein numbering refers to SEQ ID NO: 5).

Mutations can be introduced into the phosphorylation site of FGF1, for example to create a constitutively active or inactive mutant to affect nuclear signaling.

In some examples, mutations are introduced into the FGF1 nuclear export sequence, for example to decrease the amount of FGF1 in the nucleus and reduce its mitogenicity as measured by thymidine incorporation assays in cultured cells (e.g., see Nilsen et al., *J. Biol. Chem.* 282(36):26245-56, 2007). Mutations to the nuclear export sequence decrease FGF1-induced proliferation (e.g., see Nilsen et al., *J. Biol. Chem.* 282(36):26245-56, 2007). Methods of measuring FGF1 degradation are known in the art, such as measuring [$^{35}$S]Methionine-labeled FGF1 or immunoblotting for steady-state levels of FGF1 in the presence or absence of proteasome inhibitors. In one example, the assay provided by Nilsen et al., *J. Biol. Chem.* 282(36):26245-56, 2007 or Zakrzewska et al., *J. Biol. Chem.* 284:25388-403, 2009 is used to measure FGF1 degradation.

The FGF1 nuclear export sequence includes amino acids 145-152 of SEQ ID NO: 2 and 4 or amino acids 130-137 of SEQ ID NO: 5. Examples of FGF1 nuclear export sequence mutations that can be made to include but are not limited to changing the sequence ILFLPLPV (amino acids 145-152 of SEQ ID NO: 2 and 4) to AAALPLPV (SEQ ID NO: 14), ILALPLPV (SEQ ID NO: 15), ILFAPLPV (SEQ ID NO: 16), or ILFLPAPA (SEQ ID NO: 17).

In one example, mutations are introduced to improve stability of FGF1. In some examples, the sequence NYK-KPKL (amino acids 22-28 of SEQ ID NO: 2) is not altered, and in some examples ensures for structural integrity of FGF1 and increases interaction with the FGF1 receptor.

Methods of measuring FGF1 stability are known in the art, such as measuring denaturation of FGF1 or mutants by fluorescence and circular dichroism in the absence and presence of a 5-fold molar excess of heparin in the presence of 1.5 M urea or isothermal equilibrium denaturation by guanidine hydrochloride. In one example, the assay provided by Dubey et al., *J. Mol. Biol.* 371:256-268, 2007 is used to measure FGF1 stability. Examples of mutations that can be used to increase stability of the protein include, but are not limited to, one or more of Q40P, S47I and H93G (wherein the numbering refers to the sequence shown SEQ ID NO: 5).

In one example, mutations are introduced to improve the thermostability of FGF1, such as an increase of at least 10%, at least 20%, at least 50%, or at least 75%, as compared to a native FGF1 protein without the mutation (e.g., see Xia et al., *PLoS One.* 2012; 7(11):e48210 and Zakrzewska, *J Biol Chem.* 284:25388-25403, 2009). In one example, mutations are introduced to increase protease resistance of FGF1 (e.g., see Kobielak et al., *Protein Pept Lett.* 21(5):434-43, 2014). Other mutations that can be made to FGF1 include those mutations provided in Lin et al., *J Biol Chem.* 271(10):5305-8, 1996).

In some examples, the mutant FGF1 protein or chimera is PEGylated at one or more positions, such as at N95 (for example see methods of Niu et al., *J. Chromatog.* 1327:66-72, 2014, herein incorporated by reference). Pegylation consists of covalently linking a polyethylene glycol group to surface residues and/or the N-terminal amino group. N95 is known to be involved in receptor binding, thus is on the surface of the folded protein. As mutations to surface exposed residues could potentially generate immunogenic sequences, pegylation is an alternative method to abrogate a specific interaction. Pegylation is an option for any surface exposed site implicated in the receptor binding and/or proteolytic degradation. Pegylation can "cover" functional amino acids, e.g. N95, as well as increase serum stability.

In some examples, the mutant FGF1 protein or chimera includes an immunoglobin FC domain (for example see Czajkowsky et al., *EMBO Mol. Med.* 4:1015-28, 2012, herein incorporated by reference). The conserved FC fragment of an antibody can be incorporated either n-terminal or c-terminal of the mutant FGF1 protein or chimera, and can enhance stability of the protein and therefore serum half-life. The FC domain can also be used as a means to purify the proteins on protein A or Protein G sepharose beads. This makes the FGF1 mutants having heparin binding mutations easier to purify.

Variant Sequences

Variant FGF1 proteins, including variants of the sequences shown in Tables 1 and 2, and variants of SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, and 238, can contain one or more mutations, such as a single insertion, a single deletion, a single substitution. In some examples, the mutant FGF1 protein includes 1-20 insertions, 1-20 deletions, 1-20 substitutions, or any combination thereof (e.g., single insertion together with 1-19 substitutions). In some examples, the disclosure provides a variant of any disclosed mutant FGF1 protein having 1, 2, 3, 4, 5, 6, 7, 8, 9, 10, 11, 12, 13, 14, 15, 16, 17, 18, 19 or 20 amino acid changes. In some examples, SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, includes 1-8 insertions, 1-15 deletions, 1-10 substitutions, or any combination thereof (e.g., 1-15, 1-4, or 1-5 amino acid deletions together with 1-10, 1-5 or 1-7 amino acid substitutions). In some examples, the disclosure provides a variant of any of SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 and 238, having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes. In one example, such variant peptides are produced by manipulating the nucleotide sequence encoding a peptide using standard procedures such as site-directed mutagenesis or PCR. Such variants can also be chemically synthesized. Similar changes can be made to the FGFR1c dimer of SEQ ID NO: 190 (1, 2, 3, 4, 5, 6, 7, 8, 9, 10, 11, 12, 13, 14, 15, 16, 17, 18, 19 or 20 amino acid changes).

One type of modification or mutation includes the substitution of amino acids for amino acid residues having a similar biochemical property, that is, a conservative substitution (such as 1-4, 1-8, 1-10, or 1-20 conservative substitutions). Typically, conservative substitutions have little to no impact on the activity of a resulting peptide. For example, a conservative substitution is an amino acid substitution in SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, that does not substantially affect the ability of the peptide to decrease blood glucose in a mammal. An alanine scan can be used to identify which amino acid residues in a mutant FGF1 protein, such as SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, can tolerate an amino acid substitution. In one example, the blood glucose lowering activity of FGF1, or any of SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, is not altered by more than 25%, for example not more than 20%, for example not more than 10%, when an alanine, or other conservative amino acid, is substituted for 1-4, 1-8, 1-10, or 1-20 native amino acids. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed by analyzing the function of the mutant FGF1 protein, such as any of SEQ ID NOS: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, by analyzing the ability of the variant protein to decrease blood glucose in a mammal.

Generation of Proteins

Isolation and purification of recombinantly expressed mutated FGF1 proteins can be carried out by conventional means, such as preparative chromatography and immunological separations. Once expressed, mutated FGF1 proteins can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes.

In addition to recombinant methods, mutated FGF1 proteins disclosed herein can also be constructed in whole or in part using standard peptide synthesis. In one example, mutated FGF1 proteins are synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Mutated FGF1 and FGFR1c-Binding Protein Multimer Nucleic Acid Molecules and Vectors Nucleic acid molecules encoding a mutated FGF1 protein are encompassed by this disclosure. Based on the genetic code, nucleic acid sequences coding for any mutated FGF1 sequence, such as those generated using the sequences shown in Tables 1 and 2, can be routinely generated. Similarly, mutant FGF1/β-Klotho-binding, mutant FGF1/FGFR1c-binding, mutant FGF1/β-Klotho-binding/FGFR1c-binding, mutant FGF1/FGF21 or mutant FGF1/FGF19 chimeras can be generated using routine methods based on the amino acid sequences provided herein. In some examples, such a sequence is optimized for expression in a host cell, such as a host cell used to express the mutant FGF1 protein. Also provided are nucleic acid molecules encoding an FGFR1c-binding protein multimer, such as those encoding multimers of any of SEQ ID NOS: 147, 148, 149, 150, 151, 152, 153, 154, 155, 156, 157, 158, 159, 160, 161, 162, 163, 164, 165, 166, 167, or 190, as well as cells and vectors including such nucleic acids.

In one example, a nucleic acid sequence codes for a mutant FGF1 protein (or chimera including such protein) having at least 60%, at least 70%, at least 75%, at least 80%, at least 90%, at least 92%, at least 95%, at least 96%, at least 97%, at least 99% or at least 99% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238, can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same mutant FGF1 protein sequence. In one example, a mutant FGF1 nucleic acid sequence has at least 70%, at least 80%, at least 85%, at least 90%, at least 92%, at least 95%, at least 98%, or at least 99% sequence identity to SEQ ID NO: 18.

In one example, a nucleic acid sequence codes for a FGFR1c-binding protein multimer made using peptide sequences having at least 60%, at least 70%, at least 75%, at least 80%, at least 90%, at least 92%, at least 95%, at least 96%, at least 97%, at least 99% or at least 99% sequence identity to SEQ ID NO: 147, 148, 149, 150, 151, 152, 153, 154, 155, 156, 157, 158, 159, 160, 161, 162, 163, 164, 165, 166, 167, or 190.

Nucleic acid molecules include DNA, cDNA and RNA sequences which encode a mutated FGF1 peptide. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3$^{rd}$ Edition, W.H. 5 Freeman and Co., NY).

Codon preferences and codon usage tables for a particular species can be used to engineer isolated nucleic acid molecules encoding a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) that take advantage of the codon usage preferences of that particular species. For example, the FGFR1c-binding protein multimers and mutated FGF1 proteins disclosed herein can be designed to have codons that are preferentially used by a particular organism of interest.

A nucleic acid encoding a FGFR1c-binding protein multimer or a mutant FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A wide variety of cloning and in vitro amplification methodologies are well known to persons skilled in the art. In addition, nucleic acids encoding sequences encoding a FGFR1c-binding protein multimer or a mutant FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be prepared by cloning techniques. Examples of appropriate cloning and sequencing techniques, and instructions sufficient to direct persons of skill through cloning are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be prepared by any suitable method including, for example, cloning of appropriate sequences or by direct chemical synthesis by methods such as the phosphotriester method of Narang et al., *Meth. Enzymol.* 68:90-

99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

In one example, a mutant FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) is prepared by inserting the cDNA which encodes the mutant FGF1 protein into a vector. The insertion can be made so that the mutant FGF1 protein is read in frame so that the mutant FGF1 protein is produced. Similar methods can be used for a FGFR1c-binding protein multimer.

The mutated FGF1 protein nucleic acid coding sequence (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect, plant and mammalian organisms. Methods of expressing DNA sequences having eukaryotic or viral sequences in prokaryotes are well known in the art. Biologically functional viral and plasmid DNA vectors capable of expression and replication in a host are known in the art. The vector can encode a selectable marker, such as a thymidine kinase gene. Similar methods can be used for a FGFR1c-binding protein multimer.

Nucleic acid sequences encoding a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be operatively linked to expression control sequences. An expression control sequence operatively linked to a FGFR1c-binding protein multimer or mutated FGF1 protein coding sequence is ligated such that expression of the FGFR1c-binding protein multimer or mutant FGF1 protein coding sequence is achieved under conditions compatible with the expression control sequences. The expression control sequences include, but are not limited to appropriate promoters, enhancers, transcription terminators, a start codon (i.e., ATG) in front of a FGFR1c-binding protein multimer or mutated FGF1 protein-encoding gene, splicing signal for introns, maintenance of the correct reading frame of that gene to permit proper translation of mRNA, and stop codons.

In one embodiment, vectors are used for expression in yeast such as *S. cerevisiae, P. pastoris*, or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2µ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation. The nucleic acid molecules encoding a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can also be designed to express in insect cells.

A FGFR1c-binding protein multimer or mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast cell lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared that encode a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238). Exemplary viral vectors include polyoma, SV40, adenovirus, vaccinia virus, adeno-associated virus, herpes viruses including HSV and EBV, Sindbis viruses, alphaviruses and retroviruses of avian, murine, and human origin. Baculovirus (*Autographa californica* multinuclear polyhedrosis virus; AcMNPV) vectors are also known in the art, and may be obtained from commercial sources. Other suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

Viral vectors that encode a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can include at least one expression control element operationally linked to the nucleic acid sequence encoding the FGFR1c-binding protein multimer or mutated FGF1 protein. The expression control elements are inserted in the vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the mutated FGF1 protein in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the FGFR1c-binding protein multimer or mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) are known. Such techniques involve, for example, homologous recombination between the viral DNA sequences flanking the DNA sequence in a donor plasmid and homologous sequences present in the parental virus. The vector can be constructed for example by steps known in the art, such as by using a unique restriction endonuclease site that is naturally present or artificially inserted in the parental viral vector to insert the heterologous DNA.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a FGFR1c-binding protein multimer or a mutated FGF1 protein (such as one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing mutated FGF1 proteins in cells including higher eukaryotic cells such as the COS, CHO, HeLa and myeloma cell lines.

Cells Expressing Mutated FGF1 Proteins or FGFR1c-Binding Protein Multimers

A nucleic acid molecule encoding a mutated FGF1 protein disclosed herein (or chimeric protein including a mutant FGF1), or an FGFR1c-binding protein multimer disclosed herein, can be used to transform cells and make transformed cells. Thus, cells expressing a FGFR1c-binding protein multimer (such as a FGFR1c-binding protein multimer made using peptides having at least 60%, at least 70%, at least 75%, at least 80%, at least 90%, at least 92%, at least 95%, at least 96%, at least 97%, at least 99%, at least 99%, or 100% sequence identity to SEQ ID NO: 147, 148, 149, 150, 151, 152, 153, 154, 155, 156, 157, 158, 159, 160, 161, 162, 163, 164, 165, 166, 167, or 190) or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), are disclosed. Cells expressing a mutated FGF1 protein disclosed herein, or expressing an FGFR1c-binding protein multimer, can be eukaryotic or prokaryotic. Examples of such cells include, but are not limited to bacteria, archea, plant, fungal, yeast, insect, and mammalian cells, such as *Lactobacillus, Lactococcus, Bacillus* (such as *B. subtilis*), *Escherichia* (such as *E. coli*), *Clostridium, Saccharomyces* or *Pichia* (such as *S. cerevisiae* or *P. pastoris*), *Kluyveromyces lactis, Salmonella typhimurium*, SF9 cells, C129 cells, 293 cells, *Neurospora*, and immortalized mammalian myeloid and lymphoid cell lines.

Cells expressing a mutated FGF1 protein or an FGFR1c-binding protein multimer are transformed or recombinant cells. Such cells can include at least one exogenous nucleic acid molecule that encodes a mutated FGF1 protein, for example one encoding a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238. Such cells can include at least one exogenous nucleic acid molecule that encodes an FGFR1c-binding protein multimer, such as one encoding a protein made using two or more peptides having at least 90%, at least 95%, at least 95%, at least 96%, at least 97%, at least 98%, at least 99% or 100% sequence identity to SEQ ID NO: 147, 148, 149, 150, 151, 152, 153, 154, 155, 156, 157, 158, 159, 160, 161, 162, 163, 164, 165, 166, 167, or 190. It is understood that all progeny may not be identical to the parental cell since there may be mutations that occur during replication. Methods of stable transfer, meaning that the foreign DNA is continuously maintained in the host cell, are known in the art.

Transformation of a host cell with recombinant DNA may be carried out by conventional techniques as are well known. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. Techniques for the transformation of yeast cells, such as polyethylene glycol transformation, protoplast transformation and gene guns are also known in the art.

Pharmaceutical Compositions that Include Mutated FGF1 Molecules and/or FGFR1c-Binding Protein Multimers Pharmaceutical compositions that include a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) or a nucleic acid encoding these proteins, can be formulated with an appropriate pharmaceutically acceptable carrier, depending upon the particular mode of administration chosen. Similarly, the disclosure provides pharmaceutical compositions that include one or more FGFR1c-binding protein multimers, such as multimers of SEQ ID NO: 147, 148, 149, 150, 151, 152, 153, 154, 155, 156, 157, 158, 159, 160, 161, 162, 163, 164, 165, 166, or 167, such as SEQ ID NO: 190 (or sequences having at least 90%, at least 95%, at least 95%, at least 96%, at least 97%, at least 98%, at least 99% or 100% sequence identity to SEQ ID NO: 147, 148, 149, 150, 151, 152, 153, 154, 155, 156, 157, 158, 159, 160, 161, 162, 163, 164, 165, 166, 167, or 190).

In some embodiments, the pharmaceutical composition consists essentially of an FGFR1c-binding protein multimer or a mutated FGF1 protein (such as a protein generated using the sequences shown in Table 1, the sequences in any of SEQ ID NOS: 21-84, or a protein having at least 90%, at least 95%, at least 95%, at least 96%, at least 97%, at least 98%, at least 99% or 100% sequence identity to any of SEQ ID NOS: 6-13, 21-84, 87-98, 101-112, 173-175, 177-179, 181-183, 185-189, and 191-238) (or a nucleic acid encoding such a protein) and a pharmaceutically acceptable carrier. In these embodiments, additional therapeutically effective agents are not included in the compositions.

In other embodiments, the pharmaceutical composition includes an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) (or a nucleic acid encoding such a protein) and a pharmaceutically acceptable carrier. Additional therapeutic agents, such as agents for the treatment of diabetes, can be included. Thus, the pharmaceutical compositions can include a therapeutically effective amount of another agent. Examples of such agents include, without limitation, anti-apoptotic substances such as the Nemo-Binding Domain and compounds that induce proliferation such as cyclin dependent kinase (CDK)-6, CDK-4 and cyclin D1. Other active agents can be utilized, such as antidiabetic agents for example, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570, aleglitazar, farglitazar, muraglitazar, tesaglitazar, and TZD) and PPAR-γ antagonists, PPAR-gamma/alpha modulators (such as KRP 297), alpha-glucosidase inhibitors (e.g., acarbose, voglibose), dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g. exendin-4) or amylin. Additional examples include immunomodulatory factors such as anti-CD3 mAb, growth factors such as HGF, VEGF, PDGF, lactogens, and PTHrP. In some examples, the pharmaceutical compositions containing a mutated FGF1 protein can further include a therapeutically effective amount of other FGFs, such as FGF21, FGF19, or both, heparin, or combinations thereof.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

In some embodiments, an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Patent Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, 2$^{nd}$ ed., CRC Press, 2006).

In other embodiments, an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid) (PLGA), poly(ethylene glycol). Exemplary low molecular weight surfactants include sodium dodecyl sulfate, hexadecyl pyridinium chloride, polysorbates, sorbitans, poly(oxyethylene)alkyl ethers, poly(oxyethylene)alkyl esters, and combinations thereof. In one example, the nanodispersion system includes PVP and ODP or a variant thereof (such as 80/20 w/w). In some examples, the nanodispersion is prepared using the solvent evaporation method, see for example, Kanaze et al., *Drug Dev. Indus. Pharm.* 36:292-301, 2010; Kanaze et al., *J. Appl. Polymer Sci.* 102:460-471, 2006. With regard to the administration of nucleic acids, one approach to administration of nucleic acids is direct treatment with plasmid DNA, such as with a mammalian expression plasmid. As described above, the nucleotide sequence encoding an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be placed under the control of a promoter to increase expression of the protein.

Many types of release delivery systems are available and known. Examples include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or polynucleotide encoding this protein, is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as diabetes. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with nucleic acids (see U.S. Pat. No. 6,218,371). For use in vivo, nucleic acids and peptides are preferably relatively resistant to degradation (such as via endo- and exo-nucleases). Thus, modifications of the disclosed mutated FGF1 proteins, such as the inclusion of a C-terminal amide, can be used.

The dosage form of the pharmaceutical composition can be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The pharmaceutical compositions that include an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be formulated in unit dosage form, suitable for individual administration of precise dosages. In one non-limiting example, a unit dosage contains from about 1 mg to about 1 g of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), such as about 10 mg to about 100 mg, about 50 mg to about 500 mg, about 100 mg to about 900 mg, about 250 mg to about 750 mg, or about 400 mg to about 600 mg. In other examples, a therapeutically effective amount of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) is about 0.01 mg/kg to about 50 mg/kg, for example, about 0.5 mg/kg to about 25 mg/kg or about 1 mg/kg to about 10 mg/kg. In other examples, a therapeutically effective amount of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) is about 1 mg/kg to about 5 mg/kg, for example about 2 mg/kg. In a particular example, a therapeutically effective amount of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) includes about 1 mg/kg to about 10 mg/kg, such as about 2 mg/kg.

Treatment Using Mutated FGF1 or FGFR1c-Binding Protein Multimers

The disclosed FGFR1c-binding protein multimers (such as a protein made using two or more peptides having at least 90%, at least 95%, at least 95%, at least 96%, at least 97%, at least 98%, at least 99% or 100% sequence identity to SEQ ID NO: 147, 148, 149, 150, 151, 152, 153, 154, 155, 156, 157, 158, 159, 160, 161, 162, 163, 164, 165, 166, 167, or 190) and mutated FGF1 proteins and chimeras (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or nucleic acids encoding such proteins, can be administered to a subject, for example to treat a metabolic disease, for example by reducing fed and fasting blood glucose, improving insulin sensitivity and glucose tolerance, reducing systemic chronic inflammation, ameliorating hepatic steatosis in a mammal, reducing food intake, or combinations thereof.

The compositions of this disclosure that include an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) (or nucleic acids encoding these molecules) can be administered to humans or other animals by any means, including orally, intravenously, intramuscularly, intraperitoneally, intranasally, intradermally, intrathecally, subcutaneously, via inhalation or via suppository. In one non-limiting example, the composition is administered via injection. In some examples, site-specific administration of the composition can be used, for example by administering an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) (or a nucleic acid encoding these molecules) to pancreas tissue (for example by using a pump, or by implantation of a slow release form at the site of the pancreas). The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly or monthly etc.) doses over a period of a few days to months, or even years. For example, a therapeutically effective amount of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be administered in a single dose, twice daily, weekly, or in several doses, for example daily, or during a course of treatment. In a particular non-limiting example, treatment involves once daily dose or twice daily dose.

The amount of an FGFR1c-binding protein multimer or mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) administered can be dependent on the subject being treated, the severity of the affliction, and the manner of administration, and is best left to the judgment of the prescribing clinician. Within these bounds, the formulation to be administered will contain a quantity of the FGFR1c-binding protein multimer or mutated FGF1 protein in amounts effective to achieve the desired effect in the subject being treated. A therapeutically effective amount of an FGFR1c-binding protein multimer or mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be the amount of the mutant FGF1 protein or FGFR1c-binding protein multimer, or a nucleic acid encoding these molecules that is necessary to treat diabetes or reduce blood glucose levels (for example a reduction of at least 5%, at least 10% or at least 20%, for example relative to no administration of the mutant FGF1 or FGFR1c-binding protein multimer).

When a viral vector is utilized for administration of an nucleic acid encoding an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), the recipient can receive a dosage of each recombinant virus in the composition in the range of from about $10^5$ to about $10^{10}$ plaque forming units/mg mammal, although a lower or higher dose can be administered. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the pancreases in a pharmaceutically acceptable carrier.

Generally, the quantity of recombinant viral vector, carrying the nucleic acid sequence of an FGFR1c-binding protein multimer or the mutated FGF1 protein to be administered (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) is based on the titer of virus particles. An exemplary range to be administered is $10^5$ to $10^{10}$ virus particles per mammal, such as a human.

In some examples, an FGFR1c-binding protein multimer or mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or a nucleic acid encoding the FGFR1c-binding protein multimer or the mutated FGF1 protein, is administered in combination (such as sequentially or simultaneously or contemporaneously) with one or more other agents, such as those useful in the treatment of diabetes or insulin resistance.

Anti-diabetic agents are generally categorized into six classes: biguanides (e.g., metformin); thiazolidinediones (including rosiglitazone (Avandia®), pioglitazone (Actos®), rivoglitazone, and troglitazone); sulfonylureas; inhibitors of carbohydrate absorption; fatty acid oxidase inhibitors and anti-lipolytic drugs; and weight-loss agents. Any of these agents can also be used in the methods disclosed herein. The anti-diabetic agents include those agents disclosed in *Diabetes Care,* 22(4):623-634. One class of anti-diabetic agents of use is the sulfonylureas, which are believed to increase secretion of insulin, decrease hepatic glucogenesis, and increase insulin receptor sensitivity. Another class of anti-diabetic agents use the biguanide antihyperglycemics, which decrease hepatic glucose production and intestinal absorption, and increase peripheral glucose uptake and utilization, without inducing hyperinsulinemia.

In some examples, an FGFR1c-binding protein multimer or mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) can be administered in combination with effective doses of anti-diabetic agents (such as biguanides, thiazolidinediones, or incretins) and/or lipid lowering compounds (such as statins or fibrates). The term "administration in combination" or "co-administration" refers to both concurrent and sequential administration of the active agents. Administration of an FGFR1c-binding protein multimer or mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 2388) or a nucleic acid encoding such an FGFR1c-binding protein multimer or a mutant FGF1 protein, may also be in combination with lifestyle modifications, such as increased physical activity, low fat diet, low sugar diet, and smoking cessation.

Additional agents that can be used in combination with the disclosed FGFR1c-binding protein multimers and mutated FGF1 proteins include, without limitation, anti-apoptotic substances such as the Nemo-Binding Domain and compounds that induce proliferation such as cyclin dependent kinase (CDK)-6, CDK-4 and Cyclin D1. Other active agents can be utilized, such as antidiabetic agents for example, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g., acarbose, voglibose), Dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMG-CoA) reductase inhibitors (such as a statin), insulin and insulin analogues, GLP-1 and GLP-1 analogues (e.g., exendin-4) or amylin. In some embodiments the agent is an immunomodulatory factor such as anti-CD3 mAb, growth factors such as HGF, vascular endothelial growth factor (VEGF), platelet derived growth factor (PDGF), lactogens, or parathyroid hormone related protein (PTHrP). In one example, the mutated FGF1 protein is administered in combination with a therapeutically effective amount of another FGF, such as FGF21, FGF19, or both, heparin, or combinations thereof.

In some embodiments, methods are provided for treating diabetes or pre-diabetes in a subject by administering a therapeutically effective amount of a composition including an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or a nucleic acid encoding the FGFR1c-binding protein multimer or the mutated FGF1 protein, to the subject. The subject can have diabetes type I or diabetes type II. The subject can be any mammalian subject, including human subjects and veterinary subjects such as cats and dogs. The subject can be a child or an adult. The subject can also be administered insulin. The method can include measuring blood glucose levels.

In some examples, the method includes selecting a subject with diabetes, such as type I or type II diabetes, or a subject at risk for diabetes, such as a subject with pre-diabetes. These subjects can be selected for treatment with the disclosed FGFR1c-binding protein multimer or mutated FGF1 proteins (such as a protein g generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238) or nucleic acid molecules encoding such.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care* 33:S11-61, 2010).

In some examples, the subject treated with the disclosed compositions and methods has HbA1C of greater than 6.5% or greater than 7%.

In some examples, treating diabetes includes one or more of increasing glucose tolerance (such as an increase of at least 5%, at least 10%, at least 20%, or at least 50%, for example relative to no administration of the FGFR1c-binding protein multimer or mutant FGF1), decreasing insulin resistance (for example, decreasing plasma glucose levels, decreasing plasma insulin levels, or a combination thereof, such as decreases of at least 5%, at least 10%, at least 20%, or at least 50%, for example relative to no administration of the FGFR1c-binding protein multimer or mutant FGF1), decreasing serum triglycerides (such as a decrease of at least 10%, at least 20%, or at least 50%, for example relative to no administration of the FGFR1c-binding protein multimer or mutant FGF1), decreasing free fatty acid levels (such as a decrease of at least 5%, at least 10%, at least 20%, or at least 50%, for example relative to no administration of the FGFR1c-binding protein multimer or mutant FGF1), and decreasing HbA1c levels in the subject (such as a decrease of at least 0.5%, at least 1%, at least 1.5%, at least 2%, or at least 5% for example relative to no administration of the FGFR1c-binding protein multimer or mutant FGF1). In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or nucleic acid molecule encoding such, treats a metabolic disease, such as diabetes (such as type II diabetes) or pre-diabetes, by decreasing of HbA1C, such as a reduction of at least 0.5%, at least 1%, or at least 1.5%, such as a decrease of 0.5% to 0.8%, 0.5% to 1%, 1 to 1.5% or 0.5% to 2%. In some examples the target for HbA1C is less than about 6.5%, such as about 4-6%, 4-6.4%, or 4-6.2%. In some examples, such target levels are achieved within about 26 weeks, within about 40 weeks, or within about 52 weeks. Methods of measuring HbA1C are routine, and the disclosure is not limited to particular methods. Exemplary methods include HPLC, immunoassays, and boronate affinity chromatography.

In some examples, administration of an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or nucleic acid molecule encoding such, treats diabetes or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, at least 15%, at least 20%, at least 25%, at least 30%, at least 35%, or more) as compared with a control (such as no administration of any of insulin, an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or a nucleic acid molecule encoding such). In particular examples, a decrease in blood glucose level is determined relative to the starting blood glucose level of the subject (for example, prior to treatment with an FGFR1c-binding protein multimer or a mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or nucleic acid molecule encoding such). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In other embodiments, the disclosed methods include comparing one or more indicator of diabetes (such as glucose tolerance, triglyceride levels, free fatty acid levels, or HbA1c levels) to a control (such as no administration of any of insulin, any FGFR1c-binding protein multimer or any mutated FGF1 protein (such as a protein generated using the sequences shown in Tables 1 and 2, the sequences in any of SEQ ID NOS: 21-84, 113-120 and 191-238 or those encoding a protein having at least 90%, at least 95%, at least 95%, at least 96%, at least 97%, at least 98%, at least 99% or 100% sequence identity to SEQ ID NO: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 or 238), or a nucleic acid molecule encoding such), wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

The disclosure is illustrated by the following non-limiting Examples.

Example 1

Preparation of Mutated FGF1 Proteins

Mutated FGF1 proteins can be made using known methods (e.g., see Xia et al., *PLoS One.* 7(11):e48210, 2012). An example is provided below.

Briefly, a nucleic acid sequence encoding an FGF1 mutant protein (e.g., any of SEQ ID NOs: 6, 7, 8, 9, 10, 11, 12, 13, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 87, 88, 89, 90, 91, 92, 93, 94, 95, 96, 97, 98, 101, 102, 103, 104, 105, 106, 107, 108, 109, 110, 111, 112, 113, 114, 115, 116, 117, 118, 119, 120, 173, 174, 175, 177, 178, 179, 181, 182, 183, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237 and 238) can be fused downstream of an enterokinase (EK) recognition sequence ($Asp_4Lys$) preceded by a flexible 20 amino acid linker (derived from the S-tag sequence of pBAC-3) and an N-terminal $(His)_6$ tag. The resulting expressed fusion protein utilizes the $(His)_6$ tag for efficient purification and can be subsequently processed by EK digestion to yield the mutant FGF1 protein.

The mutant FGF1 protein can be expressed from an *E. coli* host after induction with isopropyl-β-D-thio-galactoside. The expressed protein can be purified utilizing sequential column chromatography on Ni-nitrilotriacetic acid (NTA) affinity resin followed by ToyoPearl HW-405 size exclusion chromatography. The purified protein can be digested with EK to remove the N-terminal $(His)_6$ tag, 20 amino acid linker, and (Asp4Lys) EK recognition sequence. A subsequent second Ni-NTA chromatographic step can be utilized to remove the released N-terminal mutant FGF1 protein (along with any uncleaved fusion protein). Final purification can be performed using HiLoad Superdex 75 size exclusion chromatography equilibrated to 50 mM $Na_2PO_4$, 100 mM NaCl, 10 mM $(NH_4)_2SO_4$, 0.1 mM ethylenediaminetetraacetic acid (EDTA), 5 mM L-Methionine, pH at 6.5 ("PBX" buffer); L-Methionine can be included in PBX buffer to limit oxidization of reactive thiols and other potential oxidative degradation.

In some examples, the enterokinase is not used, and instead, an FGF1 mutant protein (such as one that includes an N-terminal methionine) can be made and purified using heparin affinity chromatography.

For storage and use, the purified mutant FGF1 protein can be sterile filtered through a 0.22 micron filter, purged with $N_2$, snap frozen in dry ice and stored at −80° C. prior to use. The purity of the mutant FGF 1 protein can be assessed by both Coomassie Brilliant Blue and Silver Stain Plus (BIO-RAD Laboratories, Inc., Hercules Calif.) stained sodium dodecylsulfate polyacrylamide gel electrophoresis (SDS PAGE). Mutant FGF1 proteins can be prepared in the absence of heparin. Prior to IV bolus, heparin, or PBS, can be added to the protein.

Example 2

N-Terminally Truncated FGF1 Reduces Blood Glucose in Ob/Ob Mice

We have shown that administration of mature rFGF1 to ob/ob mice can lower blood glucose and have reduced adverse effects as compared to those observed with thiazolidinediones (TZDs).

To dissociate the mitogenic effects of rFGF1 from its glucose lowering activities, an FGF1 ligand was generated that lacks the first 24 residues from the N-terminus, rFGF1$^{\Delta NT}$ (SEQ ID NO: 7). Based on the crystal structures of FGF1-FGFR complexes, the truncation was predicted to reduce the binding affinity of FGF1 for selected FGFRs including FGFR4, and hence the ligand's mitogenicity.

Animals

Mice were housed in a temperature-controlled environment with a 12-hour light/12-hour dark cycle and handled according to institutional guidelines complying with U.S. legislation. Male ob/ob mice (B6.V-Lep$^{ob}$/J, Jackson laboratories) and male C57BL/6J mice received a standard or high fat diet (MI laboratory rodent diet 5001, Harlan Teklad; high fat (60%) diet F3282, Bio-Serv) and acidified water ad libitum. STZ-induced diabetic mice on the C57BL/6J background were purchased from Jackson laboratories. 0.1 mg/ml solutions in PBS of mouse FGF1 (Prospec, Ness Ziona, Israel), human FGF1 (Prospec, Ness Ziona, Israel), mouse FGF2 (Prospec, Ness Ziona, Israel), mouse FGF9 (Prospec, Ness Ziona, Israel), and mouse FGF10 (R&D systems) were injected as described.

Serum Analysis

Blood was collected by tail bleeding either in the ad libitum fed state or following overnight fasting. Free fatty acids (Wako), triglycerides (Thermo) and cholesterol (Thermo) were measured using enzymatic colorimetric methods following the manufacturer's instructions. Serum insulin levels were measured using an Ultra Sensitive Insulin ELISA kit (Crystal Chem). Plasma adipokine and cytokine levels were measured using Milliplex™ MAP and Bio-Plex Pro™ kits (Millipore and Bio-Rad).

Metabolic Studies

Glucose tolerance tests (GTT) were conducted after o/n fasting. Mice were injected i.p. with 1 g of glucose per/kg bodyweight and blood glucose was monitored at 0, 15, 30, 60, and 120 min using a OneTouch Ultra glucometer (Lifescan Inc). Insulin tolerance tests (ITT) were conducted after 3 h fasting. Mice were injected i.p. with 2 U of insulin/kg bodyweight (Humulin R; Eli Lilly) and blood glucose was monitored at 0, 15, 30, 60, and 90 min using a OneTouch Ultra glucometer (Lifescan Inc). Real-time metabolic analyses were conducted in a Comprehensive Lab Animal Monitoring System (Columbus Instruments). $CO_2$ production, 02 consumption, RQ (relative rates of carbohydrate versus fat oxidation), and ambulatory counts were determined for six consecutive days and nights, with at least 24 h for adaptation before data recording. Total body composition analysis was performed using an EchoMRI-100™ (Echo Medical Systems, LLC)

Purification of FGF and FGFR Proteins

Human FGF1 (M1 to D155; SEQ ID NO: 2) and N-terminally truncated human FGF1 (FGF1$^{\Delta NT}$ On K25 to D155; SEQ ID NO: 7) were expressed in *Escherichia coli* cells and purified from the soluble bacterial cell lysate fraction by heparin affinity, ion exchange, and size exclusion chromatographies. The minimal ligand-binding domain of human FGFR1c (D142 to R365), FGFR2b (A140 to E369), FGFR2c (N149 to E368), FGFR3c (D147 to E365), and FGFR4 (Q144 to D355) was refolded in vitro from bacterial inclusion bodies and purified by published protocols.

Mice received a standard diet (ob/ob and db/db mice) or high fat diet (C57/BL6 mice, 60% fat, F3282, Bio-Serv) and acidified water ad libitum. Blood glucose levels were monitored either in the ad libitum fed state or following overnight fasting after injection of recombinant FGF1 or rFGF1$^{\Delta NT}$ (in PBS, Prospec, Israel) using the specified delivery route and dosage. Glucose tolerance tests (GTT) and Insulin tolerance tests (ITT) were conducted after overnight and 5 hour fasting, respectively. Glucose (1 g/kg i.p.) or insulin (0.5 U insulin/kg i.p.) was injected and blood glucose monitored. Serum analyses were performed on blood collected by tail bleeding either in the ad libitum fed state or following overnight fasting.

Remarkably, parenteral delivery of rFGF1$^{\Delta NT}$ lowered blood glucose levels to the same extent as rFGF1 in both genetic- and diet-induced mouse models of diabetes (FIGS. 2A and 2B). rFGF1$^{\Delta NT}$ also retained the feeding suppression effects observed with rFGF1 (FIG. 2C). Therefore, the synthetic effects of exogenous rFGF1 on physiology, such as glucose homeostasis and feeding behavior, differ from and are independent of its classical role as a growth factor and mitogen.

Example 3

FGF1 Mutant Proteins Reduce Blood Glucose Levels in Diabetic Mice

FGF1 mutants shown in Table 3 were tested as described in Example 2.

As shown in Table 3, up to 12 N-terminal amino acids can be deleted from FGF1 without significantly affecting activity, while an FGF1 mutant lacking 14 N-terminal amino acids failed to lower glucose in diabetic mice. Mutations that increase the thermal stability of FGF1 were generally well tolerated, however glucose lowering activity was lost in a mutant with high thermal stability. Furthermore, mutations to the putative heparan sulfate binding site had minimal effect to the glucose lowering actions of FGF1. Notably, the effects of N-terminal deletions and selected stabilizing mutations appeared additive.

| FGF1 (SEQ ID NO:) | Relative activity |
|---|---|
| wt FGF1 (5) | xxx |
| Reduced mitogenic mutants | |
| FGF1$^{\Delta NT}$(10-140αα) (7) | xxxx |
| FGF1$^{\Delta NT2}$(14-140αα) (8) | inactive |
| FGF1$^{\Delta NT3}$(12-140αα) (9) | xxx (shorter duration) |
| FGF1(1-140αα) K12V, N95V (10) | xxxx |
| FGF1(1-140αα) K12V, L46V, E87V, N95V, P134V (11) | inactive |
| FGF1(7-140αα) K118N (12) | inactive |
| FGF1(7-140αα) K118E (13) | inactive |
| Stabilizing Mutants | |
| FGF1(1-140αα)K12V, P134V, C117V (22) | xxx |
| FGF1(1-140αα) L44F, C83T, C117V, F132W (28) | xxx |
| FGF1(1-140αα) L44F, M67I, L73V, V109L, L111I, C117V, A103G, R119G, Δ104-106, Δ120-122 (40) | xxx (shorter duration) |
| FGF1(1-140αα) K12V, N95V, C117V (54) | xxx (longer duration) |
| FGF1(1-140αα) K12V, L46V, E87V, N95V, P134V, C117V (212) | inactive |
| Heparan binding site mutations | |
| FGF1$^{\Delta HBS}$ K112D, K113Q, K118V (113) | xx |
| FGF1$^{\Delta HBS}$ (1-140αα) K112D, K113Q, K118V (226) | xx |
| Combination mutations | |
| FGF$^{\Delta NT1C}$ (10-140αα) K12V, N95V, C117V (225) | xxxx (longer duration) |
| FGF1 (1-140αα) K12V, Q40P, S47I, H93G, N95V (227) | xx |
| FGF1$^{\Delta NT1}$(10-140αα) K12V, Q40P, S47I, H93G, N95V (228) | xx |
| FGF1 (1-140αα) K12V, L44F, C83T, N95V, C117V, F132W (229) | xxx |
| Chimeras | |
| wtFGF1$^{\Delta HBS}$-FGF21$^{C-tail}$ (219) | xx |
| wtFGF1$^{\Delta HBS}$-FGF19$^{C-tail}$ (220) | xx |

Example 4

Effect on Intracellular Signaling with FGF1 Mutants

Peptides M1, M2, M3, M4, and M5 (see SEQ ID NO: 22, 28, 40, 54 and 212, respectively); KN (SEQ ID NO: 10), KLE (SEQ ID NO: 11), and FGF1 (SEQ ID NO: 5) were generated as described in Example 1. The NT truncations, peptides NT1 (SEQ ID NO: 7), NT2 (SEQ ID NO: 8), and NT3 (SEQ ID NO: 9), were prepared without the His tag and enterokinase cleavage, and purified with heparin affinity and ion exchange chromatography. Peptides (10 ng/ml) were incubated with serum-starved HEK293 cells for 15 minutes. Total cell lysates were subject to Western blotting with antibodies specific for pAkt, Akt, pERK and ERK.

As shown in FIG. 8, the thermostable M3 analog shows reduced ERK signaling, similar to that seen with the M5 analog, correlating with the reduced glucose lowering activity seen in ob/ob mice.

As shown in FIG. 9, deletion of 9 (NT1) or 11 (NT3) N-terminal residues of FGF1 does not significantly affecting FGFR downstream signaling, while deletion of 13 (NT2) residues severely compromises ERK phosphorylation. The introduction of the point mutations K12V, N95V reduced ERK phosphorylation, while incorporating the additional mutations L46V, E87V and P134V totally abrogates ERK signaling.

As shown in FIG. 10, deletion of 9 amino acids from the N-terminus of FGF1 (NT1, FGF1$^{\Delta NT}$) induces an ~100 fold reduction in FGFR signaling, as seen in the reduced phosphorylation of downstream ERK and AKT pathways.

Example 5

Effect on Blood Glucose with FGF1 Mutants

Peptides M1, M2, M3 (see SEQ ID NOS: 22, 28, and 40, respectively), FGF1 (SEQ ID NO: 5), NT1 (SEQ ID NO: 7) and NT2 (SEQ ID NO: 8) were generated as described in Example 4. Peptides (0.5 mg/kg) or PBS (control) were injected SQ into 5 mo old C57BL/6J ob/ob mice fed normal chow. Blood glucose levels were subsequently determined.

As shown in FIGS. 11A and 11B, peptides M1 and M2 lowered glucose as well as wild-type FGF1. Thus, FGF1 analogs can be designed with increased thermostability, and improved pharmacokinetic properties, while still having desired effects on lowering blood glucose. Thus, the FGF1 portion of the FGF2/FGF1 chimeras provided herein can include these mutations (e.g., one or more of K12V, C117V, P134V, L44F, C83T, and F132W).

As shown in FIG. 12 peptide FGF1$^{\Delta NT}$ (NT1) significantly lowered glucose, while FGF1$^{\Delta NT2}$ (NT2) lost its ability to significantly lowered glucose. Thus, FGF1 can be N-terminally truncated (such as the first 9 amino acids, but not more than 13 amino acids), while still having desired effects on lowing blood glucose. Thus, the FGF1 portion of the FGF2/FGF1 chimeras provided herein can include such a truncation.

Example 6

Glucose Lowering Correlates with FGFR Signaling

Peptides FGF1 (SEQ ID NO: 5), FGF1$^{\Delta NT}$ (SEQ ID NO: 7) and NT2 (SEQ ID NO: 8) were generated as described in Example 4. Peptides (10 ng/ml) were incubated with serum-starved HEK293 cells for 15 minutes. Total cell lysates were subject to Western blotting with antibodies specific for pAkt, Akt, pERK and ERK.

As shown in FIG. 13, comparable activation of the downstream signaling effectors ERK and AKT is seen with FGF1 and two independent preparations of FGF1$^{\Delta NT}$ that lacks the N-terminal 9 amino acids (SEQ ID NO: 7). In contrast, the deletion of an additional 4 N-terminal amino acids markedly reduces both ERK and AKT phosphorylation. These in vitro FGFR-mediated signaling results correlate with the in vivo glucose lowering effect observed in FIG. 12, supporting the hypothesis that the glucose-lowering activity is mediated through an FGF receptor.

Example 7

Effect on Blood Glucose with FGF1 Mutants

Peptides FGF1-KLE (SEQ ID NO: 11) or FGF1-KN (SEQ ID NO: 10) were generated as described in Example 1. Peptides (0.5 mg/kg) were injected SQ into 5 mo old C57BL/6J ob/ob mice fed normal chow. Blood glucose levels were subsequently determined 0 to 120 hours later.

As shown in FIG. 14, the FGF1-KN mutant retained the ability to lower glucose for 120 hrs despite a marked reduction in its mitogenic activity. In contrast, the mitogenically dead FGF1-KLE failed to lower glucose. These results indicate that the mitogenicity and glucose-lowering activity can be independently affected through targeted mutations.

Thus, the FGF1 portion of the FGF2/FGF1 chimeras provided herein can include the mutations in the KN mutant (e.g., one or more of K12V and N95V) to reduce its mitogenicity without significantly compromising its ability to lower blood glucose levels.

Example 8

Dose-Response Effects on Blood Glucose with FGF1 Mutants

Peptides rFGF1$^{\Delta NT}$ (SEQ ID NO: 7) and rFGF1 (SEQ ID NO: 5) were generated as described in Example 4 (generated with an N-terminal methionine and purified with heparin affinity and ion exchange chromatography). Peptides (0.016 to 10 ng/ml) or PBS were incubated with serum-starved HEK293 cells for 15 minutes. Total cell lysates were subject to Western blotting with antibodies specific for pFRS2α, pAkt, Akt, pERK and ERK. Peptides (0.5 mg/kg) were injected SQ into high fat diet (HFD) fed diet-induced obesity (DIO) mice or into 12 week old C57BL/6J ob/ob mice (0 to 0.5 mg/kg) fed normal chow. Blood glucose levels were subsequently determined.

As shown in FIG. 15A, deletion of 9 N-terminal amino acids of FGF1 significantly reduces FGFR downstream signaling, including phosphorylation of ERK and AKT. Dose dependent phosphorylation of the FGFR substrate FRS2a, confirms that both FGF1 and FGF1$^{\Delta NT}$ are capable of activating FGF receptors.

As shown in FIG. 15B, food intake in DIO mice after receiving, rFGF1 or rFGF1$^{\Delta NT}$ was significantly reduced, as compared to mice that received PBS alone. The similarity in the extent of the transient reduction in food intake between rFGF1 and rFGF1$^{\Delta NT}$ further supports the conclusion that both proteins achieve their in vivo glucose lowering effects by signaling through an FGF receptor.

As shown in FIG. 15C, an essentially identical dose-response curve was observed for the glucose lowering effects of rFGF1 and rFGF1$^{\Delta NT}$ (NT1) in ob/ob mice. Given the significant reduction in mitogenicity of rFGF1$^{\Delta NT}$, these results demonstrate that the glucose lowering and mitogenic activities of FGF1 can be dissociated.

Example 9

Effect of N-Terminal FGF1 Truncations on Blood Glucose Levels

Peptides NT1 (SEQ ID NO: 7), NT2 (SEQ ID NO: 8), and NT3 (SEQ ID NO: 9) were generated as described in Example 4. Peptides (0.5 mg/kg) were injected SQ into 5 mo old C57BL/6J ob/ob mice fed normal chow, or peptides (0 to 0.5 mg/kg) were injected SQ into 12 week old ob/ob mice fed normal chow. Blood glucose levels were subsequently determined (0 hr, 16 hrs, or 24 hrs).

As shown in FIG. 16 if the N-terminus is truncated at 14 amino acids, glucose lowering ability is dramatically decreased (NT2). Thus, FGF1 can be N-terminally truncated (such as the first 9, 10, or 11 amino acids), while maintaining the desired effects on lowering blood glucose. Thus, the FGF1 mutants provided herein can include such a truncation.

In another experiment, NT1 (SEQ ID NO: 7) (0.5 mg/kg) was injected SQ into 8 month old HFD-fed wildtype (FGFR1 f/f, open bars) or adipose-specific FGFR1 knockout (R1KO, aP2-Cre; FGFR1 f/f, filled bars) mice Blood glucose levels were subsequently determined (0 hr, 12 hrs, or 24 hrs).

As shown in FIGS. 17A and 17B, rFGF1$^{\Delta NT}$ (NT1) (SEQ ID NO: 7) lowers blood glucose levels in HFD-fed wildtype mice (control) but has no effect on FGFR1 KO (mutant) mice. FIG. 17A reports the changes in blood glucose, while FIG. 17B reports the data normalized to starting glucose levels at 100%. These results demonstrate that expression of FGFR1 in adipose tissue is required for rFGF1$^{\Delta NT}$ mediated glucose lowering.

As shown in FIGS. 18A and 18B mouse rFGF1 (amino acids 1-15 of SEQ ID NO: 4) lowers blood glucose levels in HFD-fed wildtype mice (FGFR1 f/f mice, filled bars) but has no effect on aP2-Cre; FGFR1 f/f (FGFR1KO, speckled bars) mice. FIG. 17A reports the changes in blood glucose, while FIG. 17B reports the data normalized to starting glucose levels at 100%. These results demonstrate that expression of FGFR1 in adipose tissue is required for rFGF1 mediated glucose lowering.

Example 10

Effect of FGF1 Point Mutations on Blood Glucose Lowering

Peptides K118E (SEQ ID NO: 13), K118N (SEQ ID NO: 12), FGF1 (SEQ ID NO: 5), and KKK (SEQ ID NO: 114) were generated as described in Example 1, while FGF1$^{\Delta NT}$ (NT1) (SEQ ID NO: 7) was expressed with an N-terminal methionine and purified using heparin affinity and ion exchange chromatography. Peptides (0.5 mg/kg) or PBS were injected SQ into 7 months HFD-fed C57BL/6J mice. Blood glucose levels were subsequently determined (0 to 120 hours). These mice are diet-induced obese (DIO) mice.

As shown in FIG. 19, mutation of the single lysine, K118, to either Asn (K118N (SEQ ID NO: 12)) or Glu (K118E (SEQ ID NO: 13)), is sufficient to abrogate glucose lowering activity in DIO mice.

As shown in FIGS. 21 and 22, mutating selected amino acids implicated in the heparin binding site of FGF1, namely amino acids K112, K113, and K118, resulted in a mutated FGF1 sequence that could lower blood glucose levels in ob/ob mice. Thus, the FGF1 mutants provided herein can include mutations at all three of K112, K113, and K118, such as a K112D, K113Q, and K118V substitution. However, while the mutation of K118 to the hydrophobic residue valine was tolerated, mutations involving a charge reversal (K118E) or to a polar residue (K118N) are not tolerated.

Example 11

Effect of FGF1 Point Mutations on Blood Glucose Lowering

Peptides KN (SEQ ID NO: 10), KKK (Salk_010, SEQ ID NO: 226), FGF1 (SEQ ID NO: 5), and KLE (Salk_011, SEQ ID NO: 11) were generated as described in Example 1, while FGF1$^{\Delta NT}$ (NT1) (SEQ ID NO: 7) and FGF1$^{\Delta NTKN}$ (Salk_009, SEQ ID NO: 225) were expressed with an N-terminal methionine and purified using heparin affinity and ion exchange chromatographies. Peptides (0.5 mg/kg) or PBS were injected SQ into 7 months HFD-fed C57BL/6J mice. Blood glucose levels were subsequently determined (0 to 120 hours).

Figure 32B:
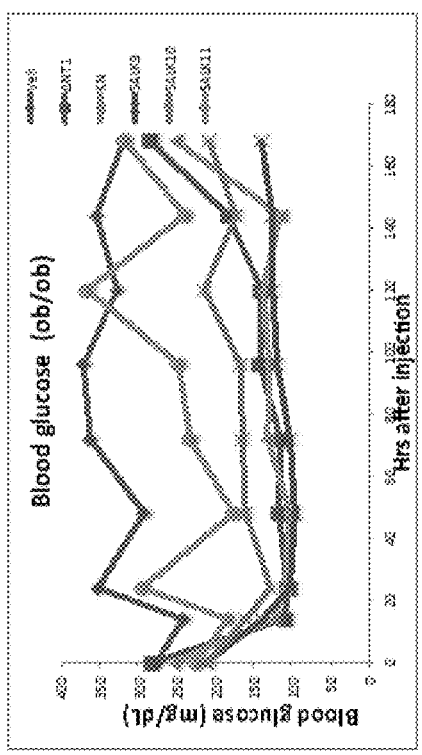
Figure 32A:
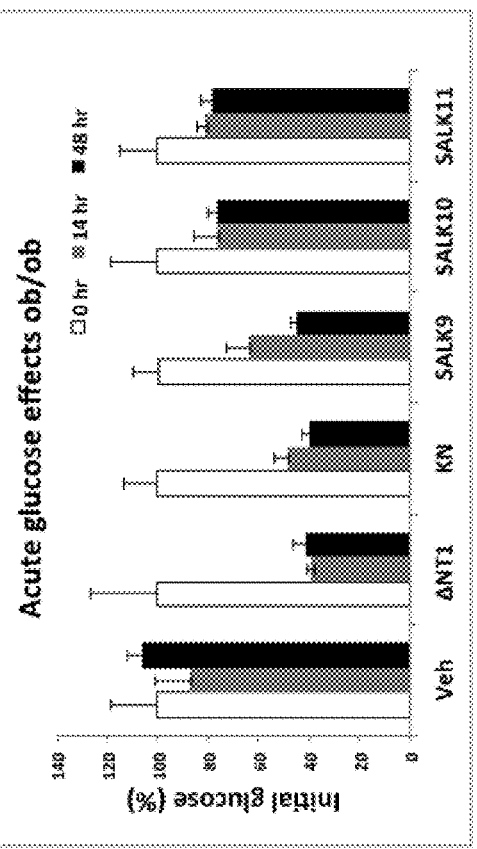
Figure 32C:
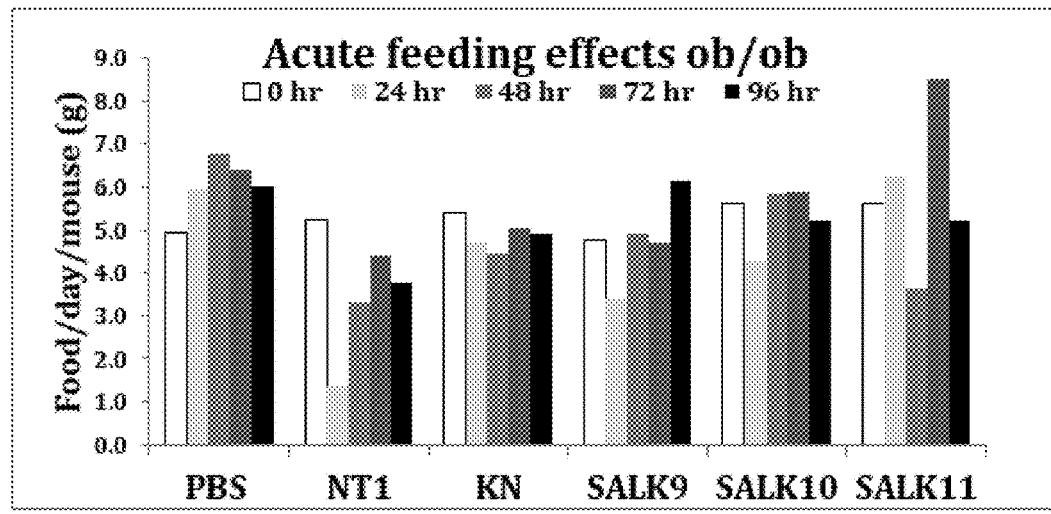
Figure 32D:
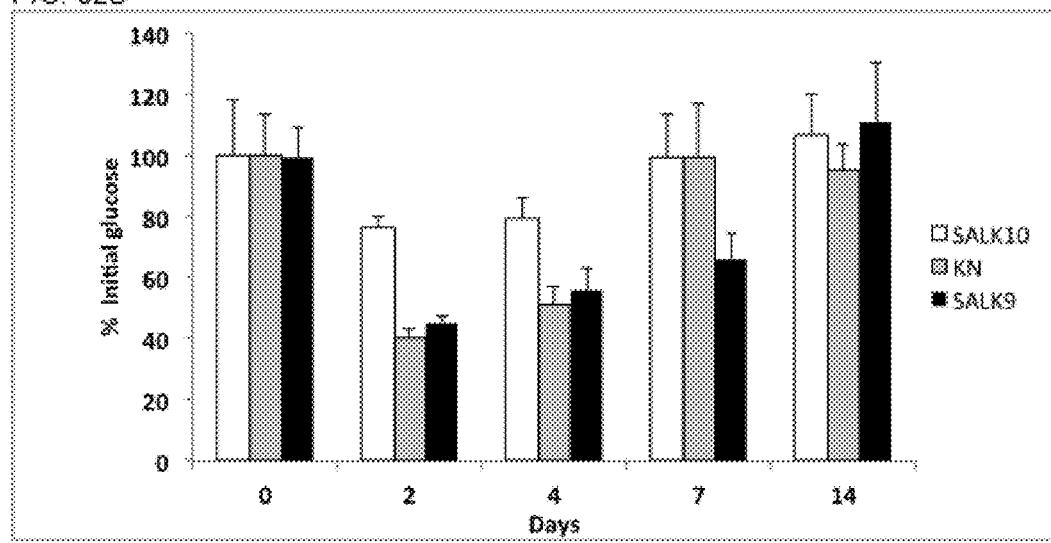

As shown in FIGS. 32A and 32B, combining the mutations K12V and N95V with the deletion of the N-terminal residues resulted in a mutated FGF1 sequence (SEQ ID NO: 225) that could lower blood glucose levels in ob/ob mice. The combined mutations of K12V N95V with the stabilizing mutations Q40P S47I H93G (SEQ ID NO: 11) also lowered blood glucose levels in ob/ob mice. Transient reductions in food intake were observed with selected FGF1 analogs (FIGS. 32C and 32D). Furthermore, a single injection of SEQ ID NO: 225 was able to sustain the low glucose levels for more than 7 days.

Example 12

Effect of FGF1 Point Mutations on Blood Glucose Lowering

Peptides FGF1 (SEQ ID NO: 5), and Salk_013 (SEQ ID NO: 31) were generated as described in Example 1, while Salk_012 (SEQ ID NO: 79) was expressed with an N-terminal methionine and purified using heparin affinity and ion exchange chromatographies. Peptides (0.5 mg/kg) or PBS were injected SQ into 7 months HFD-fed C57BL/6J mice. Blood glucose levels were subsequently determined (0 to 96 hours).

As shown in FIG. 33A, combining the mutations K12V N95V with the stabilizing mutations Q40P S47I H93G and the deletion of the N-terminal residues resulted in a mutated FGF1 sequence (Salk_012) that could lower blood glucose levels in ob/ob mice. The combined mutations of K12V N95V with the stabilizing mutations L44F, C83T, C117V, and F132W (Salk_013) also lowered blood glucose levels in ob/ob mice. Salk_012 and Salk_013 has minimal effects on food intake (FIG. 33B).

Example 13

Effect of FGF1 Point Mutations on Blood Glucose Lowering

Peptides Salk_014 (SEQ ID NO: 230), Salk_024 (SEQ ID NO: 84), Salk_025 (SEQ ID NO: 208), and Salk_026 (SEQ ID NO: 209), were generated as described in Example 1, while Salk_023 (SEQ ID NO: 38) was expressed with an N-terminal methionine and purified using heparin affinity and ion exchange chromatographies. Peptides (0.5 mg/kg) or PBS were injected SQ into 7 months HFD-fed C57BL/6J mice. Blood glucose levels were subsequently determined (0 to 72 hours).

As shown in FIG. 34A, FGF1 with the stabilizing point mutation C117V alone, or in combination with additional mutations reduces blood glucose in ob/ob mice for more than 72 hours. Various transient effects on food intake in the 24 hours after injection were observed (FIG. 34B).

Example 14

Effect of FGF1 Point Mutations on Blood Glucose Lowering

Peptides Salk_014 (SEQ ID NO: 230), Salk_022 (SEQ ID NO: 119), and Salk_027 (SEQ ID NO: 207) were generated as described in Example 1. Peptides (0.5 mg/kg) or PBS were injected SQ into 7 months HFD-fed C57BL/6J mice. Blood glucose levels were subsequently determined (0 to 24 hours).

As shown in FIG. 35A, FGF1 with the stabilizing point mutation C117V alone, or in combination with additional mutations that affect the ability to bind to heparan sulfate proteoglycans (HSPG), reduce blood glucose in ob/ob mice.

The transient suppression of food intake is lost in analogs incorporating mutations that affect HSPG binding (FIG. 35B).

Example 15

Effect of FGF1 Point Mutations on Blood Glucose Lowering

Peptides Salk_014 (SEQ ID NO: 230), was generated as described in Example 1, while Salk_032 (SEQ ID NO: 215) was expressed with an N-terminal methionine and purified using heparin affinity and ion exchange chromatographies. Peptides (0.5 mg/kg) or PBS were injected SQ into 7 months HFD-fed C57BL/6J mice. Blood glucose levels were subsequently determined (0 to 24 hours).

As shown in FIG. 36A, the K12V N95V mutations, the stabilizing cysteine mutations C12T, C83S C117V, and the deletion of the N-terminal residues can be combined to generate an FGF1 analog that is able to robustly reduce blood glucose levels with only minor effects on feeding (FIG. 36B), indicating that these effects can be differentiated.

Example 16

Effect of FGF1-FGF19 Chimeric Proteins on Blood Glucose Lowering

Peptides Salk_014 (SEQ ID NO: 230), and Salk_019 (SEQ ID NO: 224) were generated as described in Example 1. Peptides (Salk_014; 0.5 mg/kg, Salk_019; indicated doses) or PBS were injected SQ into 7 months HFD-fed C57BL/6J mice. Blood glucose levels were subsequently determined (0 to 24 hours).

As shown in FIGS. 37A and 37B, the chimeric protein (SEQ ID NO: 224) generated by fusing the β-klotho binding domain of FGF19 (SEQ ID NO: 100) to the C-terminus of FGF1 failed to affect blood glucose or to suppress food intake, even at a 5 fold higher concentration (2.5 mg/kg compared to 0.5 mg/kg). Given that a chimeric protein composed of FGF1 and the β-klotho binding region of FGF21 was active in lowering blood glucose, these results indicate that this analog is being targeted to FGFR4-β-klotho receptor complex that does not affect blood glucose levels.

Example 17

Effect of FGF1-FGF21 Chimeric Proteins on Blood Glucose Lowering

Peptides FGF1 (SEQ ID NO: 5), FGF1$^{\Delta NT}$ (SEQ ID NO: 7), FGF21 (SEQ ID 20) and FGF1-FGF21 chimera (wherein the FGF1 portion includes K112D, K113Q, and K118V mutations, thus the chimera is SEQ ID NO: 114+SEQ ID NO: 86) were generated as described in Example 1. Peptides (0.5 mg/kg,) or PBS were injected SQ into 7 months HFD-fed C57BL/6J mice. Blood glucose levels were subsequently determined (0 to 48 hours).

As shown in FIG. 38, wildtype FGF21 weakly lowers glucose compared to wildtype FGF1, and FGF1$^{\Delta NT}$. In contrast, a chimeric protein constructed from a mutant FGF1 fused to the β-klotho binding region of FGF21 (FGF1-FGF21$^{C\text{-}tail}$) was effective at lowering blood glucose.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

SEQUENCE LISTING

<160> NUMBER OF SEQ ID NOS: 238

<210> SEQ ID NO 1
<211> LENGTH: 468
<212> TYPE: DNA
<213> ORGANISM: Homo sapiens

<400> SEQUENCE: 1

```
atggctgaag gggaaatcac caccttcaca gccctgaccg agaagtttaa tctgcctcca      60
gggaattaca agaagcccaa actcctctac tgtagcaacg ggggccactt cctgaggatc     120
cttccggatg gcacagtgga tgggacaagg gacaggagcg accagcacat tcagctgcag     180
ctcagtgcgg aaagcgtggg ggaggtgtat ataaagagta ccgagactgg ccagtacttg     240
gccatggaca ccgacgggct tttatacggc tcacagacac aaatgagga atgtttgttc      300 ctggaaaggc tggaggagaa ccattacaac acctatatat ccaagaagca tgcagagaag     360
aattggtttg ttggcctcaa gaagaatggg agctgcaaac gcggtcctcg gactcactat     420
ggccagaaag caatcttgtt tctccccctg ccagtctctt ctgattaa                  468
```

<210> SEQ ID NO 2
<211> LENGTH: 155
<212> TYPE: PRT
<213> ORGANISM: Homo sapiens

<400> SEQUENCE: 2

```
Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 3
<211> LENGTH: 468
<212> TYPE: DNA
<213> ORGANISM: Mus musculus

<400> SEQUENCE: 3

```
atggctgaag gggagatcac aaccttcgca gccctgaccg agaggttcaa cctgcctcta      60
```

```
ggaaactaca aaaagcccaa actgctctac tgcagcaacg ggggccactt cttgaggatc    120
cttcctgatg gcaccgtgga tgggacaagg gacaggagcg accagcacat tcagctgcag    180
ctcagtgcgg aaagtgcggg cgaagtgtat ataaagggta cggagaccgg ccagtacttg    240
gccatggaca ccgaagggct tttatacggc tcgcagacac caaatgagga atgtctgttc    300
ctggaaaggc tggaagaaaa ccattataac acttacacct ccaagaagca tgcggagaag    360
aactggtttg tgggcctcaa gaagaacggg agctgtaagc gcggtcctcg gactcactat    420
ggccagaaag ccatcttgtt tctgcccctc ccggtgtctt ctgactag                 468
```

<210> SEQ ID NO 4
<211> LENGTH: 155
<212> TYPE: PRT
<213> ORGANISM: Mus musculus

<400> SEQUENCE: 4

```
Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 5
<211> LENGTH: 140
<212> TYPE: PRT
<213> ORGANISM: Homo sapiens

<400> SEQUENCE: 5

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
        50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95
```

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 6
<211> LENGTH: 137
<212> TYPE: PRT
<213> ORGANISM: Artificial sequence
<220> FEATURE:
<223> OTHER INFORMATION: Synthetic polypeptide

<400> SEQUENCE: 6

Pro Pro Gly Asn Tyr Lys Lys Pro Lys Leu Leu Tyr Cys Ser Asn Gly
1               5                   10                  15

Gly His Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Ala Met
    50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Asn His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Cys Lys Arg Gly Pro Arg Thr His Tyr Gly Gln Lys Ala Ile Leu
        115                 120                 125

Phe Leu Pro Leu Pro Val Ser Ser Asp
    130                 135

<210> SEQ ID NO 7
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 7

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 8
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 8

Leu Tyr Cys Ser Asn Gly Gly His Phe Leu Arg Ile Leu Pro Asp Gly
1               5                   10                  15

Thr Val Asp Gly Thr Arg Asp Arg Ser Asp Gln His Ile Gln Leu Gln
            20                  25                  30

Leu Ser Ala Glu Ser Val Gly Glu Val Tyr Ile Lys Ser Thr Glu Thr
        35                  40                  45

Gly Gln Tyr Leu Ala Met Asp Thr Asp Gly Leu Leu Tyr Gly Ser Gln
    50                  55                  60

Thr Pro Asn Glu Glu Cys Leu Phe Leu Glu Arg Leu Glu Glu Asn His
65                  70                  75                  80

Tyr Asn Thr Tyr Ile Ser Lys Lys His Ala Glu Lys Asn Trp Phe Val
                85                  90                  95

Gly Leu Lys Lys Asn Gly Ser Cys Lys Arg Gly Pro Arg Thr His Tyr
            100                 105                 110

Gly Gln Lys Ala Ile Leu Phe Leu Pro Leu Pro Val Ser Ser Asp
        115                 120                 125

<210> SEQ ID NO 9
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 9

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Cys Lys Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 10
<211> LENGTH: 140
<212> TYPE: PRT
<213> ORGANISM: Artificial sequence

```
<220> FEATURE:
<223> OTHER INFORMATION: Synthetic polypeptide

<400> SEQUENCE: 10

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 11
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 11

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Val Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Val Arg Leu Glu Glu Asn His Tyr Val Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Val Leu Pro Val Ser Ser Asp
        130                 135                 140

<210> SEQ ID NO 12
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 12
```

```
Asn Tyr Lys Lys Pro Lys Leu Leu Tyr Cys Ser Asn Gly Gly His Phe
1               5                   10                  15

Leu Arg Ile Leu Pro Asp Gly Thr Val Asp Gly Thr Arg Asp Arg Ser
            20                  25                  30

Asp Gln His Ile Gln Leu Gln Leu Ser Ala Glu Ser Val Gly Glu Val
            35                  40                  45

Tyr Ile Lys Ser Thr Glu Thr Gly Gln Tyr Leu Ala Met Asp Thr Asp
        50                  55                  60

Gly Leu Leu Tyr Gly Ser Gln Thr Pro Asn Glu Glu Cys Leu Phe Leu
65                  70                  75                  80

Glu Arg Leu Glu Glu Asn His Tyr Asn Thr Tyr Ile Ser Lys Lys His
                85                  90                  95

Ala Glu Lys Asn Trp Phe Val Gly Leu Lys Lys Asn Gly Ser Cys Asn
            100                 105                 110

Arg Gly Pro Arg Thr His Tyr Gly Gln Lys Ala Ile Leu Phe Leu Pro
            115                 120                 125

Leu Pro Val Ser Ser Asp
            130

<210> SEQ ID NO 13
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 13

Asn Tyr Lys Lys Pro Lys Leu Leu Tyr Cys Ser Asn Gly Gly His Phe
1               5                   10                  15

Leu Arg Ile Leu Pro Asp Gly Thr Val Asp Gly Thr Arg Asp Arg Ser
            20                  25                  30

Asp Gln His Ile Gln Leu Gln Leu Ser Ala Glu Ser Val Gly Glu Val
            35                  40                  45

Tyr Ile Lys Ser Thr Glu Thr Gly Gln Tyr Leu Ala Met Asp Thr Asp
        50                  55                  60

Gly Leu Leu Tyr Gly Ser Gln Thr Pro Asn Glu Glu Cys Leu Phe Leu
65                  70                  75                  80

Glu Arg Leu Glu Glu Asn His Tyr Asn Thr Tyr Ile Ser Lys Lys His
                85                  90                  95

Ala Glu Lys Asn Trp Phe Val Gly Leu Lys Lys Asn Gly Ser Cys Glu
            100                 105                 110

Arg Gly Pro Arg Thr His Tyr Gly Gln Lys Ala Ile Leu Phe Leu Pro
            115                 120                 125

Leu Pro Val Ser Ser Asp
            130

<210> SEQ ID NO 14
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 14

Ala Ala Ala Leu Pro Leu Pro Val
1               5

<210> SEQ ID NO 15
```

```
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 15

Ile Leu Ala Leu Pro Leu Pro Val
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 16

Ile Leu Phe Ala Pro Leu Pro Val
1               5

<210> SEQ ID NO 17
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 17

Ile Leu Phe Leu Pro Ala Pro Ala
1               5

<210> SEQ ID NO 18
<211> LENGTH: 414
<212> TYPE: DNA
<213> ORGANISM: Artificial sequence
<220> FEATURE:
<223> OTHER INFORMATION: Synthetic polynucleotide

<400> SEQUENCE: 18
ccgccgggta actacaaaaa accgaaactg ctgtattgca gcaacggcgg tcattttctg      60
cgtattctgc cggatggcac cgtcgacggt acgcgtgatc gcagtgacca gcacattcag     120
ctgcaactga gcgcggaatc tgtgggtgaa gtttatatca aatcaaccga acgggccag      180 tacctggcca tggataccga cggcctgctg tacggttcgc aaacgccgaa tgaagaatgc     240
ctgtttctgg aacgtctgga agaaaaccat tacaacacct acatcagtaa aaaacacgcg     300
gagaaaaact ggttcgttgg cctgaagaaa acggttcct gtaaacgcgg cccgcgcacc      360
cattacggtc aaaaagccat tctgtttctg ccgctgccgg tttcgtccga ctaa           414

<210> SEQ ID NO 19
<211> LENGTH: 939
<212> TYPE: DNA
<213> ORGANISM: Homo sapiens

<400> SEQUENCE: 19
ctgtcagctg aggatccagc cgaaagagga gccaggcact caggccacct gagtctactc      60
acctggacaa ctggaatctg caccaattc taaaccactc agcttctccg agctcacacc      120
ccggagatca cctgaggacc cgagccattg atggactcgg acgagaccgg gttcgagcac     180
tcaggactgt gggtttctgt gctggctggt ctgctgggag cctgccaggc acaccccatc     240
cctgactcca gtcctctcct gcaattcggg ggccaagtcc ggcagcggta cctctacaca     300
```

```
gatgatgccc agcagacaga agcccacctg agatcaggg aggatgggac ggtgggggc    360
gctgctgacc agagccccga aagtctcctg cagctgaaag ccttgaagcc gggagttatt   420
caaatcttgg gagtcaagac atccaggttc ctgtgccagc ggccagatgg ggccctgtat   480
ggatcgctcc actttgaccc tgaggcctgc agcttccggg agctgcttct tgaggacgga   540
tacaatgttt accagtccga agcccacggc ctcccgctgc acctgccagg gaacaagtcc   600
ccacaccggg accctgcacc ccgaggacca gctcgcttcc tgccactacc aggcctgccc   660
cccgcactcc cggagccacc cggaatcctg ccccccagc ccccgatgt gggctcctcg     720
gaccctctga gcatggtggg accttcccag ggccgaagcc ccagctacgc ttcctgaagc   780
cagaggctgt ttactatgac atctcctctt tatttattag gttatttatc ttatttattt   840
ttttattttt cttacttgag ataataaaga gttccagagg agaaaaaaaa aaaaaaaaa    900
aaaaaaaaa aaaaaaaaa aaaaaaaaa aaaaaaag                              939
```

<210> SEQ ID NO 20
<211> LENGTH: 208
<212> TYPE: PRT
<213> ORGANISM: Homo sapiens

<400> SEQUENCE: 20

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Gln Thr Glu Ala His Leu Glu Ile Arg Glu
    50                  55                  60

Asp Gly Thr Val Gly Gly Ala Ala Asp Gln Ser Pro Glu Ser Leu Leu
65                  70                  75                  80

Gln Leu Lys Ala Leu Lys Pro Gly Val Ile Gln Ile Leu Gly Val Lys
                85                  90                  95

Thr Ser Arg Phe Leu Cys Gln Arg Pro Asp Gly Ala Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala His Gly Leu Pro Leu His
    130                 135                 140

Leu Pro Gly Asn Lys Ser Pro His Arg Asp Pro Ala Pro Arg Gly Pro
145                 150                 155                 160

Ala Arg Phe Leu Pro Leu Pro Gly Leu Pro Pro Ala Leu Pro Glu Pro
                165                 170                 175

Pro Gly Ile Leu Ala Pro Gln Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 21
<211> LENGTH: 135
<212> TYPE: PRT
<213> ORGANISM: Artificial sequence
<220> FEATURE:
<223> OTHER INFORMATION: Synthetic polypeptide

<400> SEQUENCE: 21

```
Gly Gly Gln Val Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
            20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
        115                 120                 125

Pro Leu Pro Val Ser Ser Asp
    130                 135

<210> SEQ ID NO 22
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 22

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Val Leu Pro Val Ser Ser Asp
    130                 135                 140

<210> SEQ ID NO 23
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 23

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30
```

-continued

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
        50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Val Leu Pro Val Ser Ser Asp
    130                 135                 140

<210> SEQ ID NO 24
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 24

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Phe Leu Val Leu Pro Val
        115                 120                 125

Ser Ser Asp
    130

<210> SEQ ID NO 25
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 25

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly

```
                    50                  55                  60
Ser Gln Thr Pro Asn Glu Glu Cys Leu Phe Leu Glu Arg Leu Glu Glu
 65                  70                  75                  80

Asn His Tyr Asn Thr Tyr Ile Ser Lys Lys His Ala Glu Lys Asn Trp
                 85                  90                  95

Phe Val Gly Leu Lys Lys Asn Gly Ser Val Lys Arg Gly Pro Arg Thr
            100                 105                 110

His Tyr Gly Gln Lys Ala Ile Leu Phe Leu Val Leu Pro Val Ser Ser
            115                 120                 125

Asp

<210> SEQ ID NO 26
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 26

Lys Pro Val Leu Leu Tyr Cys Ser Asn Gly Gly His Phe Leu Arg Ile
 1               5                  10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
         35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Cys Leu Phe Leu Glu Arg Leu
 65                  70                  75                  80

Glu Glu Asn His Tyr Val Thr Tyr Ile Ser Lys Lys His Ala Glu Lys
                 85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Phe Leu Val Leu Pro Val
            115                 120                 125

Ser Ser Asp
        130

<210> SEQ ID NO 27
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 27

Val Leu Leu Tyr Cys Ser Asn Gly Gly His Phe Leu Arg Ile Leu Pro
 1               5                  10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
         35                  40                  45

Glu Thr Gly Gln Tyr Leu Ala Met Asp Thr Asp Gly Leu Leu Tyr Gly
         50                  55                  60

Ser Gln Thr Pro Asn Glu Glu Cys Leu Phe Leu Glu Arg Leu Glu Glu
 65                  70                  75                  80

Asn His Tyr Val Thr Tyr Ile Ser Lys Lys His Ala Glu Lys Asn Trp
```

```
                    85                  90                  95

Phe Val Gly Leu Lys Lys Asn Gly Ser Val Lys Arg Gly Pro Arg Thr
            100                 105                 110

His Tyr Gly Gln Lys Ala Ile Leu Phe Leu Val Leu Pro Val Ser Ser
        115                 120                 125

Asp

<210> SEQ ID NO 28
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 28

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Trp Leu Pro Leu Pro Val Ser Ser Asp
    130                 135                 140

<210> SEQ ID NO 29
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 29

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
```

```
            115                 120                 125
Ala Ile Leu Trp Leu Pro Leu Pro Val Ser Ser Asp
    130                 135                 140

<210> SEQ ID NO 30
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 30

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Trp Leu Pro Leu Pro Val Ser Ser Asp
    130                 135                 140

<210> SEQ ID NO 31
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 31

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Trp Leu Pro Leu Pro Val Ser Ser Asp
    130                 135                 140
```

<210> SEQ ID NO 32
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 32

```
Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
50                  55                  60

Tyr Gly Ser Gln Thr Pro Asn Glu Glu Thr Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Trp Leu Pro Leu Pro Val
        115                 120                 125

Ser Ser Asp
        130
```

<210> SEQ ID NO 33
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 33

```
Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
50                  55                  60

Ser Gln Thr Pro Asn Glu Glu Thr Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Val Lys Arg Gly Pro Arg Thr
            100                 105                 110

His Tyr Gly Gln Lys Ala Ile Leu Trp Leu Pro Leu Pro Val Ser Ser
        115                 120                 125

Asp
```

<210> SEQ ID NO 34
<211> LENGTH: 131
<212> TYPE: PRT
<213> ORGANISM: Artificial sequence
<220> FEATURE:

<223> OTHER INFORMATION: Synthetic polypeptide

<400> SEQUENCE: 34

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Thr Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Trp Leu Pro Leu Pro Val
        115                 120                 125

Ser Ser Asp
    130

<210> SEQ ID NO 35
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 35

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Thr Leu Phe Leu Glu Arg Leu Glu Glu
65                  70                  75                  80

Asn His Tyr Val Thr Tyr Ile Ser Lys Lys His Ala Glu Lys Asn Trp
                85                  90                  95

Phe Val Gly Leu Lys Lys Asn Gly Ser Val Lys Arg Gly Pro Arg Thr
            100                 105                 110

His Tyr Gly Gln Lys Ala Ile Leu Trp Leu Pro Leu Pro Val Ser Ser
        115                 120                 125

Asp

<210> SEQ ID NO 36
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 36

Lys Pro Val Leu Leu Tyr Cys Ser Asn Gly Gly His Phe Leu Arg Ile
1               5                   10                  15

-continued

```
Leu Pro Asp Gly Thr Val Asp Gly Thr Arg Asp Arg Ser Asp Gln His
             20                  25                  30

Ile Gln Phe Gln Leu Ser Ala Glu Ser Val Gly Glu Val Tyr Ile Lys
         35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Thr Leu Phe Leu Glu Arg Leu
 65                  70                  75                  80

Glu Glu Asn His Tyr Asn Thr Tyr Ile Ser Lys Lys His Ala Glu Lys
                 85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Trp Leu Pro Leu Pro Val
        115                 120                 125

Ser Ser Asp
    130
```

<210> SEQ ID NO 37
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 37

```
Val Leu Leu Tyr Cys Ser Asn Gly Gly His Phe Leu Arg Ile Leu Pro
 1               5                  10                  15

Asp Gly Thr Val Asp Gly Thr Arg Asp Arg Ser Asp Gln His Ile Gln
             20                  25                  30

Phe Gln Leu Ser Ala Glu Ser Val Gly Glu Val Tyr Ile Lys Ser Thr
         35                  40                  45

Glu Thr Gly Gln Tyr Leu Ala Met Asp Thr Asp Gly Leu Leu Tyr Gly
 50                  55                  60

Ser Gln Thr Pro Asn Glu Glu Thr Leu Phe Leu Glu Arg Leu Glu Glu
 65                  70                  75                  80

Asn His Tyr Asn Thr Tyr Ile Ser Lys Lys His Ala Glu Lys Asn Trp
                 85                  90                  95

Phe Val Gly Leu Lys Lys Asn Gly Ser Val Lys Arg Gly Pro Arg Thr
            100                 105                 110

His Tyr Gly Gln Lys Ala Ile Leu Trp Leu Pro Leu Pro Val Ser Ser
        115                 120                 125

Asp
```

<210> SEQ ID NO 38
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 38

```
Lys Pro Val Leu Leu Tyr Cys Ser Asn Gly Gly His Phe Leu Arg Ile
 1               5                  10                  15

Leu Pro Asp Gly Thr Val Asp Gly Thr Arg Asp Arg Ser Asp Gln His
             20                  25                  30

Ile Gln Phe Gln Leu Ser Ala Glu Ser Val Gly Glu Val Tyr Ile Lys
         35                  40                  45
```

-continued

Ser Thr Glu Thr Gly Gln Tyr Leu Ala Met Asp Thr Asp Gly Leu Leu
    50                  55                  60

Tyr Gly Ser Gln Thr Pro Asn Glu Glu Thr Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Trp Leu Pro Leu Pro Val
        115                 120                 125

Ser Ser Asp
    130

<210> SEQ ID NO 39
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 39

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Thr Leu Phe Leu Glu Arg Leu Glu Glu
65                  70                  75                  80

Asn His Tyr Val Thr Tyr Ile Ser Lys Lys His Ala Glu Lys Asn Trp
                85                  90                  95

Phe Val Gly Leu Lys Lys Asn Gly Ser Val Lys Arg Gly Pro Arg Thr
            100                 105                 110

His Tyr Gly Gln Lys Ala Ile Leu Trp Leu Pro Leu Pro Val Ser Ser
        115                 120                 125

Asp

<210> SEQ ID NO 40
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 40

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Ile Asp Thr Asp Gly Leu Val Tyr Gly Ser Gln Thr Pro Asn
65                  70                  75                  80

```
Glu Glu Cys Leu Phe Leu Glu Arg Leu Glu Glu Asn His Tyr Asn Thr
                85                  90                  95

Tyr Ile Ser Lys Lys His Gly Trp Phe Leu Gly Ile Lys Lys Asn Gly
            100                 105                 110

Ser Val Lys Gly Thr His Tyr Gly Gln Lys Ala Ile Leu Phe Leu Pro
        115                 120                 125

Leu Pro Val Ser Ser Asp
    130
```

<210> SEQ ID NO 41
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 41

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Ile Asp Thr Asp Gly Leu Val Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Gly Trp Phe Leu Gly Ile Lys Lys Asn Gly
            100                 105                 110

Ser Val Lys Gly Thr His Tyr Gly Gln Lys Ala Ile Leu Phe Leu Pro
        115                 120                 125

Leu Pro Val Ser Ser Asp
    130
```

<210> SEQ ID NO 42
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 42

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Ile Asp Thr Asp Gly Leu Val Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Gly Trp Phe Leu Gly Ile Lys Lys Asn Gly
```

```
                100               105               110
Ser Val Lys Gly Thr His Tyr Gly Gln Lys Ala Ile Leu Phe Leu Pro
            115                 120                 125

Leu Pro Val Ser Ser Asp
        130

<210> SEQ ID NO 43
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 43

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Ile Asp Thr Asp Gly Leu Val Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Gly Trp Phe Leu Gly Ile Lys Lys Asn Gly
            100                 105                 110

Ser Val Lys Gly Thr His Tyr Gly Gln Lys Ala Ile Leu Phe Leu Pro
        115                 120                 125

Leu Pro Val Ser Ser Asp
    130

<210> SEQ ID NO 44
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 44

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Ile Asp Thr Asp Gly Leu Val
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Gly Trp Phe
                85                  90                  95

Leu Gly Ile Lys Lys Asn Gly Ser Val Lys Gly Thr His Tyr Gly Gln
            100                 105                 110

Lys Ala Ile Leu Phe Leu Pro Leu Pro Val Ser Ser Asp
        115                 120                 125
```

<210> SEQ ID NO 45
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 45

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Ile Asp Thr Asp Gly Leu Val Tyr Gly
    50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Gly Trp Phe Leu Gly
                85                  90                  95

Ile Lys Lys Asn Gly Ser Val Lys Gly Thr His Tyr Gly Gln Lys Ala
            100                 105                 110

Ile Leu Phe Leu Pro Leu Pro Val Ser Ser Asp
        115                 120

<210> SEQ ID NO 46
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 46

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Ile Asp Thr Asp Gly Leu Val
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Gly Trp Phe
                85                  90                  95

Leu Gly Ile Lys Lys Asn Gly Ser Val Lys Gly Thr His Tyr Gly Gln
            100                 105                 110

Lys Ala Ile Leu Phe Leu Pro Leu Pro Val Ser Ser Asp
        115                 120                 125

<210> SEQ ID NO 47
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 47

Val Leu Leu Tyr Cys Ser Asn Gly Gly His Phe Leu Arg Ile Leu Pro

```
                1               5                  10                 15
Asp Gly Thr Val Asp Gly Thr Arg Asp Arg Ser Asp Gln His Ile Gln
                20                 25                 30

Phe Gln Leu Ser Ala Glu Ser Val Gly Glu Val Tyr Ile Lys Ser Thr
                35                 40                 45

Glu Thr Gly Gln Tyr Leu Ala Ile Asp Thr Asp Gly Leu Val Tyr Gly
                50                 55                 60

Ser Gln Thr Pro Asn Glu Glu Cys Leu Phe Leu Glu Arg Leu Glu Glu
65                 70                 75                 80

Asn His Tyr Asn Thr Tyr Ile Ser Lys Lys His Gly Trp Phe Leu Gly
                85                 90                 95

Ile Lys Lys Asn Gly Ser Val Lys Gly Thr His Tyr Gly Gln Lys Ala
                100                105                110

Ile Leu Phe Leu Pro Leu Pro Val Ser Ser Asp
                115                120
```

<210> SEQ ID NO 48
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 48

```
Lys Pro Lys Leu Leu Tyr Cys Ser Asn Gly Gly His Phe Leu Arg Ile
1               5                  10                 15

Leu Pro Asp Gly Thr Val Asp Gly Thr Arg Asp Arg Ser Asp Gln His
                20                 25                 30

Ile Gln Phe Gln Leu Ser Ala Glu Ser Val Gly Glu Val Tyr Ile Lys
                35                 40                 45

Ser Thr Glu Thr Gly Gln Tyr Leu Ala Ile Asp Thr Asp Gly Leu Val
                50                 55                 60

Tyr Gly Ser Gln Thr Pro Asn Glu Glu Cys Leu Phe Leu Glu Arg Leu
65                 70                 75                 80

Glu Glu Asn His Tyr Val Thr Tyr Ile Ser Lys Lys His Gly Trp Phe
                85                 90                 95

Leu Gly Ile Lys Lys Asn Gly Ser Val Lys Gly Thr His Tyr Gly Gln
                100                105                110

Lys Ala Ile Leu Phe Leu Pro Leu Pro Val Ser Ser Asp
                115                120                125
```

<210> SEQ ID NO 49
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 49

```
Lys Leu Leu Tyr Cys Ser Asn Gly Gly His Phe Leu Arg Ile Leu Pro
1               5                  10                 15

Asp Gly Thr Val Asp Gly Thr Arg Asp Arg Ser Asp Gln His Ile Gln
                20                 25                 30

Phe Gln Leu Ser Ala Glu Ser Val Gly Glu Val Tyr Ile Lys Ser Thr
                35                 40                 45

Glu Thr Gly Gln Tyr Leu Ala Ile Asp Thr Asp Gly Leu Val Tyr Gly
                50                 55                 60
```

Ser Gln Thr Pro Asn Glu Glu Cys Leu Phe Leu Glu Arg Leu Glu Glu
65                  70                  75                  80

Asn His Tyr Val Thr Tyr Ile Ser Lys Lys His Gly Trp Phe Leu Gly
                85                  90                  95

Ile Lys Lys Asn Gly Ser Val Lys Gly Thr His Tyr Gly Gln Lys Ala
            100                 105                 110

Ile Leu Phe Leu Pro Leu Pro Val Ser Ser Asp
        115                 120

<210> SEQ ID NO 50
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 50

Val Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Ile Asp Thr Asp Gly Leu Val
50                  55                  60

Tyr Gly Ser Gln Thr Pro Asn Glu Glu Cys Leu Phe Leu Glu Arg Leu
65                  70                  75                  80

Glu Glu Asn His Tyr Val Thr Tyr Ile Ser Lys Lys His Gly Trp Phe
                85                  90                  95

Leu Gly Ile Lys Lys Asn Gly Ser Val Lys Gly Thr His Tyr Gly Gln
            100                 105                 110

Lys Ala Ile Leu Phe Leu Pro Leu Pro Val Ser Ser Asp
        115                 120                 125

<210> SEQ ID NO 51
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 51

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Ile Asp Thr Asp Gly Leu Val Tyr Gly
    50                  55                  60

Ser Gln Thr Pro Asn Glu Glu Cys Leu Phe Leu Glu Arg Leu Glu Glu
65                  70                  75                  80

Asn His Tyr Val Thr Tyr Ile Ser Lys Lys His Gly Trp Phe Leu Gly
                85                  90                  95

Ile Lys Lys Asn Gly Ser Val Lys Gly Thr His Tyr Gly Gln Lys Ala
            100                 105                 110

Ile Leu Phe Leu Pro Leu Pro Val Ser Ser Asp
        115                 120

<210> SEQ ID NO 52
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 52

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Cys Asn Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 53
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 53

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Cys Glu Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 54
<211> LENGTH: 140
<212> TYPE: PRT

<213> ORGANISM: Artificial sequence
<220> FEATURE:
<223> OTHER INFORMATION: Synthetic polypeptide

<400> SEQUENCE: 54

```
Phe Asn Leu Pro Pro Gly Asn Tyr Lys Lys Pro Val Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 55
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 55

```
Phe Asn Leu Pro Pro Gly Asn Tyr Lys Lys Pro Val Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Val Asn Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 56
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 56

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
                100                 105                 110

Lys Asn Gly Ser Val Glu Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 57
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 57

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
50                  55                  60

Tyr Gly Ser Gln Thr Pro Asn Glu Glu Cys Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Cys Lys Arg Gly Pro
                100                 105                 110

Arg Thr His Tyr Gly Gln Lys Ala Ile Leu Phe Leu Pro Leu Pro Val
            115                 120                 125

Ser Ser Asp
        130

<210> SEQ ID NO 58
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 58

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
```

```
                    20                  25                  30

Leu Gln Leu Ser Ala Glu Ser Val Gly Glu Val Tyr Ile Lys Ser Thr
            35                  40                  45

Glu Thr Gly Gln Tyr Leu Ala Met Asp Thr Asp Gly Leu Leu Tyr Gly
        50                  55                  60

Ser Gln Thr Pro Asn Glu Glu Cys Leu Phe Leu Glu Arg Leu Glu Glu
65                  70                  75                  80

Asn His Tyr Val Thr Tyr Ile Ser Lys Lys His Ala Glu Lys Asn Trp
                85                  90                  95

Phe Val Gly Leu Lys Lys Asn Gly Ser Cys Lys Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 59
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 59

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 60
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 60

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
```

```
                     50                  55                  60
Ser Gln Thr Pro Asn Glu Glu Cys Leu Phe Leu Glu Arg Leu Glu Glu
 65                  70                  75                  80

Asn His Tyr Asn Thr Tyr Ile Ser Lys Lys His Ala Glu Lys Asn Trp
                 85                  90                  95

Phe Val Gly Leu Lys Lys Asn Gly Ser Cys Lys Arg Gly Pro Arg Thr
            100                 105                 110

His Tyr Gly Gln Lys Ala Ile Leu Phe Leu Pro Leu Pro Val Ser Ser
        115                 120                 125

Asp
```

```
<210> SEQ ID NO 61
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 61

Lys Pro Lys Leu Leu Tyr Cys Ser Asn Gly Gly His Phe Leu Arg Ile
 1               5                  10                  15

Leu Pro Asp Gly Thr Val Asp Gly Thr Arg Asp Arg Ser Asp Gln His
                20                  25                  30

Ile Gln Leu Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
        50                  55                  60

Tyr Gly Ser Gln Thr Pro Asn Glu Glu Cys Leu Phe Leu Glu Arg Leu
 65                  70                  75                  80

Glu Glu Asn His Tyr Val Thr Tyr Ile Ser Lys Lys His Ala Glu Lys
                 85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp
        130
```

```
<210> SEQ ID NO 62
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 62

Lys Leu Leu Tyr Cys Ser Asn Gly Gly His Phe Leu Arg Ile Leu Pro
 1               5                  10                  15

Asp Gly Thr Val Asp Gly Thr Arg Asp Arg Ser Asp Gln His Ile Gln
                20                  25                  30

Leu Gln Leu Ser Ala Glu Ser Val Gly Glu Val Tyr Ile Lys Ser Thr
            35                  40                  45

Glu Thr Gly Gln Tyr Leu Ala Met Asp Thr Asp Gly Leu Leu Tyr Gly
        50                  55                  60

Ser Gln Thr Pro Asn Glu Glu Cys Leu Phe Leu Glu Arg Leu Glu Glu
 65                  70                  75                  80

Asn His Tyr Val Thr Tyr Ile Ser Lys Lys His Ala Glu Lys Asn Trp
```

```
                    85                  90                  95
Phe Val Gly Leu Lys Lys Asn Gly Ser Cys Lys Arg Gly Pro Arg Thr
                100                 105                 110

His Tyr Gly Gln Lys Ala Ile Leu Phe Leu Pro Leu Pro Val Ser Ser
        115                 120                 125

Asp

<210> SEQ ID NO 63
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 63

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Cys Asn Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 64
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 64

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn His Tyr Val Thr Tyr Ile Ser Lys Lys His Ala Glu Lys Asn Trp
                85                  90                  95

Phe Val Gly Leu Lys Lys Asn Gly Ser Cys Glu Arg Gly Pro Arg Thr
            100                 105                 110

His Tyr Gly Gln Lys Ala Ile Leu Phe Leu Pro Leu Pro Val Ser Ser
```

115                 120                 125

Asp

<210> SEQ ID NO 65
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 65

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Asn Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 66
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 66

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Cys Glu Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 67

<211> LENGTH: 140
<212> TYPE: PRT
<213> ORGANISM: Artificial sequence
<220> FEATURE:
<223> OTHER INFORMATION: Synthetic polypeptide

<400> SEQUENCE: 67

```
Phe Asn Leu Pro Pro Gly Asn Tyr Thr Thr Pro Lys Leu Leu Tyr Cys
  1               5                  10                  15
Ser Asn Gly Gly His Phe Leu Arg Ile Leu Pro Asp Gly Thr Val Asp
             20                  25                  30
Gly Thr Arg Asp Arg Ser Asp Gln His Ile Gln Leu Gln Leu Ser Ala
         35                  40                  45
Glu Ser Val Gly Glu Val Tyr Ile Lys Ser Thr Glu Thr Gly Gln Tyr
     50                  55                  60
Leu Ala Met Asp Thr Asp Gly Leu Leu Tyr Gly Ser Gln Thr Pro Asn
 65                  70                  75                  80
Glu Glu Cys Leu Phe Leu Glu Arg Leu Glu Glu Asn His Tyr Asn Thr
                 85                  90                  95
Tyr Ile Ser Lys Lys His Ala Glu Lys Asn Trp Phe Val Gly Leu Lys
            100                 105                 110
Lys Asn Gly Ser Cys Lys Arg Gly Pro Arg Thr His Tyr Gly Gln Lys
        115                 120                 125
Ala Ile Leu Phe Leu Pro Leu Pro Val Ser Ser Asp
    130                 135                 140
```

<210> SEQ ID NO 68
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 68

```
Phe Asn Leu Pro Pro Gly Asn Tyr Thr Thr Pro Lys Leu Leu Tyr Cys
  1               5                  10                  15
Ser Asn Gly Gly His Phe Leu Arg Ile Leu Pro Asp Gly Thr Val Asp
             20                  25                  30
Gly Thr Arg Asp Arg Ser Asp Gln His Ile Gln Leu Gln Leu Ser Ala
         35                  40                  45
Glu Ser Val Gly Glu Val Tyr Ile Lys Ser Thr Glu Thr Gly Gln Tyr
     50                  55                  60
Leu Ala Met Asp Thr Asp Gly Leu Leu Tyr Gly Ser Gln Thr Pro Asn
 65                  70                  75                  80
Glu Glu Cys Leu Phe Leu Glu Arg Leu Glu Glu Asn His Tyr Val Thr
                 85                  90                  95
Tyr Ile Ser Lys Lys His Ala Glu Lys Asn Trp Phe Val Gly Leu Lys
            100                 105                 110
Lys Asn Gly Ser Cys Lys Arg Gly Pro Arg Thr His Tyr Gly Gln Lys
        115                 120                 125
Ala Ile Leu Phe Leu Pro Leu Pro Val Ser Ser Asp
    130                 135                 140
```

<210> SEQ ID NO 69
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 69

Phe Asn Leu Pro Pro Gly Asn Tyr Thr Thr Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Asn Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 70
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 70

Phe Asn Leu Pro Pro Gly Asp Gln Asp Gln Asn Gln Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 71
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 71

Lys Pro Lys Leu Leu Tyr Cys Ser Asn Gly Gly His Phe Leu Arg Ile
1               5                   10                  15

```
Leu Pro Asp Gly Thr Val Asp Gly Thr Arg Asp Arg Ser Asp Pro His
        20                  25                  30

Ile Gln Leu Gln Leu Ile Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Cys Leu Phe Leu Glu Arg Leu
 65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
            115                 120                 125

Ser Ser Asp
    130

<210> SEQ ID NO 72
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 72

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Pro His Ile Gln
            20                  25                  30

Leu Gln Leu Ile Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Cys Lys Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 73
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 73

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Pro His Ile Gln Leu Gln Leu Ile Ala
        35                  40                  45
```

Glu Ser Val Gly Glu Val Tyr Ile Lys Ser Thr Gly Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 74
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 74

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Pro His
            20                  25                  30

Ile Gln Leu Gln Leu Ile Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 75
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 75

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Pro His Ile Gln
            20                  25                  30

Leu Gln Leu Ile Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu

```
              65                  70                  75                  80
Asn His Tyr Val Thr Tyr Ile Ser Lys Lys His Ala Glu Lys Asn Trp
                    85                  90                  95

Phe Val Gly Leu Lys Lys Asn Gly Ser Cys Lys Arg Gly Pro Arg Thr
                100                 105                 110

His Tyr Gly Gln Lys Ala Ile Leu Phe Leu Pro Leu Pro Val Ser Ser
                115                 120                 125

Asp

<210> SEQ ID NO 76
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 76

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Pro His
                20                  25                  30

Ile Gln Leu Gln Leu Ile Ala Glu Ser Val Gly Glu Val Tyr Ile Lys
            35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn Gly Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
                100                 105                 110

Arg Thr His Tyr Gly Gln Lys Ala Ile Leu Phe Leu Pro Leu Pro Val
                115                 120                 125

Ser Ser Asp
    130

<210> SEQ ID NO 77
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 77

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Pro His Ile Gln
                20                  25                  30

Leu Gln Leu Ile Ala Glu Ser Val Gly Glu Val Tyr Ile Lys Ser Thr
            35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn Gly Tyr Asn Thr Tyr Ile Ser Lys Lys His Ala Glu Lys Asn Trp
                85                  90                  95

Phe Val Gly Leu Lys Lys Asn Gly Ser Cys Lys Arg Gly Pro Arg Thr
```

```
                100             105             110
His Tyr Gly Gln Lys Ala Ile Leu Phe Leu Pro Leu Pro Val Ser Ser
        115             120             125

Asp

<210> SEQ ID NO 78
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 78

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Pro His Ile Gln Leu Gln Leu Ile Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn Gly Tyr Val Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 79
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 79

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Pro His
            20                  25                  30

Ile Gln Leu Gln Leu Ile Ala Glu Ser Val Gly Glu Val Tyr Ile Lys
        35                  40                  45

Ser Thr Glu Thr Gly Gln Tyr Leu Ala Met Asp Thr Asp Gly Leu Leu
50                  55                  60

Tyr Gly Ser Gln Thr Pro Asn Glu Glu Cys Leu Phe Leu Glu Arg Leu
65                  70                  75                  80

Glu Glu Asn Gly Tyr Val Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp
```

<210> SEQ ID NO 80
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 80

Val Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Pro His Ile Gln
            20                  25                  30

Leu Gln Leu Ile Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn Gly Tyr Val Thr Tyr Ile Ser Lys Lys His Ala Glu Lys Asn Trp
                85                  90                  95

Phe Val Gly Leu Lys Lys Asn Gly Ser Cys Lys Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 81
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 81

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Pro Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 82
<211> LENGTH: 129
<212> TYPE: PRT

```
<213> ORGANISM: Artificial sequence
<220> FEATURE:
<223> OTHER INFORMATION: Synthetic polypeptide

<400> SEQUENCE: 82

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Pro Val Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 83
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 83

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Pro Val Arg Gly Pro Arg Thr His Tyr Gly Gln Lys
        115                 120                 125

Ala Ile Leu Phe Leu Pro Leu Pro Val Ser Ser Asp
        130                 135                 140

<210> SEQ ID NO 84
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 84
```

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Glu Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 85
<211> LENGTH: 145
<212> TYPE: PRT
<213> ORGANISM: Artificial sequence
<220> FEATURE:
<223> OTHER INFORMATION: Synthetic polypeptide

<400> SEQUENCE: 85

Pro Ala Leu Pro Glu Asp Gly Gly Ala Ala Phe Pro Pro Gly His Phe
1               5                   10                  15

Lys Asp Pro Lys Arg Leu Tyr Cys Lys Asn Gly Gly Phe Phe Leu Arg
            20                  25                  30

Ile His Pro Asp Gly Arg Val Asp Gly Val Arg Glu Lys Ser Asp Pro
            35                  40                  45

His Val Lys Leu Gln Leu Gln Ala Glu Glu Arg Gly Val Val Ser Ile
50                  55                  60

Lys Gly Val Cys Ala Asn Arg Tyr Leu Ala Met Lys Glu Asp Gly Arg
65                  70                  75                  80

Leu Leu Ala Ser Lys Cys Val Thr Glu Glu Cys Phe Phe Phe Glu Arg
                85                  90                  95

Leu Glu Ser Asn Asn Tyr Asn Thr Tyr Arg Ser Arg Lys Tyr Ser Ser
            100                 105                 110

Trp Tyr Val Ala Leu Lys Arg Thr Gly Gln Tyr Lys Leu Gly Ser Lys
            115                 120                 125

Thr Gly Pro Gly Gln Lys Ala Ile Leu Phe Leu Pro Met Ser Ala Lys
            130                 135                 140

Ser
145

<210> SEQ ID NO 86
<211> LENGTH: 42
<212> TYPE: PRT
<213> ORGANISM: Artificial sequence
<220> FEATURE:
<223> OTHER INFORMATION: Synthetic polypeptide

<400> SEQUENCE: 86

Pro Gly Leu Pro Pro Ala Leu Pro Glu Pro Gly Ile Leu Ala Pro
1               5                   10                  15
```

```
Gln Pro Pro Asp Val Gly Ser Ser Asp Pro Leu Ser Met Val Gly Pro
            20                  25                  30

Ser Gln Gly Arg Ser Pro Ser Tyr Ala Ser
            35                  40

<210> SEQ ID NO 87
<211> LENGTH: 177
<212> TYPE: PRT
<213> ORGANISM: Artificial sequence
<220> FEATURE:
<223> OTHER INFORMATION: Synthetic polypeptide

<400> SEQUENCE: 87

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Gly Leu Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ser Met Val Gly Pro Ser Gln Gly Arg Ser Pro Ser Tyr Ala
                165                 170                 175

Ser

<210> SEQ ID NO 88
<211> LENGTH: 168
<212> TYPE: PRT
<213> ORGANISM: Artificial sequence
<220> FEATURE:
<223> OTHER INFORMATION: Synthetic polypeptide

<400> SEQUENCE: 88

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95
```

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Gly
        115                 120                 125

Leu Pro Pro Ala Leu Pro Glu Pro Pro Gly Ile Leu Ala Pro Gln Pro
    130                 135                 140

Pro Asp Val Gly Ser Ser Asp Pro Leu Ser Met Val Gly Pro Ser Gln
145                 150                 155                 160

Gly Arg Ser Pro Ser Tyr Ala Ser
                165

<210> SEQ ID NO 89
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 89

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Cys Lys Arg Gly Pro Arg Thr
            100                 105                 110

His Tyr Gly Gln Lys Ala Ile Leu Phe Leu Pro Leu Pro Gly Leu Pro
        115                 120                 125

Pro Ala Leu Pro Glu Pro Pro Gly Ile Leu Ala Pro Gln Pro Pro Asp
    130                 135                 140

Val Gly Ser Ser Asp Pro Leu Ser Met Val Gly Pro Ser Gln Gly Arg
145                 150                 155                 160

Ser Pro Ser Tyr Ala Ser
                165

<210> SEQ ID NO 90
<211> LENGTH: 168
<212> TYPE: PRT
<213> ORGANISM: Artificial sequence
<220> FEATURE:
<223> OTHER INFORMATION: Synthetic polypeptide

<400> SEQUENCE: 90

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu

```
                50                  55                  60
Tyr Gly Ser Gln Thr Pro Asn Glu Glu Cys Leu Phe Leu Glu Arg Leu
 65                  70                  75                  80

Glu Glu Asn His Tyr Asn Thr Tyr Ile Ser Lys Lys His Ala Glu Lys
                 85                  90                  95

Asn Trp Phe Val Gly Leu Lys Lys Asn Gly Ser Val Lys Arg Gly Pro
                100                 105                 110

Arg Thr His Tyr Gly Gln Lys Ala Ile Leu Phe Leu Val Leu Pro Gly
            115                 120                 125

Leu Pro Pro Ala Leu Pro Glu Pro Pro Gly Ile Leu Ala Pro Gln Pro
        130                 135                 140

Pro Asp Val Gly Ser Ser Asp Pro Leu Ser Met Val Gly Pro Ser Gln
145                 150                 155                 160

Gly Arg Ser Pro Ser Tyr Ala Ser
                165

<210> SEQ ID NO 91
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 91

Lys Leu Leu Tyr Cys Ser Asn Gly Gly His Phe Leu Arg Ile Leu Pro
 1               5                  10                  15

Asp Gly Thr Val Asp Gly Thr Arg Asp Arg Ser Asp Gln His Ile Gln
                 20                  25                  30

Leu Gln Leu Ser Ala Glu Ser Val Gly Glu Val Tyr Ile Lys Ser Thr
             35                  40                  45

Glu Thr Gly Gln Tyr Leu Ala Met Asp Thr Asp Gly Leu Leu Tyr Gly
         50                  55                  60

Ser Gln Thr Pro Asn Glu Glu Cys Leu Phe Leu Glu Arg Leu Glu Glu
 65                  70                  75                  80

Asn His Tyr Asn Thr Tyr Ile Ser Lys Lys His Ala Glu Lys Asn Trp
                 85                  90                  95

Phe Val Gly Leu Lys Lys Asn Gly Ser Val Lys Arg Gly Pro Arg Thr
                100                 105                 110

His Tyr Gly Gln Lys Ala Ile Leu Phe Leu Val Leu Pro Gly Leu Pro
            115                 120                 125

Pro Ala Leu Pro Glu Pro Pro Gly Ile Leu Ala Pro Gln Pro Pro Asp
        130                 135                 140

Val Gly Ser Ser Asp Pro Leu Ser Met Val Gly Pro Ser Gln Gly Arg
145                 150                 155                 160

Ser Pro Ser Tyr Ala Ser
                165

<210> SEQ ID NO 92
<211> LENGTH: 177
<212> TYPE: PRT
<213> ORGANISM: Artificial sequence
<220> FEATURE:
<223> OTHER INFORMATION: Synthetic polypeptide

<400> SEQUENCE: 92

Phe Asn Leu Pro Pro Gly Asn Tyr Lys Lys Pro Val Leu Leu Tyr Cys
 1               5                  10                  15
```

```
Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Val Leu Pro Gly Leu Pro Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ser Met Val Gly Pro Ser Gln Gly Arg Ser Pro Ser Tyr Ala
                165                 170                 175

Ser

<210> SEQ ID NO 93
<211> LENGTH: 168
<212> TYPE: PRT
<213> ORGANISM: Artificial sequence
<220> FEATURE:
<223> OTHER INFORMATION: Synthetic polypeptide

<400> SEQUENCE: 93

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
                20                  25                  30

Ile Gln Phe Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Thr Leu Phe Leu Glu Arg Leu
 65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
                100                 105                 110

Arg Thr His Tyr Gly Gln Lys Ala Ile Leu Trp Leu Pro Leu Pro Gly
            115                 120                 125

Leu Pro Pro Ala Leu Pro Glu Pro Gly Ile Leu Ala Pro Gln Pro
        130                 135                 140

Pro Asp Val Gly Ser Ser Asp Pro Leu Ser Met Val Gly Pro Ser Gln
145                 150                 155                 160

Gly Arg Ser Pro Ser Tyr Ala Ser
                165

<210> SEQ ID NO 94
<211> LENGTH: 166
<212> TYPE: PRT
```

<213> ORGANISM: Artificial sequence
<220> FEATURE:
<223> OTHER INFORMATION: Synthetic polypeptide

<400> SEQUENCE: 94

```
Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
50                  55                  60

Ser Gln Thr Pro Asn Glu Glu Thr Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Val Lys Arg Gly Pro Arg Thr
            100                 105                 110

His Tyr Gly Gln Lys Ala Ile Leu Trp Leu Pro Leu Pro Gly Leu Pro
        115                 120                 125

Pro Ala Leu Pro Glu Pro Pro Gly Ile Leu Ala Pro Gln Pro Pro Asp
    130                 135                 140

Val Gly Ser Ser Asp Pro Leu Ser Met Val Gly Pro Ser Gln Gly Arg
145                 150                 155                 160

Ser Pro Ser Tyr Ala Ser
                165
```

<210> SEQ ID NO 95
<211> LENGTH: 177
<212> TYPE: PRT
<213> ORGANISM: Artificial sequence
<220> FEATURE:
<223> OTHER INFORMATION: Synthetic polypeptide

<400> SEQUENCE: 95

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Trp Leu Pro Leu Pro Gly Leu Pro Pro Ala Leu Pro Glu
    130                 135                 140

Pro Pro Gly Ile Leu Ala Pro Gln Pro Pro Asp Val Gly Ser Ser Asp
145                 150                 155                 160
```

```
Pro Leu Ser Met Val Gly Pro Ser Gln Gly Arg Ser Pro Ser Tyr Ala
                165                 170                 175
Ser

<210> SEQ ID NO 96
<211> LENGTH: 162
<212> TYPE: PRT
<213> ORGANISM: Artificial sequence
<220> FEATURE:
<223> OTHER INFORMATION: Synthetic polypeptide

<400> SEQUENCE: 96

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
                20                  25                  30

Ile Gln Phe Gln Leu Ser Ala Glu Ser Val Gly Glu Val Tyr Ile Lys
            35                  40                  45

Ser Thr Glu Thr Gly Gln Tyr Leu Ala Ile Asp Thr Asp Gly Leu Val
        50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Gly Trp Phe
                85                  90                  95

Leu Gly Ile Lys Lys Asn Gly Ser Val Lys Gly Thr His Tyr Gly Gln
            100                 105                 110

Lys Ala Ile Leu Phe Leu Pro Leu Pro Gly Leu Pro Pro Ala Leu Pro
        115                 120                 125

Glu Pro Pro Gly Ile Leu Ala Pro Gln Pro Pro Asp Val Gly Ser Ser
    130                 135                 140

Asp Pro Leu Ser Met Val Gly Pro Ser Gln Gly Arg Ser Pro Ser Tyr
145                 150                 155                 160

Ala Ser

<210> SEQ ID NO 97
<211> LENGTH: 160
<212> TYPE: PRT
<213> ORGANISM: Artificial sequence
<220> FEATURE:
<223> OTHER INFORMATION: Synthetic polypeptide

<400> SEQUENCE: 97

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
                20                  25                  30

Phe Gln Leu Ser Ala Glu Ser Val Gly Glu Val Tyr Ile Lys Ser Thr
            35                  40                  45

Glu Thr Gly Gln Tyr Leu Ala Ile Asp Thr Asp Gly Leu Val Tyr Gly
        50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Gly Trp Phe Leu Gly
                85                  90                  95

Ile Lys Lys Asn Gly Ser Val Lys Gly Thr His Tyr Gly Gln Lys Ala
            100                 105                 110

Ile Leu Phe Leu Pro Leu Pro Gly Leu Pro Pro Ala Leu Pro Glu Pro
```

```
                   115                 120                 125
Pro Gly Ile Leu Ala Pro Gln Pro Pro Asp Val Gly Ser Ser Asp Pro
            130                 135                 140
Leu Ser Met Val Gly Pro Ser Gln Gly Arg Ser Pro Ser Tyr Ala Ser
145                 150                 155                 160

<210> SEQ ID NO 98
<211> LENGTH: 171
<212> TYPE: PRT
<213> ORGANISM: Artificial sequence
<220> FEATURE:
<223> OTHER INFORMATION: Synthetic polypeptide

<400> SEQUENCE: 98

Phe Asn Leu Pro Pro Gly Asn Tyr Lys Lys Pro Lys Leu Leu Tyr Cys
1               5                   10                  15
Ser Asn Gly Gly His Phe Leu Arg Ile Leu Pro Asp Gly Thr Val Asp
            20                  25                  30
Gly Thr Arg Asp Arg Ser Asp Gln His Ile Gln Phe Gln Leu Ser Ala
        35                  40                  45
Glu Ser Val Gly Glu Val Tyr Ile Lys Ser Thr Glu Thr Gly Gln Tyr
    50                  55                  60
Leu Ala Ile Asp Thr Asp Gly Leu Val Tyr Gly Ser Gln Thr Pro Asn
65                  70                  75                  80
Glu Glu Cys Leu Phe Leu Glu Arg Leu Glu Glu Asn His Tyr Asn Thr
                85                  90                  95
Tyr Ile Ser Lys Lys His Gly Trp Phe Leu Gly Ile Lys Lys Asn Gly
            100                 105                 110
Ser Val Lys Gly Thr His Tyr Gly Gln Lys Ala Ile Leu Phe Leu Pro
        115                 120                 125
Leu Pro Gly Leu Pro Pro Ala Leu Pro Glu Pro Pro Gly Ile Leu Ala
    130                 135                 140
Pro Gln Pro Pro Asp Val Gly Ser Ser Asp Pro Leu Ser Met Val Gly
145                 150                 155                 160
Pro Ser Gln Gly Arg Ser Pro Ser Tyr Ala Ser
                165                 170

<210> SEQ ID NO 99
<211> LENGTH: 216
<212> TYPE: PRT
<213> ORGANISM: Artificial sequence
<220> FEATURE:
<223> OTHER INFORMATION: Synthetic polypeptide

<400> SEQUENCE: 99

Met Arg Ser Gly Cys Val Val Val His Val Trp Ile Leu Ala Gly Leu
1               5                   10                  15
Trp Leu Ala Val Ala Gly Arg Pro Leu Ala Phe Ser Asp Ala Gly Pro
            20                  25                  30
His Val His Tyr Gly Trp Gly Asp Pro Ile Arg Leu Arg His Leu Tyr
        35                  40                  45
Thr Ser Gly Pro His Gly Leu Ser Ser Cys Phe Leu Arg Ile Arg Ala
    50                  55                  60
Asp Gly Val Val Asp Cys Ala Arg Gly Gln Ser Ala His Ser Leu Leu
65                  70                  75                  80
Glu Ile Lys Ala Val Ala Leu Arg Thr Val Ala Ile Lys Gly Val His
                85                  90                  95
```

```
Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 100
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 100

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 101
<211> LENGTH: 183
<212> TYPE: PRT
<213> ORGANISM: Artificial sequence
<220> FEATURE:
<223> OTHER INFORMATION: Synthetic polypeptide

<400> SEQUENCE: 101

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Met Val Pro Glu Glu Pro Glu
    130                 135                 140
```

```
Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
            165                 170                 175

Arg Ser Pro Ser Phe Glu Lys
            180

<210> SEQ ID NO 102
<211> LENGTH: 174
<212> TYPE: PRT
<213> ORGANISM: Artificial sequence
<220> FEATURE:
<223> OTHER INFORMATION: Synthetic polypeptide

<400> SEQUENCE: 102

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Leu Pro
            115                 120                 125

Met Val Pro Glu Glu Pro Glu Asp Leu Arg Gly His Leu Glu Ser Asp
        130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys
                165                 170

<210> SEQ ID NO 103
<211> LENGTH: 172
<212> TYPE: PRT
<213> ORGANISM: Artificial sequence
<220> FEATURE:
<223> OTHER INFORMATION: Synthetic polypeptide

<400> SEQUENCE: 103

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
```

```
                    85                  90                  95

Phe Val Gly Leu Lys Lys Asn Gly Ser Cys Lys Arg Gly Pro Arg Thr
                100                 105                 110

His Tyr Gly Gln Lys Ala Ile Leu Phe Leu Pro Leu Pro Met Val
            115                 120                 125

Pro Glu Glu Pro Glu Asp Leu Arg Gly His Leu Glu Ser Asp Met Phe
130                 135                 140

Ser Ser Pro Leu Glu Thr Asp Ser Met Asp Pro Phe Gly Leu Val Thr
145                 150                 155                 160

Gly Leu Glu Ala Val Arg Ser Pro Ser Phe Glu Lys
                165                 170

<210> SEQ ID NO 104
<211> LENGTH: 183
<212> TYPE: PRT
<213> ORGANISM: Artificial sequence
<220> FEATURE:
<223> OTHER INFORMATION: Synthetic polypeptide

<400> SEQUENCE: 104

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
        50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Val Leu Leu Pro Met Val Pro Glu Glu Pro Glu
        130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 105
<211> LENGTH: 174
<212> TYPE: PRT
<213> ORGANISM: Artificial sequence
<220> FEATURE:
<223> OTHER INFORMATION: Synthetic polypeptide

<400> SEQUENCE: 105

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
                20                  25                  30
```

```
Ile Gln Leu Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Cys Leu Phe Leu Glu Arg Leu
 65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Phe Leu Val Leu Leu Pro
            115                 120                 125

Met Val Pro Glu Glu Pro Glu Asp Leu Arg Gly His Leu Glu Ser Asp
            130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys
                165                 170

<210> SEQ ID NO 106
<211> LENGTH: 172
<212> TYPE: PRT
<213> ORGANISM: Artificial sequence
<220> FEATURE:
<223> OTHER INFORMATION: Synthetic polypeptide

<400> SEQUENCE: 106

Val Leu Leu Tyr Cys Ser Asn Gly Gly His Phe Leu Arg Ile Leu Pro
 1               5                  10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
            35                  40                  45

Glu Thr Gly Gln Tyr Leu Ala Met Asp Thr Asp Gly Leu Leu Tyr Gly
 50                  55                  60

Ser Gln Thr Pro Asn Glu Glu Cys Leu Phe Leu Glu Arg Leu Glu Glu
 65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Val Lys Arg Gly Pro Arg Thr
            100                 105                 110

His Tyr Gly Gln Lys Ala Ile Leu Phe Leu Val Leu Leu Pro Met Val
            115                 120                 125

Pro Glu Glu Pro Glu Asp Leu Arg Gly His Leu Glu Ser Asp Met Phe
            130                 135                 140

Ser Ser Pro Leu Glu Thr Asp Ser Met Asp Pro Phe Gly Leu Val Thr
145                 150                 155                 160

Gly Leu Glu Ala Val Arg Ser Pro Ser Phe Glu Lys
                165                 170

<210> SEQ ID NO 107
<211> LENGTH: 183
<212> TYPE: PRT
<213> ORGANISM: Artificial sequence
<220> FEATURE:
<223> OTHER INFORMATION: Synthetic polypeptide

<400> SEQUENCE: 107
```

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Thr Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Trp Leu Pro Leu Leu Pro Met Val Pro Glu Glu Pro Glu
        130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 108
<211> LENGTH: 174
<212> TYPE: PRT
<213> ORGANISM: Artificial sequence
<220> FEATURE:
<223> OTHER INFORMATION: Synthetic polypeptide

<400> SEQUENCE: 108

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
50                  55                  60

Tyr Gly Ser Gln Thr Pro Asn Glu Glu Thr Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
                100                 105                 110

Arg Thr His Tyr Gly Gln Lys Ala Ile Leu Trp Leu Pro Leu Leu Pro
            115                 120                 125

Met Val Pro Glu Glu Pro Glu Asp Leu Arg Gly His Leu Glu Ser Asp
        130                 135                 140

Met Phe Ser Ser Pro Leu Glu Thr Asp Ser Met Asp Pro Phe Gly Leu
145                 150                 155                 160

Val Thr Gly Leu Glu Ala Val Arg Ser Pro Ser Phe Glu Lys
                165                 170
```

<210> SEQ ID NO 109
<211> LENGTH: 172
<212> TYPE: PRT
<213> ORGANISM: Artificial sequence
<220> FEATURE:
<223> OTHER INFORMATION: Synthetic polypeptide

<400> SEQUENCE: 109

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Phe Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Thr Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Lys Lys Asn Gly Ser Val Lys Arg Gly Pro Arg Thr
            100                 105                 110

His Tyr Gly Gln Lys Ala Ile Leu Trp Leu Pro Leu Pro Met Val
        115                 120                 125

Pro Glu Glu Pro Glu Asp Leu Arg Gly His Leu Glu Ser Asp Met Phe
    130                 135                 140

Ser Ser Pro Leu Glu Thr Asp Ser Met Asp Pro Phe Gly Leu Val Thr
145                 150                 155                 160

Gly Leu Glu Ala Val Arg Ser Pro Ser Phe Glu Lys
                165                 170

<210> SEQ ID NO 110
<211> LENGTH: 177
<212> TYPE: PRT
<213> ORGANISM: Artificial sequence
<220> FEATURE:
<223> OTHER INFORMATION: Synthetic polypeptide

<400> SEQUENCE: 110

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
    50                  55                  60

Leu Ala Ile Asp Thr Asp Gly Leu Val Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Gly Trp Phe Leu Gly Ile Lys Lys Asn Gly
                100                 105                 110

Ser Val Lys Gly Thr His Tyr Gly Gln Lys Ala Ile Leu Phe Leu Pro
            115                 120                 125

Leu Leu Pro Met Val Pro Glu Glu Pro Glu Asp Leu Arg Gly His Leu

```
                130                 135                 140
Glu Ser Asp Met Phe Ser Pro Leu Glu Thr Asp Ser Met Asp Pro
145                 150                 155                 160

Phe Gly Leu Val Thr Gly Leu Glu Ala Val Arg Ser Pro Ser Phe Glu
                165                 170                 175

Lys

<210> SEQ ID NO 111
<211> LENGTH: 168
<212> TYPE: PRT
<213> ORGANISM: Artificial sequence
<220> FEATURE:
<223> OTHER INFORMATION: Synthetic polypeptide

<400> SEQUENCE: 111

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
                20                  25                  30

Ile Gln Phe Gln Leu Ser Ala Glu Ser Val Gly Glu Val Tyr Ile Lys
                35                  40                  45

Ser Thr Glu Thr Gly Gln Tyr Leu Ala Ile Asp Thr Asp Gly Leu Val
            50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Gly Trp Phe
                85                  90                  95

Leu Gly Ile Lys Lys Asn Gly Ser Val Lys Gly Thr His Tyr Gly Gln
                100                 105                 110

Lys Ala Ile Leu Phe Leu Pro Leu Pro Met Val Pro Glu Glu Pro
                115                 120                 125

Glu Asp Leu Arg Gly His Leu Glu Ser Asp Met Phe Ser Ser Pro Leu
    130                 135                 140

Glu Thr Asp Ser Met Asp Pro Phe Gly Leu Val Thr Gly Leu Glu Ala
145                 150                 155                 160

Val Arg Ser Pro Ser Phe Glu Lys
                165

<210> SEQ ID NO 112
<211> LENGTH: 166
<212> TYPE: PRT
<213> ORGANISM: Artificial sequence
<220> FEATURE:
<223> OTHER INFORMATION: Synthetic polypeptide

<400> SEQUENCE: 112

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
                20                  25                  30

Phe Gln Leu Ser Ala Glu Ser Val Gly Glu Val Tyr Ile Lys Ser Thr
                35                  40                  45

Glu Thr Gly Gln Tyr Leu Ala Ile Asp Thr Asp Gly Leu Val Tyr Gly
            50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Gly Trp Phe Leu Gly
```

```
                85                  90                  95
Ile Lys Lys Asn Gly Ser Val Lys Gly Thr His Tyr Gly Gln Lys Ala
            100                 105                 110

Ile Leu Phe Leu Pro Leu Pro Met Val Pro Glu Glu Pro Glu Asp
            115                 120                 125

Leu Arg Gly His Leu Glu Ser Asp Met Phe Ser Ser Pro Leu Glu Thr
130                 135                 140

Asp Ser Met Asp Pro Phe Gly Leu Val Thr Gly Leu Glu Ala Val Arg
145                 150                 155                 160

Ser Pro Ser Phe Glu Lys
                165

<210> SEQ ID NO 113
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 113

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
            100                 105                 110

Gln Asn Gly Ser Cys Val Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 114
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 114

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80
```

```
Glu Glu Cys Leu Phe Leu Glu Arg Leu Glu Asn His Tyr Asn Thr
                85                  90                  95

Tyr Ile Ser Lys Lys His Ala Glu Lys Asn Trp Phe Val Gly Leu Asp
                100                 105                 110

Gln Asn Gly Ser Val Val Arg Gly Pro Arg Thr His Tyr Gly Gln Lys
            115                 120                 125

Ala Ile Leu Phe Leu Pro Leu Pro Val Ser Ser Asp
        130                 135                 140
```

<210> SEQ ID NO 115
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 115

```
Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
                20                  25                  30

Ile Gln Leu Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
50              55                  60

Tyr Gly Ser Gln Thr Pro Asn Glu Glu Cys Leu Phe Leu Glu Arg Leu
65              70                  75                  80

Glu Glu Asn His Tyr Asn Thr Tyr Ile Ser Lys Lys His Ala Glu Lys
                85                  90                  95

Asn Trp Phe Val Gly Leu Asp Gln Asn Gly Ser Cys Val Arg Gly Pro
                100                 105                 110

Arg Thr His Tyr Gly Gln Lys Ala Ile Leu Phe Leu Pro Leu Pro Val
            115                 120                 125

Ser Ser Asp
    130
```

<210> SEQ ID NO 116
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 116

```
Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
                20                  25                  30

Leu Gln Leu Ser Ala Glu Ser Val Gly Glu Val Tyr Ile Lys Ser Thr
            35                  40                  45

Glu Thr Gly Gln Tyr Leu Ala Met Asp Thr Asp Gly Leu Leu Tyr Gly
        50                  55                  60

Ser Gln Thr Pro Asn Glu Glu Cys Leu Phe Leu Glu Arg Leu Glu Glu
65              70                  75                  80

Asn His Tyr Asn Thr Tyr Ile Ser Lys Lys His Ala Glu Lys Asn Trp
                85                  90                  95

Phe Val Gly Leu Asp Gln Asn Gly Ser Cys Val Arg Gly Pro Arg Thr
                100                 105                 110
```

His Tyr Gly Gln Lys Ala Ile Leu Phe Leu Pro Leu Pro Val Ser Ser
        115                 120                 125

Asp

<210> SEQ ID NO 117
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 117

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Asp Gln Asn Gly Ser Val Val Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 118
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 118

Lys Leu Leu Tyr Cys Ser Asn Gly Gly His Phe Leu Arg Ile Leu Pro
1               5                   10                  15

Asp Gly Thr Val Asp Gly Thr Arg Asp Arg Ser Asp Gln His Ile Gln
            20                  25                  30

Leu Gln Leu Ser Ala Glu Ser Val Gly Glu Val Tyr Ile Lys Ser Thr
        35                  40                  45

Glu Thr Gly Gln Tyr Leu Ala Met Asp Thr Asp Gly Leu Leu Tyr Gly
    50                  55                  60

Ser Gln Thr Pro Asn Glu Glu Cys Leu Phe Leu Glu Arg Leu Glu Glu
65                  70                  75                  80

Asn His Tyr Asn Thr Tyr Ile Ser Lys Lys His Ala Glu Lys Asn Trp
                85                  90                  95

Phe Val Gly Leu Asp Gln Asn Gly Ser Val Val Arg Gly Pro Arg Thr
            100                 105                 110

His Tyr Gly Gln Lys Ala Ile Leu Phe Leu Pro Leu Pro Val Ser Ser
        115                 120                 125

Asp

<210> SEQ ID NO 119
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 119

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Asp
                100                 105                 110

Gln Asn Gly Ser Cys Val Arg Gly Pro Arg Thr His Tyr Gly Gln Lys
            115                 120                 125

Ala Ile Leu Phe Leu Pro Leu Pro Val Ser Ser Asp
    130                 135                 140
```

<210> SEQ ID NO 120
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 120

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Asp
                100                 105                 110

Gln Asn Gly Ser Val Val Arg Gly Pro Arg Thr His Tyr Gly Gln Lys
            115                 120                 125

Ala Ile Leu Phe Leu Pro Leu Pro Val Ser Ser Asp
    130                 135                 140
```

<210> SEQ ID NO 121
<211> LENGTH: 90
<212> TYPE: PRT
<213> ORGANISM: Artificial sequence

```
<220> FEATURE:
<223> OTHER INFORMATION: Synthetic polypeptide

<400> SEQUENCE: 121

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
        35                  40                  45

Cys Arg Ser Gly Arg Cys Ile Pro Gln His Trp Leu Cys Asp Gly Leu
50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Ser Leu
                85                  90

<210> SEQ ID NO 122
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 122

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys
        35

<210> SEQ ID NO 123
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (33)..(33)
<223> OTHER INFORMATION: Xaa = Pro or Ser
<220> FEATURE:
<221> NAME/KEY: MISC_FEATURE
<222> LOCATION: (34)..(34)
<223> OTHER INFORMATION: Xaa = Pro or Gln
<220> FEATURE:
<221> NAME/KEY: MISC_FEATURE
<222> LOCATION: (35)..(35)
<223> OTHER INFORMATION: Xaa = Ala or Gln
<220> FEATURE:
<221> NAME/KEY: MISC_FEATURE
<222> LOCATION: (36)..(36)
<223> OTHER INFORMATION: Xaa = His or no amino acid

<400> SEQUENCE: 123

Cys Gln Ser Asn Glu Phe Arg Cys Arg Ser Gly Arg Cys Ile Pro Gln
1               5                   10                  15

His Trp Leu Cys Asp Gly Leu Asn Asp Cys Gly Asp Gly Ser Asp Glu
            20                  25                  30

Xaa Xaa Xaa Xaa Cys
        35

<210> SEQ ID NO 124
```

```
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Glu, Leu, Pro, Gln or Arg
<220> FEATURE:
<221> NAME/KEY: MISC_FEATURE
<222> LOCATION: (3)..(3)
<223> OTHER INFORMATION: Xaa = Ala, Pro or Ser
<220> FEATURE:
<221> NAME/KEY: MISC_FEATURE
<222> LOCATION: (4)..(4)
<223> OTHER INFORMATION: Xaa = Asp, Gly, Ile or Asn
<220> FEATURE:
<221> NAME/KEY: MISC_FEATURE
<222> LOCATION: (5)..(5)
<223> OTHER INFORMATION: Xaa = Glu, Gly or Gln
<220> FEATURE:
<221> NAME/KEY: MISC_FEATURE
<222> LOCATION: (6)..(6)
<223> OTHER INFORMATION: Xaa = Phe or Gln
<220> FEATURE:
<221> NAME/KEY: MISC_FEATURE
<222> LOCATION: (7)..(7)
<223> OTHER INFORMATION: Xaa = Phe, Lys, Pro, Gln, Arg or Thr
<220> FEATURE:
<221> NAME/KEY: MISC_FEATURE
<222> LOCATION: (8)..(8)
<223> OTHER INFORMATION: Xaa = Glu or no amino acid
<220> FEATURE:
<221> NAME/KEY: MISC_FEATURE
<222> LOCATION: (10)..(10)
<223> OTHER INFORMATION: Xaa = Gly, Asn, Arg or Ser
<220> FEATURE:
<221> NAME/KEY: MISC_FEATURE
<222> LOCATION: (11)..(11)
<223> OTHER INFORMATION: Xaa = Asn or Ser
<220> FEATURE:
<221> NAME/KEY: MISC_FEATURE
<222> LOCATION: (13)..(13)
<223> OTHER INFORMATION: Xaa = His, Asn, Gln or Arg
<220> FEATURE:
<221> NAME/KEY: MISC_FEATURE
<222> LOCATION: (15)..(15)
<223> OTHER INFORMATION: Xaa = Ile or Val
<220> FEATURE:
<221> NAME/KEY: MISC_FEATURE
<222> LOCATION: (17)..(17)
<223> OTHER INFORMATION: Xaa = Ala, Glu, Leu, Pro, Gln, Arg or Val
<220> FEATURE:
<221> NAME/KEY: MISC_FEATURE
<222> LOCATION: (18)..(18)
<223> OTHER INFORMATION: Xaa = Ala, His, Pro, Gln, Arg or Thr
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Glu or Val
<220> FEATURE:
<221> NAME/KEY: MISC_FEATURE
<222> LOCATION: (25)..(25)
<223> OTHER INFORMATION: Xaa = Asp, Asn or Pro
<220> FEATURE:
<221> NAME/KEY: MISC_FEATURE
<222> LOCATION: (28)..(28)
<223> OTHER INFORMATION: Xaa = Gly, Leu or Gln
<220> FEATURE:
<221> NAME/KEY: MISC_FEATURE
<222> LOCATION: (30)..(30)
<223> OTHER INFORMATION: Xaa = Asp, Gly, Asn or Ser
<220> FEATURE:
<221> NAME/KEY: MISC_FEATURE
```

<222> LOCATION: (34)..(34)
<223> OTHER INFORMATION: Xaa = Ala, Glu, Lys or Thr
<220> FEATURE:
<221> NAME/KEY: MISC_FEATURE
<222> LOCATION: (35)..(35)
<223> OTHER INFORMATION: Xaa = Asp, Gly, Leu, Asn or Ser
<220> FEATURE:
<221> NAME/KEY: MISC_FEATURE
<222> LOCATION: (36)..(36)
<223> OTHER INFORMATION: Xaa = Ala or no amino acid
<220> FEATURE:
<221> NAME/KEY: MISC_FEATURE
<222> LOCATION: (37)..(37)
<223> OTHER INFORMATION: Xaa = His or no amino acid

<400> SEQUENCE: 124

Cys Xaa Xaa Xaa Xaa Xaa Xaa Xaa Cys Xaa Xaa Gly Xaa Cys Xaa Pro
1               5                   10                  15

Xaa Xaa Trp Xaa Cys Asp Gly Xaa Xaa Asp Cys Xaa Asp Xaa Ser Asp
            20                  25                  30

Glu Xaa Xaa Xaa Xaa Cys
        35

<210> SEQ ID NO 125
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Ala, Gly or Pro
<220> FEATURE:
<221> NAME/KEY: MISC_FEATURE
<222> LOCATION: (3)..(3)
<223> OTHER INFORMATION: Xaa = Ala, Pro or Ser
<220> FEATURE:
<221> NAME/KEY: MISC_FEATURE
<222> LOCATION: (4)..(4)
<223> OTHER INFORMATION: Xaa = Asp, Gly or Asn
<220> FEATURE:
<221> NAME/KEY: MISC_FEATURE
<222> LOCATION: (5)..(5)
<223> OTHER INFORMATION: Xaa = Glu or Gln
<220> FEATURE:
<221> NAME/KEY: MISC_FEATURE
<222> LOCATION: (7)..(7)
<223> OTHER INFORMATION: Xaa = Gln, Arg or Thr
<220> FEATURE:
<221> NAME/KEY: MISC_FEATURE
<222> LOCATION: (9)..(9)
<223> OTHER INFORMATION: Xaa = Gly, Asn, Arg or Ser
<220> FEATURE:
<221> NAME/KEY: MISC_FEATURE
<222> LOCATION: (10)..(10)
<223> OTHER INFORMATION: Xaa = Gly, Asn or Ser
<220> FEATURE:
<221> NAME/KEY: MISC_FEATURE
<222> LOCATION: (11)..(11)
<223> OTHER INFORMATION: Xaa = Gly or Thr
<220> FEATURE:
<221> NAME/KEY: MISC_FEATURE
<222> LOCATION: (12)..(12)
<223> OTHER INFORMATION: Xaa = Gly, Lys, Gln or Ser
<220> FEATURE:
<221> NAME/KEY: MISC_FEATURE
<222> LOCATION: (13)..(13)
<223> OTHER INFORMATION: Xaa = Ile, Lys or no amino acid
<220> FEATURE:
<221> NAME/KEY: MISC_FEATURE
<222> LOCATION: (15)..(15)
<223> OTHER INFORMATION: Xaa = Ile, Leu or Val
<220> FEATURE:
<221> NAME/KEY: MISC_FEATURE
<222> LOCATION: (17)..(17)
<223> OTHER INFORMATION: Xaa = Leu, Gln, Arg or Val
<220> FEATURE:
<221> NAME/KEY: MISC_FEATURE
<222> LOCATION: (18)..(18)
<223> OTHER INFORMATION: Xaa = Ala, Glu, His or Pro
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Leu or Val
<220> FEATURE:
<221> NAME/KEY: MISC_FEATURE
<222> LOCATION: (25)..(25)
<223> OTHER INFORMATION: Xaa = Asp or Asn
<220> FEATURE:
<221> NAME/KEY: MISC_FEATURE
<222> LOCATION: (30)..(30)
<223> OTHER INFORMATION: Xaa = Gly or Asn
<220> FEATURE:
<221> NAME/KEY: MISC_FEATURE
<222> LOCATION: (34)..(34)
<223> OTHER INFORMATION: Xaa = Ala, Glu, Lys, Pro or Ser
<220> FEATURE:
<221> NAME/KEY: MISC_FEATURE
<222> LOCATION: (35)..(35)
<223> OTHER INFORMATION: Xaa = Gly, Leu, Pro or Ser
<220> FEATURE:
<221> NAME/KEY: MISC_FEATURE
<222> LOCATION: (36)..(36)
<223> OTHER INFORMATION: Xaa = Ala, Glu, Val or no amino acid
<220> FEATURE:
<221> NAME/KEY: MISC_FEATURE
<222> LOCATION: (37)..(37)
<223> OTHER INFORMATION: Xaa = Ile, Thr or no amino acid

<400> SEQUENCE: 125

Cys Xaa Xaa Xaa Xaa Phe Xaa Cys Xaa Xaa Xaa Xaa Xaa Cys Xaa Pro
1               5                   10                  15

Xaa Xaa Trp Xaa Cys Asp Gly Xaa Xaa Asp Cys Gly Asp Xaa Ser Asp
            20                  25                  30

Glu Xaa Xaa Xaa Xaa Cys
        35

<210> SEQ ID NO 126
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 126

Cys Gln Ser Asn Glu Phe Arg Cys Arg Ser Gly Arg Cys Ile Pro Gln
1               5                   10                  15

His Trp Leu Cys Asp Gly Leu Asn Asp Cys Gly Asp Gly Ser Asp Glu
            20                  25                  30

Ser Gln Gln Cys Ser Ala Pro Ala Ser Glu Pro Pro Gly Ser Leu
        35                  40                  45

<210> SEQ ID NO 127
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 127

-continued

Cys Gln Ser Asn Glu Phe Arg Cys Arg Ser Gly Arg Cys Ile Pro Gln
1               5                   10                  15

His Trp Leu Cys Asp Gly Leu Asn Asp Cys Gly Asp Gly Ser Asp Glu
            20                  25                  30

Ser Gln Gln Cys
        35

<210> SEQ ID NO 128
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 128

Cys Arg Ala Gly Glu Phe Arg Cys Ser Asn Gly Arg Cys Val Pro Leu
1               5                   10                  15

Thr Trp Leu Cys Asp Gly Glu Asp Cys Gln Asp Asn Ser Asp Glu
            20                  25                  30

Lys Asn Cys
        35

<210> SEQ ID NO 129
<211> LENGTH: 38
<212> TYPE: PRT
<213> ORGANISM: Artificial sequence
<220> FEATURE:
<223> OTHER INFORMATION: Synthetic polypeptide

<400> SEQUENCE: 129

Cys Pro Ser Asn Gln Phe Pro Cys Arg Ser Thr Gly Ile Cys Ile Pro
1               5                   10                  15

Leu Ala Trp Val Cys Asp Gly Leu Asn Asp Cys Gly Asp Gly Ser Asp
            20                  25                  30

Glu Ser Pro Ala His Cys
        35

<210> SEQ ID NO 130
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 130

Cys Gln Ser Asn Glu Phe Arg Cys Arg Ser Gly Arg Cys Ile Pro Gln
1               5                   10                  15

His Trp Leu Cys Asp Gly Leu Asn Asp Cys Gly Asp Gly Ser Asp Glu
            20                  25                  30

Pro Pro Ala His Cys
        35

<210> SEQ ID NO 131
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (9)..(9)
<223> OTHER INFORMATION: Xaa = Ser or Gly
<220> FEATURE:
<221> NAME/KEY: MISC_FEATURE

```
<222> LOCATION: (17)..(17)
<223> OTHER INFORMATION: Xaa = His or Thr
<220> FEATURE:
<221> NAME/KEY: MISC_FEATURE
<222> LOCATION: (19)..(19)
<223> OTHER INFORMATION: Xaa = Val or Leu
<220> FEATURE:
<221> NAME/KEY: MISC_FEATURE
<222> LOCATION: (33)..(33)
<223> OTHER INFORMATION: Xaa = Pro or Ser
<220> FEATURE:
<221> NAME/KEY: MISC_FEATURE
<222> LOCATION: (36)..(36)
<223> OTHER INFORMATION: Xaa = His or Thr

<400> SEQUENCE: 131

Cys Leu Pro Asp Glu Phe Gln Cys Xaa Ser Gly Arg Cys Ile Pro Gln
1               5                   10                  15

Xaa Trp Xaa Cys Asp Gly Leu Asn Asp Cys Gly Asp Gly Ser Asp Glu
            20                  25                  30

Xaa Pro Ala Xaa Cys
        35

<210> SEQ ID NO 132
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Ala, Gly, Pro or Arg
<220> FEATURE:
<221> NAME/KEY: MISC_FEATURE
<222> LOCATION: (3)..(3)
<223> OTHER INFORMATION: Xaa = Ala or Pro
<220> FEATURE:
<221> NAME/KEY: MISC_FEATURE
<222> LOCATION: (4)..(4)
<223> OTHER INFORMATION: Xaa = Asp, Gly, Asn or Ser
<220> FEATURE:
<221> NAME/KEY: MISC_FEATURE
<222> LOCATION: (5)..(5)
<223> OTHER INFORMATION: Xaa = Glu or Gln
<220> FEATURE:
<221> NAME/KEY: MISC_FEATURE
<222> LOCATION: (7)..(7)
<223> OTHER INFORMATION: Xaa = Gln, Arg or Thr
<220> FEATURE:
<221> NAME/KEY: MISC_FEATURE
<222> LOCATION: (9)..(9)
<223> OTHER INFORMATION: Xaa = Gly, Ser, Lys
<220> FEATURE:
<221> NAME/KEY: MISC_FEATURE
<222> LOCATION: (11)..(11)
<223> OTHER INFORMATION: Xaa = Gly or Thr
<220> FEATURE:
<221> NAME/KEY: MISC_FEATURE
<222> LOCATION: (12)..(12)
<223> OTHER INFORMATION: Xaa = Gly, His or Arg
<220> FEATURE:
<221> NAME/KEY: MISC_FEATURE
<222> LOCATION: (13)..(13)
<223> OTHER INFORMATION: Xaa = Arg or no amino acid
<220> FEATURE:
<221> NAME/KEY: MISC_FEATURE
<222> LOCATION: (15)..(15)
<223> OTHER INFORMATION: Xaa = Ile, Leu or Val
<220> FEATURE:
<221> NAME/KEY: MISC_FEATURE
<222> LOCATION: (16)..(16)
<223> OTHER INFORMATION: Xaa = Pro or Ser
<220> FEATURE:
<221> NAME/KEY: MISC_FEATURE
```

```
<222> LOCATION: (17)..(17)
<223> OTHER INFORMATION: Xaa = Ala, Leu or Gln
<220> FEATURE:
<221> NAME/KEY: MISC_FEATURE
<222> LOCATION: (18)..(18)
<223> OTHER INFORMATION: Xaa = Asn, Ser or Thr
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Glu or Val
<220> FEATURE:
<221> NAME/KEY: MISC_FEATURE
<222> LOCATION: (28)..(28)
<223> OTHER INFORMATION: Xaa = Gly or Leu
<220> FEATURE:
<221> NAME/KEY: MISC_FEATURE
<222> LOCATION: (34)..(34)
<223> OTHER INFORMATION: Xaa = Ala, Glu or Thr
<220> FEATURE:
<221> NAME/KEY: MISC_FEATURE
<222> LOCATION: (35)..(35)
<223> OTHER INFORMATION: Xaa = Asp, Asn or Ser
<220> FEATURE:
<221> NAME/KEY: MISC_FEATURE
<222> LOCATION: (36)..(36)
<223> OTHER INFORMATION: Xaa = Ala or no amino acid
<220> FEATURE:
<221> NAME/KEY: MISC_FEATURE
<222> LOCATION: (37)..(37)
<223> OTHER INFORMATION: Xaa = Thr or no amino acid

<400> SEQUENCE: 132

Cys Xaa Xaa Xaa Xaa Phe Xaa Cys Xaa Asn Xaa Xaa Xaa Cys Xaa Xaa
1               5                   10                  15

Xaa Xaa Trp Xaa Cys Asp Gly Xaa Asp Asp Cys Xaa Asp Gly Ser Asp
            20                  25                  30

Glu Xaa Xaa Xaa Xaa Cys
        35

<210> SEQ ID NO 133
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 133

Cys Gly Pro Asp Gln Phe Arg Cys Ser Ser Gly Lys Cys Ile Pro Gln
1               5                   10                  15

His Trp Leu Cys Asp Gly Leu Asn Asp Cys Gly Asp Gly Ser Asp Glu
            20                  25                  30

Ser Pro Ala Thr Cys
        35

<210> SEQ ID NO 134
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 134

Cys Gly Ala Asn Glu Phe Gln Cys Arg Ser Thr Gly Ile Cys Val Pro
1               5                   10                  15

Val Glu Trp Val Cys Asp Gly Asp Asn Asp Cys Gly Asp Gly Ser Asp
```

```
                  20                  25                  30

Glu Pro Pro Val Cys
        35

<210> SEQ ID NO 135
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 135

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys
        35

<210> SEQ ID NO 136
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 136

Cys Gly Pro Asp Glu Phe Arg Cys Asn Asn Gly Gln Cys Ile Pro Leu
1               5                   10                  15

Pro Trp Arg Cys Asp Gly Val Asp Asp Cys Gly Asp Asn Ser Asp Glu
            20                  25                  30

Pro Leu Glu Ile Cys
        35

<210> SEQ ID NO 137
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 137

Cys Ala Ser Gly Glu Phe Thr Cys Asn Asn Gly Gln Cys Val Pro Leu
1               5                   10                  15

Ala Trp Arg Cys Asp Gly Val Asn Asp Cys Gln Asp Gly Ser Asp Glu
            20                  25                  30

Lys Gly Cys
        35

<210> SEQ ID NO 138
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 138

Cys Pro Pro Asp Glu Phe Gln Cys Arg Gly Thr Lys Lys Cys Leu Pro
1               5                   10                  15

Leu Ala Trp Val Cys Asp Gly Asp Asn Asp Cys Glu Asp Asp Ser Asp
            20                  25                  30

Glu Glu Ser Cys
```

<210> SEQ ID NO 139
<211> LENGTH: 37
<212> TYPE: PRT
<213> ORGANISM: Artificial sequence
<220> FEATURE:
<223> OTHER INFORMATION: Synthetic polypeptide

<400> SEQUENCE: 139

Cys Leu Pro Asp Glu Phe Gln Cys Gly Ser Gly Arg Cys Ile Pro Gln
1               5                   10                  15

His Trp Leu Cys Asp Gly Leu Asn Asp Cys Gly Asp Gly Ser Asp Glu
            20                  25                  30

Pro Pro Ala His Cys
        35

<210> SEQ ID NO 140
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 140

Cys Ala Pro Gly Glu Phe Thr Cys Lys Asn Thr Gly Arg Cys Ile Pro
1               5                   10                  15

Leu Asn Trp Arg Cys Asp Gly Asp Asp Asp Cys Gly Asp Gly Ser Asp
            20                  25                  30

Glu Thr Asp Cys
        35

<210> SEQ ID NO 141
<211> LENGTH: 29
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Ala, Gly or Pro
<220> FEATURE:
<221> NAME/KEY: MISC_FEATURE
<222> LOCATION: (3)..(3)
<223> OTHER INFORMATION: Xaa = Ala, Pro or Ser
<220> FEATURE:
<221> NAME/KEY: MISC_FEATURE
<222> LOCATION: (4)..(4)
<223> OTHER INFORMATION: Xaa = Asp, Gly or Asn
<220> FEATURE:
<221> NAME/KEY: MISC_FEATURE
<222> LOCATION: (5)..(5)
<223> OTHER INFORMATION: Xaa = Glu or Gln
<220> FEATURE:
<221> NAME/KEY: MISC_FEATURE
<222> LOCATION: (7)..(7)
<223> OTHER INFORMATION: Xaa = Gln, Arg or Thr
<220> FEATURE:
<221> NAME/KEY: MISC_FEATURE
<222> LOCATION: (9)..(9)
<223> OTHER INFORMATION: Xaa = Gly, Asn, Arg or Ser
<220> FEATURE:
<221> NAME/KEY: MISC_FEATURE
<222> LOCATION: (10)..(10)
<223> OTHER INFORMATION: Xaa = Gly, Asn or Ser
<220> FEATURE:
<221> NAME/KEY: MISC_FEATURE
<222> LOCATION: (11)..(11)
<223> OTHER INFORMATION: Xaa = Gly or Thr

```
<220> FEATURE:
<221> NAME/KEY: MISC_FEATURE
<222> LOCATION: (12)..(12)
<223> OTHER INFORMATION: Xaa = Gly, Lys, Gln or Ser
<220> FEATURE:
<221> NAME/KEY: MISC_FEATURE
<222> LOCATION: (13)..(13)
<223> OTHER INFORMATION: Xaa = Ile, Lys or no amino acid
<220> FEATURE:
<221> NAME/KEY: MISC_FEATURE
<222> LOCATION: (15)..(15)
<223> OTHER INFORMATION: Xaa = Ile, Leu or Val
<220> FEATURE:
<221> NAME/KEY: MISC_FEATURE
<222> LOCATION: (17)..(17)
<223> OTHER INFORMATION: Xaa = Leu, Gln, Arg or Val
<220> FEATURE:
<221> NAME/KEY: MISC_FEATURE
<222> LOCATION: (18)..(18)
<223> OTHER INFORMATION: Xaa = Ala, Glu, His or Pro
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Leu or Val
<220> FEATURE:
<221> NAME/KEY: MISC_FEATURE
<222> LOCATION: (25)..(25)
<223> OTHER INFORMATION: Xaa = Asp or Asn

<400> SEQUENCE: 141

Cys Xaa Xaa Xaa Phe Xaa Cys Xaa Xaa Xaa Xaa Cys Xaa Pro
1               5                   10                  15

Xaa Xaa Trp Xaa Cys Asp Gly Xaa Xaa Asp Cys Gly Asp
            20                  25

<210> SEQ ID NO 142
<211> LENGTH: 48
<212> TYPE: PRT
<213> ORGANISM: Artificial sequence
<220> FEATURE:
<223> OTHER INFORMATION: Synthetic polypeptide

<400> SEQUENCE: 142

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gly Ser Asn Glu Phe Arg
        35                  40                  45

<210> SEQ ID NO 143
<211> LENGTH: 40
<212> TYPE: PRT
<213> ORGANISM: Artificial sequence
<220> FEATURE:
<223> OTHER INFORMATION: Synthetic polypeptide

<400> SEQUENCE: 143

Cys Arg Ser Gly Arg Cys Ile Pro Gln His Trp Leu Cys Asp Gly Leu
1               5                   10                  15

Asn Asp Cys Gly Asp Gly Ser Asp Glu Ser Gln Gln Cys Ser Ala Pro
            20                  25                  30

Ala Ser Glu Pro Pro Gly Ser Leu
        35                  40
```

```
<210> SEQ ID NO 144
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Ala, Gly, Pro or Arg
<220> FEATURE:
<221> NAME/KEY: MISC_FEATURE
<222> LOCATION: (3)..(3)
<223> OTHER INFORMATION: Xaa = Ala or Pro
<220> FEATURE:
<221> NAME/KEY: MISC_FEATURE
<222> LOCATION: (4)..(4)
<223> OTHER INFORMATION: Xaa = Asp, Gly, Asn or Ser
<220> FEATURE:
<221> NAME/KEY: MISC_FEATURE
<222> LOCATION: (5)..(5)
<223> OTHER INFORMATION: Xaa = Glu or Gln
<220> FEATURE:
<221> NAME/KEY: MISC_FEATURE
<222> LOCATION: (7)..(7)
<223> OTHER INFORMATION: Xaa = Gln, Arg or Thr
<220> FEATURE:
<221> NAME/KEY: MISC_FEATURE
<222> LOCATION: (9)..(9)
<223> OTHER INFORMATION: Xaa = Gly, Ser or Lys
<220> FEATURE:
<221> NAME/KEY: MISC_FEATURE
<222> LOCATION: (11)..(11)
<223> OTHER INFORMATION: Xaa = Gly or Thr
<220> FEATURE:
<221> NAME/KEY: MISC_FEATURE
<222> LOCATION: (12)..(12)
<223> OTHER INFORMATION: Xaa = Gly, His or Arg
<220> FEATURE:
<221> NAME/KEY: MISC_FEATURE
<222> LOCATION: (13)..(13)
<223> OTHER INFORMATION: Xaa = Arg or no amino acid
<220> FEATURE:
<221> NAME/KEY: MISC_FEATURE
<222> LOCATION: (15)..(15)
<223> OTHER INFORMATION: Xaa = Ile, Leu or Val
<220> FEATURE:
<221> NAME/KEY: MISC_FEATURE
<222> LOCATION: (16)..(16)
<223> OTHER INFORMATION: Xaa = Pro or Ser
<220> FEATURE:
<221> NAME/KEY: MISC_FEATURE
<222> LOCATION: (17)..(17)
<223> OTHER INFORMATION: Xaa = Ala, Leu or Gln
<220> FEATURE:
<221> NAME/KEY: MISC_FEATURE
<222> LOCATION: (18)..(18)
<223> OTHER INFORMATION: Xaa = Asn, Ser or Thr
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Glu or Val
<220> FEATURE:
<221> NAME/KEY: MISC_FEATURE
<222> LOCATION: (28)..(28)
<223> OTHER INFORMATION: Xaa = Gly or Leu
<220> FEATURE:
<221> NAME/KEY: MISC_FEATURE
<222> LOCATION: (34)..(34)
<223> OTHER INFORMATION: Xaa = Ala, Glu or Thr
<220> FEATURE:
<221> NAME/KEY: MISC_FEATURE
<222> LOCATION: (35)..(35)
<223> OTHER INFORMATION: Xaa = Asp, Asn or Ser
```

-continued

```
<220> FEATURE:
<221> NAME/KEY: MISC_FEATURE
<222> LOCATION: (36)..(36)
<223> OTHER INFORMATION: Xaa = Ala or no amino acid
<220> FEATURE:
<221> NAME/KEY: MISC_FEATURE
<222> LOCATION: (37)..(37)
<223> OTHER INFORMATION: Xaa = Thr or no amino acid

<400> SEQUENCE: 144

Cys Xaa Xaa Xaa Xaa Phe Xaa Cys Xaa Asn Xaa Xaa Xaa Cys Xaa Xaa
1               5                   10                  15

Xaa Xaa Trp Xaa Cys Asp Gly Xaa Asp Asp Cys Xaa Asp Gly Ser Asp
            20                  25                  30

Glu Xaa Xaa Xaa Xaa Cys
            35

<210> SEQ ID NO 145
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Glu, Leu, Pro, Gln or Arg
<220> FEATURE:
<221> NAME/KEY: MISC_FEATURE
<222> LOCATION: (3)..(3)
<223> OTHER INFORMATION: Xaa = Ala, Pro or Ser
<220> FEATURE:
<221> NAME/KEY: MISC_FEATURE
<222> LOCATION: (4)..(4)
<223> OTHER INFORMATION: Xaa = Asp, Gly, Ile or Asn
<220> FEATURE:
<221> NAME/KEY: MISC_FEATURE
<222> LOCATION: (5)..(5)
<223> OTHER INFORMATION: Xaa = Glu, Gly or Gln
<220> FEATURE:
<221> NAME/KEY: MISC_FEATURE
<222> LOCATION: (6)..(6)
<223> OTHER INFORMATION: Xaa = Phe or Gln
<220> FEATURE:
<221> NAME/KEY: MISC_FEATURE
<222> LOCATION: (7)..(7)
<223> OTHER INFORMATION: Xaa = Phe, Lys, Pro, Gln, Arg or Thr
<220> FEATURE:
<221> NAME/KEY: MISC_FEATURE
<222> LOCATION: (8)..(8)
<223> OTHER INFORMATION: Xaa = Glu or no amino acid
<220> FEATURE:
<221> NAME/KEY: MISC_FEATURE
<222> LOCATION: (10)..(10)
<223> OTHER INFORMATION: Xaa = Gly, Asn, Arg or Ser
<220> FEATURE:
<221> NAME/KEY: MISC_FEATURE
<222> LOCATION: (11)..(11)
<223> OTHER INFORMATION: Xaa = Asn or Ser
<220> FEATURE:
<221> NAME/KEY: MISC_FEATURE
<222> LOCATION: (13)..(13)
<223> OTHER INFORMATION: Xaa = His, Asn, Gln or Arg
<220> FEATURE:
<221> NAME/KEY: MISC_FEATURE
<222> LOCATION: (15)..(15)
<223> OTHER INFORMATION: Xaa = Ile or Val
<220> FEATURE:
<221> NAME/KEY: MISC_FEATURE
<222> LOCATION: (17)..(17)
<223> OTHER INFORMATION: Xaa = Ala, Glu, Leu, Pro, Gln, Arg or Val
<220> FEATURE:
<221> NAME/KEY: MISC_FEATURE
<222> LOCATION: (18)..(18)
<223> OTHER INFORMATION: Xaa = Ala, His, Pro, Gln, Arg or Thr
```

```
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Glu or Val
<220> FEATURE:
<221> NAME/KEY: MISC_FEATURE
<222> LOCATION: (25)..(25)
<223> OTHER INFORMATION: Xaa = Asp, Asn or Pro
<220> FEATURE:
<221> NAME/KEY: MISC_FEATURE
<222> LOCATION: (28)..(28)
<223> OTHER INFORMATION: Xaa = Gly, Leu or Gln
<220> FEATURE:
<221> NAME/KEY: MISC_FEATURE
<222> LOCATION: (30)..(30)
<223> OTHER INFORMATION: Xaa = Asp, Gly, Asn or Ser
<220> FEATURE:
<221> NAME/KEY: MISC_FEATURE
<222> LOCATION: (34)..(34)
<223> OTHER INFORMATION: Xaa = Ala, Glu, Lys or Thr
<220> FEATURE:
<221> NAME/KEY: MISC_FEATURE
<222> LOCATION: (35)..(35)
<223> OTHER INFORMATION: Xaa = Asp, Gly, Leu, Asn or Ser
<220> FEATURE:
<221> NAME/KEY: MISC_FEATURE
<222> LOCATION: (36)..(36)
<223> OTHER INFORMATION: Xaa = Ala or no amino acid
<220> FEATURE:
<221> NAME/KEY: MISC_FEATURE
<222> LOCATION: (37)..(37)
<223> OTHER INFORMATION: Xaa = His or no amino acid

<400> SEQUENCE: 145

Cys Xaa Xaa Xaa Xaa Xaa Xaa Cys Xaa Xaa Gly Xaa Cys Xaa Pro
1               5                   10                  15

Xaa Xaa Trp Xaa Cys Asp Gly Xaa Xaa Asp Cys Xaa Asp Xaa Ser Asp
            20                  25                  30

Glu Xaa Xaa Xaa Xaa Cys
        35

<210> SEQ ID NO 146
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa = Ala, Gly or Pro
<220> FEATURE:
<221> NAME/KEY: MISC_FEATURE
<222> LOCATION: (3)..(3)
<223> OTHER INFORMATION: Xaa = Ala, Pro or Ser
<220> FEATURE:
<221> NAME/KEY: MISC_FEATURE
<222> LOCATION: (4)..(4)
<223> OTHER INFORMATION: Xaa = Asp, Gly or Asn
<220> FEATURE:
<221> NAME/KEY: MISC_FEATURE
<222> LOCATION: (5)..(5)
<223> OTHER INFORMATION: Xaa = Glu or Gln
<220> FEATURE:
<221> NAME/KEY: MISC_FEATURE
<222> LOCATION: (7)..(7)
<223> OTHER INFORMATION: Xaa = Gln, Arg or Thr
<220> FEATURE:
<221> NAME/KEY: MISC_FEATURE
<222> LOCATION: (9)..(9)
<223> OTHER INFORMATION: Xaa = Gly, Asn, Arg or Ser
```

```
<220> FEATURE:
<221> NAME/KEY: MISC_FEATURE
<222> LOCATION: (10)..(10)
<223> OTHER INFORMATION: Xaa = Gly, Asn or Ser
<220> FEATURE:
<221> NAME/KEY: MISC_FEATURE
<222> LOCATION: (11)..(11)
<223> OTHER INFORMATION: Xaa = Gly or Thr
<220> FEATURE:
<221> NAME/KEY: MISC_FEATURE
<222> LOCATION: (12)..(12)
<223> OTHER INFORMATION: Xaa = Gly, Lys, Gln or Ser
<220> FEATURE:
<221> NAME/KEY: MISC_FEATURE
<222> LOCATION: (13)..(13)
<223> OTHER INFORMATION: Xaa = Ile, Lys or no amino acid
<220> FEATURE:
<221> NAME/KEY: MISC_FEATURE
<222> LOCATION: (15)..(15)
<223> OTHER INFORMATION: Xaa = Ile, Leu or Val
<220> FEATURE:
<221> NAME/KEY: MISC_FEATURE
<222> LOCATION: (17)..(17)
<223> OTHER INFORMATION: Xaa = Leu, Gln, Arg or Val
<220> FEATURE:
<221> NAME/KEY: MISC_FEATURE
<222> LOCATION: (18)..(18)
<223> OTHER INFORMATION: Xaa = Ala, Glu, His or Pro
<220> FEATURE:
<221> NAME/KEY: MISC_FEATURE
<222> LOCATION: (20)..(20)
<223> OTHER INFORMATION: Xaa = Leu, Arg or Val
<220> FEATURE:
<221> NAME/KEY: MISC_FEATURE
<222> LOCATION: (24)..(24)
<223> OTHER INFORMATION: Xaa = Asp, Leu or Val
<220> FEATURE:
<221> NAME/KEY: MISC_FEATURE
<222> LOCATION: (25)..(25)
<223> OTHER INFORMATION: Xaa = Asp or Asn
<220> FEATURE:
<221> NAME/KEY: MISC_FEATURE
<222> LOCATION: (30)..(30)
<223> OTHER INFORMATION: Xaa = Gly or Asn
<220> FEATURE:
<221> NAME/KEY: MISC_FEATURE
<222> LOCATION: (34)..(34)
<223> OTHER INFORMATION: Xaa = Ala, Glu, Lys, Pro or Ser
<220> FEATURE:
<221> NAME/KEY: MISC_FEATURE
<222> LOCATION: (35)..(35)
<223> OTHER INFORMATION: Xaa = Gly, Leu, Pro or Ser
<220> FEATURE:
<221> NAME/KEY: MISC_FEATURE
<222> LOCATION: (36)..(36)
<223> OTHER INFORMATION: Xaa = Ala, Glu, Val or no amino acid
<220> FEATURE:
<221> NAME/KEY: MISC_FEATURE
<222> LOCATION: (37)..(37)
<223> OTHER INFORMATION: Xaa = Ile, Thr or no amino acid

<400> SEQUENCE: 146

Cys Xaa Xaa Xaa Xaa Phe Xaa Cys Xaa Xaa Xaa Xaa Xaa Cys Xaa Pro
1               5                   10                  15

Xaa Xaa Trp Xaa Cys Asp Gly Xaa Xaa Asp Cys Gly Asp Xaa Ser Asp
            20                  25                  30

Glu Xaa Xaa Xaa Xaa Cys
        35

<210> SEQ ID NO 147
<211> LENGTH: 36
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MISC_FEATURE
<222> LOCATION: (3)..(3)
<223> OTHER INFORMATION: Xaa = Ala or Glu
<220> FEATURE:
<221> NAME/KEY: MISC_FEATURE
<222> LOCATION: (4)..(4)
<223> OTHER INFORMATION: Xaa = Gly or Ser
<220> FEATURE:
<221> NAME/KEY: MISC_FEATURE
<222> LOCATION: (9)..(9)
<223> OTHER INFORMATION: Xaa = Gly or Arg
<220> FEATURE:
<221> NAME/KEY: MISC_FEATURE
<222> LOCATION: (10)..(10)
<223> OTHER INFORMATION: Xaa = Asn, Arg or Ser
<220> FEATURE:
<221> NAME/KEY: MISC_FEATURE
<222> LOCATION: (11)..(11)
<223> OTHER INFORMATION: Xaa = Ala, Ser or Thr
<220> FEATURE:
<221> NAME/KEY: MISC_FEATURE
<222> LOCATION: (12)..(12)
<223> OTHER INFORMATION: Xaa = Lys or Asn
<220> FEATURE:
<221> NAME/KEY: MISC_FEATURE
<222> LOCATION: (17)..(17)
<223> OTHER INFORMATION: Xaa = Glu, His, Gln or Ser
<220> FEATURE:
<221> NAME/KEY: MISC_FEATURE
<222> LOCATION: (18)..(18)
<223> OTHER INFORMATION: Xaa = Ala or Val
<220> FEATURE:
<221> NAME/KEY: MISC_FEATURE
<222> LOCATION: (20)..(20)
<223> OTHER INFORMATION: Xaa = Ile or Val
<220> FEATURE:
<221> NAME/KEY: MISC_FEATURE
<222> LOCATION: (24)..(24)
<223> OTHER INFORMATION: Xaa = Ile or Val
<220> FEATURE:
<221> NAME/KEY: MISC_FEATURE
<222> LOCATION: (28)..(28)
<223> OTHER INFORMATION: Xaa = Asp or Glu
<220> FEATURE:
<221> NAME/KEY: MISC_FEATURE
<222> LOCATION: (34)..(34)
<223> OTHER INFORMATION: Xaa = Asp, Lys, Met, Asn or Thr
<220> FEATURE:
<221> NAME/KEY: MISC_FEATURE
<222> LOCATION: (35)..(35)
<223> OTHER INFORMATION: Xaa = Asn, Ser or Tyr

<400> SEQUENCE: 147

Cys Gly Xaa Xaa Leu Phe Thr Cys Xaa Xaa Xaa Xaa Ile Cys Ile Ser
1               5                   10                  15

Xaa Xaa Trp Xaa Cys Asp Gly Xaa Asp Asp Cys Xaa Asp Asn Ser Asp
                20                  25                  30

Glu Xaa Xaa Cys
        35

<210> SEQ ID NO 148
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 148

Cys Gly Glu Gly Leu Phe Thr Cys Arg Ser Thr Asn Ile Cys Ile Ser
1               5                   10                  15

His Ala Trp Val Cys Asp Gly Val Asp Asp Cys Glu Asp Asn Ser Asp
                20                  25                  30
```

```
Glu Asn Asn Cys Ser Ala Pro Ala Ser Glu Pro Pro Gly Ser Leu
        35                  40                  45

<210> SEQ ID NO 149
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 149

Cys Gly Ala Gly Leu Phe Thr Cys Arg Ser Thr Asn Ile Cys Ile Ser
1               5                   10                  15

Gln Val Trp Val Cys Asp Gly Val Asp Asp Cys Glu Asp Asn Ser Asp
            20                  25                  30

Glu Asp Ser Cys
        35

<210> SEQ ID NO 150
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 150

Cys Gly Ala Gly Leu Phe Thr Cys Arg Ser Thr Asn Ile Cys Ile Ser
1               5                   10                  15

Gln Ala Trp Val Cys Asp Gly Val Asp Asp Cys Glu Asp Asn Ser Asp
            20                  25                  30

Glu Asn Tyr Cys
        35

<210> SEQ ID NO 151
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 151

Cys Gly Ala Gly Leu Phe Thr Cys Arg Ser Thr Asn Ile Cys Ile Ser
1               5                   10                  15

Gln Ala Trp Val Cys Asp Gly Val Asp Asp Cys Glu Asp Asn Ser Asp
            20                  25                  30

Glu Thr Asn Cys
        35

<210> SEQ ID NO 152
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 152

Cys Gly Glu Gly Leu Phe Thr Cys Gly Ser Thr Asn Ile Cys Ile Ser
1               5                   10                  15

Ser Ala Trp Val Cys Asp Gly Val Asp Asp Cys Glu Asp Asn Ser Asp
            20                  25                  30

Glu Asn Asn Cys
        35
```

<210> SEQ ID NO 153
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 153

Cys Gly Glu Gly Leu Phe Thr Cys Arg Ser Thr Asn Ile Cys Ile Ser
1               5                   10                  15

His Ala Trp Val Cys Asp Gly Val Asp Asp Cys Glu Asp Asn Ser Asp
            20                  25                  30

Glu Asn Asn Cys
        35

<210> SEQ ID NO 154
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 154

Cys Gly Glu Gly Leu Phe Thr Cys Arg Ser Thr Asn Ile Cys Ile Ser
1               5                   10                  15

Glu Ala Trp Ile Cys Asp Gly Val Asp Asp Cys Glu Asp Asn Ser Asp
            20                  25                  30

Glu Lys Asn Cys
        35

<210> SEQ ID NO 155
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 155

Cys Gly Ala Gly Leu Phe Thr Cys Arg Ser Ala Lys Ile Cys Ile Ser
1               5                   10                  15

His Ala Trp Val Cys Asp Gly Ile Asp Asp Cys Glu Asp Asn Ser Asp
            20                  25                  30

Glu Asn Asn Cys
        35

<210> SEQ ID NO 156
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 156

Cys Gly Ala Gly Leu Phe Thr Cys Arg Asn Ser Lys Ile Cys Ile Ser
1               5                   10                  15

Gln Ala Trp Val Cys Asp Gly Val Asp Asp Cys Asp Asp Asn Ser Asp
            20                  25                  30

Glu Lys Tyr Cys
        35

<210> SEQ ID NO 157

```
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 157

Cys Gly Ala Ser Leu Phe Thr Cys Arg Arg Ser Asn Ile Cys Ile Ser
1               5                   10                  15

Gln Ala Trp Val Cys Asp Gly Val Asp Asp Cys Glu Asp Asn Ser Asp
            20                  25                  30

Glu Met Asn Cys
        35

<210> SEQ ID NO 158
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 158

Cys Gly Ala Gly Leu Phe Thr Cys Arg Ser Thr Lys Ile Cys Ile Ser
1               5                   10                  15

Gln Ala Trp Val Cys Asp Gly Val Asp Asp Cys Glu Asp Asn Ser Asp
            20                  25                  30

Glu Lys Asn Cys
        35

<210> SEQ ID NO 159
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 159

Cys Gly Ala Gly Leu Phe Thr Cys Arg Ser Thr Asn Ile Cys Ile Ser
1               5                   10                  15

Gln Val Trp Val Cys Asp Gly Val Asp Asp Cys Glu Asp Asn Ser Asp
            20                  25                  30

Glu Asp Ser Cys Ser Ala Pro Ala Ser Glu Pro Pro Gly Ser Leu
        35                  40                  45

<210> SEQ ID NO 160
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 160

Cys Gly Ala Gly Leu Phe Thr Cys Arg Ser Thr Asn Ile Cys Ile Ser
1               5                   10                  15

Gln Ala Trp Val Cys Asp Gly Val Asp Asp Cys Glu Asp Asn Ser Asp
            20                  25                  30

Glu Asn Tyr Cys Ser Ala Pro Ala Ser Glu Pro Pro Gly Ser Leu
        35                  40                  45

<210> SEQ ID NO 161
<211> LENGTH: 47
<212> TYPE: PRT
<213> ORGANISM: Artificial sequence
```

<220> FEATURE:
<223> OTHER INFORMATION: Synthetic polypeptide

<400> SEQUENCE: 161

Cys Gly Ala Gly Leu Phe Thr Cys Arg Ser Thr Asn Ile Cys Ile Ser
1               5                   10                  15

Gln Ala Trp Val Cys Asp Gly Val Asp Asp Cys Glu Asp Asn Ser Asp
            20                  25                  30

Glu Thr Asn Cys Ser Ala Pro Ala Ser Glu Pro Pro Gly Ser Leu
        35                  40                  45

<210> SEQ ID NO 162
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 162

Cys Gly Glu Gly Leu Phe Thr Cys Gly Ser Thr Asn Ile Cys Ile Ser
1               5                   10                  15

Ser Ala Trp Val Cys Asp Gly Val Asp Asp Cys Glu Asp Asn Ser Asp
            20                  25                  30

Glu Asn Asn Cys Ser Ala Pro Ala Ser Glu Pro Pro Gly Ser Leu
        35                  40                  45

<210> SEQ ID NO 163
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 163

Cys Gly Glu Gly Leu Phe Thr Cys Arg Ser Thr Asn Ile Cys Ile Ser
1               5                   10                  15

Glu Ala Trp Ile Cys Asp Gly Val Asp Asp Cys Glu Asp Asn Ser Asp
            20                  25                  30

Glu Lys Asn Cys Ser Ala Pro Ala Ser Glu Pro Pro Gly Ser Leu
        35                  40                  45

<210> SEQ ID NO 164
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 164

Cys Gly Ala Gly Leu Phe Thr Cys Arg Ser Ala Lys Ile Cys Ile Ser
1               5                   10                  15

His Ala Trp Val Cys Asp Gly Ile Asp Asp Cys Glu Asp Asn Ser Asp
            20                  25                  30

Glu Asn Asn Cys Ser Ala Pro Ala Ser Glu Pro Pro Gly Ser Leu
        35                  40                  45

<210> SEQ ID NO 165
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 165

Cys Gly Ala Gly Leu Phe Thr Cys Arg Asn Ser Lys Ile Cys Ile Ser
1               5                   10                  15

Gln Ala Trp Val Cys Asp Gly Val Asp Asp Cys Asp Asp Asn Ser Asp
            20                  25                  30

Glu Lys Tyr Cys Ser Ala Pro Ala Ser Glu Pro Pro Gly Ser Leu
        35                  40                  45

<210> SEQ ID NO 166
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 166

Cys Gly Ala Ser Leu Phe Thr Cys Arg Arg Ser Asn Ile Cys Ile Ser
1               5                   10                  15

Gln Ala Trp Val Cys Asp Gly Val Asp Asp Cys Glu Asp Asn Ser Asp
            20                  25                  30

Glu Met Asn Cys Ser Ala Pro Ala Ser Glu Pro Pro Gly Ser Leu
        35                  40                  45

<210> SEQ ID NO 167
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 167

Cys Gly Ala Gly Leu Phe Thr Cys Arg Ser Thr Lys Ile Cys Ile Ser
1               5                   10                  15

Gln Ala Trp Val Cys Asp Gly Val Asp Asp Cys Glu Asp Asn Ser Asp
            20                  25                  30

Glu Lys Asn Cys Ser Ala Pro Ala Ser Glu Pro Pro Gly Ser Leu
        35                  40                  45

<210> SEQ ID NO 168
<211> LENGTH: 135
<212> TYPE: PRT
<213> ORGANISM: Artificial sequence
<220> FEATURE:
<223> OTHER INFORMATION: Synthetic polypeptide

<400> SEQUENCE: 168

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
        35                  40                  45

Cys Arg Ser Gly Arg Cys Ile Pro Gln His Trp Leu Cys Asp Gly Leu
    50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Cys Gly Glu Gly Leu Phe Thr Cys
            85                  90                  95

Arg Ser Thr Asn Ile Cys Ile Ser His Ala Trp Val Cys Asp Gly Val
                100                 105                 110

```
Asp Asp Cys Glu Asp Asn Ser Asp Glu Asn Asn Cys Ser Ala Pro Ala
        115                 120                 125

Ser Glu Pro Pro Gly Ser Leu
    130                 135

<210> SEQ ID NO 169
<211> LENGTH: 134
<212> TYPE: PRT
<213> ORGANISM: Artificial sequence
<220> FEATURE:
<223> OTHER INFORMATION: Synthetic polypeptide

<400> SEQUENCE: 169

Cys Leu Pro Asp Glu Phe Gln Cys Gly Ser Gly Arg Cys Ile Pro Gln
1               5                   10                  15

His Trp Leu Cys Asp Gly Leu Asn Asp Cys Gly Asp Gly Ser Asp Glu
            20                  25                  30

Pro Pro Ala His Cys Ser Ala Pro Ala Ser Glu Pro Pro Gly Ser Leu
        35                  40                  45

Cys Arg Ala Gly Glu Phe Arg Cys Ser Asn Gly Arg Cys Val Pro Leu
    50                  55                  60

Thr Trp Leu Cys Asp Gly Glu Asp Asp Cys Gln Asp Asn Ser Asp Glu
65                  70                  75                  80

Lys Asn Cys Ala Gln Pro Thr Cys Gly Glu Gly Leu Phe Thr Cys Arg
                85                  90                  95

Ser Thr Asn Ile Cys Ile Ser His Ala Trp Val Cys Asp Gly Val Asp
            100                 105                 110

Asp Cys Glu Asp Asn Ser Asp Glu Asn Asn Cys Ser Ala Pro Ala Ser
        115                 120                 125

Glu Pro Pro Gly Ser Leu
    130

<210> SEQ ID NO 170
<211> LENGTH: 136
<212> TYPE: PRT
<213> ORGANISM: Artificial sequence
<220> FEATURE:
<223> OTHER INFORMATION: Synthetic polypeptide

<400> SEQUENCE: 170

Cys Ala Pro Gly Glu Phe Thr Cys Lys Asn Thr Gly Arg Cys Ile Pro
1               5                   10                  15

Leu Asn Trp Arg Cys Asp Gly Asp Asp Cys Gly Asp Gly Ser Asp Glu
            20                  25                  30

Glu Thr Asp Cys Pro Ala Pro Thr Cys Pro Ser Asn Gln Phe Pro Cys
        35                  40                  45

Arg Ser Thr Gly Ile Cys Ile Pro Leu Ala Trp Val Cys Asp Gly Leu
    50                  55                  60

Asn Asp Cys Gly Asp Gly Ser Asp Glu Ser Pro Ala His Cys Ser Ala
65                  70                  75                  80

Pro Ala Ser Glu Pro Pro Gly Ser Leu Cys Gly Glu Gly Leu Phe Thr
                85                  90                  95

Cys Arg Ser Thr Asn Ile Cys Ile Ser His Ala Trp Val Cys Asp Gly
            100                 105                 110

Val Asp Asp Cys Glu Asp Asn Ser Asp Glu Asn Asn Cys Ser Ala Pro
        115                 120                 125

Ala Ser Glu Pro Pro Gly Ser Leu
```

130                 135

<210> SEQ ID NO 171
<211> LENGTH: 136
<212> TYPE: PRT
<213> ORGANISM: Artificial sequence
<220> FEATURE:
<223> OTHER INFORMATION: Synthetic polypeptide

<400> SEQUENCE: 171

Cys Gly Pro Asp Glu Phe Arg Cys Asn Asn Gly Gln Cys Ile Pro Leu
1               5                   10                  15

Pro Trp Arg Cys Asp Gly Val Asp Asp Cys Gly Asp Asn Ser Asp Glu
            20                  25                  30

Pro Leu Glu Ile Cys Gln Ala Pro Thr Cys Gln Ser Asn Glu Phe Arg
        35                  40                  45

Cys Arg Ser Gly Arg Cys Ile Pro Gln His Trp Leu Cys Asp Gly Leu
    50                  55                  60

Asn Asp Cys Gly Asp Gly Ser Asp Glu Pro Pro Ala His Cys Ser Ala
65                  70                  75                  80

Pro Ala Ser Glu Pro Pro Gly Ser Leu Cys Gly Glu Gly Leu Phe Thr
                85                  90                  95

Cys Arg Ser Thr Asn Ile Cys Ile Ser His Ala Trp Val Cys Asp Gly
            100                 105                 110

Val Asp Asp Cys Glu Asp Asn Ser Asp Glu Asn Asn Cys Ser Ala Pro
        115                 120                 125

Ala Ser Glu Pro Pro Gly Ser Leu
    130                 135

<210> SEQ ID NO 172
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 172

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp Cys Gly Ala Asp
    130                 135                 140

Gln Phe Arg Cys Gly Asn Gly Ser Cys Val Pro Arg Ala Trp Arg Cys
145                 150                 155                 160

Asp Gly Val Asp Asp Cys Gly Asp Gly Ser Asp Glu Ala Pro Glu Ile
            165                 170                 175

Cys Glu Thr Pro Thr Cys Gln Ser Asn Glu Phe Arg Cys Arg Ser Gly
            180                 185                 190

Arg Cys Ile Pro Gln His Trp Leu Cys Asp Gly Leu Asn Asp Cys Gly
            195                 200                 205

Asp Gly Ser Asp Glu Ser Gln Gln Cys Ser Ala Pro Ala Ser Glu Pro
            210                 215                 220

Pro Gly Ser Leu Ser Leu
225             230

<210> SEQ ID NO 173
<211> LENGTH: 221
<212> TYPE: PRT
<213> ORGANISM: Artificial sequence
<220> FEATURE:
<223> OTHER INFORMATION: Synthetic polypeptide

<400> SEQUENCE: 173

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp Cys Gly Ala Asp Gln Phe Arg Cys Gly Asn Gly Ser Cys
    130                 135                 140

Val Pro Arg Ala Trp Arg Cys Asp Gly Val Asp Asp Cys Gly Asp Gly
145                 150                 155                 160

Ser Asp Glu Ala Pro Glu Ile Cys Glu Thr Pro Thr Cys Gln Ser Asn
                165                 170                 175

Glu Phe Arg Cys Arg Ser Gly Arg Cys Ile Pro Gln His Trp Leu Cys
            180                 185                 190

Asp Gly Leu Asn Asp Cys Gly Asp Gly Ser Asp Glu Ser Gln Gln Cys
        195                 200                 205

Ser Ala Pro Ala Ser Glu Pro Pro Gly Ser Leu Ser Leu
    210                 215                 220

<210> SEQ ID NO 174
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 174

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Val Thr
                 85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp Cys Gly Ala Asp
130                 135                 140

Gln Phe Arg Cys Gly Asn Gly Ser Cys Val Pro Arg Ala Trp Arg Cys
145                 150                 155                 160

Asp Gly Val Asp Asp Cys Gly Asp Gly Ser Asp Glu Ala Pro Glu Ile
                165                 170                 175

Cys Glu Thr Pro Thr Cys Gln Ser Asn Glu Phe Arg Cys Arg Ser Gly
                180                 185                 190

Arg Cys Ile Pro Gln His Trp Leu Cys Asp Gly Leu Asn Asp Cys Gly
            195                 200                 205

Asp Gly Ser Asp Glu Ser Gln Gln Cys Ser Ala Pro Ala Ser Glu Pro
            210                 215                 220

Pro Gly Ser Leu Ser Leu
225                 230

<210> SEQ ID NO 175
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 175

Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Asp
                100                 105                 110

Gln Asn Gly Ser Cys Val Arg Gly Pro Arg Thr His Tyr Gly Gln Lys
            115                 120                 125

Ala Ile Leu Phe Leu Pro Leu Pro Val Ser Ser Asp Cys Gly Ala Asp
130                 135                 140

Gln Phe Arg Cys Gly Asn Gly Ser Cys Val Pro Arg Ala Trp Arg Cys
145                 150                 155                 160

Asp Gly Val Asp Asp Cys Gly Asp Gly Ser Asp Glu Ala Pro Glu Ile
            165                 170                 175

Cys Glu Thr Pro Thr Cys Gln Ser Asn Glu Phe Arg Cys Arg Ser Gly
            180                 185                 190

Arg Cys Ile Pro Gln His Trp Leu Cys Asp Gly Leu Asn Asp Cys Gly
        195                 200                 205

Asp Gly Ser Asp Glu Ser Gln Gln Cys Ser Ala Pro Ala Ser Glu Pro
    210                 215                 220

Pro Gly Ser Leu Ser Leu
225                 230

<210> SEQ ID NO 176
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 176

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp Cys Gly Ala Asp
    130                 135                 140

Gln Phe Arg Cys Gly Asn Gly Ser Cys Val Pro Arg Ala Trp Arg Cys
145                 150                 155                 160

Asp Gly Val Asp Asp Cys Gly Asp Gly Ser Asp Glu Ala Pro Glu Ile
            165                 170                 175

Cys Glu Thr Pro Thr Cys Gln Ser Asn Glu Phe Arg Cys Arg Ser Gly
            180                 185                 190

Arg Cys Ile Pro Gln His Trp Leu Cys Asp Gly Leu Asn Asp Cys Gly
        195                 200                 205

Asp Gly Ser Asp Glu Ser Gln Gln Cys Ser Ala Pro Ala Ser Glu Pro
    210                 215                 220

Pro Gly Ser Leu Ser Leu Cys Gly Ala Asp Gln Phe Arg Cys Gly Asn
225                 230                 235                 240

Gly Ser Cys Val Pro Arg Ala Trp Arg Cys Asp Gly Val Asp Cys
            245                 250                 255

Gly Asp Gly Ser Asp Glu Ala Pro Glu Ile Cys Glu Thr Pro Thr Cys
            260                 265                 270

```
Gln Ser Asn Glu Phe Arg Cys Arg Ser Gly Arg Cys Ile Pro Gln His
        275                 280                 285

Trp Leu Cys Asp Gly Leu Asn Asp Cys Gly Asp Gly Ser Asp Glu Ser
290                 295                 300

Gln Gln Cys Ser Ala Pro Ala Ser Glu Pro Pro Gly Ser Leu Ser Leu
305                 310                 315                 320

<210> SEQ ID NO 177
<211> LENGTH: 311
<212> TYPE: PRT
<213> ORGANISM: Artificial sequence
<220> FEATURE:
<223> OTHER INFORMATION: Synthetic polypeptide

<400> SEQUENCE: 177

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp Cys Gly Ala Asp Gln Phe Arg Cys Gly Asn Gly Ser Cys
    130                 135                 140

Val Pro Arg Ala Trp Arg Cys Asp Gly Val Asp Asp Cys Gly Asp Gly
145                 150                 155                 160

Ser Asp Glu Ala Pro Glu Ile Cys Glu Thr Pro Thr Cys Gln Ser Asn
                165                 170                 175

Glu Phe Arg Cys Arg Ser Gly Arg Cys Ile Pro Gln His Trp Leu Cys
            180                 185                 190

Asp Gly Leu Asn Asp Cys Gly Asp Gly Ser Asp Glu Ser Gln Gln Cys
        195                 200                 205

Ser Ala Pro Ala Ser Glu Pro Pro Gly Ser Leu Ser Leu Cys Gly Ala
    210                 215                 220

Asp Gln Phe Arg Cys Gly Asn Gly Ser Cys Val Pro Arg Ala Trp Arg
225                 230                 235                 240

Cys Asp Gly Val Asp Asp Cys Gly Asp Gly Ser Asp Glu Ala Pro Glu
                245                 250                 255

Ile Cys Glu Thr Pro Thr Cys Gln Ser Asn Glu Phe Arg Cys Arg Ser
            260                 265                 270

Gly Arg Cys Ile Pro Gln His Trp Leu Cys Asp Gly Leu Asn Asp Cys
        275                 280                 285

Gly Asp Gly Ser Asp Glu Ser Gln Gln Cys Ser Ala Pro Ala Ser Glu
    290                 295                 300

Pro Pro Gly Ser Leu Ser Leu
305                 310
```

<210> SEQ ID NO 178
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 178

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp Cys Gly Ala Asp
    130                 135                 140

Gln Phe Arg Cys Gly Asn Gly Ser Cys Val Pro Arg Ala Trp Arg Cys
145                 150                 155                 160

Asp Gly Val Asp Asp Cys Gly Asp Gly Ser Asp Glu Ala Pro Glu Ile
                165                 170                 175

Cys Glu Thr Pro Thr Cys Gln Ser Asn Glu Phe Arg Cys Arg Ser Gly
            180                 185                 190

Arg Cys Ile Pro Gln His Trp Leu Cys Asp Gly Leu Asn Asp Cys Gly
        195                 200                 205

Asp Gly Ser Asp Glu Ser Gln Gln Cys Ser Ala Pro Ala Ser Glu Pro
    210                 215                 220

Pro Gly Ser Leu Ser Leu Cys Gly Ala Asp Gln Phe Arg Cys Gly Asn
225                 230                 235                 240

Gly Ser Cys Val Pro Arg Ala Trp Arg Cys Asp Gly Val Asp Asp Cys
                245                 250                 255

Gly Asp Gly Ser Asp Glu Ala Pro Glu Ile Cys Glu Thr Pro Thr Cys
            260                 265                 270

Gln Ser Asn Glu Phe Arg Cys Arg Ser Gly Arg Cys Ile Pro Gln His
        275                 280                 285

Trp Leu Cys Asp Gly Leu Asn Asp Cys Gly Asp Gly Ser Asp Glu Ser
    290                 295                 300

Gln Gln Cys Ser Ala Pro Ala Ser Glu Pro Pro Gly Ser Leu Ser Leu
305                 310                 315                 320

<210> SEQ ID NO 179
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 179

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
            100                 105                 110

Gln Asn Gly Ser Cys Val Arg Gly Pro Arg Thr His Tyr Gly Gln Lys
        115                 120                 125

Ala Ile Leu Phe Leu Pro Leu Pro Val Ser Ser Asp Cys Gly Ala Asp
130                 135                 140

Gln Phe Arg Cys Gly Asn Gly Ser Cys Val Pro Arg Ala Trp Arg Cys
145                 150                 155                 160

Asp Gly Val Asp Asp Cys Gly Asp Gly Ser Asp Glu Ala Pro Glu Ile
                165                 170                 175

Cys Glu Thr Pro Thr Cys Gln Ser Asn Glu Phe Arg Cys Arg Ser Gly
            180                 185                 190

Arg Cys Ile Pro Gln His Trp Leu Cys Asp Gly Leu Asn Asp Cys Gly
        195                 200                 205

Asp Gly Ser Asp Glu Ser Gln Gln Cys Ser Ala Pro Ala Ser Glu Pro
    210                 215                 220

Pro Gly Ser Leu Ser Leu Cys Gly Ala Asp Gln Phe Arg Cys Gly Asn
225                 230                 235                 240

Gly Ser Cys Val Pro Arg Ala Trp Arg Cys Asp Gly Val Asp Asp Cys
                245                 250                 255

Gly Asp Gly Ser Asp Glu Ala Pro Glu Ile Cys Glu Thr Pro Thr Cys
            260                 265                 270

Gln Ser Asn Glu Phe Arg Cys Arg Ser Gly Arg Cys Ile Pro Gln His
        275                 280                 285

Trp Leu Cys Asp Gly Leu Asn Asp Cys Gly Asp Gly Ser Asp Glu Ser
    290                 295                 300

Gln Gln Cys Ser Ala Pro Ala Ser Glu Pro Pro Gly Ser Leu Ser Leu
305                 310                 315                 320

<210> SEQ ID NO 180
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 180

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
                20                  25                  30

Ala Pro Glu Ile Cys Glu Thr Pro Thr Cys Gln Ser Asn Glu Phe Arg

```
                35                  40                  45
Cys Arg Ser Gly Arg Cys Ile Pro Gln His Trp Leu Cys Asp Gly Leu
 50                  55                  60

Asn Asp Cys Gly Asp Gly Ser Asp Glu Ser Gln Gln Cys Ser Ala Pro
 65                  70                  75                  80

Ala Ser Glu Pro Pro Gly Ser Leu Ser Leu Phe Asn Leu Pro Pro Gly
                 85                  90                  95

Asn Tyr Lys Lys Pro Lys Leu Leu Tyr Cys Ser Asn Gly Gly His Phe
                100                 105                 110

Leu Arg Ile Leu Pro Asp Gly Thr Val Asp Gly Thr Arg Asp Arg Ser
                115                 120                 125

Asp Gln His Ile Gln Leu Gln Leu Ser Ala Glu Ser Val Gly Glu Val
130                 135                 140

Tyr Ile Lys Ser Thr Glu Thr Gly Gln Tyr Leu Ala Met Asp Thr Asp
145                 150                 155                 160

Gly Leu Leu Tyr Gly Ser Gln Thr Pro Asn Glu Glu Cys Leu Phe Leu
                165                 170                 175

Glu Arg Leu Glu Glu Asn His Tyr Asn Thr Tyr Ile Ser Lys Lys His
                180                 185                 190

Ala Glu Lys Asn Trp Phe Val Gly Leu Lys Lys Asn Gly Ser Cys Lys
                195                 200                 205

Arg Gly Pro Arg Thr His Tyr Gly Gln Lys Ala Ile Leu Phe Leu Pro
                210                 215                 220

Leu Pro Val Ser Ser Asp
225                 230

<210> SEQ ID NO 181
<211> LENGTH: 221
<212> TYPE: PRT
<213> ORGANISM: Artificial sequence
<220> FEATURE:
<223> OTHER INFORMATION: Synthetic polypeptide

<400> SEQUENCE: 181

Cys Gly Ala Asp Gln Phe Arg Cys Gly Asn Gly Ser Cys Val Pro Arg
 1                   5                  10                  15

Ala Trp Arg Cys Asp Gly Val Asp Asp Cys Gly Asp Gly Ser Asp Glu
                 20                  25                  30

Ala Pro Glu Ile Cys Glu Thr Pro Thr Cys Gln Ser Asn Glu Phe Arg
                 35                  40                  45

Cys Arg Ser Gly Arg Cys Ile Pro Gln His Trp Leu Cys Asp Gly Leu
 50                  55                  60

Asn Asp Cys Gly Asp Gly Ser Asp Glu Ser Gln Gln Cys Ser Ala Pro
 65                  70                  75                  80

Ala Ser Glu Pro Pro Gly Ser Leu Ser Leu Lys Pro Lys Leu Leu Tyr
                 85                  90                  95

Cys Ser Asn Gly Gly His Phe Leu Arg Ile Leu Pro Asp Gly Thr Val
                100                 105                 110

Asp Gly Thr Arg Asp Arg Ser Asp Gln His Ile Gln Leu Gln Leu Ser
                115                 120                 125

Ala Glu Ser Val Gly Glu Val Tyr Ile Lys Ser Thr Glu Thr Gly Gln
130                 135                 140

Tyr Leu Ala Met Asp Thr Asp Gly Leu Leu Tyr Gly Ser Gln Thr Pro
145                 150                 155                 160

Asn Glu Glu Cys Leu Phe Leu Glu Arg Leu Glu Glu Asn His Tyr Asn
```

```
                    165                 170                 175
Thr Tyr Ile Ser Lys Lys His Ala Glu Lys Asn Trp Phe Val Gly Leu
                180                 185                 190

Lys Lys Asn Gly Ser Cys Lys Arg Gly Pro Arg Thr His Tyr Gly Gln
            195                 200                 205

Lys Ala Ile Leu Phe Leu Pro Leu Pro Val Ser Ser Asp
        210                 215                 220

<210> SEQ ID NO 182
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 182

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
        35                  40                  45

Cys Arg Ser Gly Arg Cys Ile Pro Gln His Trp Leu Cys Asp Gly Leu
    50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Ser Leu Phe Asn Leu Pro Pro Gly
                85                  90                  95

Asn Tyr Lys Lys Pro Val Leu Leu Tyr Cys Ser Asn Gly Gly His Phe
            100                 105                 110

Leu Arg Ile Leu Pro Asp Gly Thr Val Asp Gly Thr Arg Asp Arg Ser
        115                 120                 125

Asp Gln His Ile Gln Leu Gln Leu Ser Ala Glu Ser Val Gly Glu Val
    130                 135                 140

Tyr Ile Lys Ser Thr Glu Thr Gly Gln Tyr Leu Ala Met Asp Thr Asp
145                 150                 155                 160

Gly Leu Leu Tyr Gly Ser Gln Thr Pro Asn Glu Glu Cys Leu Phe Leu
                165                 170                 175

Glu Arg Leu Glu Glu Asn His Tyr Val Thr Tyr Ile Ser Lys Lys His
            180                 185                 190

Ala Glu Lys Asn Trp Phe Val Gly Leu Lys Lys Asn Gly Ser Cys Lys
        195                 200                 205

Arg Gly Pro Arg Thr His Tyr Gly Gln Lys Ala Ile Leu Phe Leu Pro
    210                 215                 220

Leu Pro Val Ser Ser Asp
225                 230

<210> SEQ ID NO 183
<211> LENGTH: 230
<212> TYPE: PRT
<213> ORGANISM: Artificial sequence
<220> FEATURE:
<223> OTHER INFORMATION: Synthetic polypeptide

<400> SEQUENCE: 183

Cys Gly Ala Asp Gln Phe Arg Cys Gly Asn Gly Ser Cys Val Pro Arg
1               5                   10                  15
```

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
            35                  40                  45

Cys Arg Ser Gly Arg Cys Ile Pro Gln His Trp Leu Cys Asp Gly Leu
        50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Ser Leu Phe Asn Leu Pro Pro Gly
            85                  90                  95

Asn Tyr Lys Lys Pro Lys Leu Leu Tyr Cys Ser Asn Gly Gly His Phe
            100                 105                 110

Leu Arg Ile Leu Pro Asp Gly Thr Val Asp Gly Thr Arg Asp Arg Ser
            115                 120                 125

Asp Gln His Ile Gln Leu Gln Leu Ser Ala Glu Ser Val Gly Glu Val
            130                 135                 140

Tyr Ile Lys Ser Thr Glu Thr Gly Gln Tyr Leu Ala Met Asp Thr Asp
145                 150                 155                 160

Gly Leu Leu Tyr Gly Ser Gln Thr Pro Asn Glu Glu Cys Leu Phe Leu
            165                 170                 175

Glu Arg Leu Glu Glu Asn His Tyr Asn Thr Tyr Ile Ser Lys Lys His
            180                 185                 190

Ala Glu Lys Asn Trp Phe Val Gly Leu Asp Gln Asn Gly Ser Cys Val
            195                 200                 205

Arg Gly Pro Arg Thr His Tyr Gly Gln Lys Ala Ile Leu Phe Leu Pro
            210                 215                 220

Leu Pro Val Ser Ser Asp
225                 230

<210> SEQ ID NO 184
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 184

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
            35                  40                  45

Cys Arg Ser Gly Arg Cys Ile Pro Gln His Trp Leu Cys Asp Gly Leu
        50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Ser Leu Cys Gly Ala Asp Gln Phe
            85                  90                  95

Arg Cys Gly Asn Gly Ser Cys Val Pro Arg Ala Trp Arg Cys Asp Gly
            100                 105                 110

Val Asp Asp Cys Gly Asp Gly Ser Asp Glu Ala Pro Glu Ile Cys Glu
            115                 120                 125

Thr Pro Thr Cys Gln Ser Asn Glu Phe Arg Cys Arg Ser Gly Arg Cys
            130                 135                 140

Ile Pro Gln His Trp Leu Cys Asp Gly Leu Asn Asp Cys Gly Asp Gly
145                 150                 155                 160

Ser Asp Glu Ser Gln Gln Cys Ser Ala Pro Ala Ser Glu Pro Pro Gly
            165                 170                 175

Ser Leu Ser Leu Phe Asn Leu Pro Pro Gly Asn Tyr Lys Lys Pro Lys
        180                 185                 190

Leu Leu Tyr Cys Ser Asn Gly Gly His Phe Leu Arg Ile Leu Pro Asp
        195                 200                 205

Gly Thr Val Asp Gly Thr Arg Asp Arg Ser Asp Gln His Ile Gln Leu
210                 215                 220

Gln Leu Ser Ala Glu Ser Val Gly Glu Val Tyr Ile Lys Ser Thr Glu
225                 230                 235                 240

Thr Gly Gln Tyr Leu Ala Met Asp Thr Asp Gly Leu Leu Tyr Gly Ser
            245                 250                 255

Gln Thr Pro Asn Glu Glu Cys Leu Phe Leu Glu Arg Leu Glu Glu Asn
            260                 265                 270

His Tyr Asn Thr Tyr Ile Ser Lys Lys His Ala Glu Lys Asn Trp Phe
        275                 280                 285

Val Gly Leu Lys Lys Asn Gly Ser Cys Lys Arg Gly Pro Arg Thr His
290                 295                 300

Tyr Gly Gln Lys Ala Ile Leu Phe Leu Pro Leu Pro Val Ser Ser Asp
305                 310                 315                 320

<210> SEQ ID NO 185
<211> LENGTH: 311
<212> TYPE: PRT
<213> ORGANISM: Artificial sequence
<220> FEATURE:
<223> OTHER INFORMATION: Synthetic polypeptide

<400> SEQUENCE: 185

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
        35                  40                  45

Cys Arg Ser Gly Arg Cys Ile Pro Gln His Trp Leu Cys Asp Gly Leu
50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Ser Leu Cys Gly Ala Asp Gln Phe
            85                  90                  95

Arg Cys Gly Asn Gly Ser Cys Val Pro Arg Ala Trp Arg Cys Asp Gly
        100                 105                 110

Val Asp Asp Cys Gly Asp Gly Ser Asp Glu Ala Pro Glu Ile Cys Glu
        115                 120                 125

Thr Pro Thr Cys Gln Ser Asn Glu Phe Arg Cys Arg Ser Gly Arg Cys
130                 135                 140

Ile Pro Gln His Trp Leu Cys Asp Gly Leu Asn Asp Cys Gly Asp Gly
145                 150                 155                 160

Ser Asp Glu Ser Gln Gln Cys Ser Ala Pro Ala Ser Glu Pro Pro Gly
            165                 170                 175

Ser Leu Ser Leu Lys Pro Lys Leu Leu Tyr Cys Ser Asn Gly Gly His
        180                 185                 190

Phe Leu Arg Ile Leu Pro Asp Gly Thr Val Asp Gly Thr Arg Asp Arg
            195                 200                 205

Ser Asp Gln His Ile Gln Leu Gln Leu Ser Ala Glu Ser Val Gly Glu
    210                 215                 220

Val Tyr Ile Lys Ser Thr Glu Thr Gly Gln Tyr Leu Ala Met Asp Thr
225                 230                 235                 240

Asp Gly Leu Leu Tyr Gly Ser Gln Thr Pro Asn Glu Glu Cys Leu Phe
                245                 250                 255

Leu Glu Arg Leu Glu Glu Asn His Tyr Asn Thr Tyr Ile Ser Lys Lys
            260                 265                 270

His Ala Glu Lys Asn Trp Phe Val Gly Leu Lys Lys Asn Gly Ser Cys
        275                 280                 285

Lys Arg Gly Pro Arg Thr His Tyr Gly Gln Lys Ala Ile Leu Phe Leu
    290                 295                 300

Pro Leu Pro Val Ser Ser Asp
305                 310

<210> SEQ ID NO 186
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 186

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
        35                  40                  45

Cys Arg Ser Gly Arg Cys Ile Pro Gln His Trp Leu Cys Asp Gly Leu
    50                  55                  60

Asn Asp Cys Gly Asp Gly Ser Asp Glu Ser Gln Gln Cys Ser Ala Pro
65                  70                  75                  80

Ala Ser Glu Pro Pro Gly Ser Leu Ser Leu Cys Gly Ala Asp Gln Phe
                85                  90                  95

Arg Cys Gly Asn Gly Ser Cys Val Pro Arg Ala Trp Arg Cys Asp Gly
            100                 105                 110

Val Asp Asp Cys Gly Asp Gly Ser Asp Glu Ala Pro Glu Ile Cys Glu
        115                 120                 125

Thr Pro Thr Cys Gln Ser Asn Glu Phe Arg Cys Arg Ser Gly Arg Cys
    130                 135                 140

Ile Pro Gln His Trp Leu Cys Asp Gly Leu Asn Asp Cys Gly Asp Gly
145                 150                 155                 160

Ser Asp Glu Ser Gln Gln Cys Ser Ala Pro Ala Ser Glu Pro Pro Gly
                165                 170                 175

Ser Leu Ser Leu Phe Asn Leu Pro Gly Asn Tyr Lys Lys Pro Val
            180                 185                 190

Leu Leu Tyr Cys Ser Asn Gly Gly His Phe Leu Arg Ile Leu Pro Asp
        195                 200                 205

Gly Thr Val Asp Gly Thr Arg Asp Arg Ser Asp Gln His Ile Gln Leu
    210                 215                 220

Gln Leu Ser Ala Glu Ser Val Gly Glu Val Tyr Ile Lys Ser Thr Glu
225                 230                 235                 240

Thr Gly Gln Tyr Leu Ala Met Asp Thr Asp Gly Leu Leu Tyr Gly Ser
                245                 250                 255

Gln Thr Pro Asn Glu Glu Cys Leu Phe Leu Glu Arg Leu Glu Glu Asn
            260                 265                 270

His Tyr Val Thr Tyr Ile Ser Lys Lys His Ala Glu Lys Asn Trp Phe
        275                 280                 285

Val Gly Leu Lys Lys Asn Gly Ser Cys Lys Arg Gly Pro Arg Thr His
    290                 295                 300

Tyr Gly Gln Lys Ala Ile Leu Phe Leu Pro Leu Pro Val Ser Ser Asp
305                 310                 315                 320

<210> SEQ ID NO 187
<211> LENGTH: 320
<212> TYPE: PRT
<213> ORGANISM: Artificial sequence
<220> FEATURE:
<223> OTHER INFORMATION: Synthetic polypeptide

<400> SEQUENCE: 187

Cys Gly Ala Asp Gln Phe Arg Cys Gly Asn Gly Ser Cys Val Pro Arg
1               5                   10                  15

Ala Trp Arg Cys Asp Gly Val Asp Asp Cys Gly Asp Gly Ser Asp Glu
            20                  25                  30

Ala Pro Glu Ile Cys Glu Thr Pro Thr Cys Gln Ser Asn Glu Phe Arg
        35                  40                  45

Cys Arg Ser Gly Arg Cys Ile Pro Gln His Trp Leu Cys Asp Gly Leu
    50                  55                  60

Asn Asp Cys Gly Asp Gly Ser Asp Glu Ser Gln Cys Ser Ala Pro
65                  70                  75                  80

Ala Ser Glu Pro Pro Gly Ser Leu Ser Leu Cys Gly Ala Asp Gln Phe
                85                  90                  95

Arg Cys Gly Asn Gly Ser Cys Val Pro Arg Ala Trp Arg Cys Asp Gly
            100                 105                 110

Val Asp Asp Cys Gly Asp Gly Ser Asp Glu Ala Pro Glu Ile Cys Glu
        115                 120                 125

Thr Pro Thr Cys Gln Ser Asn Glu Phe Arg Cys Arg Ser Gly Arg Cys
    130                 135                 140

Ile Pro Gln His Trp Leu Cys Asp Gly Leu Asn Asp Cys Gly Asp Gly
145                 150                 155                 160

Ser Asp Glu Ser Gln Gln Cys Ser Ala Pro Ala Ser Glu Pro Pro Gly
                165                 170                 175

Ser Leu Ser Leu Phe Asn Leu Pro Pro Gly Asn Tyr Lys Lys Pro Lys
            180                 185                 190

Leu Leu Tyr Cys Ser Asn Gly Gly His Phe Leu Arg Ile Leu Pro Asp
        195                 200                 205

Gly Thr Val Asp Gly Thr Arg Asp Arg Ser Asp Gln His Ile Gln Leu
    210                 215                 220

Gln Leu Ser Ala Glu Ser Val Gly Glu Val Tyr Ile Lys Ser Thr Glu
225                 230                 235                 240

Thr Gly Gln Tyr Leu Ala Met Asp Thr Asp Gly Leu Leu Tyr Gly Ser
                245                 250                 255

Gln Thr Pro Asn Glu Glu Cys Leu Phe Leu Glu Arg Leu Glu Glu Asn
            260                 265                 270

His Tyr Asn Thr Tyr Ile Ser Lys Lys His Ala Glu Lys Asn Trp Phe
        275                 280                 285

```
Val Gly Leu Asp Gln Asn Gly Ser Cys Val Arg Gly Pro Arg Thr His
            290                 295                 300

Tyr Gly Gln Lys Ala Ile Leu Phe Leu Pro Leu Pro Val Ser Ser Asp
305                 310                 315                 320

<210> SEQ ID NO 188
<211> LENGTH: 178
<212> TYPE: PRT
<213> ORGANISM: Artificial sequence
<220> FEATURE:
<223> OTHER INFORMATION: Synthetic polypeptide

<400> SEQUENCE: 188

Lys Pro Lys Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Cys Lys Arg Gly Pro
            100                 105                 110

Arg Thr His Tyr Gly Gln Lys Ala Ile Leu Phe Leu Pro Leu Pro Val
        115                 120                 125

Ser Ser Asp Cys Gly Glu Gly Leu Phe Thr Cys Arg Ser Thr Asn Ile
    130                 135                 140

Cys Ile Ser His Ala Trp Val Cys Asp Gly Val Asp Asp Cys Glu Asp
145                 150                 155                 160

Asn Ser Asp Glu Asn Asn Cys Ser Ala Pro Ala Ser Glu Pro Pro Gly
                165                 170                 175

Ser Leu

<210> SEQ ID NO 189
<211> LENGTH: 178
<212> TYPE: PRT
<213> ORGANISM: Artificial sequence
<220> FEATURE:
<223> OTHER INFORMATION: Synthetic polypeptide

<400> SEQUENCE: 189

Cys Gly Glu Gly Leu Phe Thr Cys Arg Ser Thr Asn Ile Cys Ile Ser
1               5                   10                  15

His Ala Trp Val Cys Asp Gly Val Asp Asp Cys Glu Asp Asn Ser Asp
            20                  25                  30

Glu Asn Asn Cys Ser Ala Pro Ala Ser Glu Pro Pro Gly Ser Leu Lys
        35                  40                  45

Pro Lys Leu Leu Tyr Cys Ser Asn Gly Gly His Phe Leu Arg Ile Leu
    50                  55                  60

Pro Asp Gly Thr Val Asp Gly Thr Arg Asp Arg Ser Asp Gln His Ile
65                  70                  75                  80

Gln Leu Gln Leu Ser Ala Glu Ser Val Gly Glu Val Tyr Ile Lys Ser
                85                  90                  95
```

```
Thr Glu Thr Gly Gln Tyr Leu Ala Met Asp Thr Asp Gly Leu Leu Tyr
            100                 105                 110

Gly Ser Gln Thr Pro Asn Glu Glu Cys Leu Phe Leu Glu Arg Leu Glu
        115                 120                 125

Glu Asn His Tyr Asn Thr Tyr Ile Ser Lys Lys His Ala Glu Lys Asn
    130                 135                 140

Trp Phe Val Gly Leu Lys Lys Asn Gly Ser Cys Lys Arg Gly Pro Arg
145                 150                 155                 160

Thr His Tyr Gly Gln Lys Ala Ile Leu Phe Leu Pro Leu Pro Val Ser
                165                 170                 175

Ser Asp

<210> SEQ ID NO 190
<211> LENGTH: 47
<212> TYPE: PRT
<213> ORGANISM: Artificial sequence
<220> FEATURE:
<223> OTHER INFORMATION: Synthetic polypeptide

<400> SEQUENCE: 190

Cys Gly Glu Gly Leu Phe Thr Cys Arg Ser Thr Asn Ile Cys Ile Ser
1               5                   10                  15

His Ala Trp Val Cys Asp Gly Val Asp Asp Cys Glu Asp Asn Ser Asp
            20                  25                  30

Glu Asn Asn Cys Ser Ala Pro Ala Ser Glu Pro Pro Gly Ser Leu
        35                  40                  45

<210> SEQ ID NO 191
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 191

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Glu Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 192
<211> LENGTH: 140
<212> TYPE: PRT
<213> ORGANISM: Artificial sequence
<220> FEATURE:
```

<223> OTHER INFORMATION: Synthetic polypeptide

<400> SEQUENCE: 192

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Glu Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
                100                 105                 110

Gln Asn Gly Ser Val Val Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 193
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 193

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Glu Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 194
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 194

Lys Pro Lys Leu Leu Tyr Cys Ser Asn Gly Gly His Phe Leu Arg Ile

```
Leu Pro Asp Gly Thr Val Asp Gly Thr Glu Asp Arg Ser Asp Gln His
            20                  25                  30

Ile Gln Leu Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                      55                  60

Tyr Gly Ser Gln Thr Pro Asn Glu Glu Cys Leu Phe Leu Glu Arg Leu
 65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Phe Leu Pro Leu Pro Val
            115                 120                 125

Ser Ser Asp
    130

<210> SEQ ID NO 195
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 195

Lys Pro Val Leu Leu Tyr Cys Ser Asn Gly Gly His Phe Leu Arg Ile
 1               5                  10                  15

Leu Pro Asp Gly Thr Val Asp Gly Thr Glu Asp Arg Ser Asp Gln His
            20                  25                  30

Ile Gln Leu Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                      55                  60

Tyr Gly Ser Gln Thr Pro Asn Glu Glu Cys Leu Phe Leu Glu Arg Leu
 65                  70                  75                  80

Glu Glu Asn His Tyr Val Thr Tyr Ile Ser Lys Lys His Ala Glu Lys
                85                  90                  95

Asn Trp Phe Val Gly Leu Asp Gln Asn Gly Ser Val Val Arg Gly Pro
            100                 105                 110

Arg Thr His Tyr Gly Gln Lys Ala Ile Leu Phe Leu Pro Leu Pro Val
            115                 120                 125

Ser Ser Asp
    130

<210> SEQ ID NO 196
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 196

Phe Asn Leu Pro Pro Gly Asn Tyr Lys Lys Pro Val Leu Leu Tyr Cys
 1               5                  10                  15

Ser Asn Gly Gly His Phe Leu Arg Ile Leu Pro Asp Gly Thr Val Asp
            20                  25                  30
```

```
Gly Thr Glu Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Val Thr
                 85                  90                  95

Tyr Ile Ser Lys Lys His Ala Glu Lys Asn Trp Phe Val Gly Leu Asp
                100                 105                 110

Gln Asn Gly Ser Val Val Arg Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 197
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 197

Lys Pro Val Leu Leu Tyr Cys Ser Asn Gly Gly His Phe Leu Arg Ile
 1               5                  10                  15

Leu Pro Asp Gly Thr Val Asp Gly Thr Glu Asp Arg Ser Asp Gln His
                20                  25                  30

Ile Gln Phe Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Thr Leu Phe Leu Glu Arg Leu
 65                  70                  75                  80

Glu Glu Asn His Tyr Val Thr Tyr Ile Ser Lys Lys His Ala Glu Lys
                 85                  90                  95

Asn Trp Phe Val Gly Leu Lys Lys Asn Gly Ser Val Lys Arg Gly Pro
                100                 105                 110

Arg Thr His Tyr Gly Gln Lys Ala Ile Leu Trp Leu Pro Leu Pro Val
            115                 120                 125

Ser Ser Asp
    130

<210> SEQ ID NO 198
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 198

Lys Pro Val Leu Leu Tyr Cys Ser Asn Gly Gly His Phe Leu Arg Ile
 1               5                  10                  15

Leu Pro Asp Gly Thr Val Asp Gly Thr Glu Asp Arg Ser Asp Gln His
                20                  25                  30

Ile Gln Phe Gln Leu Ser Ala Glu Ser Val Gly Glu Val Tyr Ile Lys
            35                  40                  45

Ser Thr Glu Thr Gly Gln Tyr Leu Ala Met Asp Thr Asp Gly Leu Leu
 50                  55                  60
```

Tyr Gly Ser Gln Thr Pro Asn Glu Glu Thr Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Asp Gln Asn Gly Ser Val Val Arg Gly Pro
            100                 105                 110

Arg Thr His Tyr Gly Gln Lys Ala Ile Leu Trp Leu Pro Leu Pro Val
        115                 120                 125

Ser Ser Asp
    130

<210> SEQ ID NO 199
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 199

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Val Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
        130                 135                 140

<210> SEQ ID NO 200
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 200

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Val Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr

```
                    85                  90                  95

Tyr Ile Ser Lys Lys His Ala Glu Lys Asn Trp Phe Val Gly Leu Asp
                100                 105                 110

Gln Asn Gly Ser Val Val Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 201
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 201

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Val Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 202
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 202

Lys Pro Lys Leu Leu Tyr Cys Ser Asn Gly Gly His Phe Leu Arg Ile
1               5                   10                  15

Leu Pro Asp Gly Thr Val Asp Gly Thr Val Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys His Ala Glu Lys
                85                  90                  95

Asn Trp Phe Val Gly Leu Lys Lys Asn Gly Ser Val Lys Arg Gly Pro
                100                 105                 110
```

```
Arg Thr His Tyr Gly Gln Lys Ala Ile Leu Phe Leu Pro Leu Pro Val
            115                 120                 125

Ser Ser Asp
    130

<210> SEQ ID NO 203
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 203

Lys Pro Val Leu Leu Tyr Cys Ser Asn Gly Gly His Phe Leu Arg Ile
1               5                   10                  15

Leu Pro Asp Gly Thr Val Asp Gly Thr Val Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Asp Gln Asn Gly Ser Val Val Arg Gly Pro
            100                 105                 110

Arg Thr His Tyr Gly Gln Lys Ala Ile Leu Phe Leu Pro Leu Pro Val
        115                 120                 125

Ser Ser Asp
    130

<210> SEQ ID NO 204
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 204

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Val Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys His Ala Glu Lys Asn Trp Phe Val Gly Leu Asp
            100                 105                 110

Gln Asn Gly Ser Val Val Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 205
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 205

Lys Pro Val Leu Leu Tyr Cys Ser Asn Gly Gly His Phe Leu Arg Ile
1               5                   10                  15

Leu Pro Asp Gly Thr Val Asp Gly Thr Val Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Thr Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Trp Leu Pro Leu Pro Val
        115                 120                 125

Ser Ser Asp
    130

<210> SEQ ID NO 206
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 206

Lys Pro Val Leu Leu Tyr Cys Ser Asn Gly Gly His Phe Leu Arg Ile
1               5                   10                  15

Leu Pro Asp Gly Thr Val Asp Gly Thr Val Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Thr Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Asp Gln Asn Gly Ser Val Val Arg Gly Pro
            100                 105                 110

Arg Thr His Tyr Gly Gln Lys Ala Ile Leu Trp Leu Pro Leu Pro Val
        115                 120                 125

Ser Ser Asp
    130

<210> SEQ ID NO 207
<211> LENGTH: 140
<212> TYPE: PRT

<213> ORGANISM: Artificial sequence
<220> FEATURE:
<223> OTHER INFORMATION: Synthetic polypeptide

<400> SEQUENCE: 207

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
            100                 105                 110

Gln Asn Gly Ser Val Val Val Gly Pro Arg Thr His Tyr Gly Gln Lys
            115                 120                 125

Ala Ile Leu Phe Leu Pro Leu Pro Val Ser Ser Asp
130                 135                 140
```

<210> SEQ ID NO 208
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 208

```
Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Val Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
130                 135                 140
```

<210> SEQ ID NO 209
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 209

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Val Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 210
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 210

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Val Arg Leu Glu Glu Asn His Val Asn Thr
                85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 211
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 211

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp

```
                20                  25                  30
Gly Thr Arg Asp Arg Ser Asp Gln His Ile Gln Leu Gln Leu Ser Ala
             35                  40                  45

Glu Ser Val Gly Glu Val Tyr Ile Lys Ser Thr Glu Thr Gly Gln Tyr
         50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Val Val Thr
                 85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 212
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 212

Phe Asn Leu Pro Pro Gly Asn Tyr Lys Lys Pro Val Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Val Ser Ala
         35                  40                  45

Glu Ser Val Gly Glu Val Tyr Ile Lys Ser Thr Glu Thr Gly Gln Tyr
         50                  55                  60

Leu Ala Met Asp Thr Asp Gly Leu Leu Tyr Gly Ser Gln Thr Pro Asn
 65                  70                  75                  80

Glu Glu Cys Leu Phe Leu Val Arg Leu Glu Glu Asn His Tyr Val Thr
                 85                  90                  95

Tyr Ile Ser Lys Lys His Ala Glu Lys Asn Trp Phe Val Gly Leu Lys
                100                 105                 110

Lys Asn Gly Ser Val Lys Arg Gly Pro Arg Thr His Tyr Gly Gln Lys
            115                 120                 125

Ala Ile Leu Phe Leu Val Leu Pro Val Ser Ser Asp
        130                 135                 140

<210> SEQ ID NO 213
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 213

Phe Asn Leu Pro Pro Gly Asn Tyr Lys Lys Pro Lys Leu Leu Tyr Cys
 1               5                  10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
         35                  40                  45
```

```
Glu Ser Val Gly Glu Val Tyr Ile Lys Ser Thr Glu Thr Gly Gln Tyr
         50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Val Val Arg Gly Pro Arg Thr His Tyr Gly Gln Lys
                115                 120                 125

Ala Ile Leu Phe Leu Pro Leu Pro Val Ser Ser Asp
            130                 135                 140

<210> SEQ ID NO 214
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 214

Lys Pro Val Leu Leu Tyr Cys Ser Asn Gly Gly His Phe Leu Arg Ile
  1               5                  10                  15

Leu Pro Asp Gly Thr Val Asp Gly Thr Arg Asp Arg Ser Asp Gln His
                 20                  25                  30

Ile Gln Leu Gln Leu Ser Ala Glu Ser Val Gly Glu Val Tyr Ile Lys
             35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Thr Leu Phe Leu Glu Arg Leu
 65                  70                  75                  80

Glu Glu Asn His Tyr Val Thr Tyr Ile Ser Lys Lys His Ala Glu Lys
                 85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Phe Leu Pro Leu Pro Val
            115                 120                 125

Ser Ser Asp
    130

<210> SEQ ID NO 215
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 215

Lys Pro Val Leu Leu Tyr Thr Ser Asn Gly Gly His Phe Leu Arg Ile
  1               5                  10                  15

Leu Pro Asp Gly Thr Val Asp Gly Thr Arg Asp Arg Ser Asp Gln His
                 20                  25                  30

Ile Gln Leu Gln Leu Ser Ala Glu Ser Val Gly Glu Val Tyr Ile Lys
             35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Ser Leu Phe Leu Glu Arg Leu
 65                  70                  75                  80
```

```
Glu Glu Asn His Tyr Val Thr Tyr Ile Ser Lys Lys His Ala Glu Lys
                85                  90                  95

Asn Trp Phe Val Gly Leu Lys Lys Asn Gly Ser Ala Lys Arg Gly Pro
           100                 105                 110

Arg Thr His Tyr Gly Gln Lys Ala Ile Leu Phe Leu Pro Leu Pro Val
           115                 120                 125

Ser Ser Asp
       130

<210> SEQ ID NO 216
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 216

Lys Pro Lys Leu Leu Tyr Cys Ser Asn Gly Gly Tyr Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Asn Thr Tyr Ile Ser Lys Lys Tyr Ala Glu Lys
                85                  90                  95

Asn Trp Tyr Val Gly Leu Lys Lys Asn Gly Ser Val Lys Arg Gly Pro
           100                 105                 110

Arg Thr His Tyr Gly Gln Lys Ala Ile Leu Phe Leu Pro Leu Pro Val
           115                 120                 125

Ser Ser Asp
       130

<210> SEQ ID NO 217
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 217

Lys Pro Val Leu Leu Tyr Cys Ser Asn Gly Gly Tyr Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65                  70                  75                  80

Glu Glu Asn His Tyr Val Thr Tyr Ile Ser Lys Lys Tyr Ala Glu Lys
                85                  90                  95

Asn Trp Tyr Val Gly Leu Lys Lys Asn Gly Ser Val Lys Arg Gly Pro
```

```
                    100                 105                 110
Arg Thr His Tyr Gly Gln Lys Ala Ile Leu Phe Leu Pro Leu Pro Val
            115                 120                 125

Ser Ser Asp
        130

<210> SEQ ID NO 218
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 218

Phe Asn Leu Pro Pro Gly Asn Tyr Lys Lys Pro Val Leu Leu Tyr Cys
1               5                   10                  15

Ser Asn Gly Gly Tyr Phe Leu Arg Ile Leu Pro Asp Gly Thr Val Asp
            20                  25                  30

Gly Thr Arg Asp Arg Ser Asp Gln His Ile Gln Phe Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Val Thr
                85                  90                  95

Tyr Ile Ser Lys Lys Tyr Ala Glu Lys Asn Trp Tyr Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 219
<211> LENGTH: 177
<212> TYPE: PRT
<213> ORGANISM: Artificial sequence
<220> FEATURE:
<223> OTHER INFORMATION: Synthetic polypeptide

<400> SEQUENCE: 219

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
            100                 105                 110

Gln Asn Gly Ser Cys Val Arg Gly Pro Arg Thr His Tyr Gly Gln Lys
        115                 120                 125
```

```
Ala Ile Leu Phe Leu Pro Leu Pro Gly Leu Pro Pro Ala Leu Pro Glu
        130                 135                 140

Pro Pro Gly Ile Leu Ala Pro Gln Pro Pro Asp Val Gly Ser Ser Asp
145                 150                 155                 160

Pro Leu Ser Met Val Gly Pro Ser Gln Gly Arg Ser Pro Ser Tyr Ala
                165                 170                 175

Ser

<210> SEQ ID NO 220
<211> LENGTH: 183
<212> TYPE: PRT
<213> ORGANISM: Artificial sequence
<220> FEATURE:
<223> OTHER INFORMATION: Synthetic polypeptide

<400> SEQUENCE: 220

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
            100                 105                 110

Gln Asn Gly Ser Cys Val Arg Gly Pro Arg Thr His Tyr Gly Gln Lys
        115                 120                 125

Ala Ile Leu Phe Leu Pro Leu Pro Met Val Pro Glu Glu Pro Glu
    130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 221
<211> LENGTH: 147
<212> TYPE: PRT
<213> ORGANISM: Artificial sequence
<220> FEATURE:
<223> OTHER INFORMATION: Synthetic polypeptide

<400> SEQUENCE: 221

His Pro Ile Pro Asp Ser Ser Pro Leu Leu Gln Phe Gly Gly Gln Val
1               5                   10                  15

Lys Pro Lys Leu Leu Tyr Cys Ser Asn Gly Gly His Phe Leu Arg Ile
            20                  25                  30

Leu Pro Asp Gly Thr Val Asp Gly Thr Arg Asp Arg Ser Asp Gln His
        35                  40                  45

Ile Gln Leu Gln Leu Ser Ala Glu Ser Val Gly Glu Val Tyr Ile Lys
    50                  55                  60
```

```
Ser Thr Glu Thr Gly Gln Tyr Leu Ala Met Asp Thr Asp Gly Leu Leu
 65                  70                  75                  80

Tyr Gly Ser Gln Thr Pro Asn Glu Glu Cys Leu Phe Leu Glu Arg Leu
                 85                  90                  95

Glu Glu Asn His Tyr Asn Thr Tyr Ile Ser Lys Lys His Ala Glu Lys
            100                 105                 110

Asn Trp Phe Val Gly Leu Lys Lys Asn Gly Ser Val Lys Arg Gly Pro
        115                 120                 125

Arg Thr His Tyr Gly Gln Lys Ala Ile Leu Phe Leu Pro Leu Pro Val
    130                 135                 140

Ser Ser Asp
145

<210> SEQ ID NO 222
<211> LENGTH: 135
<212> TYPE: PRT
<213> ORGANISM: Artificial sequence
<220> FEATURE:
<223> OTHER INFORMATION: Synthetic polypeptide

<400> SEQUENCE: 222

Gly Gly Gln Val Lys Pro Lys Leu Leu Tyr Cys Ser Asn Gly Gly His
  1               5                  10                  15

Phe Leu Arg Ile Leu Pro Asp Gly Thr Val Asp Gly Thr Arg Asp Arg
             20                  25                  30

Ser Asp Gln His Ile Gln Leu Gln Leu Ser Ala Glu Ser Val Gly Glu
         35                  40                  45

Val Tyr Ile Lys Ser Thr Glu Thr Gly Gln Tyr Leu Ala Met Asp Thr
 50                  55                  60

Asp Gly Leu Leu Tyr Gly Ser Gln Thr Pro Asn Glu Glu Cys Leu Phe
 65                  70                  75                  80

Leu Glu Arg Leu Glu Glu Asn His Tyr Asn Thr Tyr Ile Ser Lys Lys
                 85                  90                  95

His Ala Glu Lys Asn Trp Phe Val Gly Leu Lys Lys Asn Gly Ser Val
            100                 105                 110

Lys Arg Gly Pro Arg Thr His Tyr Gly Gln Lys Ala Ile Leu Phe Leu
        115                 120                 125

Pro Leu Pro Val Ser Ser Asp
    130                 135

<210> SEQ ID NO 223
<211> LENGTH: 177
<212> TYPE: PRT
<213> ORGANISM: Artificial sequence
<220> FEATURE:
<223> OTHER INFORMATION: Synthetic polypeptide

<400> SEQUENCE: 223

Phe Asn Leu Pro Pro Gly Asn Tyr Lys Lys Pro Lys Leu Leu Tyr Cys
  1               5                  10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80
```

```
Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
               100                 105                 110

Lys Asn Gly Ser Cys Lys Arg Gly Pro Arg Thr His Tyr Gly Gln Lys
               115                 120                 125

Ala Ile Leu Phe Leu Pro Leu Pro Gly Leu Pro Pro Ala Leu Pro Glu
130                 135                 140

Pro Pro Gly Ile Leu Ala Pro Gln Pro Pro Asp Val Gly Ser Ser Asp
145                 150                 155                 160

Pro Leu Ser Met Val Gly Pro Ser Gln Gly Arg Ser Pro Ser Tyr Ala
               165                 170                 175

Ser

<210> SEQ ID NO 224
<211> LENGTH: 183
<212> TYPE: PRT
<213> ORGANISM: Artificial sequence
<220> FEATURE:
<223> OTHER INFORMATION: Synthetic polypeptide

<400> SEQUENCE: 224

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
               20                  25                  30

Gly Thr Arg Asp Arg Ser Asp Gln His Ile Gln Leu Gln Leu Ser Ala
               35                  40                  45

Glu Ser Val Gly Glu Val Tyr Ile Lys Ser Thr Glu Thr Gly Gln Tyr
50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
               100                 105                 110

Lys Asn Gly Ser Cys Lys Arg Gly Pro Arg Thr His Tyr Gly Gln Lys
               115                 120                 125

Ala Ile Leu Phe Leu Pro Leu Pro Met Val Pro Glu Glu Pro Glu
130                 135                 140

Asp Leu Arg Gly His Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
               165                 170                 175

Arg Ser Pro Ser Phe Glu Lys
               180

<210> SEQ ID NO 225
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 225

Lys Pro Val Leu Leu Tyr Cys Ser Asn Gly Gly His Phe Leu Arg Ile
1               5                   10                  15
```

```
Leu Pro Asp Gly Thr Val Asp Gly Thr Arg Asp Arg Ser Asp Gln His
         20                  25                  30

Ile Gln Leu Gln Leu Ser Ala Glu Ser Val Gly Glu Val Tyr Ile Lys
             35                  40                  45

Ser Thr Glu Thr Gly Gln Tyr Leu Ala Met Asp Thr Asp Gly Leu Leu
 50                  55                  60

Tyr Gly Ser Gln Thr Pro Asn Glu Glu Cys Leu Phe Leu Glu Arg Leu
 65                  70                  75                  80

Glu Glu Asn His Tyr Val Thr Tyr Ile Ser Lys His Ala Glu Lys
                 85                  90                  95

Asn Trp Phe Val Gly Leu Lys Lys Asn Gly Ser Val Lys Arg Gly Pro
             100                 105                 110

Arg Thr His Tyr Gly Gln Lys Ala Ile Leu Phe Leu Pro Leu Pro Val
             115                 120                 125

Ser Ser Asp
    130

<210> SEQ ID NO 226
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 226

Phe Asn Leu Pro Pro Gly Asn Tyr Lys Lys Pro Lys Leu Leu Tyr Cys
 1               5                   10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
             85                  90                  95

Tyr Ile Ser Lys Lys His Ala Glu Lys Asn Trp Phe Val Gly Leu Asp
             100                 105                 110

Gln Asn Gly Ser Cys Val Arg Gly Pro Arg Thr His Tyr Gly Gln Lys
             115                 120                 125

Ala Ile Leu Phe Leu Pro Leu Pro Val Ser Ser Asp
             130                 135                 140

<210> SEQ ID NO 227
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 227

Phe Asn Leu Pro Pro Gly Asn Tyr Lys Lys Pro Val Leu Leu Tyr Cys
 1               5                   10                  15

Ser Asn Gly Gly His Phe Leu Arg Ile Leu Pro Asp Gly Thr Val Asp
             20                  25                  30

Gly Thr Arg Asp Arg Ser Asp Pro His Ile Gln Leu Gln Leu Ile Ala
```

```
                35                  40                  45
Glu Ser Val Gly Glu Val Tyr Ile Lys Ser Thr Glu Thr Gly Gln Tyr
 50                  55                  60
Leu Ala Met Asp Thr Asp Gly Leu Leu Tyr Gly Ser Gln Thr Pro Asn
 65                  70                  75                  80
Glu Glu Cys Leu Phe Leu Glu Arg Leu Glu Asn Gly Tyr Val Thr
                 85                  90                  95
Tyr Ile Ser Lys Lys His Ala Glu Lys Asn Trp Phe Val Gly Leu Lys
                100                 105                 110
Lys Asn Gly Ser Cys Lys Arg Gly Pro Arg Thr His Tyr Gly Gln Lys
                115                 120                 125
Ala Ile Leu Phe Leu Pro Leu Pro Val Ser Ser Asp
                130                 135                 140

<210> SEQ ID NO 228
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 228

Lys Pro Val Leu Leu Tyr Cys Ser Asn Gly Gly His Phe Leu Arg Ile
  1               5                  10                  15
Leu Pro Asp Gly Thr Val Asp Gly Thr Arg Asp Arg Ser Asp Pro His
                 20                  25                  30
Ile Gln Leu Gln Leu Ile Ala Glu Ser Val Gly Glu Val Tyr Ile Lys
                 35                  40                  45
Ser Thr Glu Thr Gly Gln Tyr Leu Ala Met Asp Thr Asp Gly Leu Leu
 50                  55                  60
Tyr Gly Ser Gln Thr Pro Asn Glu Glu Cys Leu Phe Leu Glu Arg Leu
 65                  70                  75                  80
Glu Glu Asn Gly Tyr Val Thr Tyr Ile Ser Lys Lys His Ala Glu Lys
                 85                  90                  95
Asn Trp Phe Val Gly Leu Lys Lys Asn Gly Ser Cys Lys Arg Gly Pro
                100                 105                 110
Arg Thr His Tyr Gly Gln Lys Ala Ile Leu Phe Leu Pro Leu Pro Val
                115                 120                 125
Ser Ser Asp
        130

<210> SEQ ID NO 229
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 229

Phe Asn Leu Pro Pro Gly Asn Tyr Lys Lys Pro Val Leu Leu Tyr Cys
  1               5                  10                  15
Ser Asn Gly Gly His Phe Leu Arg Ile Leu Pro Asp Gly Thr Val Asp
                 20                  25                  30
Gly Thr Arg Asp Arg Ser Asp Gln His Ile Gln Phe Gln Leu Ser Ala
                 35                  40                  45
Glu Ser Val Gly Glu Val Tyr Ile Lys Ser Thr Glu Thr Gly Gln Tyr
 50                  55                  60
```

```
Leu Ala Met Asp Thr Asp Gly Leu Leu Tyr Gly Ser Gln Thr Pro Asn
 65                  70                  75                  80

Glu Glu Thr Leu Phe Leu Glu Arg Leu Glu Glu Asn His Tyr Val Thr
                 85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Trp Leu Pro Leu Pro Val Ser Ser Asp
    130                 135                 140

<210> SEQ ID NO 230
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 230

Phe Asn Leu Pro Pro Gly Asn Tyr Lys Lys Pro Lys Leu Leu Tyr Cys
  1               5                  10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
     50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 231
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 231

Phe Asn Leu Pro Pro Gly Asn Tyr Lys Lys Pro Val Leu Leu Tyr Cys
  1               5                  10                  15

Ser Asn Gly Gly His Phe Leu Arg Ile Leu Pro Asp Gly Thr Val Asp
             20                  25                  30

Gly Thr Arg Asp Arg Ser Asp Gln His Ile Gln Leu Gln Leu Ser Ala
         35                  40                  45

Glu Ser Val Gly Glu Val Tyr Ile Lys Ser Thr Glu Thr Gly Gln Tyr
     50                  55                  60

Leu Ala Met Asp Thr Asp Gly Leu Leu Tyr Gly Ser Gln Thr Pro Asn
 65                  70                  75                  80

Glu Glu Cys Leu Phe Leu Glu Arg Leu Glu Glu Asn His Tyr Val Thr
                 85                  90                  95
```

Tyr Ile Ser Lys Lys His Ala Glu Lys Asn Trp Phe Val Gly Leu Asp
            100                 105                 110

Gln Asn Gly Ser Val Val Arg Gly Pro Arg Thr His Tyr Gly Gln Lys
        115                 120                 125

Ala Ile Leu Phe Leu Pro Leu Pro Val Ser Ser Asp
        130                 135                 140

<210> SEQ ID NO 232
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 232

Lys Pro Val Leu Leu Tyr Cys Ser Asn Gly Gly His Phe Leu Arg Ile
1               5                   10                  15

Leu Pro Asp Gly Thr Val Asp Gly Thr Arg Asp Arg Ser Asp Gln His
            20                  25                  30

Ile Gln Phe Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Thr Leu Phe Leu Glu Arg Leu
65                  70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Val Lys Arg Gly Pro
            100                 105                 110

Arg Thr His Tyr Gly Gln Lys Ala Ile Leu Trp Leu Pro Leu Pro Val
        115                 120                 125

Ser Ser Asp
    130

<210> SEQ ID NO 233
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 233

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Glu Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys

```
                115                 120                 125
Ala Ile Leu Phe Leu Pro Leu Pro Val Ser Ser Asp
    130                 135                 140

<210> SEQ ID NO 234
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 234

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Val Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 235
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 235

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Val Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140
```

```
<210> SEQ ID NO 236
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 236

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Asp
                100                 105                 110

Gln Asn Gly Ser Val Val Val Gly Pro Arg Thr His Tyr Gly Gln Lys
            115                 120                 125

Ala Ile Leu Phe Leu Pro Leu Pro Val Ser Ser Asp
            130                 135                 140

<210> SEQ ID NO 237
<211> LENGTH: 140
<212> TYPE: PRT
<213> ORGANISM: Artificial sequence
<220> FEATURE:
<223> OTHER INFORMATION: Synthetic polypeptide

<400> SEQUENCE: 237

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
                20                  25                  30

Gly Thr Glu Asp Arg Ser Asp Gln His Ile Gln Leu Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Phe Asn Leu Pro Pro Gly Asn Tyr Lys Lys
65                  70                  75                  80

Pro Val Leu Leu Tyr Cys Ser Asn Gly Gly His Phe Leu Arg Ile Leu
                85                  90                  95

Pro Asp Gly Thr Val Asp Gly Thr Glu Asp Arg Ser Asp Gln His Ile
                100                 105                 110

Gln Leu Gln Leu Ser Ala Glu Ser Val Gly Glu Val Tyr Ile Lys Ser
            115                 120                 125

Thr Glu Thr Gly Gln Tyr Leu Ala Met Asp Thr Asp
            130                 135                 140

<210> SEQ ID NO 238
<211> LENGTH: 131
<212> TYPE: PRT
<213> ORGANISM: Artificial sequence
```

```
<220> FEATURE:
<223> OTHER INFORMATION: Synthetic polypeptide

<400> SEQUENCE: 238

Lys Pro Val Leu Leu Tyr Cys Ser Asn Gly Gly His Phe Leu Arg Ile
1               5                   10                  15

Leu Pro Asp Gly Thr Val Asp Gly Thr Glu Asp Arg Ser Asp Gln His
            20                  25                  30

Ile Gln Leu Gln Leu Ser Ala Glu Ser Val Gly Glu Val Tyr Ile Lys
        35                  40                  45

Ser Thr Glu Thr Gly Gln Tyr Leu Ala Met Asp Thr Asp Gly Leu Leu
    50                  55                  60

Tyr Gly Ser Gln Thr Pro Asn Glu Glu Cys Leu Phe Leu Glu Arg Leu
65              70                  75                  80

Glu Glu Asn His Tyr Val Thr Tyr Ile Ser Lys Lys His Ala Glu Lys
                85                  90                  95

Asn Trp Phe Val Gly Leu Lys Lys Asn Gly Ser Val Lys Arg Gly Pro
                100                 105                 110

Arg Thr His Tyr Gly Gln Lys Ala Ile Leu Phe Leu Pro Leu Pro Val
        115                 120                 125

Ser Ser Asp
    130
```

We claim:

1. An isolated mutated mature fibroblast growth factor (FGF) 1 protein comprising at least 90% sequence identity to the amino acid sequence shown in SEQ ID NO: 234 wherein the isolated mutated mature FGF1 protein comprises a Y94V mutation, and wherein the amino acid numbering is based on SEQ ID NO: 5.

2. The isolated protein of claim 1, wherein the isolated mutated mature FGF1 protein further comprises a mutation at K12, and wherein the amino acid numbering is based on SEQ ID NO: 5.

3. The isolated protein of claim 2, wherein the mutation at K12 is K12V, and wherein the amino acid numbering is based on SEQ ID NO: 5.

4. The isolated protein of claim 1, wherein the isolated mutated mature FGF1 protein further comprises a mutation at C117, and wherein the amino acid numbering is based on SEQ ID NO: 5.

5. The isolated protein of claim 4, wherein the mutation at C117 is C117V, and wherein the amino acid numbering is based on SEQ ID NO: 5.

6. The isolated protein of claim 1, wherein the isolated mutated mature FGF1 protein further comprises a mutation at K12 and C117, and wherein the amino acid numbering is based on SEQ ID NO: 5.

7. The isolated protein of claim 6, wherein the mutation at K12 is K12V, the mutation at C117 is C117V, and amino acid numbering is based on SEQ ID NO: 5.

8. The isolated protein of claim 1, wherein the isolated mutated mature FGF1 protein comprises at least 95% sequence identity to the amino acid sequence shown in SEQ ID NO: 234, wherein the isolated mutated mature FGF1 protein comprises a Y94V mutation, and wherein the amino acid numbering is based on SEQ ID NO: 5.

9. The isolated protein of claim 1, wherein the isolated mutated mature FGF1 protein comprises at least 98% sequence identity to the amino acid sequence shown in SEQ ID NO: 234, wherein the isolated mutated mature FGF1 protein comprises a Y94V mutation, and wherein the amino acid numbering is based on SEQ ID NO: 5.

10. The isolated protein of claim 1, wherein the isolated mutated mature FGF1 protein comprises at least 99% sequence identity to the amino acid sequence shown in SEQ ID NO: 234, wherein the isolated mutated mature FGF1 protein comprises a Y94V mutation, and wherein the amino acid numbering is based on SEQ ID NO: 5.

11. The isolated protein of claim 1, wherein the isolated mutated mature FGF1 protein comprises the amino acid sequence shown in SEQ ID NO: 234.

12. The isolated protein of claim 1, wherein the isolated mutated mature FGF1 protein consists of the amino acid sequence shown in SEQ ID NO: 234.

13. An isolated nucleic acid encoding the isolated protein of claim 1.

14. A nucleic acid vector comprising the isolated nucleic acid of claim 13.

15. A host cell comprising the nucleic acid vector of claim 14.

* * * * *